(12) United States Patent
Upasani et al.

(10) Patent No.: US 12,129,275 B2
(45) Date of Patent: Oct. 29, 2024

(54) NEUROACTIVE STEROIDS, COMPOSITIONS, AND USES THEREOF

(71) Applicant: SAGE THERAPEUTICS, INC., Cambridge, MA (US)

(72) Inventors: Ravindra B. Upasani, San Jose, CA (US); Boyd L. Harrison, Princeton Junction, NJ (US); Benny C. Askew, Marshfield, MA (US); Jean-Cosme Dodart, Brookline, MA (US); Francesco G. Salituro, Marlborough, MA (US); Albert Jean Robichaud, Boston, MA (US)

(73) Assignee: SAGE THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 17/707,303

(22) Filed: Mar. 29, 2022

(65) Prior Publication Data

US 2023/0192756 A1    Jun. 22, 2023

Related U.S. Application Data

(63) Continuation of application No. 16/942,235, filed on Jul. 29, 2020, now abandoned, which is a (Continued)

(51) Int. Cl.
*C07J 41/00*     (2006.01)
*C07J 1/00*      (2006.01)
(Continued)

(52) U.S. Cl.
CPC ............. *C07J 41/00* (2013.01); *C07J 1/00* (2013.01); *C07J 1/0029* (2013.01); *C07J 3/00* (2013.01);
(Continued)

(58) Field of Classification Search
CPC ....... C07J 3/00; C07J 7/007; C07J 9/00; C07J 9/005; C07J 41/0055
See application file for complete search history.

(56) References Cited

U.S. PATENT DOCUMENTS 2,259,698 A    10/1941  Johannessohn et al.
2,594,323 A     4/1952  Levin et al.
(Continued)

FOREIGN PATENT DOCUMENTS

AU       728843    1/2001
CN      1257077    6/2000
(Continued)

OTHER PUBLICATIONS

Magyar et al., Stereoselective reaction of (20R)-3,20-dihydroxy-(3',4'-dihydro-2'H-pyranyl)-5-pregnene derivatives from 27-nor-3,20,23,26-tetrahydroxy-cholesten-22-ones and related bromo ketones. Steroids, vol. 69(1), pp. 35-42 (Year: 2004).*

(Continued)

*Primary Examiner* — Barbara P Badio
(74) *Attorney, Agent, or Firm* — HALEY GUILIANO LLP; Karen Mangasarian; Mihaela D. Danca

(57) ABSTRACT

Compounds are provided according to Formula (I) and pharmaceutically acceptable salts thereof, wherein Z is a group of the formula (i), (ii), (iii), (iv), or (v), and wherein $L^1$, $L^2$, $L^3$, $X^1$, $X^2$, Y, $R^{z4}$, $R^{z5}$, $R^{z6}$, n, $R^1$, $R^2$, $R^{3a}$, $R^{3b}$, $R^{4a}$, $R^{4b}$, $R^{6a}$, $R^{6b}$, $R^{7a}$, $R^{7b}$, $R^{11a}$, $R^{11b}$, $R^{14}$, $R^{17}$, $R^{19}$, $R^{20}$, $R^{23a}$, $R^{23b}$, and $R^{24}$ are as defined herein, and pharmaceutical compositions thereof. Compounds of the present invention are contemplated useful for the prevention and treatment of a variety of CNS-related conditions in mammals.

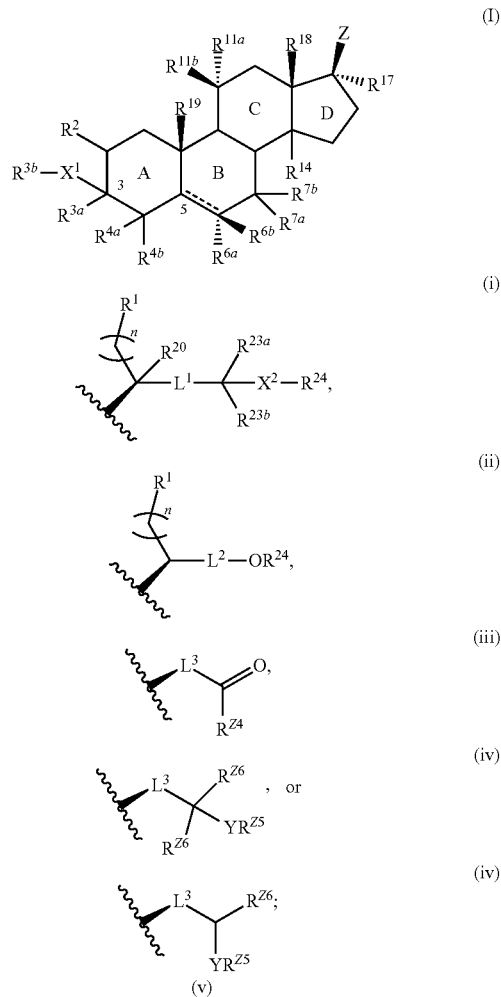

18 Claims, No Drawings

Related U.S. Application Data continuation of application No. 16/114,791, filed on Aug. 28, 2018, now Pat. No. 10,759,828, which is a continuation of application No. 14/343,603, filed as application No. PCT/US2012/054261 on Sep. 7, 2012, now abandoned.

(60) Provisional application No. 61/532,427, filed on Sep. 8, 2011.

(51) Int. Cl.
| | | |
|---|---|---|
| *C07J 3/00* | (2006.01) | |
| *C07J 7/00* | (2006.01) | |
| *C07J 9/00* | (2006.01) | |
| *C07J 31/00* | (2006.01) | |
| *C07J 43/00* | (2006.01) | |
| *C07J 75/00* | (2006.01) | |

(52) U.S. Cl.
CPC ............... *C07J 7/007* (2013.01); *C07J 9/00* (2013.01); *C07J 9/005* (2013.01); *C07J 31/003* (2013.01); *C07J 31/006* (2013.01); *C07J 41/0005* (2013.01); *C07J 41/0011* (2013.01); *C07J 41/0055* (2013.01); *C07J 43/003* (2013.01); *C07J 75/00* (2013.01)

(56) References Cited

U.S. PATENT DOCUMENTS

| | | |
|---|---|---|
| 2,673,206 A | 3/1954 | Ryer |
| 3,079,385 A | 2/1963 | Bertin et al. |
| 3,206,459 A | 9/1965 | Cross |
| 3,463,779 A | 8/1969 | Bowie et al. |
| 4,071,625 A | 1/1978 | Grunwell et al. |
| 4,174,345 A | 11/1979 | Kaiser |
| 4,183,852 A | 1/1980 | Kaiser |
| 4,868,165 A | 9/1989 | Ikekawa |
| 5,232,917 A | 8/1993 | Bolger et al. |
| 5,376,645 A | 12/1994 | Stella et al. |
| 5,512,570 A | 4/1996 | Dorn et al. |
| 5,595,996 A | 1/1997 | Graham et al. |
| 5,888,996 A | 3/1999 | Farb |
| 5,925,630 A | 7/1999 | Upasani et al. |
| 6,407,086 B2 | 6/2002 | Faarup et al. |
| 6,645,953 B2 | 11/2003 | Gronvald et al. |
| 6,884,796 B2 | 4/2005 | Faarup et al. |
| 6,933,312 B2 | 8/2005 | Price et al. |
| 8,034,798 B2 | 10/2011 | Baulieu et al. |
| 8,247,436 B2 | 8/2012 | Baettig et al. |
| 8,604,011 B2 | 12/2013 | Mellon |
| 8,673,843 B2 | 3/2014 | Moskal et al. |
| 8,829,213 B2 | 9/2014 | Peng et al. |
| 10,201,550 B2 | 2/2019 | Salituro et al. |
| 10,227,375 B2 | 3/2019 | Botella et al. |
| 10,259,840 B2 | 4/2019 | Harrison et al. |
| 10,696,712 B2 | 6/2020 | Salituro et al. |
| 10,723,758 B2 | 7/2020 | Harrison et al. |
| 10,752,653 B2 | 8/2020 | Martinez Botella et al. |
| 10,759,828 B2 | 9/2020 | Upasani et al. |
| 10,765,685 B2 | 9/2020 | Salituro et al. |
| 10,781,231 B2 | 9/2020 | Salituro et al. |
| 11,104,701 B2 | 8/2021 | Botella et al. |
| 11,111,266 B2 | 9/2021 | Salituro et al. |
| 11,149,054 B2 | 10/2021 | Salituro et al. |
| 2004/0048838 A1 | 3/2004 | Gronvald et al. |
| 2005/0101573 A1 | 5/2005 | Faarup et al. |
| 2006/0142241 A1 | 6/2006 | Yoo |
| 2006/0199790 A1 | 9/2006 | Baulieu et al. |
| 2007/0032464 A1 | 2/2007 | Lia et al. |
| 2008/0193423 A1 | 8/2008 | Brunton et al. |
| 2008/0269183 A1 | 10/2008 | Mellon et al. |
| 2008/0319026 A1 | 12/2008 | Gant et al. |
| 2010/0034781 A1 | 2/2010 | Parhami et al. |
| 2010/0087411 A1 | 4/2010 | Barraclough et al. |
| 2011/0112077 A1 | 5/2011 | Kuduk et al. |
| 2011/0160223 A1 | 6/2011 | Dingledine et al. |
| 2011/0190249 A1 | 8/2011 | Rees et al. |
| 2012/0035156 A1 | 2/2012 | Alberati et al. |
| 2012/0040916 A1 | 2/2012 | Moon et al. |
| 2012/0041016 A1 | 2/2012 | Frincke |
| 2012/0115169 A1 | 5/2012 | Mullenix et al. |
| 2013/0210792 A1 | 8/2013 | Song et al. |
| 2014/0045943 A1 | 2/2014 | Khan et al. |
| 2014/0148412 A1 | 5/2014 | Hogenkamp |
| 2014/0235600 A1 | 8/2014 | Covey et al. |
| 2014/0335050 A1 | 11/2014 | Haggerty et al. |
| 2015/0158903 A1 | 6/2015 | Upasani et al. |
| 2015/0291654 A1 | 10/2015 | Upasani et al. |
| 2015/0376225 A1 | 12/2015 | Dugar et al. |
| 2016/0022701 A1 | 1/2016 | Reddy et al. |
| 2016/0031930 A1 | 2/2016 | Botella et al. |
| 2017/0247405 A1 | 8/2017 | Harrison et al. |
| 2017/0304321 A1 | 10/2017 | Quirk et al. |
| 2017/0305960 A1 | 10/2017 | Botella et al. |
| 2018/0194797 A1 | 7/2018 | Salituro et al. |
| 2018/0200267 A1 | 7/2018 | Salituro et al. |
| 2018/0201643 A1 | 7/2018 | Salituro et al. |
| 2018/0237470 A1 | 8/2018 | Botella et al. |
| 2018/0362573 A1 | 12/2018 | Upasani et al. |
| 2018/0371009 A1 | 12/2018 | Pellicciari et al. |
| 2019/0125764 A1 | 5/2019 | Salituro et al. |
| 2019/0127414 A1 | 5/2019 | Botella et al. |
| 2019/0135854 A1 | 5/2019 | Harrison et al. |
| 2019/0160078 A1 | 5/2019 | Masuoka et al. |
| 2019/0233465 A1 | 8/2019 | Robichaud et al. |
| 2019/0248829 A1 | 8/2019 | Salituro et al. |
| 2019/0330259 A1 | 10/2019 | Robichaud et al. |
| 2019/0359646 A1 | 11/2019 | Botella et al. |
| 2020/0002371 A1 | 1/2020 | Salituro et al. |
| 2020/0024300 A1 | 1/2020 | Salituro et al. |
| 2020/0123195 A1 | 4/2020 | Salituro et al. |
| 2021/0040138 A1 | 2/2021 | Harrison et al. |
| 2021/0101925 A1 | 4/2021 | Salituro et al. |
| 2021/0145848 A1 | 5/2021 | Salituro et al. |
| 2021/0147468 A1 | 5/2021 | Salituro et al. |
| 2021/0147470 A1 | 5/2021 | Upasani et al. |
| 2021/0171567 A1 | 6/2021 | Botella et al. |
| 2021/0380631 A1 | 12/2021 | Salituro et al. |
| 2022/0024968 A1 | 1/2022 | Salituro et al. |
| 2022/0081465 A1 | 3/2022 | Salituro et al. |

FOREIGN PATENT DOCUMENTS

| | | |
|---|---|---|
| CN | 1254716 | 5/2008 |
| FR | 2850023 | 7/2004 |
| GB | 1564806 | 4/1980 |
| JP | 50140435 | 11/1975 |
| JP | 53082766 | 7/1978 |
| JP | 54163565 | 12/1979 |
| JP | 57035597 | 2/1982 |
| JP | 61254599 | 11/1986 |
| JP | 62187485 | 8/1987 |
| JP | 08268917 | 10/1996 |
| JP | 09328498 | 12/1997 |
| JP | H11509844 A | 8/1999 |
| JP | 2005508368 | 3/2005 |
| JP | 2009545535 | 12/2009 |
| JP | 2014526469 | 10/2014 |
| JP | 2016513663 | 5/2016 |
| JP | 2016514967 | 5/2016 |
| RU | 2194712 | 12/2002 |
| RU | 2458065 C2 | 8/2012 |
| RU | 2665571 C2 | 8/2018 |
| WO | WO1980002562 | 11/1980 |
| WO | 89/02272 A1 | 3/1989 |
| WO | WO1994027608 | 12/1994 |
| WO | WO1995002409 | 1/1995 |
| WO | WO1995013287 | 5/1995 |
| WO | WO1995021617 | 8/1995 |
| WO | WO1996012705 | 5/1996 |
| WO | WO1996016076 | 5/1996 |
| WO | WO1996040043 | 12/1996 |
| WO | WO1996040151 | 12/1996 |

(56) References Cited

FOREIGN PATENT DOCUMENTS

| WO | WO1997000884 | | 1/1997 |
|---|---|---|---|
| WO | WO1997003677 | | 2/1997 |
| WO | WO1997042215 | | 11/1997 |
| WO | WO1998005337 | | 2/1998 |
| WO | WO1998007740 | | 2/1998 |
| WO | WO1999058497 | | 11/1999 |
| WO | WO2000063228 | | 10/2000 |
| WO | 00/66614 A1 | | 11/2000 |
| WO | WO2000068246 | | 11/2000 |
| WO | WO2001049703 | | 7/2001 |
| WO | WO2002011708 | | 2/2002 |
| WO | WO2002053577 | | 7/2002 |
| WO | WO2002079221 | | 10/2002 |
| WO | WO2002090375 | | 11/2002 |
| WO | WO2003039480 | | 5/2003 |
| WO | WO2003049685 | | 6/2003 |
| WO | WO2003082893 | | 10/2003 |
| WO | WO2004055201 | | 7/2004 |
| WO | WO2005079810 | | 9/2005 |
| WO | WO2008041003 | | 4/2008 |
| WO | WO2008063128 | | 5/2008 |
| WO | WO2009001097 | | 12/2008 |
| WO | WO2009059239 | * | 5/2009 |
| WO | WO2009059961 | | 5/2009 |
| WO | WO2009073186 | | 6/2009 |
| WO | WO2009090063 | | 7/2009 |
| WO | WO2010075282 | | 7/2010 |
| WO | WO2010088414 | | 8/2010 |
| WO | WO2011014661 | | 2/2011 |
| WO | WO2011028794 | | 3/2011 |
| WO | WO2011067501 | | 6/2011 |
| WO | WO2011092127 | | 8/2011 |
| WO | WO2012064501 | | 5/2012 |
| WO | WO2012142039 | | 10/2012 |
| WO | WO2013019711 | | 2/2013 |
| WO | WO2013036835 | | 3/2013 |
| WO | WO2013056181 | | 4/2013 |
| WO | WO2013163455 | | 10/2013 |
| WO | WO2014025942 | | 2/2014 |
| WO | WO2014115167 | | 7/2014 |
| WO | WO2014120786 | | 8/2014 |
| WO | WO2014160441 | | 10/2014 |
| WO | WO2014160480 | | 10/2014 |
| WO | WO2015120280 | | 8/2015 |
| WO | WO2015195967 | | 12/2015 |
| WO | WO2016007762 | | 1/2016 |
| WO | WO2016057713 | | 4/2016 |
| WO | WO2017007832 | | 1/2017 |
| WO | WO2017007836 | | 1/2017 |
| WO | WO2017007840 | | 1/2017 |
| WO | WO2017037465 | | 3/2017 |
| WO | WO2017173358 | | 10/2017 |
| WO | WO2018064649 | | 4/2018 |
| WO | WO2018075698 | | 4/2018 |
| WO | WO2018075699 | | 4/2018 |
| WO | WO2018170336 | | 9/2018 |
| WO | WO2020243027 | | 12/2020 |

OTHER PUBLICATIONS

Iida et al., Preparation of glycine-conjugated bile acids and their gas/liquid chromatographic analysis on an aluminum-clad flexible fused silica capillary column. Biomedical Chromatography, vol. 6(1), pp. 4-8 (Year: 1992).*
U.S. Appl. No. 14/775,401, filed Sep. 11, 2015, Kiran Reddy et al., Abandoned.
U.S. Appl. No. 15/319,504, filed Dec. 16, 2016, Boyd L. Harrison et al., Issued.
U.S. Appl. No. 16/028,790, filed Jul. 6, 2018, Boyd L. Harrison et al., Issued.
U.S. Appl. No. 16/902,730, filed Jun. 16, 2020, Boyd L. Harrison et al., Abandoned.
U.S. Appl. No. 18/116,557, filed Mar. 2, 2023, Boyd L. Harrison et al., Pending.
U.S. Appl. No. 14/343,603, filed Nov. 25, 2014, Ravindra B. Upasani et al., Abandoned.
U.S. Appl. No. 16/114,791, filed Aug. 28, 2018, Ravindra B. Upasani et al., Issued.
U.S. Appl. No. 16/942,235, filed Jul. 29, 2020, Ravindra B. Upasani et al., Abandoned.
U.S. Appl. No. 14/775,678, filed Sep. 12, 2015, Gabriel Martinez Botella et al., Abandoned.
U.S. Appl. No. 15/588,305, filed May 5, 2017, Gabriel Martinez Botella et al., Abandoned.
U.S. Appl. No. 15/917,263, filed Mar. 9, 2018, Gabriel Martinez Botella et al., Issued.
U.S. Appl. No. 15/917,272, filed Mar. 9, 2018, Gabriel Martinez Botella et al., Abandoned.
U.S. Appl. No. 16/227,013, filed Dec. 20, 2018, Gabriel Martinez Botella et al., Issued.
U.S. Appl. No. 17/381,829, filed Jul. 21, 2021, Gabriel Martinez Botella et al., Pending.
U.S. Appl. No. 15/517,886, filed Apr. 7, 2017, Michael C. Quirk et al., Abandoned.
U.S. Appl. No. 17/947,844, filed Sep. 19, 2022, Michael C. Quirk et al., Pending.
U.S. Appl. No. 15/742,422, filed Jan. 5, 2018, Francesco G. Salituro et al., Issued.
U.S. Appl. No. 16/879,460, filed May 20, 2020, Francesco G. Salituro et al., Abandoned.
U.S. Appl. No. 17/749,976, filed May 20, 2022, Francesco G. Salituro et al., Pending.
U.S. Appl. No. 15/742,424, filed Jan. 5, 2018, Francesco G. Salituro et al., Issued.
U.S. Appl. No. 17/396,034, filed Aug. 6, 2021, Francesco G. Salituro et al., Pending.
U.S. Appl. No. 15/742,425, filed Jan. 5, 2018, Francesco G. Salituro et al., Issued.
U.S. Appl. No. 16/227,099, filed Dec. 20, 2018, Francesco G. Salituro et al., Issued.
U.S. Appl. No. 16/942,245, filed Jul. 29, 2020, Francesco G. Salituro et al., Pending.
U.S. Appl. No. 16/315,250, filed Jan. 4, 2019, Francesco G. Salituro et al., Issued.
U.S. Appl. No. 16/943,649, filed Jul. 30, 2020, Francesco G. Salituro et al., Issued.
U.S. Appl. No. 16/099,122, filed Nov. 5, 2018, Gabriel Martinez Botella et al., Issued.
U.S. Appl. No. 16/930,047, filed Jul. 15, 2020, Gabriel Martinez Botella et al., Issued.
U.S. Appl. No. 17/860,816, filed Jul. 8, 2022, Gabriel Martinez Botella et al, Pending.
U.S. Appl. No. 16/089,896, filed Sep. 28, 2018, Albert Jean Robichaud et al., Abandoned.
U.S. Appl. No. 17/242,860, filed Apr. 28, 2021, Albert Jean Robichaud et al., Pending.
U.S. Appl. No. 16/343,235, filed Apr. 18, 2019, Francesco G. Salituro et al., Issued.
U.S. Appl. No. 17/395,155, filed Aug. 5, 2021, Francesco G. Salituro et al., Pending.
U.S. Appl. No. 16/343,238, filed Apr. 18, 2019, Francesco G. Salituro et al., Issued.
U.S. Appl. No. 17/386,364, filed Jul. 27, 2021, Francesco G. Salituro et al., Issued.
U.S. Appl. No. 18/106,073, filed Feb. 6, 2023, Francesco G. Salituro et al., Pending.
U.S. Appl. No. 16/338,315, filed Mar. 29, 2019, Francesco G. Salituro et al., Issued.
U.S. Appl. No. 17/476,153, filed Sep. 15, 2021, Francesco G. Salituro et al., Pending.
U.S. Appl. No. 16/938,348, filed Jul. 24, 2020, James J. Doherty, Abandoned.
U.S. Appl. No. 18/077,031, filed Dec. 7, 2022, James J. Doherty, Pending.
"Sage Therapeutics—FutureCast—An R&D and Portfolio Review", Sage Therapeutics, URL: https://investor.sagerx.com/static-files/2729f420-42bd-4aa1-aede-d3bdafc4eeca (Sep. 9, 2020) (44 pages).

(56) References Cited

OTHER PUBLICATIONS

Akhapkina et al., "Fundamentals of the modulatory concept and classification of modulatory drugs," Breast Cancer, 19:93 (2012) (English language translation) (40 pages).
Berge et al., "Pharmaceutical salts," Journal of Pharmaceutical Sciences, 66(1):1-19 (1977).
Bjorkhem et al., "Oxysterols in the circulation of patients with the Smith-Lemli-Opitz syndrome: abnormal levels of 24S- and 27-hydroxycholesterol," Journal of Lipid Research, 42(3):366-371 (2001).
Bukelis et al., "Smith-Lemli-Opitz syndrome and autism spectrum disorder," American Journal of Psychiatry, 164(11):1655-1661 (2007).
Cais et al., "Temperature dependence of NR1/NR2B NMDA receptor channels," Neuroscience, 151(2):428-438 (2008).
Cancer [online], [retrieved on Jul. 6, 2007]. Retrieved from the internet, URL http://www.nlm.nih.gov/medlineplus/ cancer.html> (11 pages).
Chen et al., "The chemical biology of clinically tolerated NMDA receptor antagonists," Journal of Neurochemistry, 97(6):1611-1626 (2006).
Citraro et al., "Effects of some neurosteroids injected into some brain areas of WAG/Rij rats, an animal model of generalized absence epilepsy," Neuropharmacology, 50(8):1059-1071 (2006).
ClinicalTrials.gov, "A Study to Evaluate the Safety and Tolerability of SAGE-718 in Participants with Mild Cognitive Impairement or Mild Dementia Due to Alzheimer's Disease (AD)", retrieved from URL: https://clinicaltrials.gov/ct2/history/NCT04602624?v_6= View#StudyPageTop (May 11, 2021) (7 pages).
Collingridge et al., "The NMDA receptor as a target for cognitive enhancement," Neuropharmacology, 64:13-26 (2013).
Connick et al., "Program No. 613 1/B86," 2009 Neuroscience Meeting Planner, Chicago, IL: Society for Neuroscience (2009) (2 pages).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metabolism and Disposition, 37(10):2069-2078 (2009).
Corman et al., "Structure-activity relationships for side chain oxysterol agonists of the hedgehog signaling pathway," ACS Medicinal Chemistry Letters, 3(10):828-833 (2012).
Costa et al., "A novel family of negative and positive allosteric modulators of NMDA receptors," Journal of Pharmacology and Experimental Therapeutics, 335(3):614-621 (2010).
Cross et al., "Steroids CCLXXIN[1]. Biologically-active labile ethers IV[2]. The synthesis of 22-oxa-25-azacholesterol and related compounds," Steroids, 5(5):585-598 (1965).
Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).
Dayal et al., "Stereospecific synthesis of 3 beta-hydroxylated bile alcohols," Journal of Lipid Research, 25(6):646-650 (1984).
Deng et al., "Fluoro analogs of bioactive oxy-steroids: Synthesis of an $EBI_2$ agonist with enhanced metabolic stability," Bioorganic and Medicinal Chemistry Letters, 26(2):4888-4891 (2016).
Domasio, "Alzheimer's disease and related dementias," Cecil Textbook of Medicine, 20th edition, 2:1992-1996 (1996).
EESR for European Application No. 14774060.9, dated Aug. 17, 2016 (11 pages).
EESR for European Application No. 14775126.7, dated Sep. 14, 2016 (7 pages).
EESR for European Application No. 14775126.7, Dec. 15, 2016 (7 pages).
EESR for European Application No. 15809462.3, dated Nov. 29, 2017 (8 pages).
EESR for European Application No. 15849514.3, dated May 23, 2018 (7 pages).
EESR for European Application No. 16821920.2, dated Jan. 31, 2019 (12 pages).
EESR for European Application No. 16821924.4, dated Jan. 31, 2019 (12 pages).
EESR for European Application No. 16821926.9, dated Jan. 31, 2019 (10 pages).
Elbarbry et al., "Cyclosporine-induced changes in drug metabolizing enzymes in hyperlipemic rabbit kidneys could explain its toxicity," Xenobiotica, 40(11):772-781 (2010).
FDA mulls drug to slow late-stage Alzheimer's [online] (cnn.com/health), [retrieved on Sep. 23, 2003]. Retrieved from the Internet, URL; http://www.cnn.com/2003/HEALTH/conditions/09/24/alzheimers.drug.ap/indexhtml> (2 pages).
Ferriz et al., "Prodrug Design of Phenolic Drugs", Current Pharmaceutical Designs 16:2033-2052 (2010).
Festa et al., "Exploitation of cholane scaffold for the discovery of potent and selective farnesoid X receptor (FXR) and G-protein coupled bile acid receptor 1 ($GP-BAR_1$) ligands," Journal of Medicinal Chemistry, 57(20):8477-8495 (2014).
Foster et al., "Effect of steroids on beta-adrenoceptor-mediated relaxation of pig bronchus," British Journal of Pharmacology, 78(2):441-445 (1983).
Fukuto et al., "Determination of the Mechanism of Demethylenation of (methylenedioxy)phenyl compounds by cytochrome P450 using deuterium isotope effects," Journal of Medicinal Chemistry, 34(9):2871-2876 (1991).
Gee et al., "GABA-dependent modulation of the Cl-ionophore by steroids in rat brain," European Journal of Pharmacology, 136(3):419-423 (1987).
Golub et al., "Molecular classification of cancer: class discovery and class prediction by gene expression monitoring," Science, 286(5439):531-537 (1999).
Groden et al., "Determination of Fura-2 dissociation constants following adjustment of the apparent Ca-EGTA association constant for temperature and ionic strength," Cell Calcium, 12(4):279-287 (1991).
Grynkiewicz et at., "A new generation of Ca2+ indicators with greatly improved fluorescence properties," Journal of Biological Chemistry, 260(6):3440-3445 (1985).
Gunatilaka et al., "Bioactive ergost-5-ene-3 beta, 7 alpha-diol derivatives from *Pseudobersama mossambicensis*," Journal of Natural Products, 55(11):1648-1654 (1992).
Guthrie et al., "Morphological and biochemical differences expressed in separate dissociated cell cultures of dorsal and ventral halves of the mouse spinal cord," Brain Research, 420(2):313-323 (1987).
Hill et al., "SAGE-718: A First-in-Class N-Methyl-D-Aspartate Receptor Positive Allosteric Modulator for the Potential Treatment of Cognitive Impairement", Journal of Medicinal Chemistry, URL: https://pubs.acs.org/doi/pdf/10.1021/acs.jmedchem.2c00313 (Jul. 2, 2022) (13 pages).
Hoeve et al., "The design of resolving agents. Chiral cyclic phosphoric acids," Journal of Organic Chemistry, 50(23):4508-4514 (1985).
Hoffmeister et al., "Zur chemie des ecdysons, III: Vergleichende spektrometrische untersuchungen an a.b-ungesättigten steroidketonen," Chemische Berichte, 98(7):2361-2375 (1965).
Hogg et al., "An automated system for intracellular and intranuclear injection," Journal of Neuroscience, Methods, 169(1):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs—from serendipity to rational design," Pharmacological Reviews, 63(3):750-771 (2011).
Iida et al., "An improved method for the capillary gas chromatographic derivatization of polyhydroxylated steroids having tert-hydroxyl groups," Analytical Sciences, 19(9):1317-1321 (2003).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).

(56) References Cited

OTHER PUBLICATIONS

Jurman et al., "Visual identification of individual transfected cells for electrophysiology using antibody-coated beads," Biotechniques, 17(5):876-881 (1994).
Karaki et al., "Structure-activity relationship studies of Niemann-Pick type C1-like 1 (NPC1L1) ligands identified by screening assay monitoring pharmacological chaperone effect," Bioorganic and Medicinal Chemistry, 21(17):5297-5309 (2013).
Kasper et al, "Management of mild cognitive impairement (MCI): the need for national and international guidelines", World Journal of Biological Psychiatry 21(8): 579-594 (2020).
Khripach et al., "Synthesis of (24S)-hydroxy-and (24S)-24,25-epoxycholesterol analogues, potential agonists of nuclear LXR receptors," Russian Journal of Bioorganic Chemistry, 32(6):586-594 (2006).
Knoppert et al., "Position paper: Paediatric age categories to be used in differentiating between listing on a model essential medicines list for children," pp. 1-5 (2007).
Koenig et al., "Cognitive performance after repeated administration of the NMDA positive allosteric modulator SAGE-718 in healthy volunteers", Neuropsychopharmacology 44(1):152-153 (2019).
Kurosawa et al., "Synthesis of 19-hydroxylated bile acids and identification of 3 alpha,7 alpha,12 alpha,19-tetrahydroxy-5 beta-cholan-24oic acid in human neonatal urine," Chemical and Pharmaceutical Bulletin, 43(9):1551-1557 (1995).
Lakhan et al., "NMDA receptor activity in neuropsychiatric disorders," Frontiers in Psychiatry, 4:1-7 (2013).
Lala et al., "Role of nitric oxide in tumor progression: Lessons from experimental tumors," Cancer and Metastasis Reviews, 17(1):91-106 (1998).
Layzer, "Section five-degenerative diseases of the nervous system," Cecil Textbook of Medicine, 20th edition, 2:2050-2057 (1996).
Leoni et al., "Changes in human plasma levels of the brain specific oxysterol 24S-hydroxycholesterol during progression of multiple sclerosis," Neuroscience Letters, 331(3):163-166 (2002).
Leoni et al., "Oxysterols as biomarkers in neurodegenerative diseases," Chemistry and Physics of Lipids, 164(6):515-524 (2011).
Lettré et al., "Mehrwertige alkohole aus sterinen und sterinderivaten, VI Steroide mit strukturmerkmalen des ecdysons und der elatericine," Justus Liebigs Annalen der Chemie, 758:89-110 (1972) (English Abstract).
Li et al., "Synthesis of 7alpha-hydroxy derivatives of regulatory oxysterols," Steroids, 65(9):529-535 (2000).
Linsenbardt et al., "Different oxysterols have opposing actions at N-methyl-D-aspartate receptors," Neuropharmacology, 85:232-242 (2014).
Lutjohann et al., "Cholesterol homeostasis in human brain: evidence for an age-dependent flux of 24S-hydroxycholesterol from the brain into the circulation," PNAS, 93(18):9799-804 (1996).
Luu et al., "Oxysterols: Old Tale, New Twists," Annual Review of Pharmacology and Toxicology, 56:447-467 (2016).
Madau et al., Program No. 613.2/B87. 2009 Neuroscience Meeting Planner. Chicago, IL: Society for Neuroscience (2009) (3 pages).
Mateos et al., "Activity-regulated cytoskeleton-associated protein in rodent brain is down regulated by high fat diet in vivo and by 27-hydroxycholesterol in vitro," Brain Pathology, 19(1):69-80 (2009).
Meljon et al., "Analysis by liquid chromatography-mass spectrometry of sterols and oxysterols in brain of the newborn Dhcr7(Δ3-5/T93M) mouse: a model of Smith-Lemli-Opitz syndrome," Biochemical Pharmacology, 86(1):43-55 (2013).
Monyer et al., "Heteromeric NMDA receptors: molecular and functional distinction of subtypes," Science, 256(5060):1217-1221 (1992).
Mourino et al., "Studies on vitamin D (calciferol) and its analogs. 15. 24-nor-la,25-dihydroxyvitamin D3 and 24-nor-25-hydroxy-5,6-trans-vitamin D3," Journal of Medicinal Chemistry, 21(10):1025-1029 (1978).
Nagano et al., "Chemistry and biochemistry of Chinese drugs. Part II. Hydroxylated sterols, cytotoxic towards cancerous cells: synthesis and testing," Journal of Chemical Research, 9:218 (1977).
Nagasaka et al., "Oxysterol changes along with cholesterol and vitamin D changes in adult phenylketonuric patients diagnosed by newborn mass-screening," Clinica Chimica Acta, 416:54-59 (2013).
Niemann-Pick diagnosis-treatment [online] retrieved from the internet on Jul. 17, 2021 (URL: https://www.mayoclinic.org/diseases-conditions/niemann-pick/diagnosis-treatment/drc-20355890) (2 pages).
Niemann-Pick overview [online] retrieved from the internet on Jul. 17, 2021 (URL: https://www.mayoclinic.org/diseases-conditions/niemann-pick/symptoms-causes/syc-20355887) (4 pages).
Olkkonen et al., "Oxysterols and their cellular effectors," Biomolecules, 2(1):76-103 (2012).
Papassotiropoulos, et al., "Plasma 24S-hydroxycholesterol a peripheral indicator of neuronal degeneration and potential state marker for Alzheimer's disease", NeuroReport 11(9): 1959-1962 (2000).
Park-Chung et al., "Distinct sites for inverse modulation of N-methyl-D-aspartate receptors by sulfated steroids," Molecular Pharmacology, 52(6):1113-1123 (1997).
Paul et al., "The major brain cholesterol metabolite 24(S)-hydroxycholesterol is a potent allosteric modulator of N-methyl-D-aspartate receptors," The Journal of Neuroscience, 33(44):17290-17300 (2013).
PCT International Search Report and Written Opinion for corresponding International Application No. PCT/US2012/054261, dated Nov. 28, 2012 (10 pages).
PCT International Search Report and Written Opinion for corresponding International Application No. PCT/US2014/026633, dated Jul. 14, 2014 (6 pages).
PCT International Search Report and Written Opinion for corresponding International Application No. PCT/US2014/026784, dated Jul. 8, 2014 (13 pages).
PCT International Search Report and Written Opinion for corresponding International Application No. PCT/US2015/036510, dated Sep. 15, 2015 (7 pages).
PCT International Search Report and Written Opinion for corresponding International Application No. PCT/US2015/054551, dated Jan. 8, 2016 (10 pages).
PCT International Search Report and Written Opinion for corresponding International Application No. PCT/US2016/041160, dated Oct. 28, 2016 (7 pages).
PCT International Search Report and Written Opinion for corresponding International Application No. PCT/US2016/041168, dated Sep. 15, 2016 (6 pages).
PCT International Search Report and Written Opinion for corresponding International Application No. PCT/US2016/041175, dated Sep. 16, 2016 (6 pages).
PCT International Search Report and Written Opinion for corresponding International Application No. PCT/US2017/025535, dated Jul. 3, 2017 (7 pages).
PCT International Search Report and Written Opinion for corresponding International Application No. PCT/US2017/031374, dated Aug. 14, 2017 (8 pages).
PCT International Search Report and Written Opinion for corresponding International Application No. PCT/US2017/041199, dated Aug. 29, 2017 (12 pages).
PCT International Search Report and Written Opinion for corresponding International Application No. PCT/US2017/054657, dated Nov. 21, 2017 (18 pages).
PCT International Search Report and Written Opinion for corresponding International Application No. PCT/US2017/057276, dated Dec. 11, 2017 (13 pages).
PCT International Search Report and Written Opinion for corresponding International Application No. PCT/US2017/057277, dated Feb. 20, 2018 (19 pages).
PCT Invitation to Correct Fees and Partial International Search Report and Provisional Opinion for corresponding International Application No. PCT/US2017/057277, dated Dec. 20, 2017 (13 pages).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883):1306-1308 (1988).

(56) References Cited

OTHER PUBLICATIONS

Pubchem, CID 00065094, 25-Hydroxycholesterol, Nov. 18, 2016 (17 pages).
Pubchem, CID 0132021, Ergostan-3,24-diol, Mar. 5, 2018 (15 pages).
Pubchem, CID 54083335, Schembl4961477, Nov. 8, 2016 (13 pages).
Pubchem, CID 54160779, Schembl4961477, Nov. 8, 2016 (13 pages).
Pubchem, CID 58455549, Schembl12198161, Nov. 8, 2016 (13 pages).
Pubchem, CID 66966798, Cholane-3alpha,24,-diol, Nov. 8, 2016 (11 pages).
Pubchem, CID 70604305, Schembl11528874, Nov. 8, 2016 (13 pages).
Pubchem, CID 71508953, Mar. 5, 2018 (13 pages).
Reddy, "Pharmacology of endogenous neuroactive steroids," Critical Reviews in Neurobiology, 15(3-4):197-234 (2013).
Registry (STN) [online] CAS Registration No. 1392266-35-1; 13392266-34-0; 1271523-00-2; 185138-08-3; 185138-00-5; 1851387-82-0; 66450-87-1 (2012).
Roh et al., "Neuroprotective effects of ginsenoside Rg3 against 24-OH-cholesterol-induced cytotoxicity in cortical neurons," Journal of Ginseng Research, 34(3):246-253 (2010).
Schmidt et al., "Inhibitory effect of oxygenated cholestan-3b-ol derivatives on the growth of *Mycobacterium tuberculosis*," Bioorganic & Medicinal Chemistry Letters, 23(22):6111-6113 (2013).
Segal, "Pat hippocampal Neurons in Culture: Responses to Electrical and Chemical Stimuli," Journal of Neurophysiology, 50(6):1249-1264 (1983).
Sepe et al., "Total synthesis and pharmacological characterization of solomonsterol A, a potent marine pregnane-X-receptor agonist endowed with anti-inflammatory activity," Journal of Medicinal Chemistry, 54:4590-4599 (2011).
Solomon, et al., "Plasma levels of 24S-hydroxycholesterol reflect brain volumes in patients without objective cognitive impairment but not in those with Alzheimer's disease", Neuroscience Letters 462(1): 89-93 (2009).
Stamp et al., "Plasma levels and therapeutic effect of 25-hydroxycholecalciferol in epileptic patients taking anticonvulsant drugs," British Medical Journal 4(5831): 9-12 (1972).
Stastna et al., "Synthesis of C3, C5, and C7 pregnane derivatives and their effect on NMDA receptor responses in cultured rat hippocampal neurons," Steroids, 74(2):256-263 (2008).
Steinrauf et al., "Synthesis and evaluation of sulfur-containing steroids against methylmercuric chloride toxicity," Journal of Pharmaceutical Sciences, 67(12):1739-1743 (1978).
Svoboda et al., "Treatment of Smith-Lemli-Opitz syndrome and other sterol disorders," American Journal of Medical Genetics Part C: Seminars in Medical Genetics, 160C(4): 285-294 (2012).
Takahashi et al., "Stereochemistry of reduction of the C-24,25 double bond in the conversion of desmosterol into cholesterol," Tetrahedron Letters, 44(2):341-344 (2003).
Takano et al., "Simple synthesis of 3b,24-dihydroxychol-5-en-7-one by oxidative cleavage of the side chain of cholesterol," Chemistry Letters, 14(8):1265-1266 (1985).
Tierney et al., "Abnormalities of cholesterol metabolism in autism spectrum disorders," American Journal of Medical Genetics Part B: Neuropsychiatric Genetics, 141B(6):666-668 (2006).
Tomek et al., "NMDA receptor modulators in the treatment of drug addiction," Pharmaceuticals (Basel), 6(2):251-258 (2013).
Verdoorn et al., "Functional properties of recombinant rat GABAA receptors depend upon subunit composition," Neuron, 4(6):919-928 (1990).
Vyklicky et al., "Calcium-mediated modulation of N-methyl-D-aspartate (NMDA) responses in cultured rat hippocampal neurones," Journal of Physiology, 470:575-600 (1993).
Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).
Wilen et al., "Strategies in Optical Resolutions," Tetrahedron, 33:2725-2736 (1977).
Wolozin et al., "The cellular biochemistry of cholesterol and statins: Insights into the pathophysiology and therapy of Alzheimer's disease," CNS Drug Review, 10(2):127-146 (2004).
Wong et al., "An efficient and convenient transformation of a-haloketones to a-hydroxyketones using cesium formate," Journal of Organometallic Chemistry, 694(21):3452-3455 (2004).
Xiangdong et al., "Highly stereoselective synthesis of 24R,25- and 24S, 25-dihydroxysteroid," Database Chemical Abstracts Service, Database accession No. 2001:174431 (2000) (4 pages).
Xilouri et al., "Neuroprotective effects of steroid analogues on P19-N neurons," Neurochemistry International, 50(4):660-670 (2007).
Yan et al., "Characterization of a synthetic steroid 24-keto-cholest-5-en-3b,19-diol as a neuroprotectant," CNS Neuroscience & Therapeutics, 21(6):486-495 (2015).
Yang et al., "New cytotoxic oxygenated sterols from marine bryozoan *Bugula neritina*," Natural Product Research, 25(16):1505-1511 (2011).
Zhou et al., "Properties of HERG channels stably expressed in HEK 293 cells studied at physiological temperature," Biophysical Journal, 74(1):230-241 (1998).
Zuliani et al., "Plasma 24S-hydroxycholesterol levels in elderly subjects with late onset Alzheimer's disease or vascular dementia: a case-control study," BMC Neurology 11(121): 1-8 (2011).
U.S. Appl. No. 16/902,730, filed Jun. 16, 2020, Boyd L. Harrison et al., Pending.
U.S. Appl. No. 17/386,364, filed Jul. 27, 2021, Francesco G. Salituro et al., Allowed.
U.S. Appl. No. 17/947,844, filed Sep. 19, 2022, Michael C. Quirk, Pending.
U.S. Appl. No. 18/106,073, filed Feb. 6, 2023, Francesco G. Salituro, Pending.
U.S. Appl. No. 16/879,460, filed May 20, 2020, Francesco G. Salituro et al., Pending.
U.S. Appl. No. 16/930,047, filed Jul. 15, 2020, Gabriel Martinez Botella et al., Allowed.
U.S. Appl. No. 16/938,348, filed Jul. 24, 2020, James J. Doherty, Pending.
U.S. Appl. No. 17/386,364, filed Jul. 27, 2021, Francesco G. Salituro et al., Pending.
Berardelli et al., "EFNS/MDS-ES/ENS [corrected] recommendations for the diagnosis of Parkinson's disease," European Journal of Neurology, 20(1):16-34 (2013).
Dubois et al., "Research criteria for the diagnosis of Alzheimer's disease: revising the NINCDS-ADRDA criteria," Lancet Neurology, 6(8):734-736 (2007).
Dubois et al., "Revising the definition of Alzheimer's disease: a new lexicon," Lancet Neurology, 9(11):1118-27 (2010).
Jack et al., "Hypothetical model of dynamic biomarkers of the Alzheimer's pathological cascade," Lancet. Neurology, 9(1):119-128 (2010).
Jack et al., "Introduction to the recommendations from the National Institute on Aging-Alzheimer's Association workgroups on diagnostic guidelines for Alzheimer's disease," Alzheimer's & Dementia, 7(3):257-62 (2011).
Litvan et al., "Diagnostic criteria for mild cognitive impairment in Parkinson's disease: Movement Disorder Society Task Force guidelines," Movement Disorders, 27(3):349-56 (2012).
Litvan et al., "MDS Task Force on mild cognitive impairment in Parkinson's disease: critical review of PD-MCI," Movement Disorders, 26(10):1814-1824 (2011).
Nasreddine et al., "The Montreal Cognitive Assessment, MoCA: a brief screening tool for mild cognitive impairment," Journal of the American Geriatrics Society, 53(4):695-699 (2005).

* cited by examiner

NEUROACTIVE STEROIDS, COMPOSITIONS, AND USES THEREOF

RELATED APPLICATIONS

This application is a continuation of U.S. patent application Ser. No. 16/942,235, filed on Jul. 29, 2020, which is a continuation of U.S. patent application Ser. No. 16/114,791, filed on Aug. 28, 2018, now U.S. Pat. No. 10,759,828, which is a continuation of U.S. patent application Ser. No. 14/343,603, filed on Nov. 25, 2014, which is a national stage application under 35 U.S.C. § 371 of International Application No. PCT/US2012/054261, filed on Sep. 7, 2012, which claims priority under 35 U.S.C § 119(e) to U.S. Provisional Application No. 61/532,427, filed on Sep. 8, 2011. The contents of each of the foregoing applications are incorporated herein by reference in their entirety.

BACKGROUND

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released as a result of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase the membrane permeability of $Na^+$ ions. The reduced membrane potential stimulates neuronal excitability in the form of a postsynaptic action potential.

NMDA receptors are highly expressed in the CNS and are involved in excitatory synaptic transmission and synaptic plasticity as well as excitotoxicity. These receptors are ligand-gated ion channels that admit $Ca^{2+}$ after binding of the neurotransmitter glutamate and are fundamental to excitatory neurotransmission and normal CNS function. NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. These modulators may be useful as therapeutic agents with potential clinical uses as cognitive enhancers and in the treatment of psychiatric disorders in which glutamatergic transmission is reduced or defective (see, e.g., Horak et al., *J. of Neuroscience*, 2004, 24(46), 10318-10325).

Neuroactive steroids such as pregnenolone sulfate (PS) have been shown to exert direct modulatory effects on several types of neurotransmitter receptors, such as $GABA_A$, glycine, AMPA-kainate, and NMDA receptors. NMDA receptors are positively modulated by PS; however, the degree of modulation varies considerably.

In addition to PS, several other 3β-hydroxy steroids have been shown to potentiate NMDA receptors (see, e.g., Paul et al., *J. Pharm. and Exp. Ther.* 1994, 271, 677-682). Recently, a 3β-hydroxy-ergost-5-ene steroid derivative (1) was reported as positive modulator of NMDA (NR1a/NR2A). Compound (1) (also referred to as Org-1) was found to selectively modulate NMDA over $GABA_A$ (see, e.g., Madau et al., Program No. 613.2/B87. 2009 Neuroscience Meeting Planner. Chicago, IL: Society for Neuroscience, 2009; Connick et al., Program No. 613.1/B86. 2009 Neuroscience Meeting Planner. Chicago, IL: Society for Neuroscience, 2009).

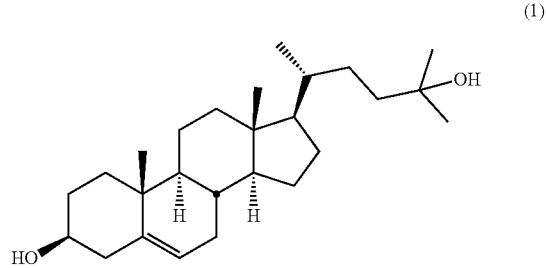

(1)

New and improved neuroactive steroids are needed that modulate brain excitability for the prevention and treatment of CNS-related conditions. The compounds, compositions, and methods described herein are directed toward this end.

SUMMARY OF THE INVENTION

New 3-α and 3β-hydroxy steroids described herein are potential NMDA receptor modulators and thus are useful for preventing and/or treating a broad range of CNS-related conditions, including but not limited to schizophrenia, depression, bipolar disorder (e.g., I and/or II), schizoaffective disorder, mood disorders, anxiety disorders, personality disorders, psychosis, compulsive disorders, post-traumatic stress disorder (PTSD), Autism spectrum disorder (ASD), dysthymia (mild depression), social anxiety disorder, obsessive compulsive disorder (OCD), pain (e.g., a painful syndrome or disorder), sleep disorders, memory disorders, dementia, Alzheimer's Disease, a seizure disorder (e.g., epilepsy), traumatic brain injury, stroke, addictive disorders (e.g., addiction to opiates, cocaine, and/or alcohol), autism, Huntington's Disease, insomnia, Parkinson's disease, withdrawal syndromes, or tinnitus. These compounds are expected to show improved in vivo potency, pharmacokinetic (PK) properties, oral bioavailability, formulatability, stability, and/or safety.

In one aspect, provided are compounds according to Formula (I):

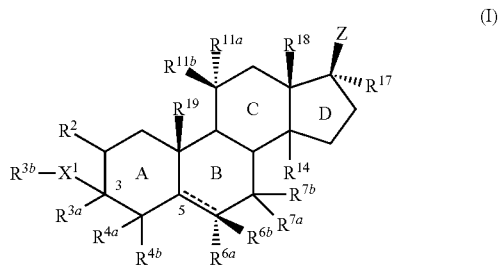

(I)

or a pharmaceutically acceptable salt, solvate, prodrug, stereoisomer, tautomer, isotopic variant, or N-oxide thereof, or a combination thereof;

wherein:

Z is a group of the formula (i), (ii), (iii), (iv), or (v):

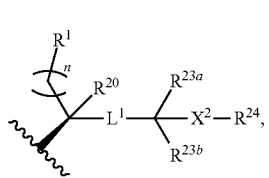
(i)

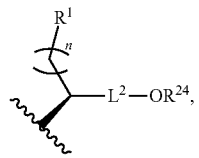
(ii)

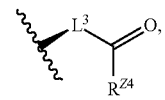
(iii)

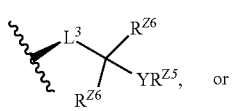
(iv)

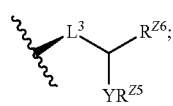
(v)

$L^1$, $L^2$, $L^3$, $X^1$, $X^2$, Y, $R^{Z4}$, $R^{Z5}$, $R^{Z6}$, n, $R^1$, $R^2$, $R^{3a}$, $R^{3b}$, $R^{4a}$, $R^{4b}$, $R^{6a}$, $R^{6b}$, $R^{7a}$, $R^{7b}$, $R^{11a}$, $R^{11b}$, $R^{14}$, $R^{17}$, $R^{19}$, $R^{20}$, $R^{23a}$, $R^{23b}$, and $R^{24}$ are as defined herein; and the group —$XR^{3b}$ at the C3 position is alpha or beta.

For example, in certain embodiments, the compound of Formula (I) is of Formula (I-w):

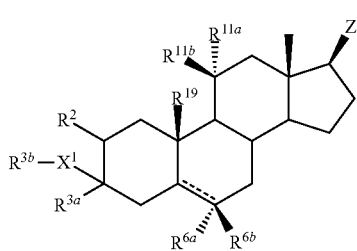
(I-w)

or a pharmaceutically acceptable salt thereof;
wherein:

Z is a group of the formula (i), (ii), (iii), (iv), or (v):

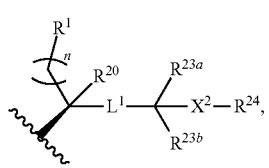
(i)

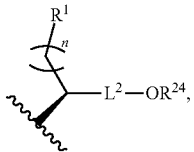
(ii)

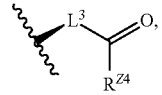
(iii)

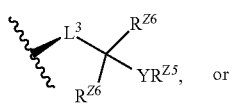
(iv)

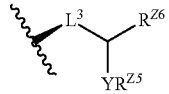
(v)

$L^1$ and $L^2$ are selected from a group consisting of a bond, a substituted or unsubstituted $C_1$-$C_6$ alkylene, a substituted or unsubstituted $C_2$-$C_6$ alkenylene, substituted or unsubstituted $C_2$-$C_6$ alkynylene, a substituted or unsubstituted hetero $C_1$-$C_6$ alkylene, a substituted or unsubstituted hetero $C_2$-$C_6$ alkenylene, and a substituted or unsubstituted hetero $C_2$-$C_6$ alkynylene;

$L^3$ is a substituted or unsubstituted $C_1$-$C_6$ alkylene, a substituted or unsubstituted $C_2$-$C_6$ alkenylene, substituted or unsubstituted $C_2$-$C_6$ alkynylene, a substituted or unsubstituted hetero $C_1$-$C_6$ alkylene, a substituted or unsubstituted hetero $C_2$-$C_6$ alkenylene, or a substituted or unsubstituted hetero $C_2$-$C_6$ alkynylene;

each instance of $X^1$ and $X^2$ is independently —O—, —S—, or —NH—;

$R^1$ is hydrogen or substituted or unsubstituted alkyl;

$R^{3b}$ is hydrogen;

$R^{3a}$ is hydrogen, substituted or unsubstituted alkyl, substituted or unsubstituted alkenyl, or substituted or unsubstituted alkynyl;

each instance of $R^2$, $R^{11a}$, and $R^{11b}$ is independently hydrogen or —$OR^{B1}$, wherein wherein $R^{B1}$ is hydrogen or substituted or unsubstituted alkyl, or $R^{11a}$ and $R^{11b}$ are joined to form an oxo (=O) group;

each of $R^{6a}$ and $R^{6b}$ is independently hydrogen, halo, or substituted or unsubstituted alkyl, and ====== represents a single or double bond, provided if a double bond is present, then one of $R^{6a}$ or $R^{6b}$ is absent, and provided if a single bond is present, then the hydrogen at C5 is in the alpha or beta position;

each instance of $R^{19}$ and $R^{20}$ is independently hydrogen or —$CH_3$;

and each instance of $R^{23a}$ and $R^{23b}$ is independently hydrogen, halogen, or substituted or unsubstituted alkyl, or $R^{23a}$ and $R^{23b}$ are joined together to form substituted or unsubstituted $C_3$-$C_6$ cycloalkyl;

$R^{24}$ is hydrogen or substituted or unsubstituted alkyl;

Y is —O—, —S—, or —$NR^{Z5}$—;

$R^{Z4}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{Z5}$, —$SR^{Z5}$, or —$N(R^{Z5})_2$;

each instance of $R^{Z5}$ is independently hydrogen or substituted or unsubstituted alkyl; and each instance of $R^{Z6}$ is independently hydrogen or substituted or unsubstituted alkyl, or two $R^{Z6}$ groups are joined to form a $C_{3-6}$ carbocyclic ring; and the subscript n is 0 or 1;

provided the following compounds are specifically excluded:

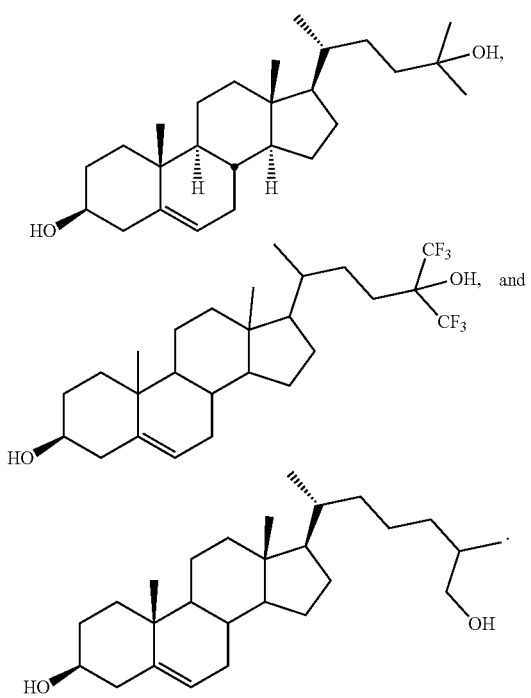

In certain embodiments, Z is a group of formula:

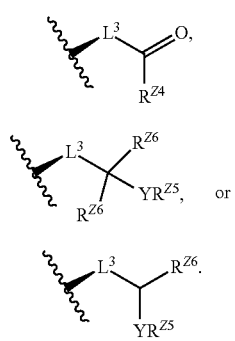

In certain embodiments, $L^3$ is a group of formula:

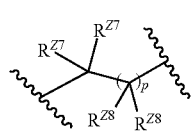

wherein p is 1, 2, or 3; and each instance of $R^{Z7}$ and $R^{Z8}$ is, independently, hydrogen, halo, substituted or unsubstituted $C_{1-6}$ alkyl, or $—OR^{Z5}$.

In certain embodiments, $L^3$ is a group of formula:

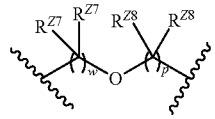

wherein w is 0 or 1 and p is 1, 2, or 3, or w is 1 and p is 0, 1, 2, or 3; and each instance of $R^{Z7}$ and $R^{Z8}$ is independently hydrogen, halo, substituted or unsubstituted $C_{1-6}$ alkyl, or $—OR^{Z5}$.

In certain embodiments, $L^3$ is a group of formula:

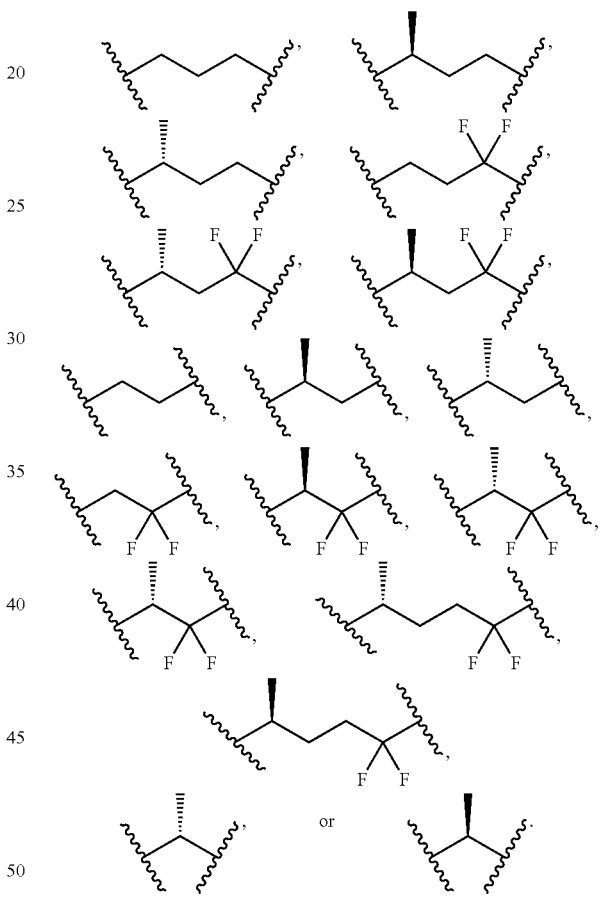

In certain embodiments, $L^3$ is a group of formula:

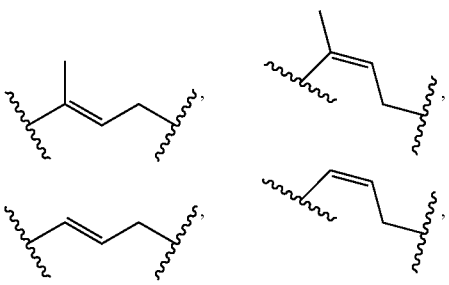

-continued
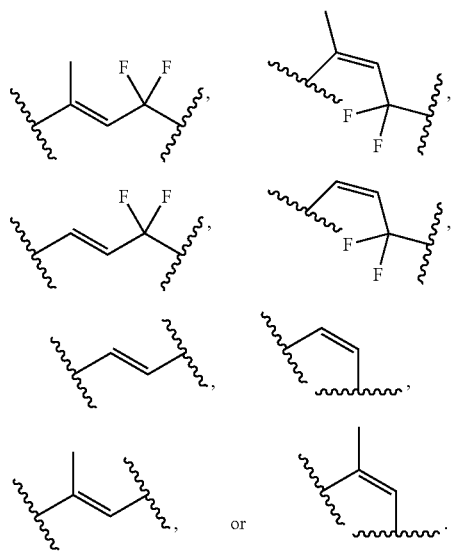
In certain embodiments, L³ is a group of formula:
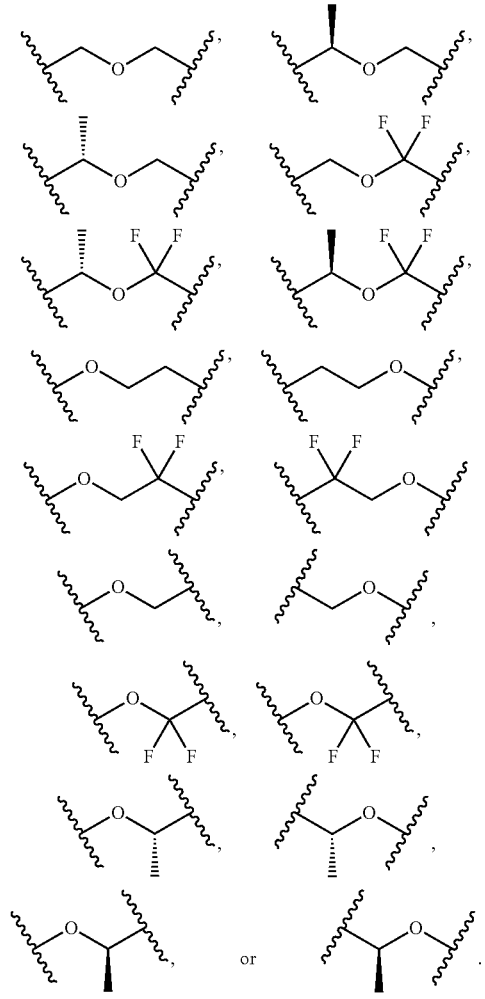
In certain embodiments, Z is of formula
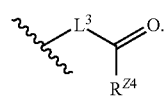
In certain embodiments, the group
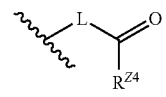
is of the formula:
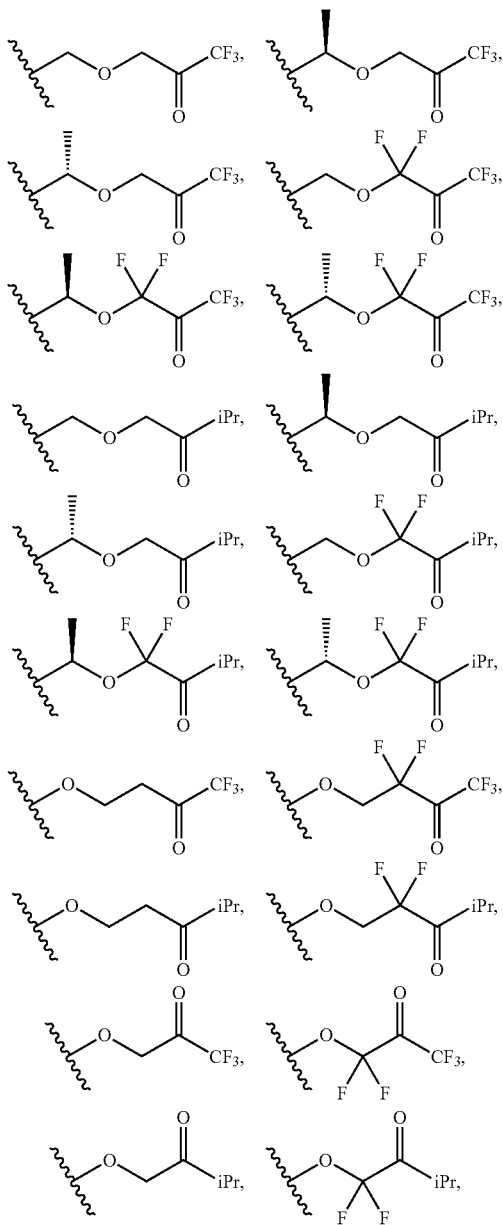

-continued
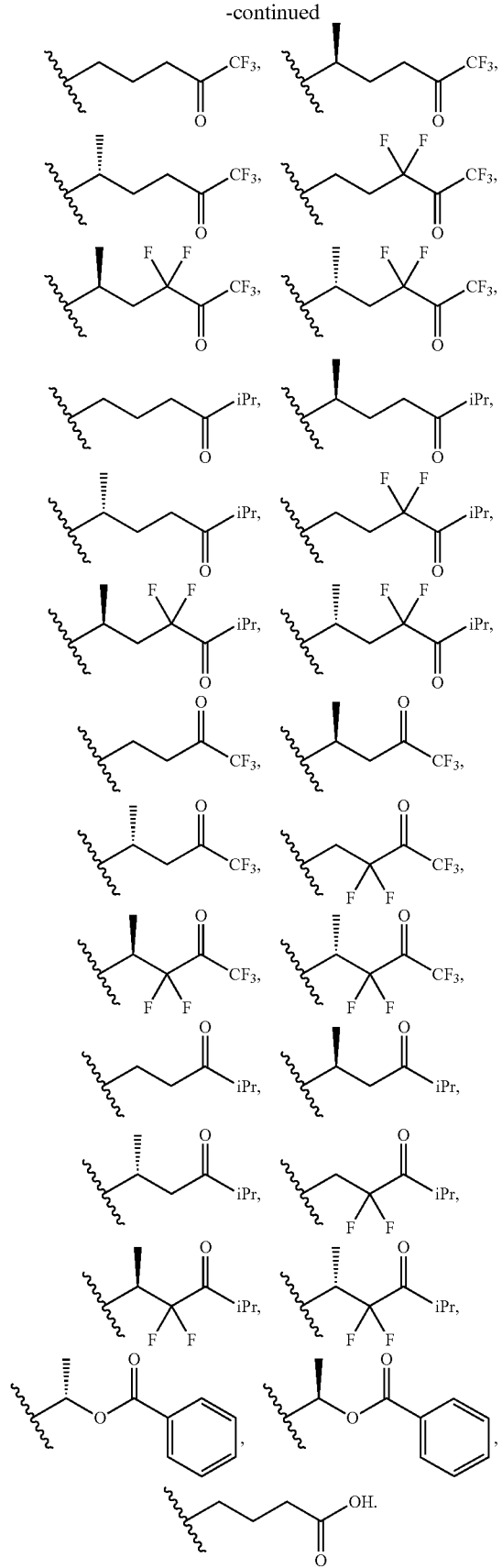
In certain embodiments, Z is of formula
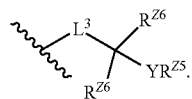
In certain embodiments, wherein Y is —O— and $L^3$ is an alkylene or heteroalkylene group.
In certain embodiments, the group
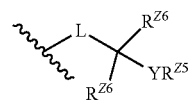
is of the formula:
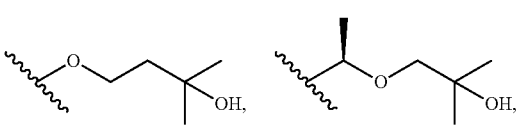
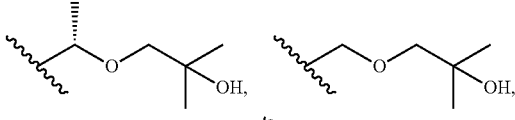
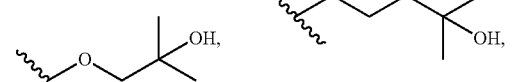
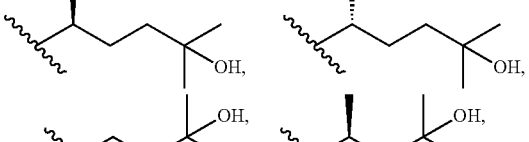
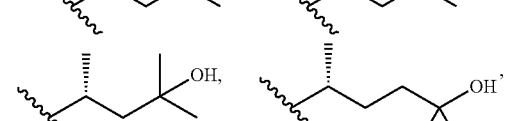
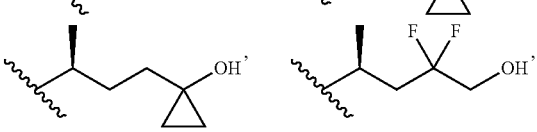
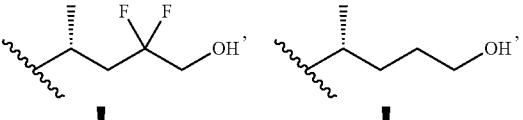
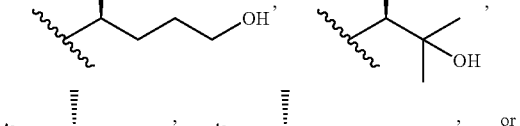
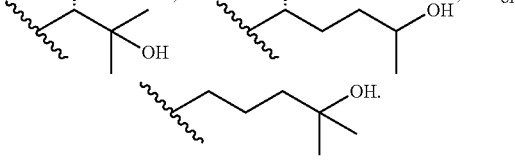

In certain embodiments, Z is of formula

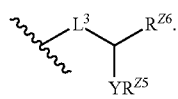

In certain embodiments, Y is —O— and $L^3$ is an alkylene or heteroalkylene.

In certain embodiments, the group

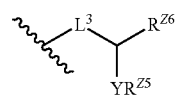

is of the formula:

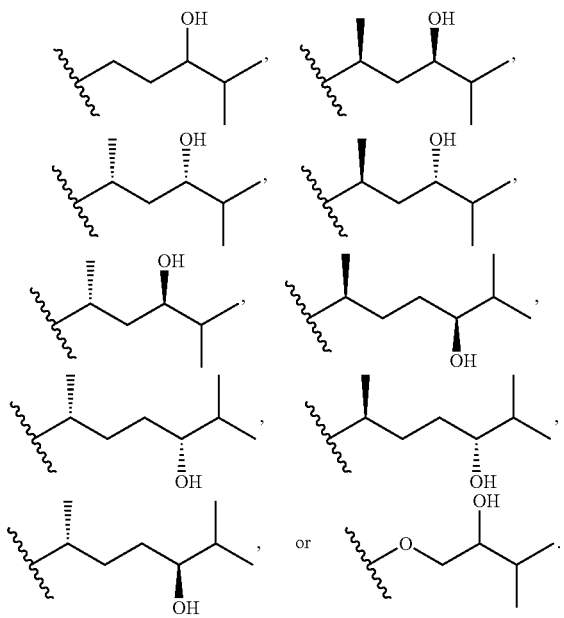

In certain embodiments, the group —$X^1R^{3b}$ is in the beta position, and $R^{3a}$ is in the alpha position. In certain embodiments, —$X^1R^{3b}$ is —OH. In certain embodiments, $R^{3a}$ is hydrogen. In certain embodiments, $R^{3a}$ is substituted or unsubstituted alkyl. In certain embodiments, $R^{6b}$ is halogen or substituted or unsubstituted alkyl. In certain embodiments, $R^2$ is hydrogen or —$OR^{B1}$. In certain embodiments, $R^{11b}$ is hydrogen or —$OR^{B1}$, and $R^{11a}$ is hydrogen. In certain embodiments, $R^{11a}$ and $R^{11b}$ together form an oxo group. In certain embodiments, ===== represents a single bond, and the hydrogen at C5 is in the alpha position. In certain embodiments, ===== represents a double bond. In certain embodiments, $R^{19}$ is —$CH_3$.

In another aspect, provided is a pharmaceutical composition comprising a compound of the present invention and a pharmaceutically acceptable carrier. In certain embodiments, the compound of the present invention is provided in an effective amount. In certain embodiments, the compound of the present invention is provided in a therapeutically effective amount. In certain embodiments, the compound of the present invention is provided in a prophylactically effective amount.

In certain aspects, compounds of the present invention are provided as negative allosteric modulators (NAM) of NMDA receptor and thus are useful for preventing and/or treating a broad range of CNS conditions including but not limited to schizophrenia, depression, bipolar disorder (I and II), schizoaffective disorder, mood disorders, anxiety disorders, personality disorders, psychosis, compulsive disorders, post-traumatic stress disorder (PTSD), Autism spectrum disorder (ASD), dysthymia (mild depression), social anxiety disorder, obsessive compulsive disorder (OCD), all pain syndromes and disorders, sleep disorders, memory disorders and dementia including Alzheimer's Disease, epilepsy and any seizure disorders, traumatic brain injury (TBI), stroke, addictive disorders including opiates and cocaine and alcohol, autism, Huntington's Disease, insomnia, Parkinson's disease, withdrawal syndromes, or tinnitus. For example, in one aspect, provided is a method of NMDA receptor modulation comprising administering an effective amount of a compound of the present invention to a subject in need thereof. In another aspect, provided is a method of modulating CNS-activity comprising administering an effective amount of a compound of the present invention to a subject in need thereof. In yet another aspect, provided is a method of modulating brain excitability comprising administering an effective amount of a compound of the present invention to a subject in need thereof.

Other objects and advantages will become apparent to those skilled in the art from a consideration of the ensuing detailed description, examples, and claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268

(E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("C2-6 alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

As used herein, "alkylene," "alkenylene," and "alkynylene," refer to a divalent radical of an alkyl, alkenyl, and alkynyl group, respectively. When a range or number of carbons is provided for a particular "alkylene," "alkenylene," and "alkynylene" group, it is understood that the range or number refers to the range or number of carbons in the linear carbon divalent chain. "Alkylene," "alkenylene," and "alkynylene" groups may be substituted or unsubstituted with one or more substituents as described herein.

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, (—$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like.

"Alkenyl" refers to a radical of a straight-chain or branched hydrocarbon group having from 2 to 20 carbon atoms, one or more carbon-carbon double bonds (e.g., 1, 2, 3, or 4 double bonds), and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkenylene" refers to an alkenyl group wherein two hydrogens are removed to provide a divalent radical, and which may be substituted or unsubstituted. Exemplary unsubstituted divalent alkenylene groups include, but are not limited to, ethenylene (—CH=CH—) and propenylene (e.g., —CH=CHCH$_2$—, —CH$_2$—CH=CH—). Exemplary substituted alkenylene groups, e.g., substituted with one or more alkyl (methyl) groups, include but are not limited to, substituted ethylene (—C(CH$_3$)=CH—, —CH=C ($CH_3$)—), substituted propylene (e.g., —C($CH_3$)=CHCH$_2$—, —CH=C($CH_3$)CH$_2$—, —CH=CHCH($CH_3$)—, —CH=CHC($CH_3$)$_2$—, —CH($CH_3$)—CH=CH—, —C($CH_3$)$_2$—CH=CH—, —CH$_2$—C($CH_3$)=CH—, —CH$_2$—CH=C($CH_3$)—), and the like.

"Alkynyl" refers to a radical of a straight-chain or branched hydrocarbon group having from 2 to 20 carbon atoms, one or more carbon-carbon triple bonds (e.g., 1, 2, 3, or 4 triple bonds), and optionally one or more double bonds (e.g., 1, 2, 3, or 4 double bonds) ("$C_{2-20}$ alkynyl"). An alkynyl group that has one or more triple bonds and one or more double bonds is also referred to as an "ene-yene" group. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

"Alkynylene" refers to a linear alkynyl group wherein two hydrogens are removed to provide a divalent radical, and which may be substituted or unsubstituted. Exemplary divalent alkynylene groups include, but are not limited to, substituted or unsubstituted ethynylene, substituted or unsubstituted propynylene, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("heteroC$_{1-10}$ alkyl"). In some embodiments, a heteroalkyl group is a saturated group having 1 to 9 carbon atoms and 1, 2, 3, or 4 heteroatoms ("heteroC$_{1-9}$ alkyl"). In some embodiments, a heteroalkyl group is a saturated group having 1 to 8 carbon atoms and 1, 2, 3, or 4 heteroatoms ("heteroC$_{1-8}$ alkyl"). In some embodiments, a heteroalkyl group is a saturated group having 1 to 7 carbon atoms and 1, 2, 3, or 4 heteroatoms ("heteroC$_{1-7}$ alkyl"). In some embodiments, a heteroalkyl group is a group having 1 to 6 carbon atoms and 1, 2, or 3 heteroatoms ("heteroC$_{1-6}$ alkyl"). In some embodiments, a heteroalkyl group is a saturated group having 1 to 5 carbon atoms and 1 or 2 heteroatoms ("heteroC$_{1-5}$ alkyl"). In some embodiments, a heteroalkyl group is a saturated group having 1 to 4 carbon atoms and 1 or 2 heteroatoms ("heteroC$_{1-4}$ alkyl"). In some embodiments, a heteroalkyl group is a saturated group having 1 to 3 carbon atoms and 1 heteroatom ("heteroC$_{1-3}$ alkyl"). In some embodiments, a heteroalkyl group is a saturated group having 1 to 2 carbon atoms and 1 heteroatom ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "heteroalkenyl," as used herein, refers to an alkenyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkenyl group refers to a group having from 2 to 10 carbon atoms, at least one double bond, and 1, 2, 3, or 4 heteroatoms ("heteroC$_{2-10}$ alkenyl"). In some embodiments, a heteroalkenyl group has 2 to 9 carbon atoms at least one double bond, and 1, 2, 3, or 4 heteroatoms ("heteroC$_{2-9}$ alkenyl"). In some embodiments, a heteroalkenyl group has 2 to 8 carbon atoms, at least one double bond, and 1, 2, 3, or 4 heteroatoms ("heteroC$_{2-8}$ alkenyl"). In some embodiments, a heteroalkenyl group has 2 to 7 carbon atoms, at least one double bond, and 1, 2, 3, or 4 heteroatoms ("heteroC$_{2-7}$ alkenyl"). In some embodiments, a heteroalkenyl group has 2 to 6 carbon atoms, at least one double bond, and 1, 2, or 3 heteroatoms ("heteroC$_{2-6}$ alkenyl"). In some embodiments, a heteroalkenyl group has 2 to 5 carbon atoms, at least one double bond, and 1 or 2 heteroatoms ("heteroC$_{2-5}$ alkenyl"). In some embodiments, a heteroalkenyl group has 2 to 4 carbon atoms, at least one double bond, and 1 or 2 heteroatoms ("heteroC$_{2-4}$ alkenyl"). In some embodiments, a heteroalkenyl group has 2 to 3 carbon atoms, at least one double bond, and 1 heteroatom ("heteroC$_{2-3}$ alkenyl"). In some embodiments, a heteroalkenyl group has 2 to 6 carbon atoms, at least one double bond, and 1 or 2 heteroatoms ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "heteroalkynyl," as used herein, refers to an alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkynyl group refers to a group having from 2 to 10 carbon atoms, at least one triple bond, and 1, 2, 3, or 4 heteroatoms ("heteroC$_{2-10}$ alkynyl"). In some embodiments, a heteroalkynyl group has 2 to 9 carbon atoms, at least one triple bond, and 1, 2, 3, or 4 heteroatoms ("heteroC$_{2-9}$ alkynyl"). In some embodiments, a heteroalkynyl group has 2 to 8 carbon atoms, at least one triple bond, and 1, 2, 3, or 4 heteroatoms ("heteroC$_{2-8}$ alkynyl"). In some embodiments, a heteroalkynyl group has 2 to 7 carbon atoms, at least one triple bond, and 1, 2, 3, or 4 heteroatoms ("heteroC$_{2-7}$ alkynyl"). In some embodiments, a heteroalkynyl group has 2 to 6 carbon atoms, at least one triple bond, and 1, 2, or 3 heteroatoms ("heteroC$_{2-6}$ alkynyl"). In some embodiments, a heteroalkynyl group has 2 to 5 carbon atoms, at least one triple bond, and 1 or 2 heteroatoms ("heteroC$_{2-5}$ alkynyl"). In some embodiments, a heteroalkynyl group has 2 to 4 carbon atoms, at least one triple bond, and 1 or 2 heteroatoms ("heteroC$_{2-4}$ alkynyl"). In some embodiments, a heteroalkynyl group has 2 to 3 carbon atoms, at least one triple bond, and 1 heteroatom ("heteroC$_{2-3}$ alkynyl"). In some embodiments, a heteroalkynyl group has 2 to 6 carbon atoms, at least one triple bond, and 1 or 2 heteroatoms ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "alkylene," "alkenylene," "alkynylene," "heteroalkylene," "heteroalkenylene," and "heteroalkynylene," refer to a divalent radical of an alkyl, alkenyl, alkynyl group, heteroalkyl, heteroalkenyl, and heteroalkynyl group respectively. When a range or number of carbons is provided for a particular "alkylene," "alkenylene," "alkynylene," "heteroalkylene," "heteroalkenylene," or "heteroalkynylene," group, it is understood that the range or number refers to the range or number of carbons in the linear carbon divalent chain. "Alkylene," "alkenylene," "alkynylene," "heteroalkylene," "heteroalkenylene," and "heteroalkynylene" groups may be substituted or unsubstituted with one or more substituents as described herein.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has six ring carbon atoms ("C$_6$ aryl"; e.g., phenyl). In some embodiments, an aryl group has ten ring carbon atoms ("C$_{10}$ aryl"; e.g., naphthyl such as 1-naphthyl and 2-naphthyl). In some embodiments, an aryl group has fourteen ring carbon atoms ("C$_{1-4}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted C$_{6-14}$ aryl. In certain embodiments, the aryl group is substituted C$_{6-14}$ aryl.

In certain embodiments, an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

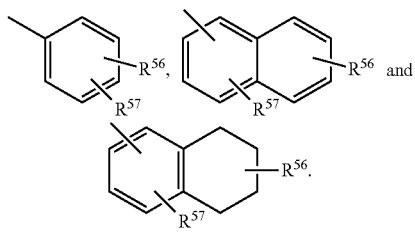

wherein one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocyclyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$ NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O, or S. R$^{60}$ and R$^{61}$ are independently hydrogen, C$_1$-C$_8$ alkyl, C$_1$-C$_4$haloalkyl, C$_3$-C$_{10}$ cycloalkyl, 4-10 membered heterocyclyl, C$_6$-C$_{10}$ aryl, substituted C$_6$-C$_{10}$ aryl, 5-10 membered heteroaryl, or substituted 5-10 membered heteroaryl.

Other representative aryl groups having a fused heterocyclyl group include the following:

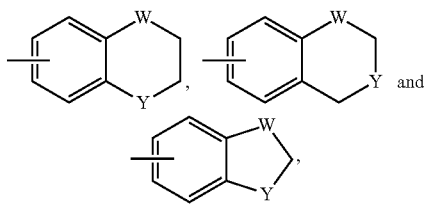

wherein each W is selected from C(R$^{66}$)$_2$, NR$^{66}$, O, and S; and each Y is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

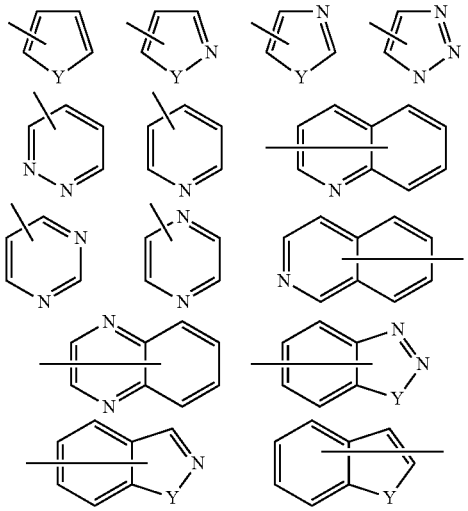

wherein each Y is selected from carbonyl, N, $NR^{65}$, O, and S; and $R^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-4}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-4}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Particular examples of heterocyclyl groups are shown in the following illustrative examples:

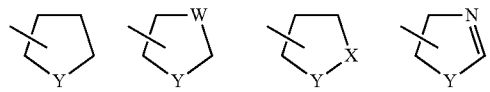

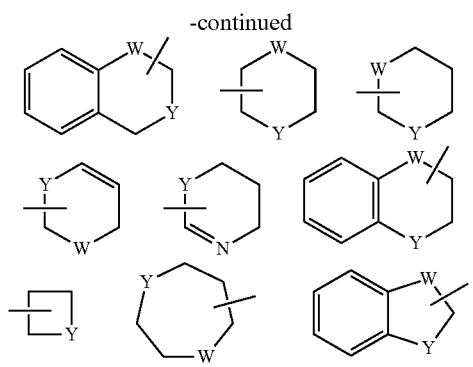

wherein each W is selected from CR$^{67}$, C(R$^{67}$)$_2$, NR$^{67}$, O, and S; and each Y is selected from NR$^{67}$, O, and S; and R$^{67}$ is independently hydrogen, C$_1$-C$_8$ alkyl, C$_3$-C$_{10}$ cycloalkyl, 4-10 membered heterocyclyl, C$_6$-C$_{10}$ aryl, 5-10 membered heteroaryl. These heterocyclyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g. heteroaryl, cycloalkenyl, e.g. cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, R$^2$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Acylamino" refers to a radical —NR$^{22}$C(O)R$^{23}$, where each instance of R$^{22}$ and R23 is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein, or R$^2$ is an amino protecting group. Exemplary "acylamino" groups include, but are not limited to, formylamino, acetylamino, cyclohexylcarbonylamino, cyclohexylmethyl-carbonylamino, benzoylamino and benzylcarbonylamino. Particular exemplary "acylamino" groups are —NR$^{24}$C(O)—C$_1$-C$_5$ alkyl, —NR$^{24}$C(O)—(CH$_2$)$_t$(C$_6$-C$_{10}$ aryl), —NR$^{24}$C(O)—(CH$_2$)$_t$(5-10 membered heteroaryl), —NR$^{24}$C(O)—(CH$_2$)$_t$(C$_3$-C$_{10}$ cycloalkyl), and —NR$^{24}$C(O)—(CH$_2$)$_t$(4-10 membered heterocyclyl), wherein t is an integer from 0 to 4, and each R$^{24}$ independently represents H or C$_1$-C$_8$ alkyl. In certain embodiments, R$^{25}$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and R$^{26}$ is H, C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl; provided at least one of R$^{25}$ and R$^{26}$ is other than H.

"Acyloxy" refers to a radical —OC(O)R$^{27}$, where R$^{27}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. Representative examples include, but are not limited to, formyl, acetyl, cyclohexylcarbonyl, cyclohexylmethylcarbonyl, benzoyl and benzylcarbonyl. In certain embodiments, R$^{28}$ is C$_1$-C$_8$ alkyl, substituted with halo or hydroxy; C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —$OCF_3$, —$OCH_2CF_3$, —$OCH_2Ph$, —$OCH_2$-cyclopropyl, —$OCH_2CH_2OH$, and —$OCH_2CH_2NMe_2$.

"Amino" refers to the radical —$NH_2$.

"Substituted amino" refers to an amino group of the formula —$N(R^{38})_2$ wherein $R^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{38}$ is not a hydrogen. In certain embodiments, each $R^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)_t(C_6$-$C_{10}$ aryl), —$(CH_2)_t$(5-10 membered heteroaryl), —$(CH_2)_t$($C_3$-$C_{10}$ cycloalkyl), or —$(CH_2)_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t(C_6$-$C_{10}$ aryl), —$NR^{39}$—$(CH_2)_t$(5-10 membered heteroaryl), —$NR^{39}$—$(CH_2)_t$($C_3$-$C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Azido" refers to the radical —$N_3$.

"Carbamoyl" or "amido" refers to the radical —$C(O)NH_2$.

"Substituted carbamoyl" or "substituted amido" refers to the radical —$C(O)N(R^{62})_2$ wherein each $R^{62}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of $R^{62}$ is not a hydrogen. In certain embodiments, $R^{62}$ is selected from H, $C_1$-$C_8$ alkyl, $C_3$-$C_{10}$ cycloalkyl, 4-10 membered heterocyclyl, $C_6$-$C_{10}$ aryl, aralkyl, 5-10 membered heteroaryl, and heteroaralkyl; or $C_1$-$C_8$ alkyl substituted with halo or hydroxy; or $C_3$-$C_{10}$ cycloalkyl, 4-10 membered heterocyclyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; provided that at least one $R^{62}$ is other than H.

Exemplary "substituted carbamoyl" groups include, but are not limited to, —$C(O)$ $NR^{64}$—$C_1$-$C_8$ alkyl, —$C(O)NR^{64}$—$(CH_2)_t(C_6$-$C_{10}$ aryl), —$C(O)N^{64}$—$(CH_2)_t$(5-10 membered heteroaryl), —$C(O)NR^{64}$—$(CH_2)_t$($C_3$-$C_{10}$ cycloalkyl), and —$C(O)NR^{64}$—$(CH_2)_t$(4-10 membered heterocyclyl), wherein t is an integer from 0 to 4, each $R^{64}$ independently represents H or $C_1$-$C_8$ alkyl and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Carboxy" refers to the radical —$C(O)OH$.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —$NO_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Cycloalkenyl" refers to substituted or unsubstituted carbocyclyl group having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Fused cycloalkenyl" refers to a cycloalkenyl having two of its ring carbon atoms in common with a second aliphatic or aromatic ring and having its olefinic unsaturation located to impart aromaticity to the cycloalkenyl ring.

"Ethenyl" refers to substituted or unsubstituted —(C=C)—.

"Ethylene" refers to substituted or unsubstituted —(C—C)—.

"Ethynyl" refers to —(C≡C)—.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal Rd substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-4}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH (C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on a nitrogen atom is an amino protecting group (also referred to herein as a nitrogen protecting group). Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., $-S(=O)_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is an sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

"Compounds of the present invention", and equivalent expressions, are meant to embrace the compounds as hereinbefore described, in particular compounds according to any of the Formula herein recited and/or described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

These and other exemplary substituents are described in more detail in the Detailed Description, Examples, and claims. The invention is not intended to be limited in any manner by the above exemplary listing of substituents.

Other Definitions

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counterion of an acidic functional group. Such cations are exemplified by sodium, potassium, calcium, magnesium, ammonium, tetraalkylammonium cations, and the like (see, e.g., Berge, et al., *J. Pharm. Sci.* 66(1): 1-79 (January "77).

"Pharmaceutically acceptable vehicle" refers to a diluent, adjuvant, excipient or carrier with which a compound of the invention is administered.

"Pharmaceutically acceptable metabolically cleavable group" refers to a group which is cleaved in vivo to yield the parent molecule of the structural Formula indicated herein. Examples of metabolically cleavable groups include —COR, —COOR, —CONRR and —CH$_2$OR radicals, where R is selected independently at each occurrence from alkyl, trialkylsilyl, carbocyclic aryl or carbocyclic aryl substituted with one or more of alkyl, halogen, hydroxy or alkoxy. Specific examples of representative metabolically cleavable groups include acetyl, methoxycarbonyl, benzoyl, methoxymethyl and trimethylsilyl groups.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

An "effective amount" means the amount of a compound that, when administered to a subject for treating or preventing a disease, is sufficient to effect such treatment or prevention. The "effective amount" can vary depending on the compound, the disease and its severity, and the age, weight, etc., of the subject to be treated. A "therapeutically effective amount" refers to the effective amount for therapeutic treatment. A "prophylatically effective amount" refers to the effective amount for prophylactic treatment.

"Preventing" or "prevention" or "prophylactic treatment" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

The term "prophylaxis" is related to "prevention," and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Treating" or "treatment" or "therapeutic treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e., $^3H$, and carbon-14, i.e., $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy. All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base. Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R"

form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

Detailed Description of Certain Embodiments of the Invention

In certain aspects, provided herein are 3-α and 3β-hydroxy steroid compounds as NMDA receptor modulators and thus, useful for preventing and/or treating a broad range of CNS conditions, among them, schizophrenia, depression, bipolar disorder (e.g., I and/or II), schizoaffective disorder, mood disorders, anxiety disorders, personality disorders, psychosis, compulsive disorders, post-traumatic stress disorder (PTSD), Autism spectrum disorder (ASD), dysthymia (mild depression), social anxiety disorder, obsessive compulsive disorder (OCD), pain (e.g., a painful syndrome or disorder), sleep disorders, memory disorders, dementia, Alzheimer's Disease, a seizure disorder (e.g., epilepsy), traumatic brain injury, stroke, addictive disorders (e.g., addiction to opiates, cocaine, and/or alcohol), autism, Huntington's Disease, insomnia, Parkinson's disease, withdrawal syndromes, or tinnitus. These compounds are expected to show improved in vivo potency, pharmacokinetic properties (PK) properties, oral bioavailability, formulatability, stability, and/or safety.

Compounds

In one aspect, provided herein are compounds according to Formula (I):

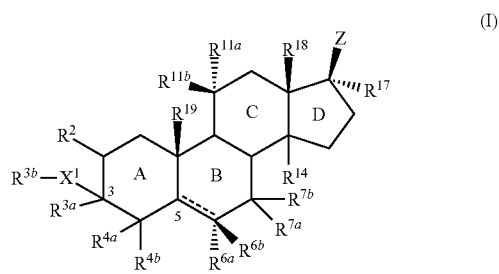

or a pharmaceutically acceptable salt, solvate, prodrug, stereoisomer, tautomer, isotopic variant, or N-oxide thereof, or a combination thereof;

wherein:

Z is a group of the formula (i), (ii), (iii), (iv), or (v):

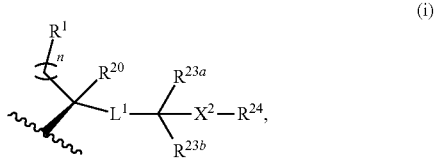

-continued

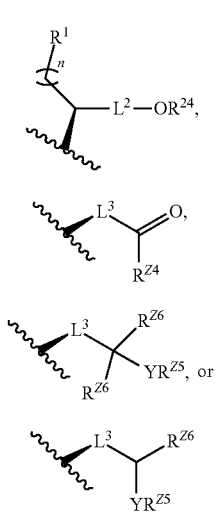

(ii)

(iii)

(iv)

(v)

L¹ and L² are selected from a group consisting of a bond, a substituted or unsubstituted $C_1$-$C_6$ alkylene, a substituted or unsubstituted $C_2$-$C_6$ alkenylene, substituted or unsubstituted $C_2$-$C_6$ alkynylene, a substituted or unsubstituted hetero $C_1$-$C_6$ alkylene, a substituted or unsubstituted hetero $C_2$-$C_6$ alkenylene, and a substituted or unsubstituted hetero $C_2$-$C_6$ alkynylene;

L³ is a substituted or unsubstituted $C_1$-$C_6$ alkylene, a substituted or unsubstituted $C_2$-$C_6$ alkenylene, substituted or unsubstituted $C_2$-$C_6$ alkynylene, a substituted or unsubstituted hetero $C_1$-$C_6$ alkylene, a substituted or unsubstituted hetero $C_2$-$C_6$ alkenylene, or a substituted or unsubstituted hetero $C_2$-$C_6$ alkynylene;

each instance of $X^1$ and $X^2$ is independently —O—, —S—, —N($R^X$)—, wherein each instance of $R^X$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroalkyl, or an amino protecting group;

$R^1$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, halo, —$N_3$, —$NO_2$, —SCN, —CN, —$OR^{41}$, —$SR^{41}$, —$N(R^{41})_2$, —N=$NR^{41}$, —N=$C(R^{41})_2$, —$N(OR^{41})(R_{41})$, —$C(=O)R^{41}$, —$C(=O)OR^{41}$, —$OC(=O)SR^{41}$, —$OC(=O)N(R^{41})_2$, —$C(=O)N(OR^{41})(R^{41})$, —$OC(=O)R^{41}$, —$OC(=O)OR^{41}$, —$OC(=O)SR^{41}$, —$OC(=O)N(R^{41})_2$, —$NR^{41}C(=O)R^{41}$, —$NR^{41}C(=O)OR^{41}$, —$NR^{41}C(=O)SR^{41}$, —$NR^{41}C(=O)N(R^{41})_2$, —$SC(=O)R^{42}$, —$SC(=O)OR^{41}$, —$SC(=O)SR^{41}$, —$SC(=O)N(R^{41})_2$, —$OS(=O)_2R^{42}$, —$OS(=O)_2OR^{41}$, —S—$S(=O)_2R^{42}$, —S—$S(=O)_2OR^{41}$, —$S(=O)R^{42}$, —$SO_2R^{42}$, —$NR^{41}SO_2R^{42}$, or —$SO_2N(R^{41})_2$, wherein $R^{41}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two $R^{41}$ groups are joined to form an substituted or unsubstituted heterocyclic ring; and $R^{42}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or an $R^{41}$ group and an $R^{42}$ group are joined to form an substituted or unsubstituted heterocyclic ring;

each instance of $R^2$, $R^{4a}$, $R^{4b}$, $R^{7a}$, $R^{7b}$, $R^{11a}$, and $R^{11b}$ is independently hydrogen, —OH, halo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$N_3$, —$NO_2$, —SCN, —CN, —$OR^{B1}$, —$SR^{B1}$, —$N(R^{B1})_2$, —N=$NR^{B1}$, —N=$C(R^{B1})_2$, —$N(OR^{B1})(R^{B1})$, —$C(=O)R^{B1}$, —$C(=O)OR^{B1}$, —$C(=O)SR^{B1}$, —$C(=O)N(R^{b1})$, —$C(=O)N(OR^{B1})(R^{B1})$, —$OC(=O)R^{B1}$, —$OC(=O)OR^{B1}$, —$OC(=O)SR^{B1}$, —$OC(=O)N(R^{B1})_2$, —$NR^{B1}C(=O)R^{B1}$, —$NR^{B1}C(=O)OR^{B1}$, —$NR^{B1}C(=O)SR^{B1}$, —$NR^{B1}C(=O)N(R^{B1})_2$, —$SC(=O)R^{B2}$, —$SC(=O)OR^{B1}$, —$SC(=O)SR^{B1}$, —$SC(=O)N(R^{B1})_2$, —$OS(=O)_2R^{B2}$, —$OS(=O)_2OR^{B1}$, —S—$S(=O)_2R^{B2}$, —S—$S(=O)_2OR^{B1}$, —$S(=O)R^{B2}$, —$SO_2R^{B2}$, —$NR^{B1}SO_2R^{B2}$, or —$SO_2N(R^{B1})_2$, wherein $R^{B1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two $R^{B1}$ groups are joined to form an substituted or unsubstituted heterocyclic ring; and $R^{B2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or an $R^{B1}$ group and an $R^{B2}$ group are joined to form an substituted or unsubstituted heterocyclic ring; or optionally wherein each of $R^{4a}$ and $R^{4b}$, and/or $R^{7a}$ and $R^{7b}$, and/or $R^{11a}$ and $R^{11b}$ are joined to form an oxo (=O) group;

$R^{3a}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^{3b}$ is hydrogen, —$C(=O)R^{C1}$, —$C(=O)OR^{C1}$, —$C(=O)SR^{C1}$, —$C(=O)N(R^{C1})_2$, —$S(=O)_2R^{C1}$, —$S(=O)_2OR^{C1}$, —$P(=O)_2R^{C1}$, —$P(=O)_2OR^{C1}$, —$P(=O)(OR^{C1})_2$, —$P(=O)(R^{C2})_2$, or —$P(=O)(R^{C2})(OR^{C1})$, wherein $R^{C1}$ is hydrogen or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two $R^{C1}$ groups are joined to form an substituted or unsubstituted heterocyclic ring; and $R^{C2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each of $R^{6a}$ and $R^{6b}$ is independently hydrogen, halo, substituted or unsubstituted alkyl, substituted or unsubstituted alkenyl, or substituted or unsubstituted alkynyl, and ----- represents a single or double bond, provided if a double bond is present in Ring B, then one of $R^{6a}$ or $R^{6b}$ is absent, and provided if a single bond is present in Ring B, then the hydrogen at C5 is in the alpha or beta position;

$R^{14}$ is hydrogen or substituted or unsubstituted alkyl;

$R^{17}$ is hydrogen, halo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or $-OR^{D1}$, wherein $R^{D1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

each instance of $R^{18}$, $R^{19}$, and $R^{20}$ is independently hydrogen or substituted or unsubstituted alkyl;

and each instance of $R^{23a}$ and $R^{23b}$ is independently hydrogen, halogen, or substituted or unsubstituted alkyl, or $R^{23a}$ and $R^{23b}$ are joined together to form substituted or unsubstituted $C_3$-$C_6$ cycloalkyl;

$R^{24}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-C(=O)R^{E1}$, $-C(=O)OR^{E1}$, $-C(=O)SR^{E1}$, $-C(=O)N(R^{E1})_2$, $-S(=O)_2R^{E2}$, $-S(=O)_2OR^{E1}$, $-P(=O)_2R^{E2}$, $-P(=O)_2OR^{E1}$, $-P(=O)(OR^{E1})_2$, $-P(=O)(R^{E2})_2$, or $-P(=O)(R^{E2})(OR^{E1})$, wherein $R^{E1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two $R^{E1}$ groups are joined to form an substituted or unsubstituted heterocyclic ring; and $R^{E2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

Y is $-O-$, $-S-$, or $-NR^{Z5}-$;

$R^{Z4}$ is independently substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{Z5}$, $-SR^{Z5}$, or $-N(R^{Z5})_2$;

each instance of $R^{Z5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, an oxygen protecting group when attached to an oxygen atom, a sulfur protecting group when attached to a sulfur atom, a nitrogen protecting group when attached to a nitrogen atom, or two $R^{Z5}$ groups are joined to form a substituted or unsubstituted heterocyclic ring; and each instance of $R^{Z6}$ is independently hydrogen or substituted or unsubstituted alkyl, or two $R^{Z6}$ groups are joined to form a $C_{3-6}$ carbocyclic ring; and the subscript n is 0, 1, 2, or 3.

In certain embodiments, when $R^{3a}$ is H, n is 1, and $R^{19}$ is Me; then $R^1$ is other than H, alkyl, alkenyl, or alkynyl. In certain embodiments, when $R^{3a}$ is H, $R^{3b}$ is $-COMe$, $R^{19}$ is Me, and n is 0; then $R^1$ is OH. In certain embodiments, when $R^{3a}$ is H, n is 0, and $R^{20}$ is alkyl; then $R^1$ is other than OH. In certain embodiments, when $R^{19}$ is Me; then $R^1$ is other than H, alkyl, alkenyl, or alkynyl. In certain embodiments, $R^1$ is H; and $R^{19}$ is other than Me. In certain embodiments, each $R^1$ and $R^{3a}$ is H; and $R^{19}$ is other than Me.

In certain embodiments, when $R^{3a}$ is H, then $R^1$ is other than H, substituted or unsubstituted alkyl, substituted or unsubstituted alkenyl, or substituted or unsubstituted alkynyl. In certain embodiments, when $R^{3a}$ is H, then $R^1$ is substituted or unsubstituted carbocyclyl, substituted or unsubstituted heterocyclyl, substituted or unsubstituted aryl, substituted or unsubstituted heteroaryl, halo, $-N_3$, $-NO_2$, $-SCN$, $-CN$, $-OR^{41}$, $-SR^{41}$, $-N(R^{41})_2$, $-N=NR^{41}$, $-N=C(R^{41})_2$, $-N(OR^{41})(R^{41})$, $-C(=O)R^{41}$, $-C(=O)OR^{41}$, $-C(=O)SR^{41}$, $-C(=O)N(R^{41})_2$, $-C(=O)N(OR^{41})(R^{41})$, $-OC(=O)R^{41}$, $-OC(=O)OR^{41}$, $-OC(=O)SR^{41}$, $-OC(=O)N(R^{41})_2$, $-NR^{41}C(=O)R^{41}$, $-NR^{41}C(=O)OR^{41}$, $-NR^{41}C(=O)SR^{41}$, $-NR^{41}C(=O)N(R^{41})_2$, $-SC(=O)R^{42}$, $-SC(=O)OR^{41}$, $-SC(=O)SR^{41}$, $-SC(=O)N(R^{41})_2$, $-OS(=O)_2R^{42}$, $-OS(=O)_2OR^{41}$, $-S-S(=O)_2R^{42}$, $-S-S(=O)_2OR^{41}$, $-S(=O)R^{42}$, $-SO_2R^{42}$, $-NR^{41}SO_2R^{42}$, or $-SO_2N(R^{41})_2$.

In certain further embodiments, the following compounds are specifically excluded:

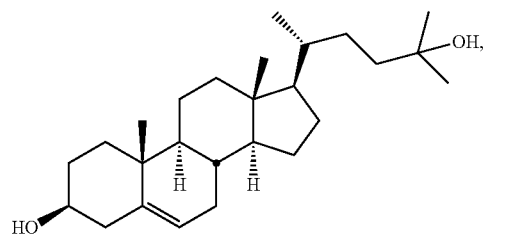

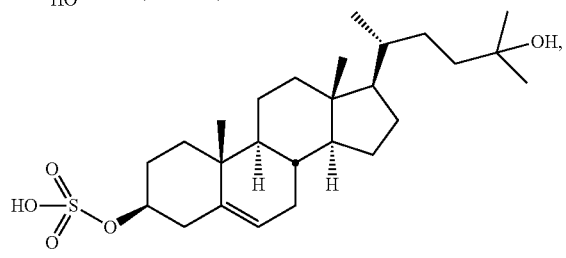

43
-continued

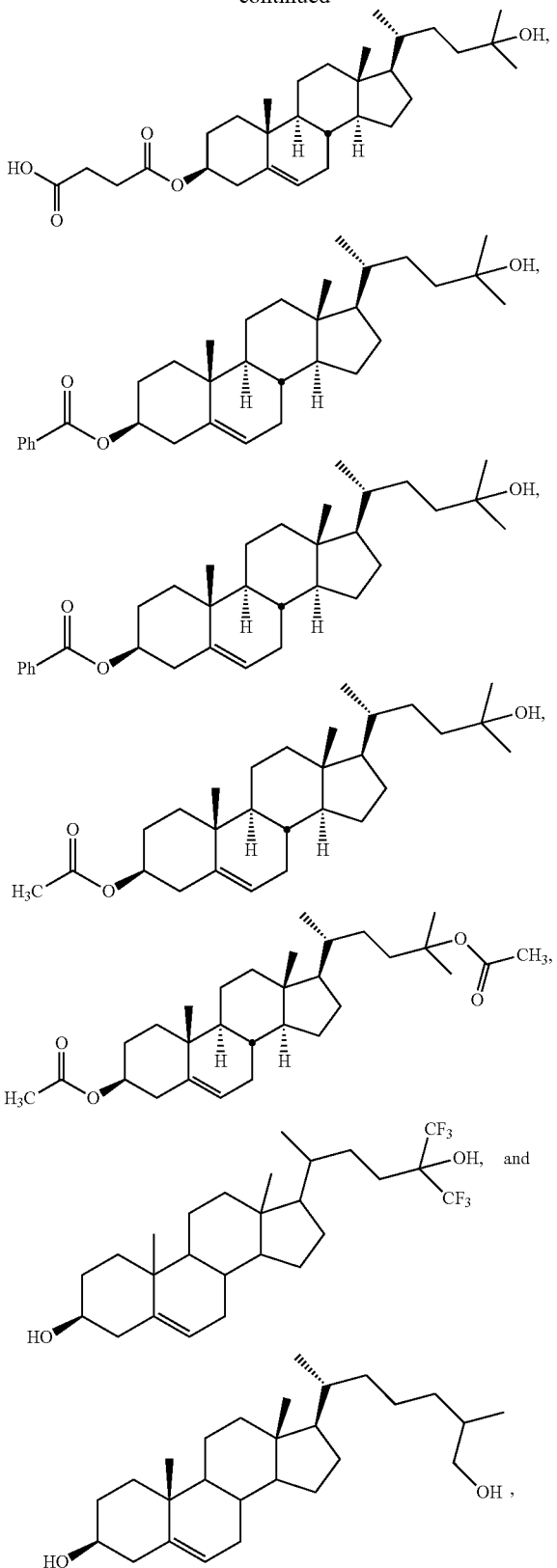

and pharmaceutically acceptable salt, solvate, prodrug, stereoisomer, tautomer, isotopic variant, or N-oxide thereof, or a combination thereof.

44

Various Embodiments of $R^{3a}$

As generally defined above, $R^{3a}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. It is generally understood that $R^{3a}$ may be in the alpha (down) or beta (up) position. In certain embodiments, $R^{3a}$ is alpha. In certain embodiments, $R^{3a}$ is beta.

In certain embodiments, $R^{3a}$ is hydrogen.

In certain embodiments, $R^{3a}$ is substituted or unsubstituted alkyl, e.g., substituted or unsubstituted $C_{1-6}$ alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^{3a}$ $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), $C_{1-6}$ alkyl substituted with 1, 2, 3, 4, 5, 6, 7, 8, 9, 10, or more fluoro groups (e.g., —$CF_3$, —$CH_2F$, —$CHF_2$, difluoroethyl, and 2,2,2-trifluoro-1,1-dimethyl-ethyl), $C_{1-6}$ alkyl substituted with 1, 2, 3, 4, 5, 6, 7, 8, 9, 10, or more chloro groups (e.g., —$CH_2Cl$, —$CHCl_2$), and $C_{1-4}$ alkyl substituted with alkoxy groups (e.g., —$CH_2OCH_3$ and —$CH_2OCH_2CH_3$). In certain embodiments, $R^{3a}$ is substituted alkyl, e.g., $R^{3a}$ is haloalkyl, alkoxyalkyl, or aminoalkyl. In certain embodiments, $R^{3a}$ is Me, Et, n-Pr, n-Bu, i-Bu, fluoromethyl, chloromethyl, difluoromethyl, trifluoromethyl, trifluoroethyl, difluoroethyl, 2,2,2-trifluoro-1,1-dimethyl-ethyl, methoxymethyl, methoxyethyl, or ethoxymethyl. In certain embodiments, $R^{3a}$ is Me, Et, n-Pr, n-Bu, or i-Bu. In certain embodiments, $R^{3a}$ is methoxymethyl, ethoxymethyl, propoxymethyl, methoxyethyl, or ethoxyethyl. In certain embodiments, $R^{3a}$ is trifluoromethoxymethyl. In certain embodiments, $R^{3a}$ is fluoromethyl, chloromethyl, difluoromethyl, trifluoromethyl, difluoroethyl, trifluoroethyl, or 2,2,2-trifluoro-1,1-dimethyl-ethyl. In certain embodiments, $R^{3a}$ is trifluoromethyl.

In certain embodiments, $R^{3a}$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, or substituted or unsubstituted $C_{5-6}$alkenyl. In certain embodiments, $R^{3a}$ is ethenyl ($C_2$), propenyl ($C_3$), or butenyl ($C_4$), unsubstituted or substituted with one or more substituents selected from the group consisting of alkyl, halo, haloalkyl, alkoxyalkyl, or hydroxyl. In certain embodiments, $R^{3a}$ is ethenyl, propenyl, or butenyl, unsubstituted or substituted with alkyl, halo, haloalkyl, alkoxyalkyl, or hydroxy. In certain embodiments, $R^{3a}$ is ethenyl.

In certain embodiments, $R^{3a}$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, or substituted or unsubstituted $C_{4-6}$alkynyl. Exemplary substituted or unsubstituted $R^{3a}$ alkynyl groups include, but are not limited to, ethynyl, propynyl, or butynyl, unsubstituted or substituted with alkyl, halo, haloalkyl (e.g., $CF_3$), alkoxyalkyl, cycloalkyl (e.g., cyclopropyl or cyclobutyl), or hydroxyl. In certain embodiments, $R^{3a}$ is selected from the group consisting of trifluoroethynyl, cyclopropylethynyl, cyclobutylethynyl, and propynyl, fluoropropynyl, and chloroethynyl. In certain embodiments, $R^{3a}$ is ethynyl ($C_2$), propynyl ($C_3$), or butynyl ($C_4$), unsubstituted or substituted with one or more substituents selected from the group consisting of substituted or unsubstituted aryl, substituted or unsubstituted heteroaryl, substituted or unsubstituted carbocyclyl, and substituted or unsubstituted heterocyclyl. In certain embodiments, $R^{3a}$ is ethynyl ($C_2$), propynyl ($C_3$), or butynyl ($C_4$) substituted with substituted phenyl. In certain embodiment, the phenyl substitutent is further substituted with one or more substituents selected from the group consisting of halo, alkyl, trifluoroalkyl, alkoxy, acyl, amino or amido. In certain embodiments, $R^{3a}$ is ethynyl ($C_2$), propynyl ($C_3$), or butynyl ($C_4$) substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, or tetrazolyl.

In certain embodiments, $R^{3a}$ is ethynyl, propynyl, or butynyl, unsubstituted or substituted with alkyl, halo, haloalkyl, alkoxyalkyl, or hydroxyl. In certain embodiments, $R^{3a}$ is ethynyl or propynyl, substituted with substituted or unsubstituted aryl. In certain embodiments, $R^{3a}$ is ethynyl or propynyl, substituted with phenyl unsubstituted or substituted with halo, alkyl, alkoxy, haloalkyl, trihaloalkyl, or acyl. In certain embodiments, $R^{3a}$ is ethynyl or propynyl, substituted with substituted or unsubstituted carbocyclyl. In certain embodiments, $R^{3a}$ is ethynyl or propynyl, substituted with substituted or unsubstituted cyclopropyl, cyclobutyl, cyclopentyl, or cyclohexyl. In certain embodiments, $R^{3a}$ is ethynyl or propynyl, substituted with substituted or unsubstituted heteroaryl. In certain embodiments, $R^{3a}$ is ethynyl or propynyl, substituted with substituted or unsubstituted pyridinyl, or pyrimidinyl. In certain embodiments, $R^{3a}$ is ethynyl or propynyl, substituted with substituted or unsubstituted pyrrolyl, imidazolyl, pyrazolyl, oxazoyl, thiazolyl, isoxazoyl, 1,2,3-triazolyl, 1,2,4-triazolyl, oxadiazolyl, thiadiazolyl, tetrazolyl. In certain embodiments, $R^{3a}$ is ethynyl or propynyl, substituted with substituted or unsubstituted heterocyclyl. In certain embodiments, $R^{3a}$ is ethynyl or propynyl, substituted with substituted or unsubstituted pyrrolidinyl, piperidinyl, piperazinyl, or mopholinyl. In certain embodiments, $R^{3a}$ is propynyl or butynyl, substituted with hydroxyl or alkoxy. In certain embodiments, $R^{3a}$ is propynyl or butynyl, substituted with methoxy or ethoxy. In certain embodiments, $R^{3a}$ is ethynyl or propynyl, substituted with Cl. In certain embodiments, $R^{3a}$ is ethynyl or propynyl, substituted with trifluoromethyl.

In certain embodiments, $R^{3a}$ is substituted or unsubstituted carbocyclyl, e.g., substituted or unsubstituted $C_{3-4}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, $R^{3a}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, $R^{3a}$ is substituted or unsubstituted aryl. In certain embodiments, $R^{3a}$ is substituted or unsubstituted phenyl.

In certain embodiments, $R^{3a}$ is substituted or unsubstituted heteroaryl, e.g., optionally substituted 5- to 6-membered heteroaryl.

Further embodiments of $R^{3a}$, as a substituted or unsubstituted alkyl, substituted or unsubstituted alkenyl, and substituted or unsubstituted alkynyl groups, are depicted below:

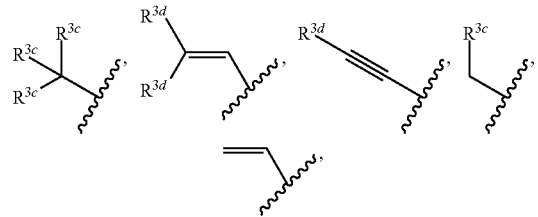

wherein each instance of $R^{3c}$ is hydrogen, halo, or $-OR^{F1}$, wherein $R^{F1}$ is substituted or unsubstituted alkyl; and each instance of $R^{3d}$ is hydrogen, halo, or substituted or unsubstituted alkyl, substituted or unsubstituted carbocyclyl, or substituted or unsubstituted heterocyclyl.

In certain embodiments, at least one $R^{3c}$, is hydrogen. In certain embodiments, at least two $R^{3c}$, is hydrogen. In certain embodiments, each $R^{3c}$, is hydrogen. In certain embodiments, at least one $R^{3c}$, is halogen (e.g., fluoro, chloro, bromo, iodo). In certain embodiments, at least two $R^{3c}$ are halogen (e.g., fluoro, chloro, bromo, iodo). In certain embodiments, each $R^{3c}$, is halogen (e.g., fluoro, to provide the group $-CF_3$). In certain embodiments, at least one $R^{3c}$ is $-OR^{F1}$ (e.g., OMe or OEt). In certain embodiments, at least two $R^{3c}$ is $-OR^{F1}$ (e.g., OMe or OEt). In certain embodiments, at least one $R^{3c}$, is hydrogen, F, $-OMe$, or $-OEt$. In certain embodiments, one of $R^{3c}$ is F, $-OMe$, or OEt; and the rest are H.

In certain embodiments, at least one $R^{3d}$ is hydrogen. In certain embodiments, each $R^{2c}$ is hydrogen. In certain embodiments, at least one $R^{3d}$ is halogen (e.g., fluoro, chloro, bromo, iodo). In certain embodiments, each $R^{3d}$ is halogen (e.g., fluoro, chloro, bromo, iodo). In certain embodiments, each of $R^{3d}$ is alkyl, e.g., each of $R^{2c}$ is Me. In certain embodiments, one of $R^{3d}$ is alkyl; and the other is hydrogen, e.g., one of $R^{3d}$ is Me; and the other is hydrogen. In certain embodiments, one of $R^{3d}$ is substituted or unsubstituted carbocyclyl, e.g., cyclopropyl or cyclobutyl, and the other is hydrogen. In certain embodiments, at least one $R^{3d}$ is hydrogen, $-F$, $-Br$, $-Cl$, $-I$, $-CH_3$, $-CF_3$, cyclopropyl, or cyclobutyl. In certain embodiments, each instance of $R^{3d}$ is H. In certain embodiments, each instance of $R^{3d}$ is halogen (e.g., fluoro, chloro, bromo, iodo). In certain embodiments, each instance of $R^{3d}$ is alkyl, e.g., $-CH_3$, $-CF_3$, $-CH_2CH_2Cl$. In certain embodiments, each instance of $R^{3d}$ is substituted or unsubstituted carbocyclyl, e.g., cyclopropyl or cyclobutyl. In certain embodiments, $R^{3d}$ is substituted or unsubstituted cyclopropyl. In certain embodiments, each instance of $R^{3d}$ is hydrogen, $-F$, $-Br$, $-Cl$, $-I$, $-CH_3$, $-CF_3$, $-CH_2CH_2Cl$, cyclopropyl, or cyclobutyl. In certain embodiments, $R^{3d}$ is Me or Cl. In certain embodiments, $R^{3d}$ is substituted or unsubstituted heterocyclyl.

Various Embodiments of $-X^1-R^{3b}$

As generally defined above, for group $-X^1R^{3b}$, X is independently $-O-$, $-S-$, or $-N(R^X)-$, wherein each instance of $R^X$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroalkyl, or an amino protecting group; and $R^{3b}$ is hydrogen, $-C(=O)R^{C1}$, $-C(=O)OR^{C1}$, $-C(=O)SR^{C1}$, $-C(=O)N(R^{C1})_2$, $-S(=O)_2R^{C1}$, $-S(=O)_2OR^{C1}$, —P(=O)$_2$R$^{C1}$, —P(=O)$_2$OR$^{C1}$, —P(=O)(OR$^{C1}$)$_2$, —P(=O)(R$^{C1}$)$_2$, or —P(=O)(R$^{C1}$)(OR$^{C1}$), wherein R$^{C1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two R$^{C1}$ groups are joined to form an substituted or unsubstituted heterocyclic ring. It is generally understood that the group —X$^1$—R$^{3b}$ may be in the alpha (down) or beta (up) position. In certain embodiments, the group —X$^1$—R$^{3b}$ is alpha. In certain embodiments, the group —X$^1$—R$^{3b}$ is beta.

In certain embodiments, X$^1$ is —O—. In certain embodiments, X$^1$ is —S—. In certain embodiments, X$^1$ is —N(R$^X$)—. In certain embodiments, R$^X$ is alkyl. In certain embodiments, R$^X$ is Me, Et, or i-Pr. In certain embodiments, R$^X$ is H, i.e., wherein X$^1$ is —NH—.

In certain embodiments, R$^{3b}$ is hydrogen. For example, in certain embodiments, the group —X$^1$R$^{3b}$ is —OH. In certain embodiments, the group —X$^1$R$^{3b}$ is —SH. In certain embodiments, the group —X$^1$R$^{3b}$ is —NH$_2$ or —NHR$^X$.

In certain embodiments, R$^{3b}$ is —C(=O)R$^{C1}$, —C(=O)OR$^{C1}$, —C(=O)SR$^{C1}$, —C(=O)N(R$^{C1}$)$_2$, —S(=O)$_2$R$^{C1}$, —S(=O)$_2$OR$^{C1}$, —P(=O)$_2$R$^{C1}$, —P(=O)$_2$OR$^{C1}$, —P(=O)(OR$^{C1}$)$_2$, —P(=O)(R$^{C1}$)$_2$, or —P(=O)(R$^{C1}$)(OR$^{C1}$).

In certain embodiments, at least one instance of R$^{C1}$ is hydrogen or a protecting group, i.e., an oxygen protecting group when attached to an oxygen atom, sulfur protecting group when attached to an sulfur atom, or a nitrogen protecting group when attached to a nitrogen atom. In certain embodiments, at least one instance of R$^{C1}$ is hydrogen.

In certain embodiments, at least one instance of R$^{C1}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^{C1}$ C$_{1-6}$alkyl groups include, but are not limited to, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), n-hexyl (C$_6$), C$_{1-6}$ alkyl substituted with 1, 2, 3, 4, 5, 6, 7, 8, 9, 10, or more fluoro groups (e.g., —CF$_3$, —CH$_2$F, —CHF$_2$, difluoroethyl, and 2,2,2-trifluoro-1,1-dimethyl-ethyl), C$_{1-6}$ alkyl substituted with 1, 2, 3, 4, 5, 6, 7, 8, 9, 10, or more chloro groups (e.g., —CH$_2$Cl, —CHCl$_2$), and C$_{1-6}$ alkyl substituted with alkoxy groups (e.g., —CH$_2$OCH$_3$ and —CH$_2$OCH$_2$CH$_3$).

In certain embodiments, at least one instance of R$^{C1}$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl.

In certain embodiments, at least one instance of R$^{C1}$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl.

In certain embodiments, at least one instance of R$^{C1}$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, at least one instance of R$^{C1}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, at least one instance of R$^{C1}$ is substituted or unsubstituted aryl, e.g., substituted or unsubstituted phenyl.

In certain embodiments, at least one instance of R$^{C1}$ is substituted or unsubstituted heteroaryl, e.g., optionally substituted 5- to 6-membered heteroaryl.

In certain embodiments, two R$^{C1}$ groups are joined to form a substituted or unsubstituted heterocyclic ring, e.g., a substituted or unsubstituted piperidinyl, substituted or unsubstituted piperazinyl, or substituted or unsubstituted morpholinyl ring.

In certain embodiments, R$^{3b}$ is —C(=O)R$^{C1}$, —C(=O)OR$^{C1}$, —C(=O)N(R$^{C1}$)$_2$ or —C(=O)N(OR$^{C1}$)(R$^{C1}$), wherein R$^{C1}$ is as defined herein.

In certain embodiments, R$^{3b}$ is —C(=O)R$^{C1}$, e.g., for example, wherein R$^{C1}$ is, for example, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), or n-hexyl (C$_6$). In certain embodiments, R$^{3b}$ is —C(=O)CH$_3$. In certain embodiments, R$^{3b}$ is —C(=O)(CH$_2$)$_m$CO$_2$H, wherein m is an integer between 2 and 5, inclusive. In certain embodiments, m is 2. In certain embodiments, m is 3. In certain embodiments, m is 4. In certain embodiments, m is 5. In certain embodiments, R$^{3b}$ is —C(=O)CH$_2$CH$_2$C(=O)OH.

In certain embodiments, R$^{3b}$ is —C(=O)OR$^{C1}$, e.g., for example, wherein R$^{C1}$ is, for example, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), or n-hexyl (C$_6$).

In certain embodiments, R$^{3b}$ is —C(=O)SR$^{C1}$, e.g., for example, wherein R$^{C1}$ is, for example, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), or n-hexyl (C$_6$).

In certain embodiments, R$^{3b}$ is —C(=O)N(R$^{C1}$)$_2$, e.g., —C(=O)NH$_2$ or —C(=O)NHR$^{C1}$, wherein R$^{C1}$ is, for example, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), or n-hexyl (C$_6$), or R$^1$ is —C(=O)N(R$^{C1}$)$_2$ wherein the two R$^{C1}$ groups are joined to form a substituted or unsubstituted heterocyclic ring, e.g., substituted or unsubstituted piperidinyl, substituted or unsubstituted piperazinyl, or substituted or unsubstituted morpholinyl ring.

In certain embodiments, R$^{3b}$ is —S(=O)$_2$R$^{C1}$ or —S(=O)$_2$OR$^{C1}$, wherein R$^{C1}$ is, for example, hydrogen, or substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), or n-hexyl (C$_6$), or substituted or unsubstituted phenyl. In certain embodiments, R$^{3b}$ is —S(=O)$_2$R$^{C1}$. In certain embodiments, R$^{3b}$ is —S(=O)$_2$OR$^{C1}$, e.g., —SO$_3$H.

In certain embodiments, R$^{3b}$ is —P(=O)$_2$R$^{C1}$, —P(=O)$_2$OR$^{C1}$, —P(=O)(OR$^{C1}$)$_2$, —P(=O)(R$^{C1}$)$_2$, or —P(=O)(R$^{C1}$)(OR$^{C1}$), wherein each R$^{C1}$ is, for example, independently hydrogen, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), or n-hexyl (C$_6$), or substituted or unsubstituted phenyl. In certain embodiments, R$^{3b}$ is —P(=O)$_2$R$^{C1}$. In certain embodiments, R$^1$ is —P(=O)$_2$OR$^{C1}$. In certain embodiments, R$^{3b}$ is —P(=O)(OR$^{C1}$)$_2$. In certain embodiments, R$^1$ is —P(=O)(R$^{C1}$)$_2$. In certain embodiments, R$^{3b}$ is —P(=O)(R$^{C1}$)(OR$^{C1}$).

Various Embodiments Wherein Z is a Group of Formula (i) or (ii)

In certain embodiments, Z is a group of formula (i):

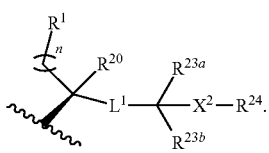

(i)

In other embodiments, Z is a group of formula (ii):

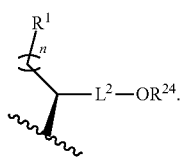

(ii)

As generally defined above, L$^1$ and L$^2$ is a bond (i.e., in other words, is absent) or is a substituted or unsubstituted C$_1$-C$_6$ alkylene, a substituted or unsubstituted C$_2$-C$_6$ alkenylene, substituted or unsubstituted C$_2$-C$_6$ alkynylene, a substituted or unsubstituted hetero C$_1$-C$_6$ alkylene, a substituted or unsubstituted hetero C$_2$-C$_6$ alkenylene, or a substituted or unsubstituted hetero C$_2$-C$_6$ alkynylene.

In certain embodiments, L$^1$ or L$^2$ is a bond.

In certain embodiments, L$^1$ or L$^2$ is a substituted or unsubstituted C$_1$-C$_6$ alkylene. In certain embodiments, L$^1$ or L$^2$ is a substituted or unsubstituted C$_1$-C$_4$ alkylene. In certain embodiments, L$^1$ or L$^2$ is a substituted or unsubstituted C$_1$-C$_3$ alkylene. In certain embodiments, L$^1$ or L$^2$ is a substituted or unsubstituted C$_1$-C$_2$ alkylene. In certain embodiments, L$^1$ or L$^2$ is a substituted or unsubstituted C$_1$ alkylene. In certain embodiments, L$^1$ or L$^2$ is a substituted or unsubstituted C2 alkylene. In certain embodiments, L$^1$ or L$^2$ is a substituted or unsubstituted C$_3$ alkylene. In certain embodiments, L$^1$ or L$^2$ is a substituted or unsubstituted C$_4$ alkylene. In certain embodiments, L$^1$ or L$^2$ is a substituted or unsubstituted C$_5$ alkylene. In certain embodiments, L$^1$ or L$^2$ is a substituted or unsubstituted C$_6$ alkylene. In certain embodiments, L$^1$ or L$^2$ is an alkylene group, as described above, substituted with one or more substituents selected from the group consisting of substituted or unsubstituted alkyl and halo. In certain embodiments, L$^1$ or L$^2$ is —CH$_2$—, —CHMe-, —CMe$_2$-, —CH$_2$—CH$_2$—, —CF$_2$—CH$_2$—, —CH$_2$—CMe$_2$-, —CH$_2$—CH$_2$—CH$_2$—, or —CH$_2$—CH$_2$—CMe$_2$-.

In certain embodiments, L$^1$ or L$^2$ is a substituted or unsubstituted C$_2$-C$_6$ alkenylene. In certain embodiments, L$^1$ or L$^2$ is a substituted or unsubstituted C$_2$-C$_5$ alkenylene. In certain embodiments, L$^1$ or L$^2$ is a substituted or unsubstituted C$_2$-C$_4$ alkenylene. In certain embodiments, L$^1$ or L$^2$ is a substituted or unsubstituted C$_2$-C$_3$ alkenylene. In certain embodiments, L$^1$ or L$^2$ is a substituted or unsubstituted C$_2$ alkenylene. In certain embodiments, L$^1$ or L$^2$ is a substituted or unsubstituted C$_3$ alkenylene. In certain embodiments, L$^1$ or L$^2$ is a substituted or unsubstituted C$_4$ alkenylene. In certain embodiments, L$^1$ or L$^2$ is a substituted or unsubstituted C$_5$ alkenylene. In certain embodiments, L$^1$ or L$^2$ is a substituted or unsubstituted C$_6$ alkenylene. In certain embodiments, L$^1$ or L$^2$ is an alkenylene group, as described above, substituted with one or more substituents selected from the group consisting of substituted or unsubstituted alkyl and halo.

In certain embodiments, L$^1$ or L$^2$ is a substituted or unsubstituted C$_2$-C$_6$ alkynylene. In certain embodiments, L$^1$ or L$^2$ is a substituted or unsubstituted C$_2$-C$_5$ alkynylene. In certain embodiments, L$^1$ or L$^2$ is a substituted or unsubstituted C$_2$-C$_4$ alkynylene. In certain embodiments, L$^1$ or L$^2$ is a substituted or unsubstituted C$_2$-C$_3$ alkynylene. In certain embodiments, L$^1$ or L$^2$ is a substituted or unsubstituted C$_2$ alkynylene. In certain embodiments, L$^1$ or L$^2$ is a substituted or unsubstituted C$_3$ alkynylene. In certain embodiments, L$^1$ or L$^2$ is a substituted or unsubstituted C$_4$ alkynylene. In certain embodiments, L$^1$ is a substituted or unsubstituted C$_5$ alkynylene. In certain embodiments, L$^1$ or L$^2$ is a substituted or unsubstituted C$_6$ alkynylene. In certain embodiments, L$^1$ or L$^2$ is an alkynylene group, as described above, substituted with one or more substituents selected from the group consisting of substituted or unsubstituted alkyl and halo.

Furthermore, in certain embodiments, L$^1$ or L$^2$ is substituted or unsubstituted heteroC$_{1-6}$alkylene, e.g., substituted or unsubstituted heteroC$_{1-2}$alkylene, substituted or unsubstituted heteroC$_{2-3}$alkylene, substituted or unsubstituted heteroC$_{3-4}$alkylene, substituted or unsubstituted heteroC$_{4-5}$alkylene, or substituted or unsubstituted heteroC$_{5-6}$alkylene. In certain embodiments, L$^1$ or L$^2$ is substituted or unsubstituted heteroC$_{2-6}$alkyenlene, e.g., substituted or unsubstituted heteroC$_{2-3}$alkenylene, substituted or unsubstituted heteroC$_{3-4}$alkenylene, substituted or unsubstituted heteroC$_{4-5}$alkenylene, or substituted or unsubstituted heteroC$_{5-6}$alkenylene. In certain embodiments, L$^1$ or L$^2$ is substituted or unsubstituted heteroC$_{2-6}$alkynylene, e.g., substituted or unsubstituted heteroC$_{2-3}$alkynylene, substituted or unsubstituted heteroC$_{3-4}$alkynylene, substituted or unsubstituted heteroC$_{4-5}$alkynylene, or substituted or unsubstituted heteroC$_{5-6}$alkynylene. In any of the above instances, in certain embodiments, L$^1$ or L$^2$ is heteroalkylene, heteroalkenylene, or heteroalkynylene unsubstituted or substituted with halo (e.g., fluoro) or substituted or unsubstituted C$_{1-6}$ alkyl.

As generally defined above, R$^1$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, halo, —N$_3$, —NO$_2$, —SCN, —CN, —OR$^{41}$, —SR$^{41}$, —N(R$^{41}$)$_2$, —N=NR$^{41}$, —N=C(R$^{41}$)$_2$, —N(OR$^{A1}$)(R$^{A1}$), —C(=O)R$^{A1}$, —C(=O)OR$^{A1}$, —C(=O)SR$^{A1}$, —C(=O)N(R$^{A1}$)$_2$, —C(=O)N(OR$^{A1}$)(R$^{A1}$), —OC(=O)R$^{A1}$, —OC(=O)OR$^{A1}$, —OC(=O)SR$^{A1}$, —OC(=O)N(R$^{A1}$)$_2$, —NR$^{A1}$C(=O)R$^{A1}$, —NR$^{A1}$C(=O)OR$^{A1}$, —NR$^{A1}$C(=O)SR$^{A1}$, —NR$^{A1}$C(=O)N(R$^{A1}$)$_2$, —SC(=O)R$^{A2}$, —SC(=O)OR$^{A1}$, —SC(=O)SR$^{A1}$, —SC(=O)N(R$^{A1}$)$_2$, —OS(=O)$_2$R$^{A2}$, —OS(=O)$_2$OR$^{A1}$, —S—S(=O)$_2$R$^{A2}$, —S—S(=O)$_2$OR$^{A1}$, —S(=O)R$^{A2}$, —SO$_2$R$^{A2}$, —NR$^{A1}$SO$_2$R$^{A2}$, or —SO$_2$N(R$^{A1}$)$_2$, wherein R$^{A1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two R$^{A1}$ groups are joined to form an substituted or unsubstituted heterocyclic ring; and R$^{A2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or an R$^{A1}$ group and an R$^{A2}$ group are joined to form an substituted or unsubstituted heterocyclic ring.

In certain embodiments, R$^1$ is hydrogen.

In certain embodiments, R$^1$ is substituted or unsubstituted alkyl, substituted or unsubstituted alkenyl or substituted or unsubstituted alkynyl. In certain embodiments, R$^1$ is substituted or unsubstituted alkyl, e.g., Me, Et, or i-Pr. In certain embodiments, R$^1$ is substituted or unsubstituted alkenyl, e.g., substituted or unsubstituted ethenyl or substituted or unsubstituted propenyl. In certain embodiments, R$^1$ is substituted or unsubstituted alkynyl.

In certain embodiments, R$^1$ is selected from substituted or unsubstituted carbocyclyl or substituted or unsubstituted heterocyclyl.

In certain embodiments, R$^1$ is substituted or unsubstituted aryl, e.g., phenyl.

In certain embodiments, R$^1$ is substituted or unsubstituted heteroaryl, e.g., a substituted or unsubstituted heteroaryl selected from pyrrolyl, imidazolyl, pyrazolyl, oxazoyl, thiazolyl, isoxazoyl, 1,2,3-triazolyl, 1,2,4-triazolyl, oxadiazolyl, thiadiazolyl, tetrazolyl, pyridinyl, pyrimidinyl, pyrazinyl, quinolinyl, isoquinolinyl, quinazonyl, quinoxilinyl, naphthyridinyl, indolyl, indazolyl, benzimidazloyl, pyrrolopyridinyl, pyrrolopyrimidinyl, pyridopyrimidinyl, or purinyl. In certain embodiments, the heteroaryl group is substituted with one or more groups selected from substituted or unsubstituted alkyl, haloalkyl, alkenyl, substituted or unsubstituted alkynyl, oxo, hydoxy, halo, alkoxy, —S-alkyl, substituted or unsubstituted aryl, substituted or unsubstituted heteroaryl, substituted or unsubstituted —SO— alkyl, substituted or unsubstituted —SO$_2$-alkyl, substituted or unsubstituted —SO-aryl, substituted or unsubstituted —SO$_2$-aryl, substituted or unsubstituted —SO-heteroaryl, substituted or unsubstituted —SO$_2$-heteroaryl, amino, cyano, and acyl. In certain embodiments, R$^1$ is imidazolyl, pyrazolyl, 1,2,3-triazolyl, 1,2,4-triazolyl, oxadiazolyl, thiadiazolyl, or tetrazolyl; each unsubstituted or substituted with one or two groups independently selected from oxo, Me, F, Cl, —CN, and —CF$_3$. In certain embodiments, R$^1$ is quinolinyl, isoquinolinyl or purinyl; each unsubstituted or substituted with one or two groups independently selected from oxo, Me, F, Cl, —CN, and —CF$_3$.

In certain embodiments, R$^1$ is —OR$^{A1}$. In certain embodiments, R$^1$ is —O— quinolinyl, —O-isoquinolinyl, —O-purinyl, each unsubstituted or substituted with one or two groups independently selected from Me, F, Cl, —CN, and —CF$_3$. In certain embodiments, R$^1$ is —OH or —O—CO—CH$_2$—CH$_2$—CO$_2$H.

In certain embodiments, R$^1$ is —SR$^{A1}$. In certain embodiments, R$^1$ is S-quinolinyl, —S-isoquinolinyl, or —S-purinyl, each unsubstituted or substituted with one or two groups independently selected from Me, F, Cl, —CN, and —CF$_3$. In certain embodiments, R$^1$ is —SH.

In certain embodiments, R$^1$ is —OS(=O)$_2$R$^{A2}$. In certain embodiments, R$^1$ is —OS(=O)$_2$OR$^{A1}$; e.g., —O—SO$_3$H. In certain embodiments, R$^1$ is —S—S(=O)$_2$R$^{A2}$. In certain embodiments, R$^1$ is —S—S(=O)$_2$OR$^{A1}$; e.g., —S—SO$_3$H.

As generally defined above, R$^{20}$ is independently hydrogen or substituted or unsubstituted alkyl. In certain embodiments, R$^{20}$ is hydrogen. In certain embodiments, R$^{20}$ is substituted or unsubstituted alkyl (e.g., —CH$_3$).

As generally defined above each instance of R$^{23a}$ and R$^{23b}$ is independently hydrogen, halogen, or substituted or unsubstituted alkyl, or R$^{23a}$ and R$^{23b}$ are joined together to form substituted or unsubstituted C$_3$-C$_6$ cycloalkyl. In certain embodiments, each instance of R$^{23a}$ and R$^{23b}$ is hydrogen. In certain embodiments, one of R$^{23a}$ and R$^{23b}$ is halogen, e.g., fluoro, and the other of R$^{23a}$ and R$^{23b}$ is hydrogen, halogen, or substituted or unsubstituted alkyl. In certain embodiments, each instance of R$^{23a}$ and R$^{23b}$ is halogen, e.g., fluoro. In certain embodiments, each instance of R$^{23a}$ and R$^{23b}$ is independently substituted or unsubstituted alkyl. In certain embodiments, each of R$^{23a}$ and R$^{23b}$ is Me. In certain embodiments, one of R$^{23a}$ and R$^{23b}$ is H. In certain embodiments, one of R$^{23a}$ and R$^{23b}$ is H; and the other is substituted or unsubstituted alkyl. In certain embodiments, one of R$^{23a}$ and R$^{23b}$ is H; and the other is Me or Et. In certain embodiments, R$^{23a}$ and R$^{23b}$ are joined together to form substituted or unsubstituted C$_3$-C$_6$ cycloalkyl. In certain embodiments, R$^{23a}$ and R$^{23b}$ are joined together to form a substituted or unsubstituted cyclopropyl.

In certain embodiments, the group

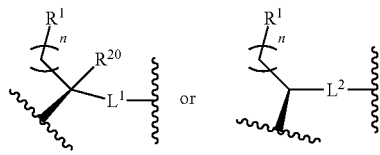

is of the formula:

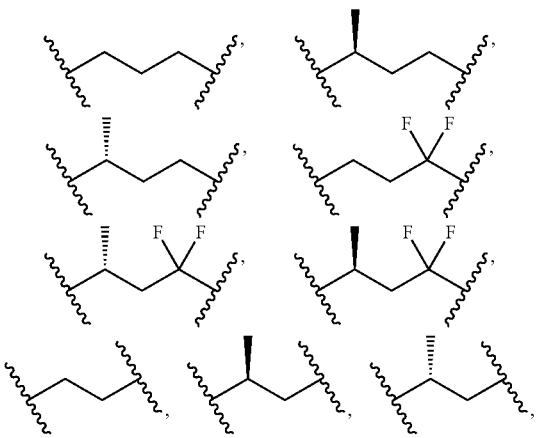

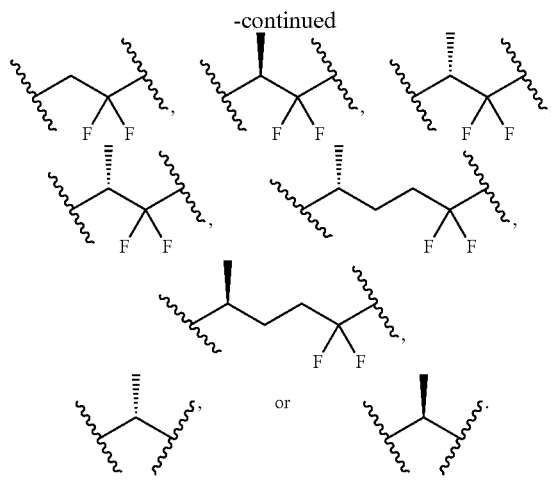

As generally defined above, $X^2$ is independently —O—, —S—, or —N($R^X$)—, wherein each instance of $R^X$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroalkyl, or an amino protecting group.

In certain embodiments, $X^2$ is —O—. In certain embodiments, $X^2$ is —S—. In certain embodiments, $X^2$ is —N($R^X$)—. In certain embodiments, $R^X$ is alkyl. In certain embodiments, $R^X$ is Me, Et, or i-Pr. In certain embodiments, $R^X$ is hydrogen.

In certain embodiments, $X^1$ is —O— and $X^2$ is —O—. In certain embodiments, $X^1$ is —O— and $X^2$ is —S—. In certain embodiments, $X^1$ is —O— and $X^2$ is —N($R^X$)—. In certain embodiments, $X^1$ is —S— and $X^2$ is —O—. In certain embodiments, $X^1$ is —S— and $X^2$ is —S—. In certain embodiments, $X^1$ is —S— and $X^2$ is —N($R^X$)—. In certain embodiments, $X^1$ is —N($R^X$)— and $X^2$ is —O—. In certain embodiments, $X^1$ is —N($R^X$)— and $X^2$ is —S—. In certain embodiments, $X^1$ is —N($R^X$)— and $X^2$ is —N($R^X$)—.

As generally defined above, $R^{24}$ is H, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —C(=O)$R^{E1}$, —C(=O)O$R^{E1}$, —C(=O)S$R^{E1}$, —C(=O)N($R^{E1}$)$_2$, —S(=O)$_2R^{E2}$, —S(=O)$_2$O$R^{E1}$, —P(=O)$_2R^{E2}$, —P(=O)$_2$O$R^{E1}$, —P(=O)(O$R^{E1}$)$_2$, —P(=O)($R^{E2}$)$_2$, or —P(=O)($R^{E2}$)(O$R^{E1}$).

In certain embodiments, $R^{24}$ is hydrogen.

In certain embodiments, $R^{24}$ is substituted or unsubstituted alkyl. In certain embodiments, $R^{24}$ is alkyl unsubstituted or substituted with one or more substituents selected from the group consisting of halo or and hydroxyl. In certain embodiments, $R^{24}$ is substituted or unsubstituted alkenyl. In certain embodiments, $R^{24}$ is substituted or unsubstituted alkynyl. In certain embodiments, $R^{24}$ is substituted or unsubstituted carbocyclyl. In certain embodiments, $R^{24}$ is substituted or unsubstituted heterocyclyl. In certain embodiments, $R^{24}$ is substituted or unsubstituted aryl. In certain embodiments, $R^{24}$ is substituted or unsubstituted heteroaryl.

In certain embodiments, $R^{24}$ is —C(=O)$R^{E1}$, e.g., $R^{24}$ is —C(=O)(CH$_2$)$_p$CO$_2$H, wherein p is an integer between 2 and 5, inclusive. In certain embodiments, p is 2. In certain embodiments, p is 3. In certain embodiments, p is 4. In certain embodiments, p is 5. In certain embodiments, $R^{24}$ is —C(=O)O$R^{E1}$. In certain embodiments, $R^{24}$ is —C(=O)S$R^{E1}$. In certain embodiments, $R^{24}$ is —C(=O)N($R^{E1}$)$_2$. In certain embodiments, $R^{24}$ is —S(=O)$_2R^{E2}$. In certain embodiments, $R^{24}$ is —S(=O)$_2$O$R^{E1}$; e.g., —SO$_3$H. In certain embodiments, $R^{24}$ is —P(=O)$_2R^{E2}$. In certain embodiments, $R^{24}$ is —P(=O)$_2$O$R^{E1}$. In certain embodiments, $R^{24}$ is —P(=O)(O$R^{E1}$)$_2$. In certain embodiments, $R^{24}$ is —P(=O)($R^{E2}$)$_2$. In certain embodiments, $R^{24}$ is —P(=O)($R^{E2}$)(O$R^{E1}$).

As generally defined above, the subscript n is 0, 1, 2, or 3. In certain embodiments, n is 0. In certain embodiments, n is 1. In certain embodiments, n is 2. In certain embodiments, n is 3.

Various Embodiments Wherein Z is a Group of Formula (iii), (iv), or (v)

In certain embodiments, Z is a group of formula (iii), (iv), or (v):

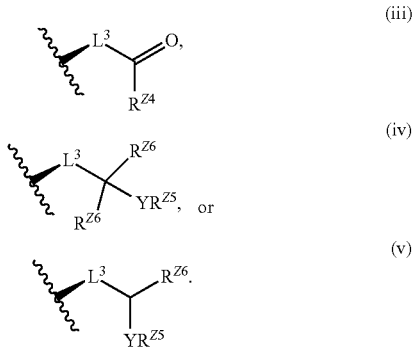

In certain embodiments, $L^3$ is substituted or unsubstituted $C_{1-6}$alkylene, e.g., substituted or unsubstituted $C_{1-2}$alkylene, substituted or unsubstituted $C_{2-3}$alkylene, substituted or unsubstituted $C_{3-4}$alkylene, substituted or unsubstituted $C_{4-5}$alkylene, or substituted or unsubstituted $C_{5-6}$alkylene. In certain embodiments, $L^3$ is substituted or unsubstituted $C_{2-6}$alkyenlene, e.g., substituted or unsubstituted $C_{2-3}$alkenylene, substituted or unsubstituted $C_{3-4}$alkenylene, substituted or unsubstituted $C_{4-5}$alkenylene, or substituted or unsubstituted $C_{5-6}$alkenylene. In certain embodiments, $L^3$ is substituted or unsubstituted $C_{2-6}$alkynylene, e.g., substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene. In any of the above instances, in certain embodiments, $L^3$ is alkylene, alkenylene, or alkynylene unsubstituted or substituted with halo (e.g., fluoro), substituted or unsubstituted $C_{1-6}$ alkyl, and/or —O$R^{Z5}$.

Furthermore, in certain embodiments, $L^3$ is substituted or unsubstituted heteroC$_{1-6}$alkylene, e.g., substituted or unsubstituted heteroC$_{1-2}$alkylene, substituted or unsubstituted heteroC$_{2-3}$alkylene, substituted or unsubstituted heteroC$_{3-4}$alkylene, substituted or unsubstituted heteroC$_{4-5}$alkylene, or substituted or unsubstituted heteroC$_{5-6}$alkylene. In certain embodiments, $L^3$ is substituted or unsubstituted heteroC$_{2-6}$alkyenlene, e.g., substituted or unsubstituted heteroC$_{2-3}$alkenylene, substituted or unsubstituted heteroC$_{3-4}$alkenylene, substituted or unsubstituted heteroC$_{4-5}$alkenylene, or substituted or unsubstituted heteroC$_{5-6}$alkenylene. In certain embodiments, L$^3$ is substituted or unsubstituted heteroC$_{2-6}$alkynylene, e.g., substituted or unsubstituted heteroC$_{2-3}$alkynylene, substituted or unsubstituted heteroC$_{3-4}$alkynylene, substituted or unsubstituted heteroC$_{4-5}$alkynylene, or substituted or unsubstituted heteroC$_{5-6}$alkynylene. In any of the above instances, in certain embodiments, L$^3$ is heteroalkylene, heteroalkenylene, or heteroalkynylene unsubstituted or substituted with halo (e.g., fluoro), substituted or unsubstituted C$_{1-6}$ alkyl, and/or —OR$^{Z5}$.

In any of the above or below instances, in certain embodiments, at least one R$^{Z5}$ is hydrogen.

In any of the above or below instances, in certain embodiments, at least one instance of R$^{Z5}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^{Z5}$ C$_{1-6}$alkyl groups include, but are not limited to, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), n-hexyl (C$_6$), C$_{1-4}$ alkyl substituted with 1, 2, 3, 4, 5, 6, 7, 8, 9, 10, or more fluoro groups (e.g., —CF$_3$, —CH$_2$F, —CHF$_2$, difluoroethyl, and 2,2,2-trifluoro-1,1-dimethyl-ethyl), C$_{1-6}$ alkyl substituted with 1, 2, 3, 4, 5, 6, 7, 8, 9, 10, or more chloro groups (e.g., —CH$_2$Cl, —CHCl$_2$), and C$_{1-6}$ alkyl substituted with alkoxy groups (e.g., —CH$_2$OCH$_3$ and —CH$_2$OCH$_2$CH$_3$).

In any of the above or below instances, in certain embodiments, at least one instance of R$^{Z5}$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl.

In any of the above or below instances, in certain embodiments, at least one instance of R$^{Z5}$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-4}$alkynyl.

In any of the above or below instances, in certain embodiments, at least one instance of R$^{Z5}$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In any of the above or below instances, in certain embodiments, at least one instance of R$^{Z5}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In any of the above or below instances, in certain embodiments, at least one instance of R$^{Z5}$ is substituted or unsubstituted aryl, e.g., substituted or unsubstituted phenyl.

In any of the above or below instances, in certain embodiments, at least one instance of R$^{Z5}$ is substituted or unsubstituted heteroaryl, e.g., optionally substituted 5-6 membered heteroaryl.

In any of the above or below instances, in certain embodiments, R$^{Z5}$ is a protecting group, e.g., an oxygen protecting group when attached to an oxygen atom, a sulfur protecting group when attached to a sulfur atom, a nitrogen protecting group when attached to a nitrogen atom.

In certain embodiments, wherein two R$^{Z5}$ are attached to a nitrogen atom, the two R$^{Z5}$ groups are joined to form a substituted or unsubstituted heterocyclic ring, e.g., a substituted or unsubstituted piperidinyl, substituted or unsubstituted piperazinyl, or substituted or unsubstituted morpholinyl ring.

Furthermore, in any of the above or below instances, in certain embodiments, each instance of R$^{Z6}$ is independently hydrogen, substituted or unsubstituted alkyl, or two R$^{Z6}$ groups are joined to form a C$_{3-6}$ carbocyclic ring.

In certain embodiments, at least one instance of R$^{Z6}$ is hydrogen.

In certain embodiments, at least one instance of R$^{Z6}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^{Z4}$ C$_{1-6}$alkyl groups include, but are not limited to, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), n-hexyl (C$_6$), C$_{1-6}$ alkyl substituted with 1, 2, 3, 4, 5, 6, 7, 8, 9, 10, or more fluoro groups (e.g., —CF$_3$, —CH$_2$F, —CHF$_2$, difluoroethyl, and 2,2,2-trifluoro-1,1-dimethyl-ethyl), C$_{1-6}$ alkyl substituted with 1, 2, 3, 4, 5, 6, 7, 8, 9, 10, or more chloro groups (e.g., —CH$_2$Cl, —CHCl$_2$), and C$_{1-6}$ alkyl substituted with alkoxy groups (e.g., —CH$_2$OCH$_3$ and —CH$_2$OCH$_2$CH$_3$).

In certain embodiments, two R$^{Z6}$ groups are joined to form a C$_{3-4}$ carbocyclic ring, e.g., for example, a substituted or unsubstituted cyclopropyl, substituted or unsubstituted cyclobutyl, substituted or unsubstituted cyclopentyl, or substituted or unsubstituted cyclohexyl ring.

In certain embodiments, R$^{Z4}$ is substituted or unsubstituted alkyl, e.g., substituted or unsubstituted C$_{1-6}$alkyl, substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^{Z4}$ C$_{1-6}$alkyl groups include, but are not limited to, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), n-hexyl (C$_6$), C$_{1-6}$ alkyl substituted with 1, 2, 3, 4, 5, 6, 7, 8, 9, 10, or more fluoro groups (e.g., —CF$_3$, —CH$_2$F, —CHF$_2$, difluoroethyl, and 2,2,2-trifluoro-1,1-dimethyl-ethyl), C$_{1-6}$ alkyl substituted with 1, 2, 3, 4, 5, 6, 7, 8, 9, 10, or more chloro groups (e.g., —CH$_2$Cl, —CHCl$_2$), and C$_{1-6}$ alkyl substituted with alkoxy groups (e.g., —CH$_2$OCH$_3$ and —CH$_2$OCH$_2$CH$_3$).

In certain embodiments, R$^{Z4}$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, or substituted or unsubstituted C$_{5-6}$alkenyl.

In certain embodiments, R$^{Z4}$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, or substituted or unsubstituted C$_{5-6}$alkynyl.

In certain embodiments, R$^{Z4}$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, $R^{Z4}$ is substituted or unsubstituted heterocyclyl, e.g., substituted or unsubstituted 3-6 membered heterocyclyl, substituted or unsubstituted 3-4 membered heterocyclyl, substituted or unsubstituted 4-5 membered heterocyclyl, or substituted or unsubstituted 5-6 membered heterocyclyl.

In certain embodiments, $R^{Z4}$ is substituted or unsubstituted aryl, e.g., substituted or unsubstituted phenyl.

In certain embodiments, $R^{Z4}$ is substituted or unsubstituted heteroaryl, e.g., optionally substituted 5- to 6-membered heteroaryl.

In certain embodiments, $R^{Z4}$ is $-OR^{Z5}$, wherein $R^{Z5}$ is as defined herein, e.g., for example, $R^{Z5}$ is hydrogen, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, $R^{Z4}$ is $-SR^{Z5}$, wherein $R^{Z5}$ is as defined herein, e.g., for example, $R^{Z5}$ is hydrogen, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, $R^{Z4}$ is $-N(R^{Z5})_2$, e.g., $R^{Z4}$ is $-NH_2$, or $-NHR^{Z5}$, wherein $R^{Z5}$ is as defined herein, e.g., for example, $R^{Z5}$ is hydrogen, methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$), or $R^{Z4}$ is $-N(R^{Z5})_2$ wherein the two $R^{Z5}$ groups are joined to form a substituted or unsubstituted heterocyclic ring, e.g., a substituted or unsubstituted piperidinyl, substituted or unsubstituted piperazinyl, or substituted or unsubstituted morpholinyl ring.

Specific $L^3$ alkylene groups are contemplated herein. For example, in certain embodiments, $L^3$ is an alkylene group of the formula:

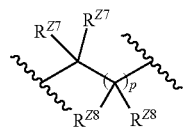

wherein p is 1, 2, or 3; and each instance of $R^{Z7}$ and $R^{Z8}$ is, independently, hydrogen, halo, substituted or unsubstituted $C_{1-4}$ alkyl, or $-OR^{Z5}$. In certain embodiments, p is 1. In certain embodiments, p is 2. In certain embodiments, p is 3.

Specific $L^3$ alkenylene groups are also contemplated herein. For example, in certain embodiments, $L^3$ is an alkenylene group of the formula:

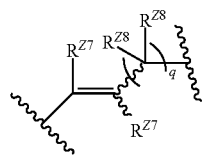

wherein q is 0, 1, or 2; and each instance of $R^{Z7}$ and $R^{Z8}$ is, independently, hydrogen, halo, substituted or unsubstituted $C_{1-4}$ alkyl, or $-OR^{Z5}$. In certain embodiments, q is 0. In certain embodiments, q is 1. In certain embodiments, q is 2.

Specific $L^3$ heteroalkylene groups are also contemplated herein, e.g., for example, in certain embodiments, $L^3$ is a heteroalkylene group of the formula:

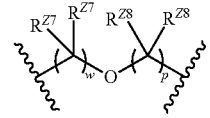

wherein w is 0 or 1 and p is 1, 2, or 3, or w is 1 and p is 0, 1, 2, or 3; and each instance of $R^{Z7}$ and $R^{Z8}$ is independently hydrogen, halo, substituted or unsubstituted $C_{1-6}$ alkyl, or $-OR^{Z5}$.

In certain embodiments, p is 0. In certain embodiments, p is 1. In certain embodiments, p is 2. In certain embodiments, p is 3. In certain embodiments, w is 0. In certain embodiments, w is 1. In certain embodiments, w is 0, and p is 1. In certain embodiments, w is 0, and p is 2. In certain embodiments, w is 0, and p is 3. In certain embodiments, w is 1, and p is 1. In certain embodiments, w is 1, and p is 2. In certain embodiments, w is 1, and p is 3.

For example, in certain embodiments wherein w is 0, provided is an $L^3$ heteroalkylene group of the formula:

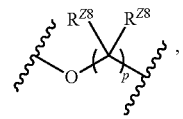

wherein p and $R^{Z8}$ are as defined herein.

In certain embodiments wherein w is 1, provided is an $L^3$ heteroalkylene group of the formula:

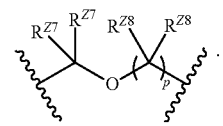

wherein p, $R^{Z7}$, and $R^{Z8}$ are as defined herein.

In certain embodiments, at least one instance of $R^{Z7}$ is hydrogen. In any of the above instances, in certain embodiments, at least one instance of $R^{Z7}$ is halo, e.g., fluoro. In any of the above instances, in certain embodiments, at least one instance of $R^{Z7}$ is substituted or unsubstituted $C_{1-6}$ alkyl, e.g., substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl. Exemplary $R^{Z7}$ $C_{1-6}$alkyl groups include, but are not limited to, substituted or unsubstituted methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), n-hexyl ($C_6$), $C_{1-6}$ alkyl substituted with 1, 2, 3, 4, 5, 6, 7, 8, 9, 10, or more fluoro groups (e.g., $-CF_3$, $-CH_2F$, $-CHF_2$, difluoroethyl, and 2,2,2-trifluoro-1,1-dimethyl-ethyl), $C_{1-6}$ alkyl substituted with 1, 2, 3, 4, 5, 6, 7, 8, 9, 10, or more chloro groups (e.g., $-CH_2Cl$, $-CHCl_2$), and $C_{1-4}$ alkyl substituted with alkoxy groups (e.g., $-CH_2OCH_3$ and $-CH_2OCH_2CH_3$). In any of the above instances, in certain embodiments, at least one instance of $R^{Z7}$ is $-CH_3$, $-CF_3$, $-CH_2CH_3$ (Et), or —CH(CH$_3$)$_2$ (iPr). In any of the above instances, in certain embodiments, at least one instance of R$^{Z7}$ is —OR$^{Z5}$, e.g., —OH.

In certain embodiments, at least one instance of R$^{Z8}$ is hydrogen. In any of the above instances, in certain embodiments, at least one instance of R$^{Z8}$ is halo, e.g., fluoro. In any of the above instances, in certain embodiments, at least one instance of R$^{Z8}$ is substituted or unsubstituted C$_{1-6}$ alkyl, e.g., substituted or unsubstituted C$_{1-2}$alkyl, substituted or unsubstituted C$_{2-3}$alkyl, substituted or unsubstituted C$_{3-4}$alkyl, substituted or unsubstituted C$_{4-5}$alkyl, or substituted or unsubstituted C$_{5-6}$alkyl. Exemplary R$^{Z8}$ C$_{1-6}$alkyl groups include, but are not limited to, substituted or unsubstituted methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), n-hexyl (C$_6$), C$_{1-6}$ alkyl substituted with 1, 2, 3, 4, 5, 6, 7, 8, 9, 10, or more fluoro groups (e.g., —CF$_3$, —CH$_2$F, —CHF$_2$, difluoroethyl, and 2,2,2-trifluoro-1,1-dimethyl-ethyl), C$_{1-6}$ alkyl substituted with 1, 2, 3, 4, 5, 6, 7, 8, 9, 10, or more chloro groups (e.g., —CH$_2$Cl, —CHCl$_2$), and C$_{1-4}$ alkyl substituted with alkoxy groups (e.g., —CH$_2$OCH$_3$ and —CH$_2$OCH$_2$CH$_3$). In any of the above instances, in certain embodiments, at least one instance of R$^{Z8}$ is —CH$_3$, —CF$_3$, —CH$_2$CH$_3$ (Et), or —CH(CH$_3$)$_2$ (iPr). In any of the above instances, in certain embodiments, at least one instance of R$^{Z8}$ is —OR$^{Z5}$, e.g., —OH.

Exemplary L$^3$ alkylene groups include, but are not limited to:

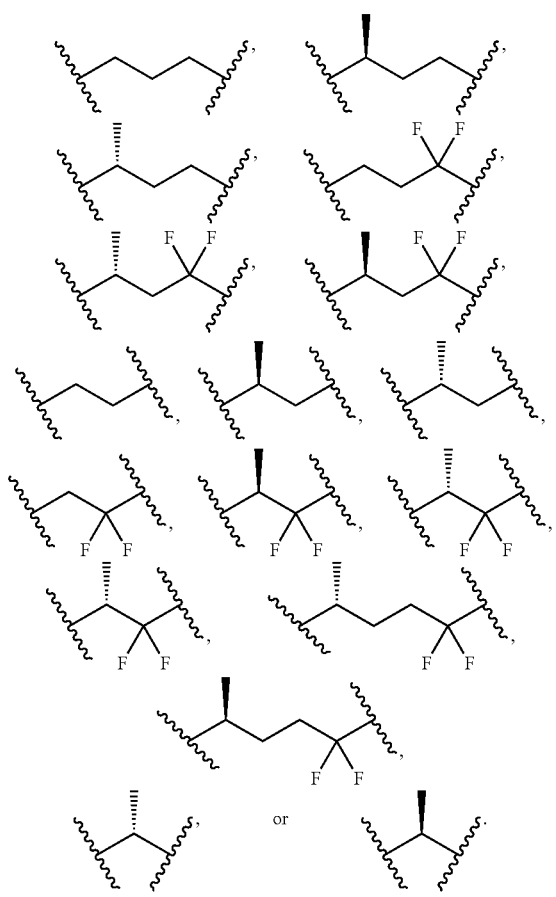

Exemplary L$^3$ alkenylene groups include, but are not limited to:

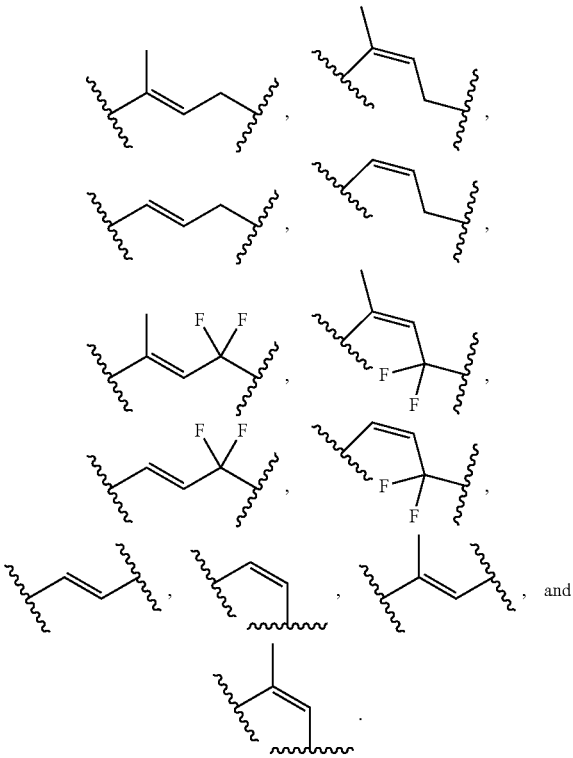

Exemplary L$^3$ heteroalkylene groups include, but are not limited to:

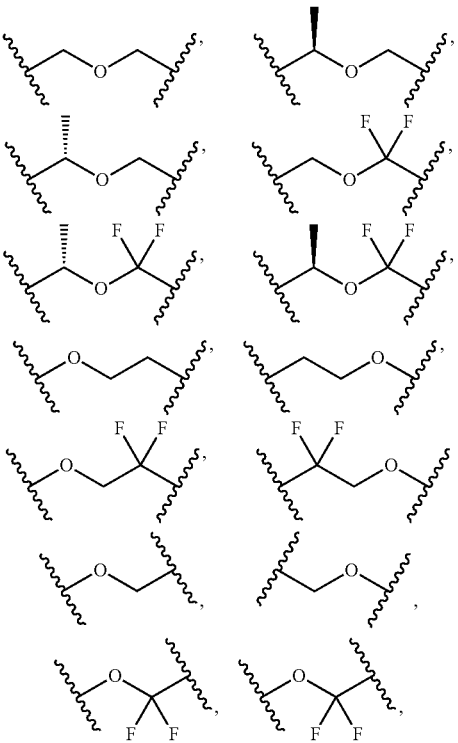

-continued
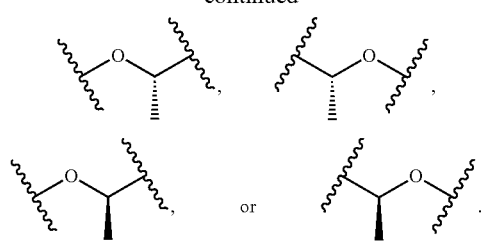
In certain embodiments, the group
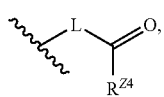
wherein L³ is an alkylene or heteroalkylene group, is of the formula:
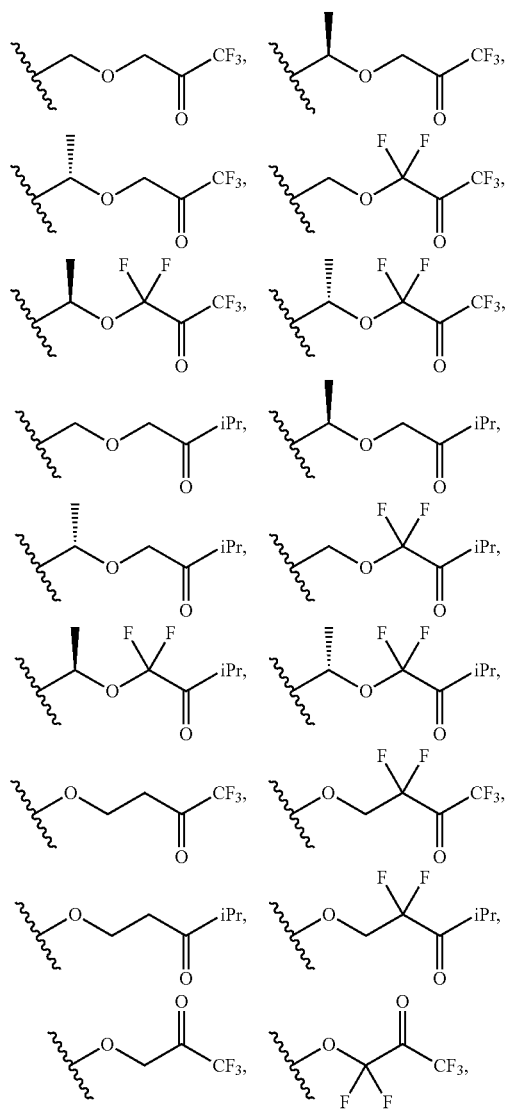
-continued
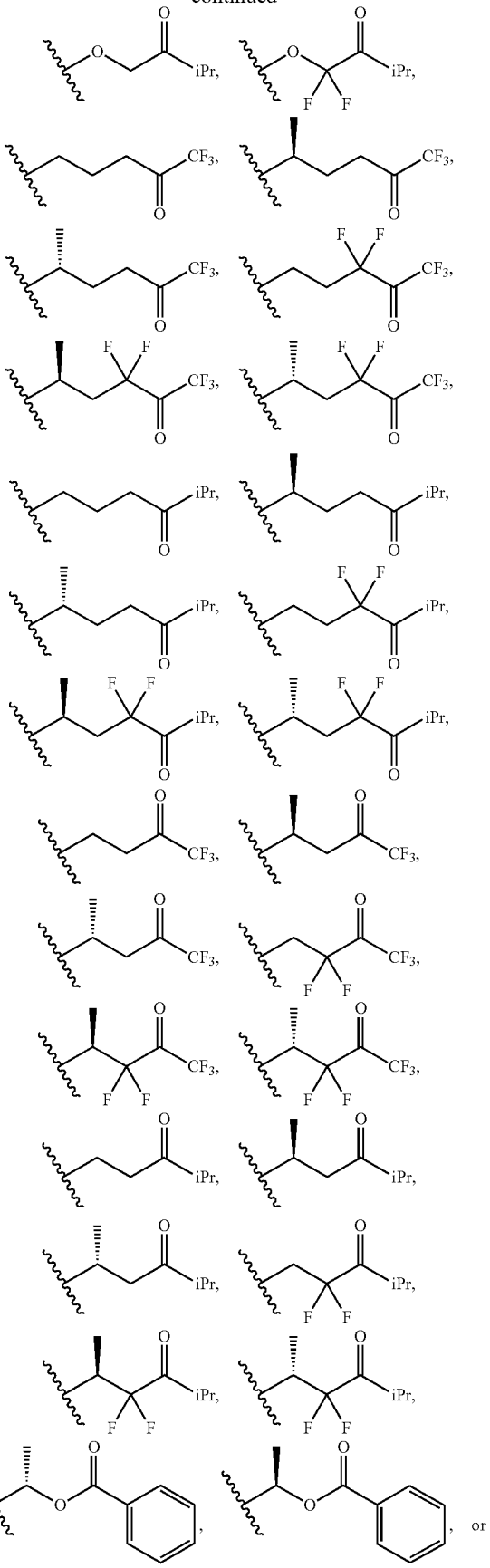

-continued
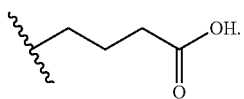
In certain embodiments, the group
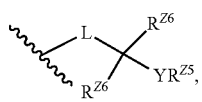
wherein Y is —O— and $L^3$ is an alkylene or heteroalkylene group, is of the formula:
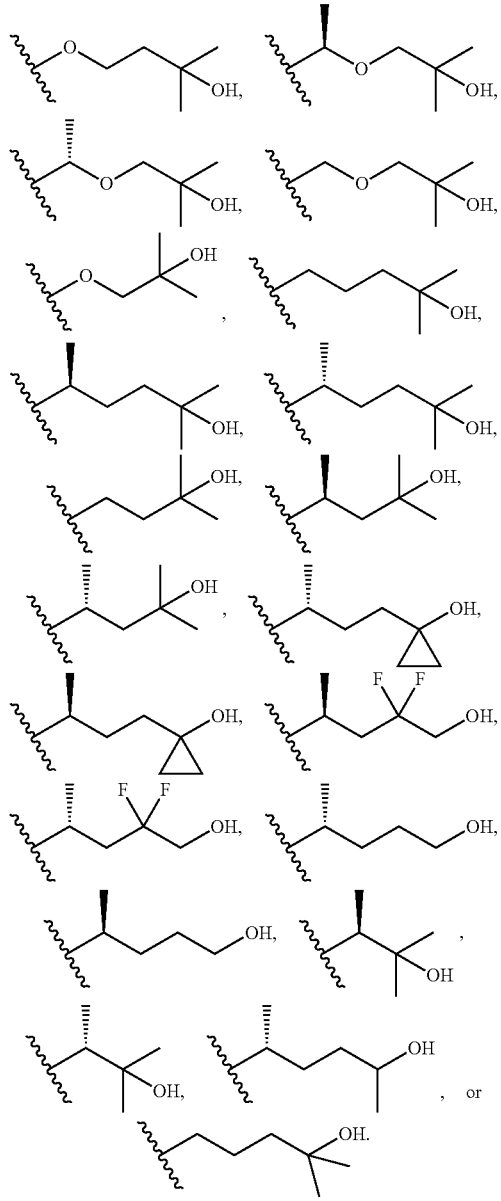
In certain embodiments, the group
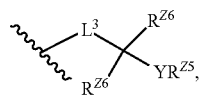
wherein Y is —NH— and $L^3$ is an alkylene or heteroalkylene group, is of the formula
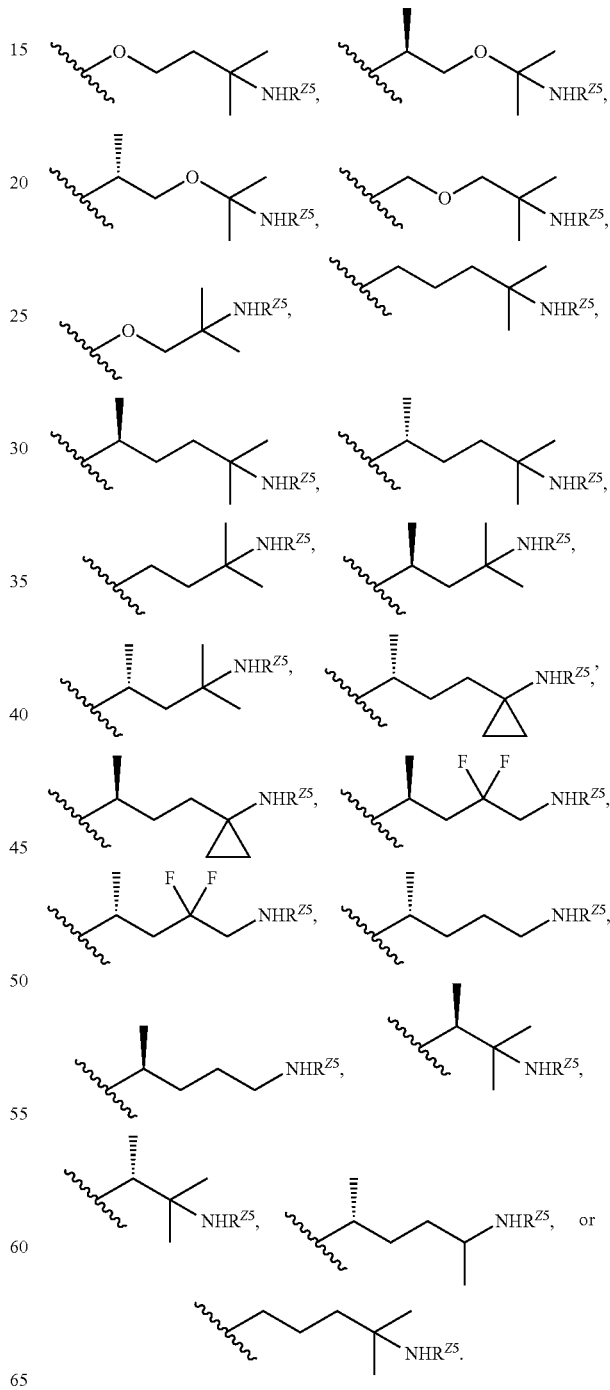

In certain embodiments, the group

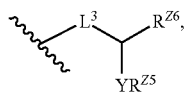

wherein Y is —O— and L³ is an alkylene or heteroalkylene group, is of the formula:

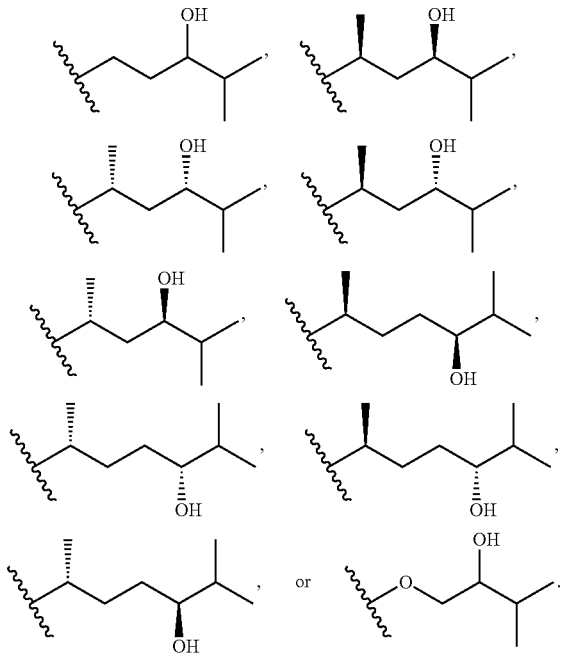

In certain embodiments, the group

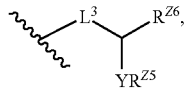

wherein Y is —NH— and L³ is an alkylene or heteroalkylene group, is of the formula:

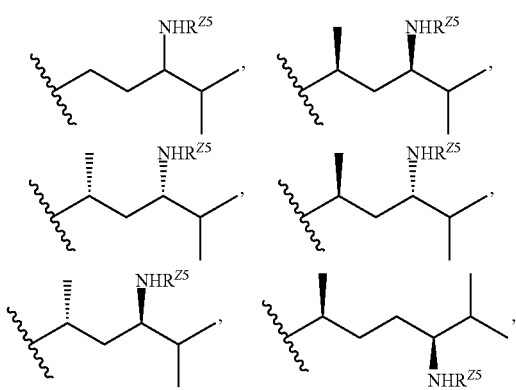

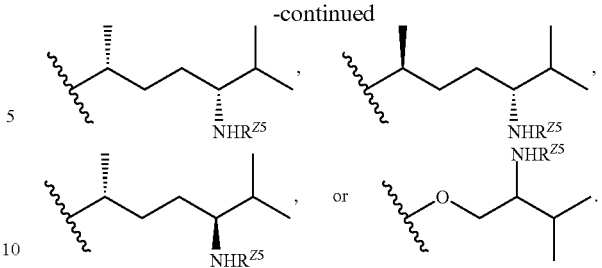

Various Embodiments of $R^2$, $R^{11a}$, and $R^{11b}$

As generally defined above, each instance of $R^2$, $R^{11a}$, and $R^{11b}$ is independently H, —OH, halo, substituted or unsubstituted alkyl, substituted or unsubstituted alkenyl, or substituted or unsubstituted alkynyl, substituted or unsubstituted carbocyclyl, substituted or unsubstituted heterocyclyl, substituted or unsubstituted aryl, substituted or unsubstituted heteroaryl, —N₃, —NO₂, —SCN, —CN, —OR^{B1}, —SR^{B1}, —N(R^{B1})₂, —N=NR^{B1}, —N=C(R^{B1})₂, —N(OR^{B1})(R^{B1}), —C(=O)R^{B1}, —C(=O)OR^{B1}, —C(=O)SR^{B1}, —C(=O)N(R^{B1})₂, —C(=O)N(OR^{B1})(R^{B1}), —OC(=O)R^{B1}, —OC(=O)OR^{B1}, —OC(=O)SR^{B1}, —OC(=O)N(R^{B1})₂, —NR^{B1}C(=O)R^{B1}, —NR^{B1}C(=O)OR^{B1}, —NR^{B1}C(=O)SR^{B1}, —NR^{B1}C(=O)N(R^{B1})₂, —SC(=O)R^{B2}, —SC(=O)OR^{B1}, —SC(=O)SR^{B1}, —SC(=O)N(R^{B1})₂, —OS(=O)₂R^{B2}, —OS(=O)₂OR^{B1}, —S—S(=O)₂R^{B2}, —S—S(=O)₂OR^{B1}, —S(=O)R^{B2}, —SO₂R^{B2}, —NR^{B1}SO₂R^{B2}, or —SO₂N(R^{B1})₂, and/or $R^{11a}$ and $R^{11b}$ are joined to form an oxo (=O) group In certain embodiments, $R^2$ is H. In certain embodiments, $R^2$ is substituted or unsubstituted alkyl. In certain embodiments, $R^2$ is substituted or unsubstituted alkenyl. In certain embodiments, $R^2$ is substituted or unsubstituted alkynyl. In certain embodiments, $R^2$ is —OR^{B1}. In certain embodiments, $R^2$ is —SR^{B1}. In certain embodiments, $R^2$ is —N(R^{B1})₂. In certain embodiments, $R^2$ is H, halo, substituted or unsubstituted alkyl, substituted or unsubstituted alkenyl, substituted or unsubstituted alkynyl, —OR^{B1}, —SR^{B1}, or —N(R^{B1})₂. In certain embodiments, $R^2$ is F, Cl, Me, Et, n-Pr, methoxy, ethoxy, propoxy, butoxy, ethynyl, hydroxybutynyl, methoxypropynyl, chloroethynyl, or cyclopropynyl. In certain embodiments, $R^2$ is CF₃, amino, or dimethylamino. In certain embodiments, $R^2$ is a non-hydrogen group in the alpha position. In certain embodiments, $R^2$ is a non-hydrogen group in the beta position.

In certain embodiments, each instance of $R^{11a}$ and $R^{11b}$ is hydrogen. In certain embodiments, one of $R^{11a}$ and $R^{11b}$ is hydrogen. In certain embodiments, one of $R^{11a}$ and R is hydrogen; and the other is —OR^{B1}, —SR^{B1}, or —N(R^{B1})₂. In certain embodiments, one of $R^{11a}$ and $R^{11b}$ is H; and the other is —OH, —OMe, amino, or dialkylamino. In certain embodiments, $R^{11b}$ is a non-hydrogen group, and $R^{11a}$ is hydrogen. In certain embodiments, $R^{11a}$ is a non-hydrogen group, and $R^{11b}$ is hydrogen.

In certain embodiments, $R^{11a}$ and $R^{11b}$ together form an oxo group.

Various Embodiments of $R^{4a}$, $R^{4b}$, $R^6$, $R^{7a}$, $R^{7b}$, $R^{14}$, $R^{17}$, $R^{18}$, and $R^{19}$ As generally defined above, each instance of $R^{4a}$, $R^{4b}$, $R^{7a}$, and $R^{7b}$ is independently hydrogen, —OH, halo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$N_3$, —$NO_2$, —SCN, —CN, —$OR^{B1}$, —$SR^{B1}$, —$N(R^{B1})_2$, —N=$NR^{B1}$, —N=$C(R^{B1})_2$, —$N(OR^{B1})(R^{B1})$, —$C(=O)R^{B1}$, —$C(=O)OR^{B1}$, —$C(=O)SR^{B1}$, —$C(=O)N(R^{b1})_2$, —$C(=O)N(OR^{B1})(R^{B1})$, —$OC(=O)R^{B1}$, —$OC(=O)OR^{B1}$, —$OC(=O)SR^{B1}$, —$OC(=O)N(R^{B1})_2$, —$NR^{B1}C(=O)R^{B1}$, —$NR^{B1}C(=O)OR^{B1}$, —$NR^{B1}C(=O)SR^{B1}$, —$NR^{B1}C(=O)N(R^{B1})_2$, —$SC(=O)R^{B2}$, —$SC(=O)OR^{B1}$, —$SC(=O)SR^{B1}$, —$SC(=O)N(R^{B1})_2$, —$OS(=O)_2R^{B2}$, —$OS(=O)_2OR^{B1}$, —S—$S(=O)_2R^{B2}$, —S—$S(=O)_2OR^{B1}$, —$S(=O)R^{B2}$, —$SO_2R^{B2}$, —$NR^{B1}SO_2R^{B2}$, or —$SO_2N(R^{B1})_2$, wherein $R^{B1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group when attached to an oxygen atom, a sulfur protecting group when attached to a sulfur atom, a nitrogen protecting group when attached to a nitrogen atom, or two $R^{B1}$ groups are joined to form an substituted or unsubstituted heterocyclic ring; and $R^{B2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or an $R^{B1}$ group and an $R^{B2}$ group are joined to form an substituted or unsubstituted heterocyclic ring; or optionally wherein each of $R^{4a}$ and $R^{4b}$, and/or $R^{7a}$ and $R^{7b}$ are joined to form an oxo (=O) group.

In certain embodiments, each instance of $R^{4a}$ and $R^{4b}$ is hydrogen. In certain embodiments, one of $R^{4a}$ and $R^{4b}$ is hydrogen. In certain embodiments, one of $R^{4a}$ and $R^{4b}$ is hydrogen; and the other is substituted or unsubstituted alkyl, substituted or unsubstituted alkenyl, or substituted or unsubstituted alkynyl. In certain embodiments, one of $R^{4a}$ and $R^{4b}$ is hydrogen; and the other is Me, Et, ethenyl, ethynyl, propenyl, or propynyl. In certain embodiments, each of $R^{4a}$ and $R^{4b}$ is independently substituted or unsubstituted alkyl. In certain embodiments, each of $R^{4a}$ and $R^{4b}$ is Me.

In certain embodiments, each instance of $R^{7a}$ and $R^{7b}$ is hydrogen.

As generally defined above, each of $R^{6a}$ and $R^{6b}$ is independently hydrogen, halo, substituted or unsubstituted alkyl, substituted or unsubstituted alkenyl, or substituted or unsubstituted alkynyl, and ====== represents a single or double bond, provided if a double bond is present in Ring B, then one of $R^{6a}$ or $R^{6b}$ is absent, and provided if a single bond is present in Ring B, then the hydrogen at C5 is in the alpha or beta position.

In certain embodiments, wherein ====== represents a single bond, each instance of $R^{6a}$ and $R^{6b}$ is hydrogen. In certain embodiments, each instance of $R^{6a}$ and $R^{6b}$ is halo, e.g., fluoro.

In certain embodiments, wherein ====== represents a single bond, $R^{6a}$ is hydrogen, and $R^{6b}$ is halo, substituted or unsubstituted alkyl, substituted or unsubstituted alkenyl, or substituted or unsubstituted alkynyl. In certain embodiments, $R^{6a}$ is hydrogen, and $R^{6b}$ is halo (e.g., fluoro). In certain embodiments, $R^{6a}$ is hydrogen, and $R^{6b}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, e.g., methyl, ethyl, propyl, or isopropyl. In certain embodiments, $R^{6a}$ is hydrogen, and $R^{6b}$ is substituted or unsubstituted alkenyl. In certain embodiments, $R^{6a}$ is hydrogen, and $R^{6b}$ is substituted or unsubstituted alkynyl.

In certain embodiments, wherein ====== represents a single bond, $R^{6b}$ is hydrogen, and $R^{6a}$ is halo, substituted or unsubstituted alkyl, substituted or unsubstituted alkenyl, or substituted or unsubstituted alkynyl. In certain embodiments, $R^{6b}$ is hydrogen, and $R^{6a}$ is halo (e.g., fluoro). In certain embodiments, $R^{6b}$ is hydrogen, and $R^{6a}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, e.g., methyl, ethyl, propyl, or isopropyl. In certain embodiments, $R^{6b}$ is hydrogen, and $R^{6a}$ is substituted or unsubstituted alkenyl. In certain embodiments, $R^{6b}$ is hydrogen, and $R^{6a}$ is substituted or unsubstituted alkynyl.

In certain embodiments, wherein ====== represents a double bond, $R^{6a}$ is hydrogen. In certain embodiments, wherein ====== represents a double bond, $R^{6a}$ is halo, e.g., fluoro. In certain embodiments, wherein ====== represents a double bond, $R^{6a}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, or substituted or unsubstituted $C_{5-6}$alkyl, e.g., methyl, ethyl, propyl, or isopropyl. In certain embodiments, wherein ====== represents a double bond, $R^{6a}$ is substituted or unsubstituted alkenyl. In certain embodiments, wherein ====== represents a double bond, $R^{6a}$ is substituted or unsubstituted alkynyl.

As generally defined above, $R^{17}$ is hydrogen, halo, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or —$OR^{D1}$. In certain embodiments, $R^{17}$ is hydrogen. In certain embodiments, $R^{17}$ is halo. In certain embodiments, $R^{17}$ is substituted or unsubstituted alkyl. In certain embodiments, $R^{17}$ is substituted or unsubstituted alkenyl. In certain embodiments, $R^{17}$ is substituted or unsubstituted alkynyl. In certain embodiments, $R^{17}$ is substituted or unsubstituted carbocyclyl. In certain embodiments, $R^{17}$ is substituted or unsubstituted heterocyclyl. In certain embodiments, $R^{17}$ is substituted or unsubstituted aryl. In certain embodiments, $R^{17}$ is substituted or unsubstituted heteroaryl. In certain embodiments, $R^{17}$ is —$OR^{D1}$ (e.g., —OH).

As generally defined above, $R^{14}$ is H or substituted or unsubstituted alkyl. In certain embodiments, $R^{14}$ is H. In certain embodiments, $R^{14}$ is substituted or unsubstituted alkyl (e.g., —$CH_3$).

As generally defined above, $R^{18}$ is independently hydrogen or substituted or unsubstituted alkyl. In certain embodiments, $R^{18}$ is hydrogen. In certain embodiments, $R^{18}$ is substituted or unsubstituted alkyl (e.g., —$CH_3$).

As generally defined above, $R^{19}$ is independently hydrogen or substituted or unsubstituted alkyl. In certain embodiments, $R^{19}$ is hydrogen. In certain embodiments, $R^{19}$ is substituted or unsubstituted alkyl (e.g., —$CH_3$).

In certain embodiments, $R^{14}$ is hydrogen, $R^{18}$ is —$CH_3$ and $R^{19}$ is —$CH_3$.

In certain embodiments, $R^{14}$ is hydrogen, $R^{18}$ is —CH$_3$ and $R^{19}$ is hydrogen.

Additional Embodiments of Formula (I)

Various combinations of the above embodiments are further contemplated herein. For example, in certain embodiments, the compound of Formula (I) is of Formula (I-w):

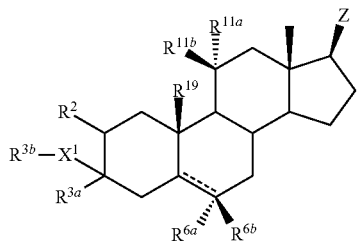

(I-w)

or a pharmaceutically acceptable salt, solvate, prodrug, stereoisomer, tautomer, isotopic variant, or N-oxide thereof, or a combination thereof. In certain embodiments, $R^{3b}$ is hydrogen. In certain embodiments, the group —X$^1$R$^{3b}$ at the C3 position is beta. In certain embodiments, $R^{3a}$ is hydrogen or substituted or unsubstituted alkyl. In certain embodiments, $R^2$ is hydrogen or —OR$^{B1}$. In certain embodiments, $R^{11a}$ is hydrogen and $R^{11b}$ is hydrogen or —OR$^{B1}$. In certain embodiments, ===== represents a single bond, $R^5$ is alpha (down) and $R^{6a}$ is hydrogen. In certain embodiments, ===== represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro. In certain embodiments, $R^{19}$ is methyl.

In certain embodiments, the compound of Formula (I) is of Formula (I-x):

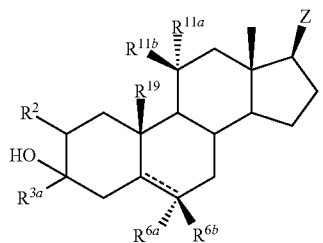

(I-x)

or a pharmaceutically acceptable salt, solvate, prodrug, stereoisomer, tautomer, isotopic variant, or N-oxide thereof, or a combination thereof. In certain embodiments, the group —OH at the C3 position is beta. In certain embodiments, $R^{3a}$ is hydrogen or substituted or unsubstituted alkyl. In certain embodiments, $R^2$ is hydrogen or —OR$^{B1}$. In certain embodiments, $R^{11a}$ is hydrogen and $R^{11b}$ is hydrogen or —OR$^{B1}$. In certain embodiments, ===== represents a single bond, $R^5$ is alpha (down) and $R^{6a}$ is hydrogen. In certain embodiments, ===== represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro. In certain embodiments, $R^{19}$ is methyl.

In certain embodiments, the compound of Formula (I) is of Formula (I-y):

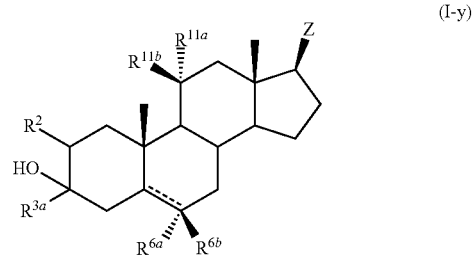

(I-y)

or a pharmaceutically acceptable salt, solvate, prodrug, stereoisomer, tautomer, isotopic variant, or N-oxide thereof, or a combination thereof. In certain embodiments, the group —OH at the C3 position is beta. In certain embodiments, $R^{3a}$ is hydrogen or substituted or unsubstituted alkyl. In certain embodiments, $R^2$ is hydrogen or —OR$^{B1}$. In certain embodiments, $R^{11a}$ is hydrogen and $R^{11b}$ is hydrogen or —OR$^{B1}$. In certain embodiments, ===== represents a single bond, $R^5$ is alpha (down) and $R^{6a}$ is hydrogen. In certain embodiments, ===== represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro.

In certain embodiments, the compound of Formula (I) is of Formula (I-z):

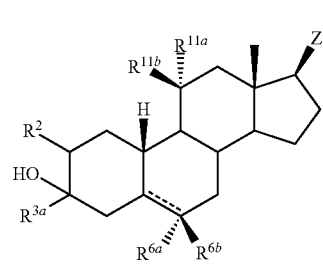

(I-z)

or a pharmaceutically acceptable salt, solvate, prodrug, stereoisomer, tautomer, isotopic variant, or N-oxide thereof, or a combination thereof. In certain embodiments, the group —OH at the C3 position is beta. In certain embodiments, $R^{3a}$ is hydrogen or substituted or unsubstituted alkyl. In certain embodiments, $R^2$ is hydrogen or —OR$^{B1}$. In certain embodiments, $R^{11a}$ is hydrogen and $R^{11b}$ is hydrogen or —OR$^{B1}$. In certain embodiments, ===== represents a single bond, $R^5$ is alpha (down) and $R^{6a}$ is hydrogen. In certain embodiments, ===== represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro.

In certain embodiments, the compound of Formula (I) is of Formula (I-a1), (I-a2), or (I-a3):

(I-a1)

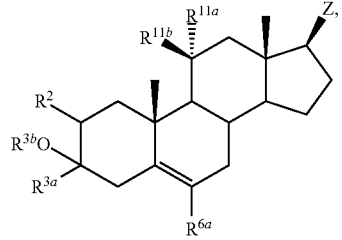

(I-a2)

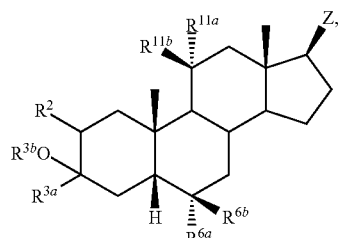

(I-a3)

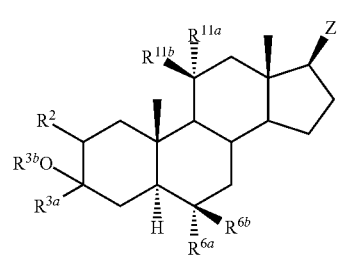

or a pharmaceutically acceptable salt, solvate, prodrug, stereoisomer, tautomer, isotopic variant, or N-oxide thereof, or a combination thereof. In certain embodiments, $R^{3b}$ is hydrogen. In certain embodiments, the group —$OR^{3b}$ at the C3 position is beta. In certain embodiments, $R^{3a}$ is hydrogen or substituted or unsubstituted alkyl. In certain embodiments, $R^2$ is hydrogen or —$OR^{B1}$. In certain embodiments, $R^{11a}$ is hydrogen and $R^{11b}$ is hydrogen or —$OR^{B1}$. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro.

In certain embodiments, the compound of Formula (I) is of Formula (I-b1), (I-b2), or (I-b3):

(I-b1)

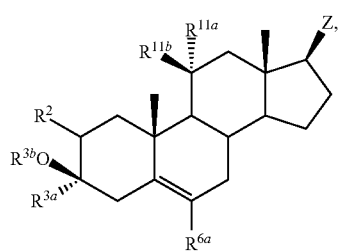

(I-b2)

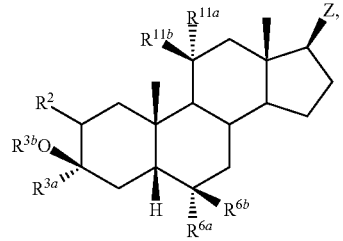

(I-b3)

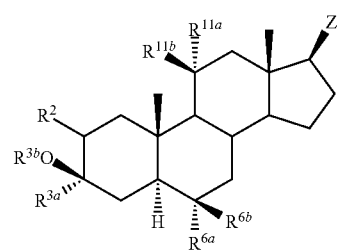

or a pharmaceutically acceptable salt, solvate, prodrug, stereoisomer, tautomer, isotopic variant, or N-oxide thereof, or a combination thereof. In certain embodiments, $R^{3b}$ is hydrogen. In certain embodiments, $R^{3a}$ is hydrogen or substituted or unsubstituted alkyl. In certain embodiments, $R^2$ is hydrogen or —$OR^{B1}$. In certain embodiments, $R^{11a}$ is hydrogen and $R^{11b}$ is hydrogen or —$OR^{B1}$. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro.

In certain embodiments, the compound of Formula (I) is of Formula (I-c1), (I-c2), or (I-c3):

(I-c1)

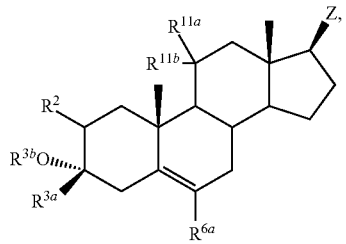

(I-c2)

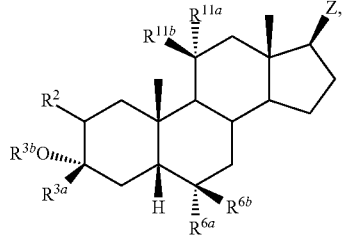

-continued

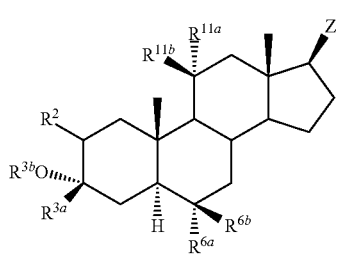

(I-c3)

or a pharmaceutically acceptable salt, solvate, prodrug, stereoisomer, tautomer, isotopic variant, or N-oxide thereof, or a combination thereof. In certain embodiments, $R^{3b}$ is hydrogen. In certain embodiments, $R^{3a}$ is hydrogen or substituted or unsubstituted alkyl. In certain embodiments, $R^2$ is hydrogen or —$OR^{B1}$. In certain embodiments, $R^{11a}$ is hydrogen and $R^{11b}$ is hydrogen or —$OR^{B1}$. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro.

In certain embodiments, the compound is of Formula (I-d):

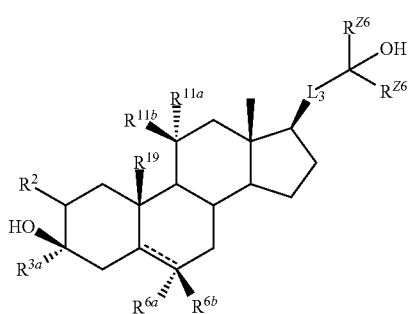

(I-d)

or a pharmaceutically acceptable salt, solvate, prodrug, stereoisomer, tautomer, isotopic variant, or N-oxide thereof, or a combination thereof. In certain embodiments, $R^{3b}$ is hydrogen. In certain embodiments, the group —$X^1R^{3b}$ at the C3 position is beta. In certain embodiments, $R^{3a}$ is hydrogen or substituted or unsubstituted alkyl. In certain embodiments, $R^2$ is hydrogen or —$OR^{B1}$. In certain embodiments $R^{11a}$ is hydrogen and $R^{11b}$ is hydrogen or —$OR^{B1}$. In certain embodiments, ------ represents a single bond, $R^5$ is alpha (down) and $R^{6a}$ is hydrogen. In certain embodiments, ------ represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro. In certain embodiments, $R^{19}$ is methyl. In certain embodiments, each $R^6$ is independently hydrogen or methyl.

In certain embodiments, the compound is of Formula (I-e):

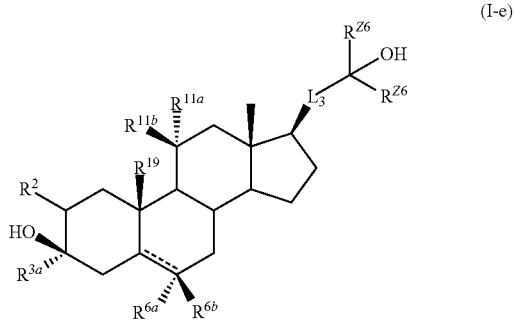

(I-e)

or a pharmaceutically acceptable salt, solvate, prodrug, stereoisomer, tautomer, isotopic variant, or N-oxide thereof, or a combination thereof. In certain embodiments, $R^{3a}$ is hydrogen or substituted or unsubstituted alkyl. In certain embodiments, $R^2$ is hydrogen or —$OR^{B1}$. In certain embodiments, $R^{11a}$ is hydrogen and $R^{11b}$ is hydrogen or —$OR^{B1}$. In certain embodiments, ------ represents a single bond, $R^5$ is alpha (down) and $R^{6a}$ is hydrogen. In certain embodiments, ------ represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro. In certain embodiments, $R^{19}$ is methyl. In certain embodiments, each $R^{Z6}$ is independently hydrogen or methyl.

In certain embodiments, the compound is of Formula (I-f):

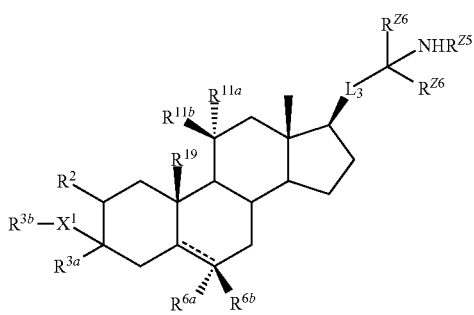

(I-f)

or a pharmaceutically acceptable salt, solvate, prodrug, stereoisomer, tautomer, isotopic variant, or N-oxide thereof, or a combination thereof. In certain embodiments, $R^{3b}$ is hydrogen. In certain embodiments, the group —$X^1R^{3b}$ at the C3 position is beta. In certain embodiments, $R^{3a}$ is hydrogen or substituted or unsubstituted alkyl. In certain embodiments, $R^2$ is hydrogen or —$OR^{B1}$. In certain embodiments, $R^{11a}$ is hydrogen and $R^{11b}$ is hydrogen or —$OR^{B1}$. In certain embodiments, ------ represents a single bond, $R^5$ is alpha (down) and $R^{6a}$ is hydrogen. In certain embodiments, ------ represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro. In certain embodiments, $R^{19}$ is methyl. In certain embodiments, each $R^{Z6}$ is independently hydrogen or methyl. In certain embodiments, $R^{Z5}$ is hydrogen or methyl.

In certain embodiments, the compound is of Formula (I-g):

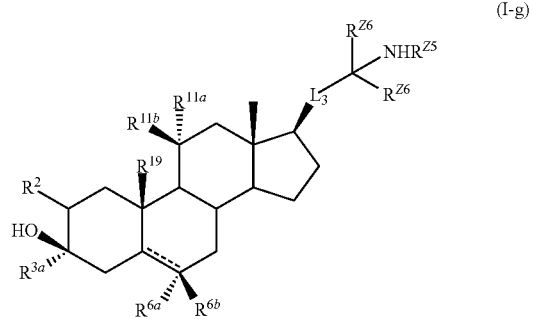

(I-g)

or a pharmaceutically acceptable salt, solvate, prodrug, stereoisomer, tautomer, isotopic variant, or N-oxide thereof, or a combination thereof. In certain embodiments, $R^{3a}$ is hydrogen or substituted or unsubstituted alkyl. In certain embodiments, $R^2$ is hydrogen or —$OR^{B1}$. In certain embodiments, $R^{11a}$ is hydrogen and $R^{11b}$ is hydrogen or —$OR^{B1}$. In certain embodiments, ===== represents a single bond, $R^5$ is alpha (down) and $R^{6a}$ is hydrogen. In certain embodiments, ------ represents a double bond. In certain embodiments, $R^{6a}$ and $R^{6b}$ are both hydrogen. In certain embodiments, Ra is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro. In certain embodiments, $R^{19}$ is methyl. In certain embodiments, each $R^6$ is independently hydrogen or methyl. In certain embodiments, $R^{Z5}$ is hydrogen or methyl.

In certain embodiments, the compound is of Formula (I-h):

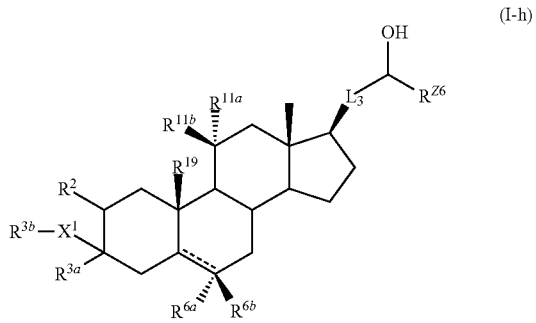

(I-h)

or a pharmaceutically acceptable salt, solvate, prodrug, stereoisomer, tautomer, isotopic variant, or N-oxide thereof, or a combination thereof. In certain embodiments, $R^{3b}$ is hydrogen. In certain embodiments, the group —$X^1R^{3b}$ at the C3 position is beta. In certain embodiments, $R^{3a}$ is hydrogen or substituted or unsubstituted alkyl. In certain embodiments, $R^2$ is hydrogen or —$OR^{B1}$. In certain embodiments, $R^{11a}$ is hydrogen and $R^{11b}$ is hydrogen or —$OR^{B1}$. In certain embodiments, ===== represents a single bond, $R^5$ is alpha (down) and $R^{6a}$ is hydrogen. In certain embodiments, ------ represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro. In certain embodiments, $R^{19}$ is methyl. In certain embodiments, $R^{Z6}$ is isopropyl.

In certain embodiments, the compound is of Formula (I-i):

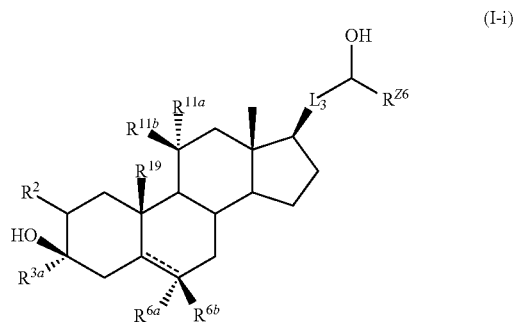

(I-i)

or a pharmaceutically acceptable salt, solvate, prodrug, stereoisomer, tautomer, isotopic variant, or N-oxide thereof, or a combination thereof. In certain embodiments, $R^{3a}$ is hydrogen or substituted or unsubstituted alkyl. In certain embodiments, $R^2$ is hydrogen or —$OR^{B1}$. In certain embodiments, $R^{11a}$ is hydrogen and $R^{11b}$ is hydrogen or —$OR^{B1}$. In certain embodiments, ===== represents a single bond, $R^5$ is alpha (down) and $R^{6a}$ is hydrogen. In certain embodiments, ------ represents a double bond. In certain embodiments, $R^{6a}$ and $R^{6b}$ are both hydrogen. In certain embodiments, $R^{6a}$ is halo, e.g., fluoro, or alkyl. In certain embodiments, $R^{6b}$ is halo, e.g., fluoro, or alkyl, and $R^{6a}$ is hydrogen. In certain embodiments, $R^{6a}$ and $R^{6b}$ are both halo, e.g., fluoro. In certain embodiments, $R^{19}$ is methyl. In certain embodiments, $R^{Z6}$ is isopropyl.

Additional embodiments of Formula (I) include compounds of the following formula:

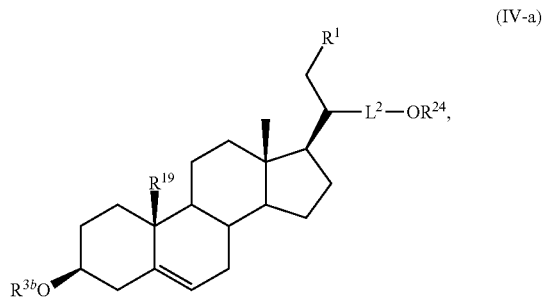

(IV-a)

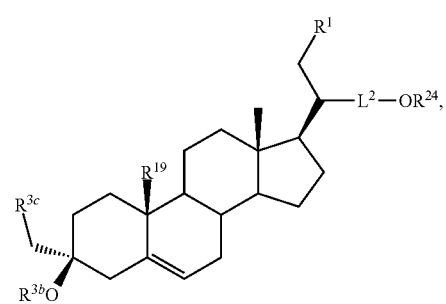
(IV-b)
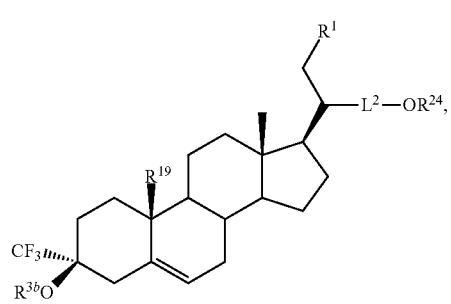
(IV-c)
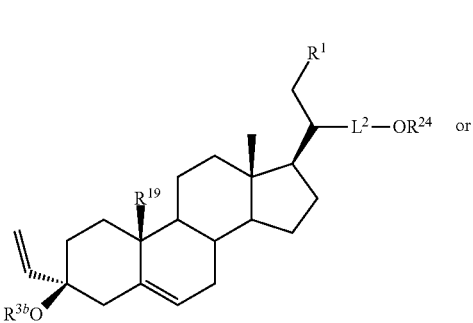
(IV-d) or
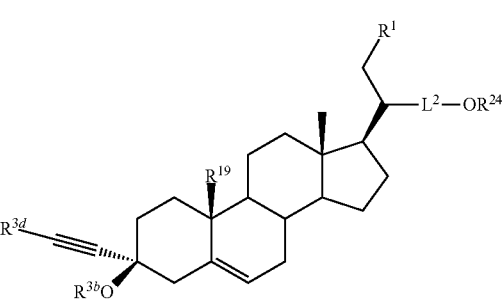
(IV-e)
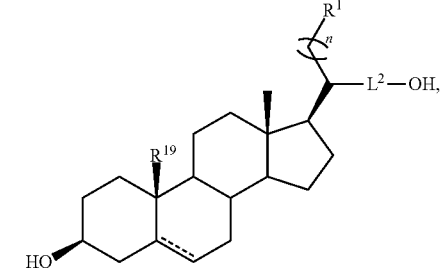
(V-a)
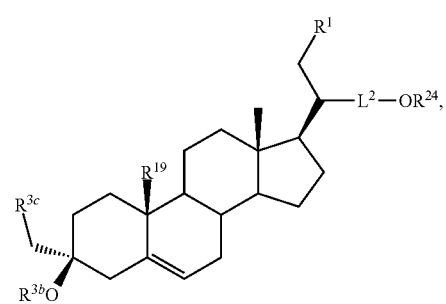
(V-b)
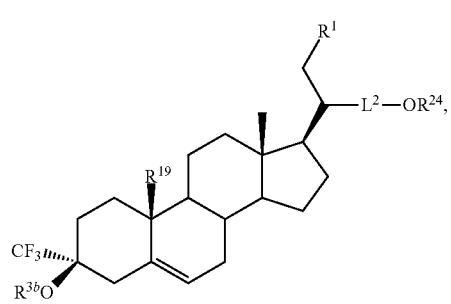
(V-c)
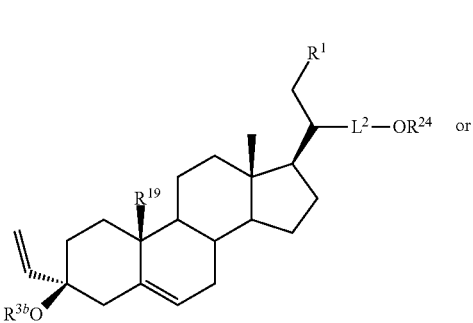
(V-d) or
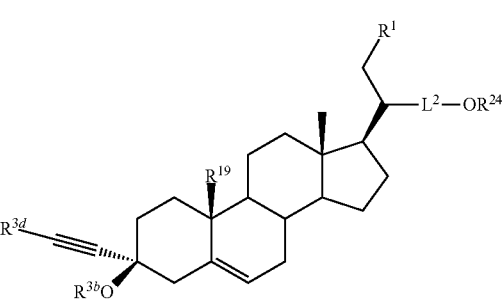
(V-e)
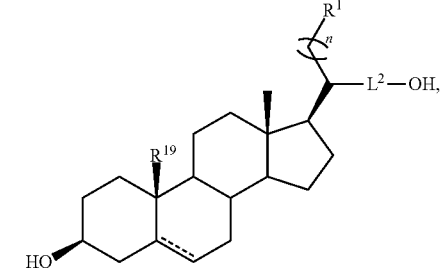
(VI-a)

(VI-b)
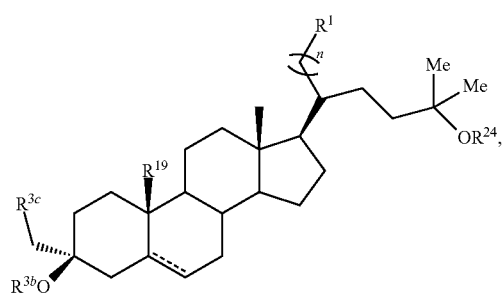
(VI-c)
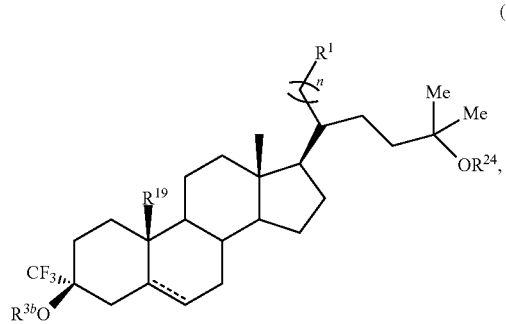
(VI-d)
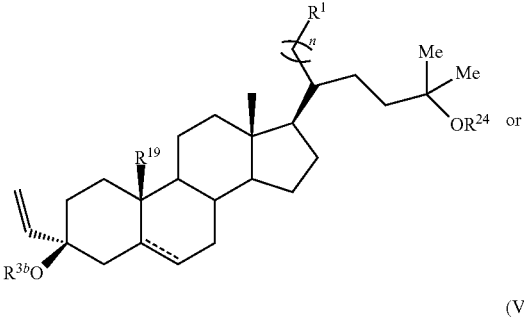
(VI-e)
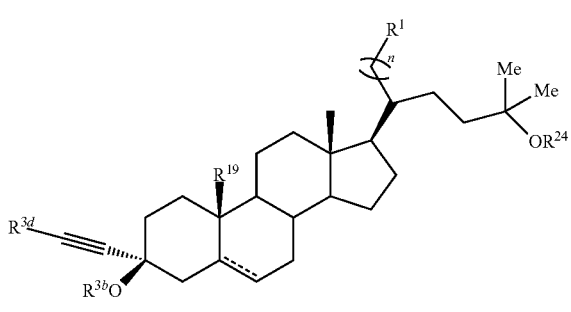
(VII-a)
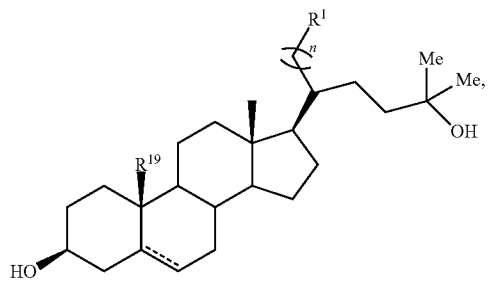
(VII-b)
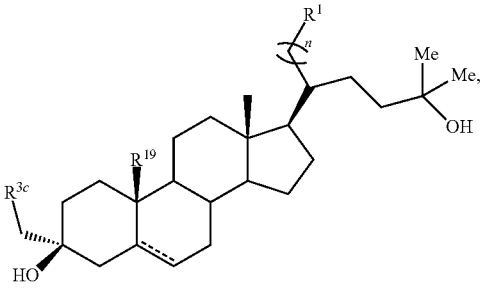
(VII-c)
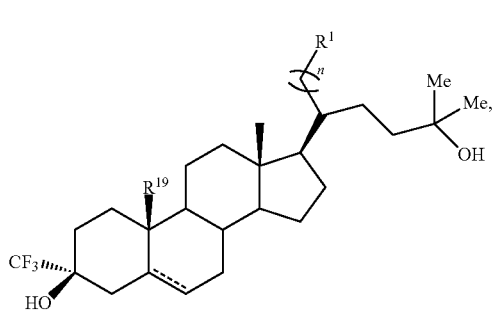
(VII-d)
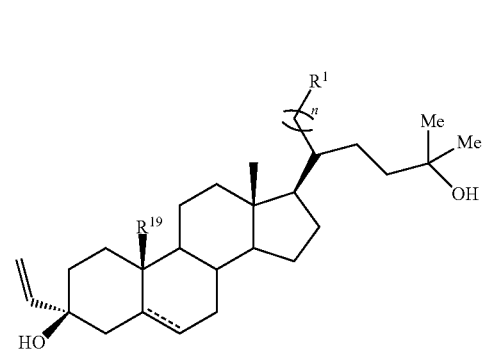
(VII-e)
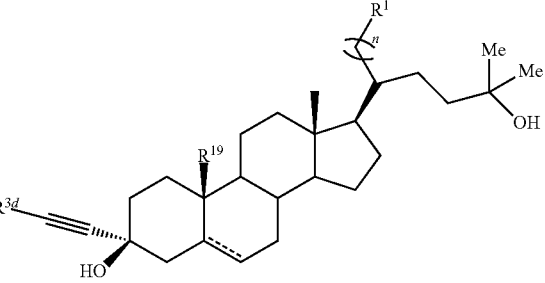
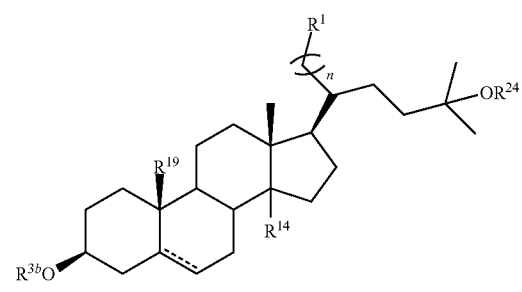

(IX)
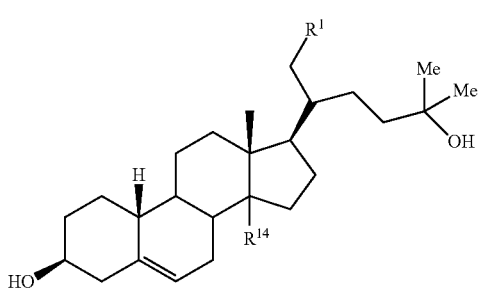
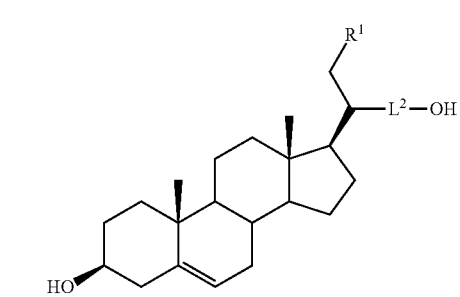
X
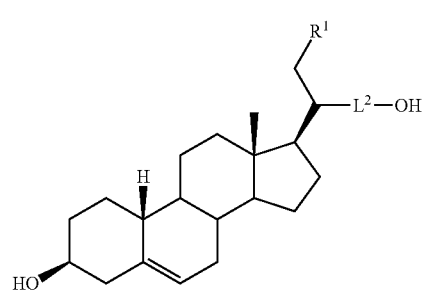
XI
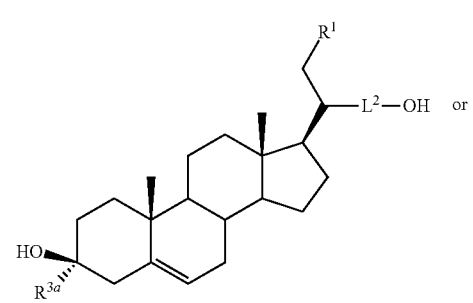 or
XIIa
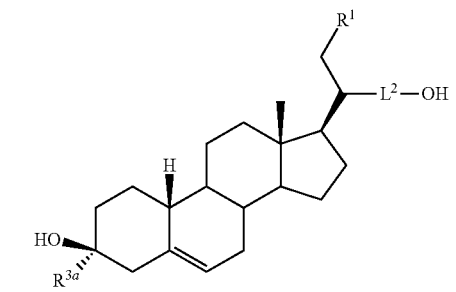
XIIb
In certain embodiments the compound is any one of the following compounds:
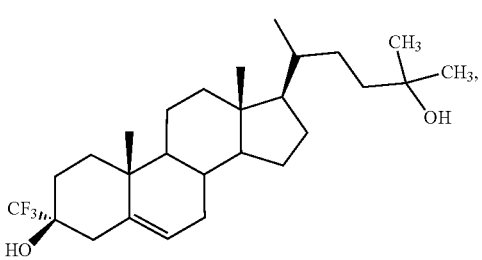
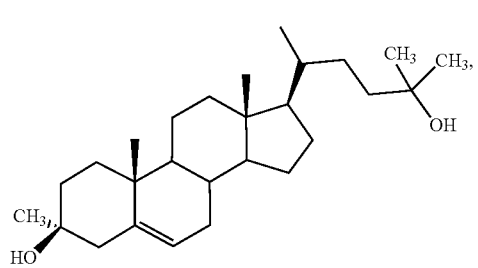
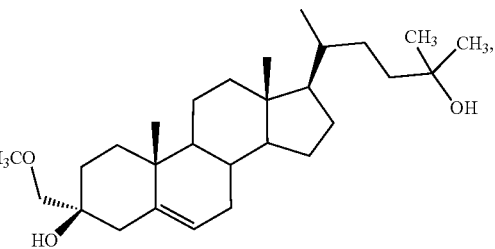
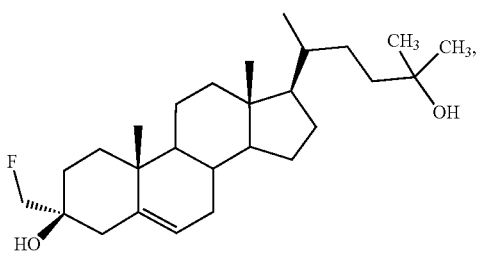
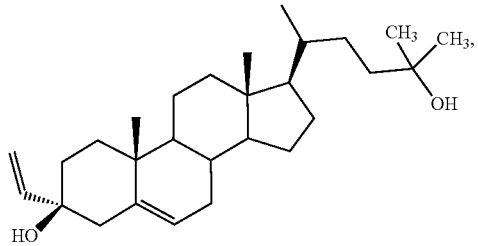
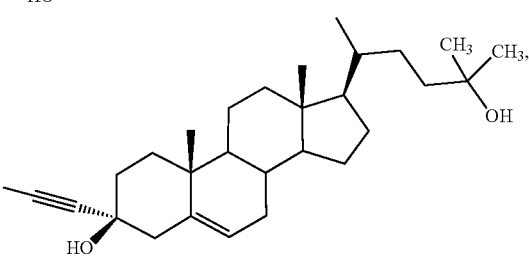

-continued
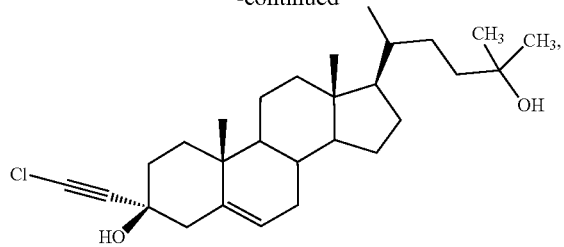
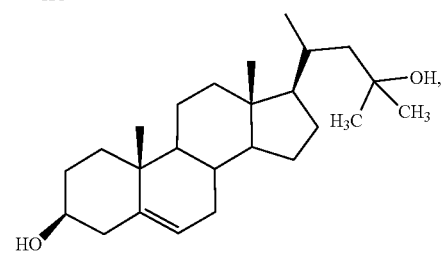
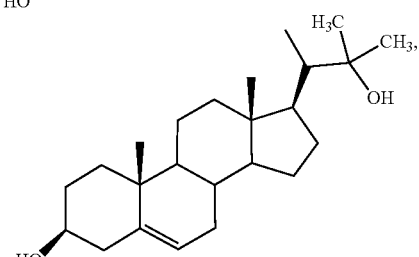
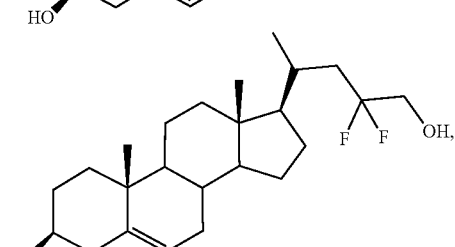
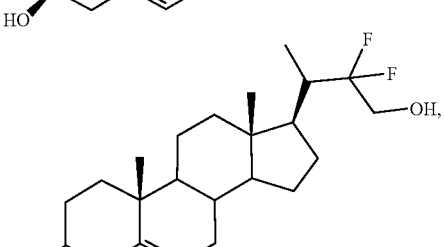
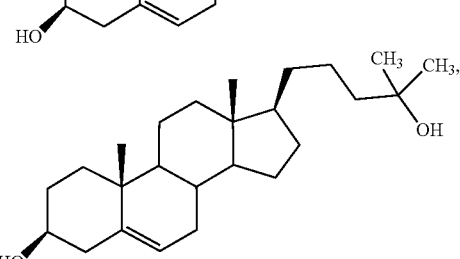
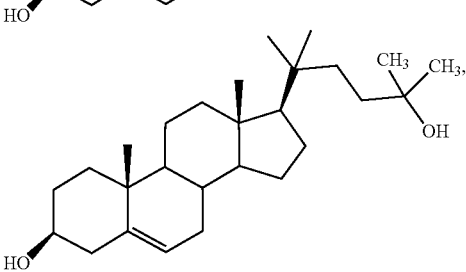
-continued
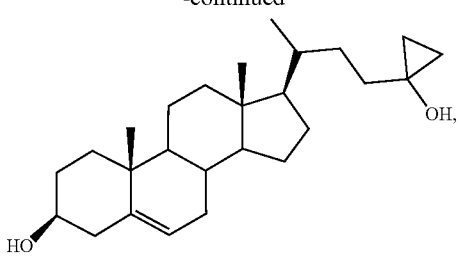
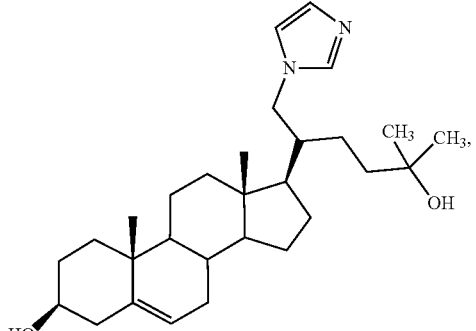
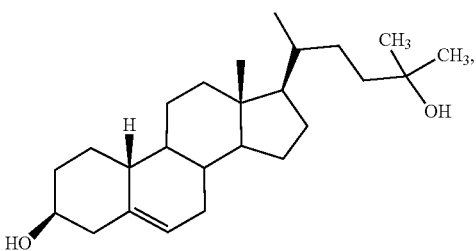
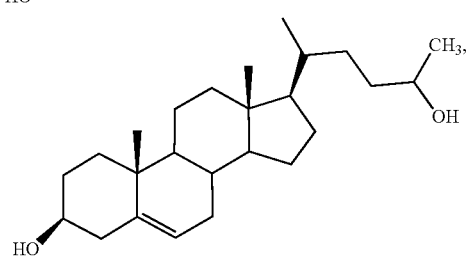
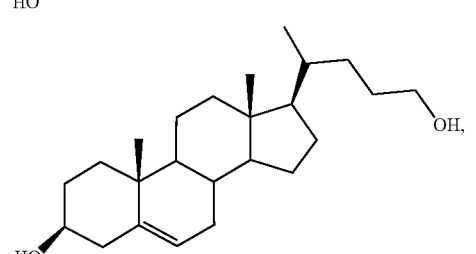
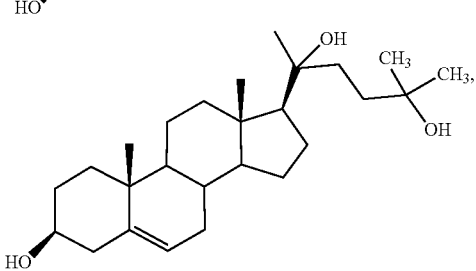

85
-continued
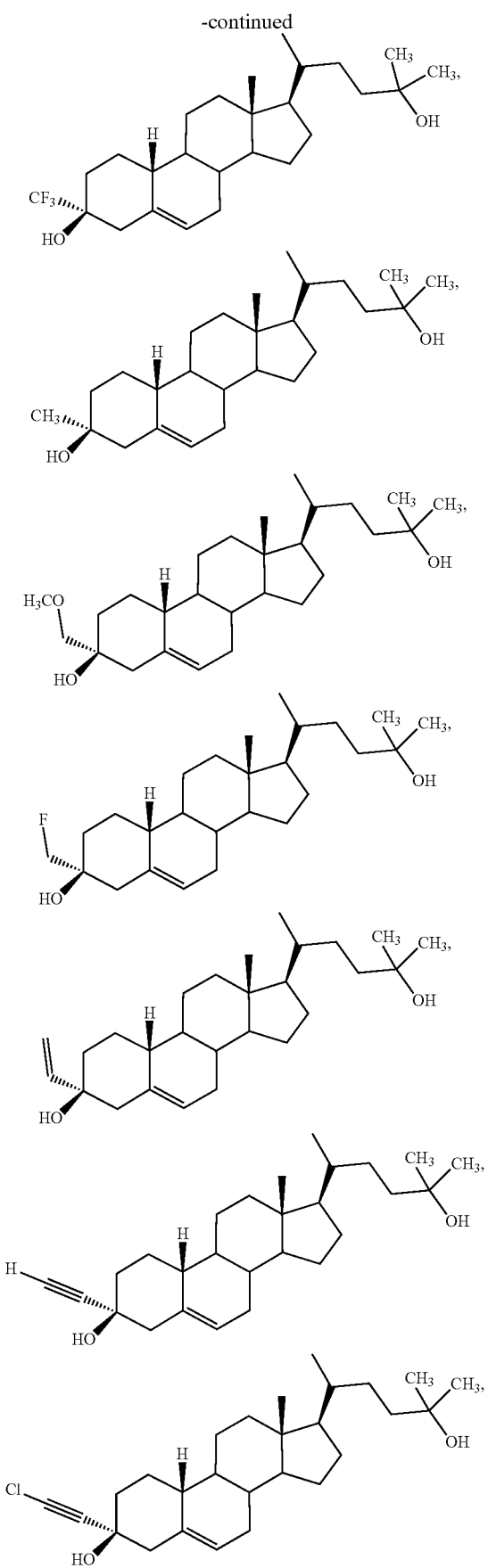
86
-continued
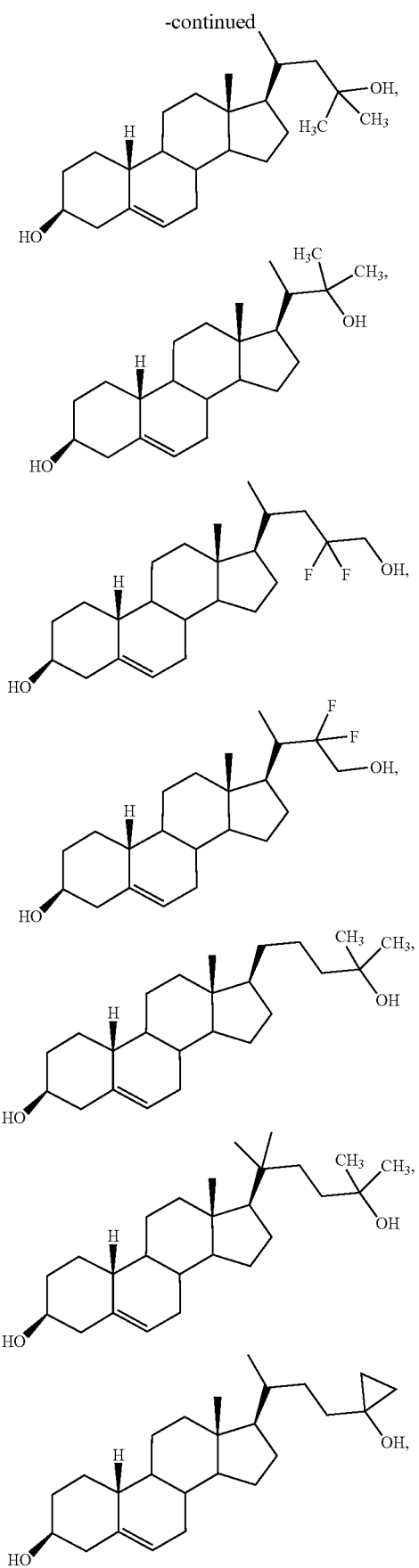

87
-continued
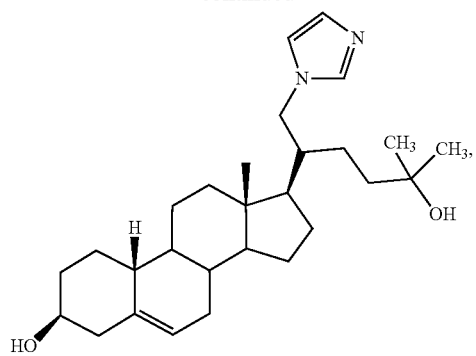
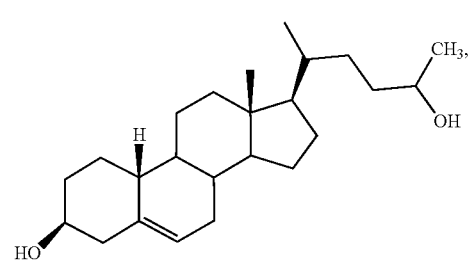
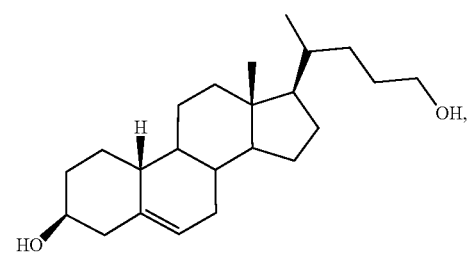
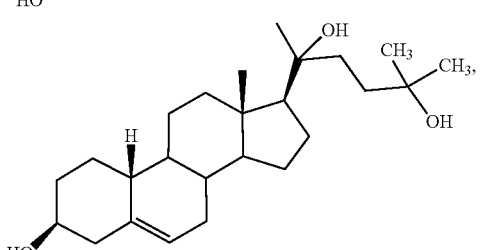
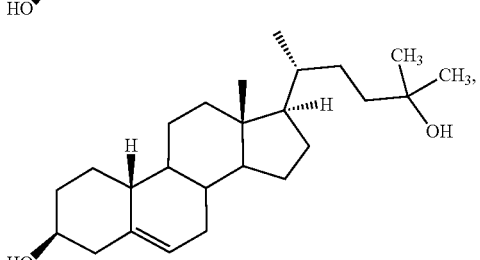
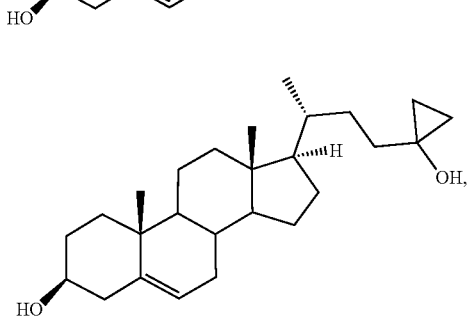
88
-continued
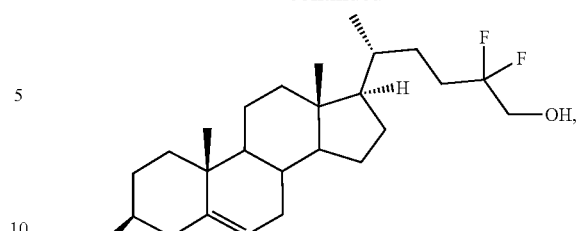
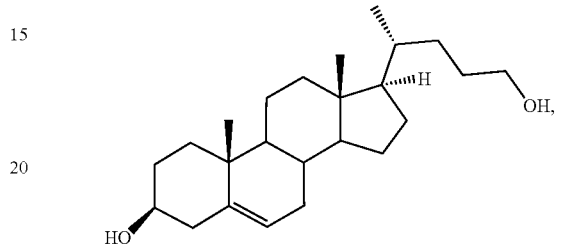
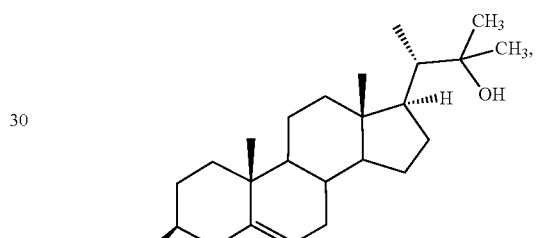
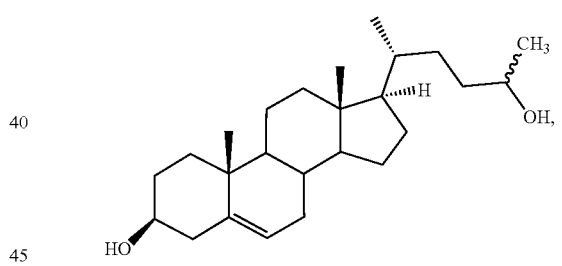
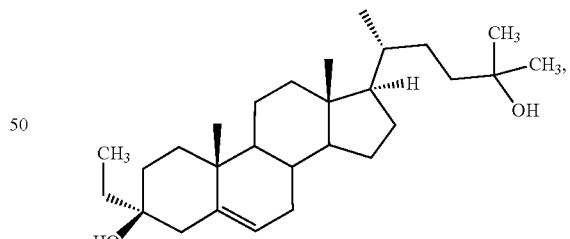
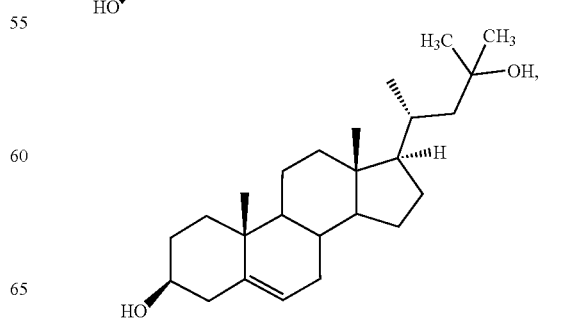

89
-continued
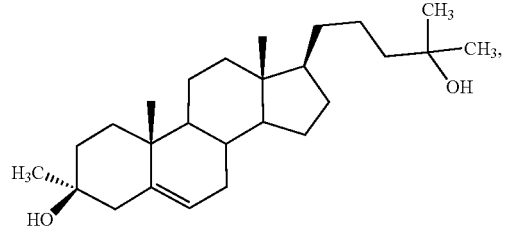
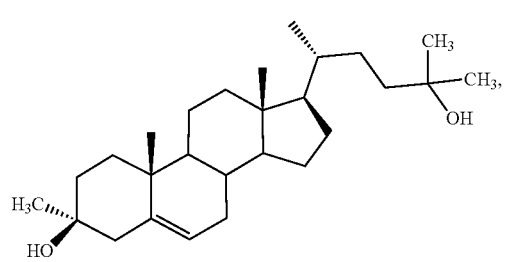
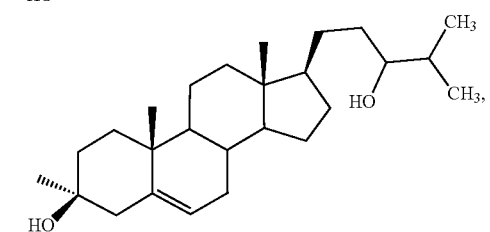
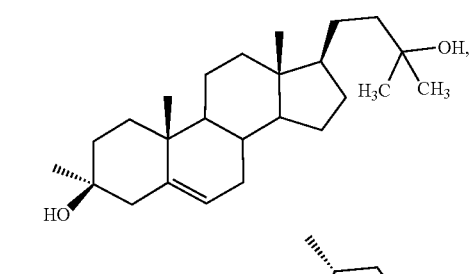
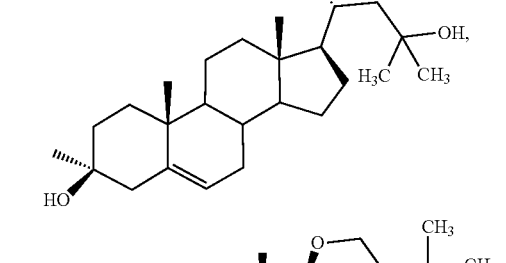
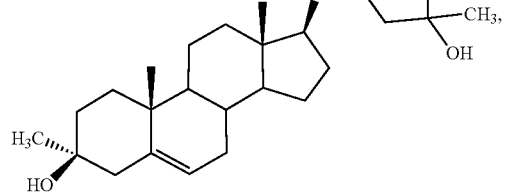
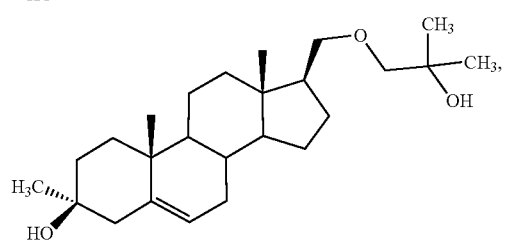
90
-continued
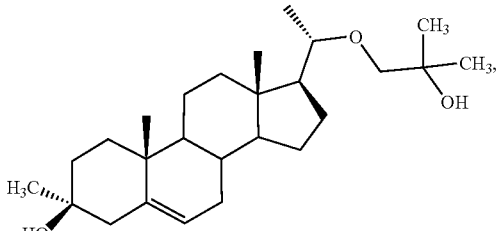
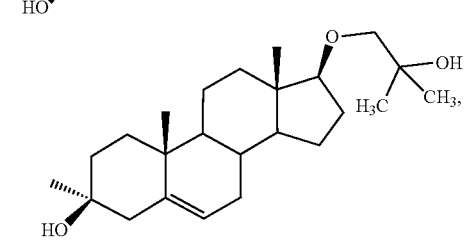
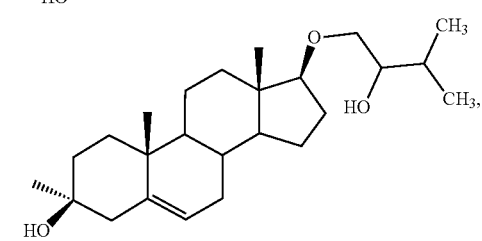
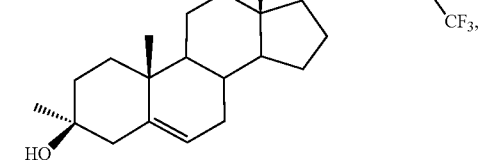
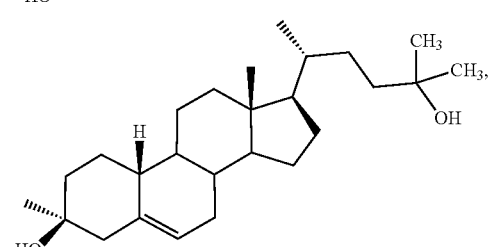
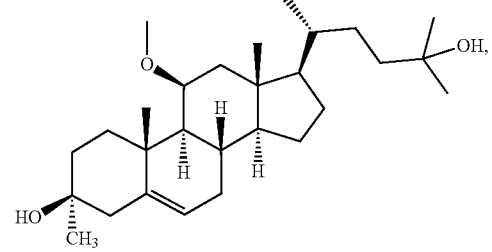

-continued
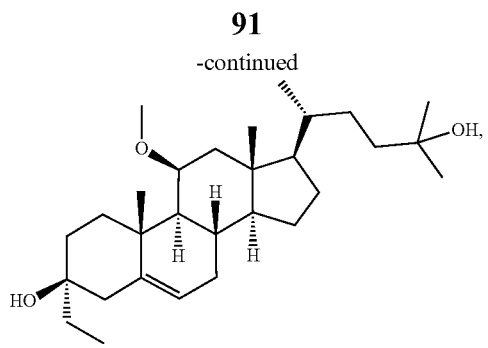
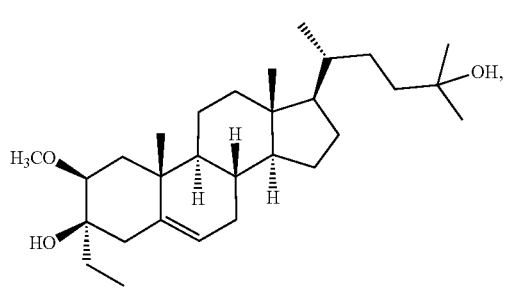
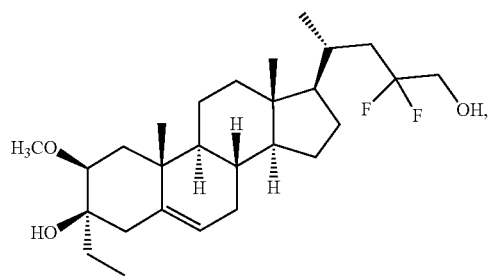
or a pharmaceutically acceptable salt, solvate, prodrug, stereoisomer, tautomer, isotopic variant, or N-oxide thereof, or a combination thereof.
In certain embodiments the compound is any one of the following compounds:
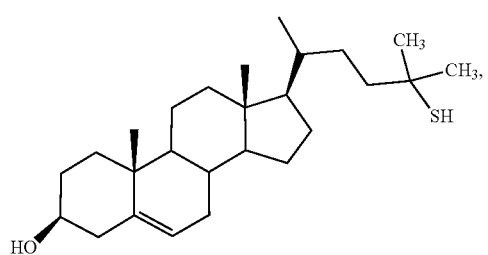
-continued
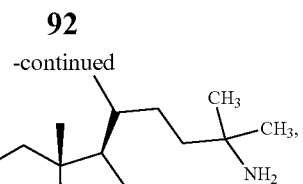
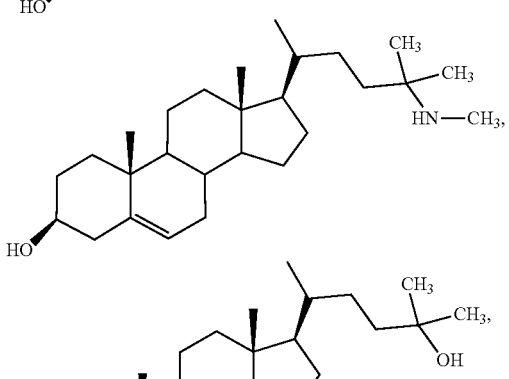
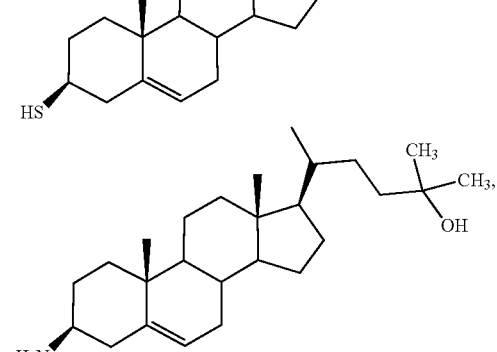
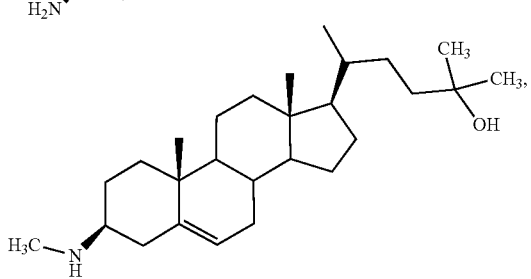
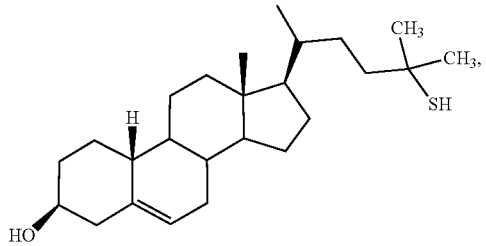

93
-continued
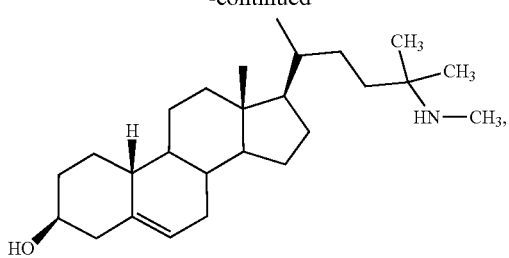
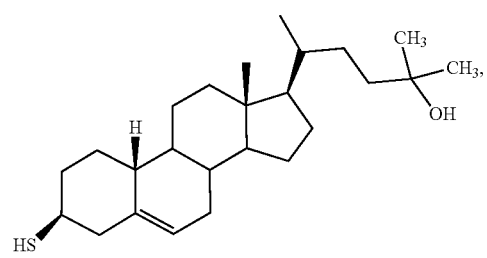
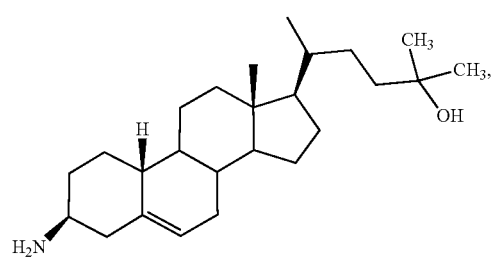
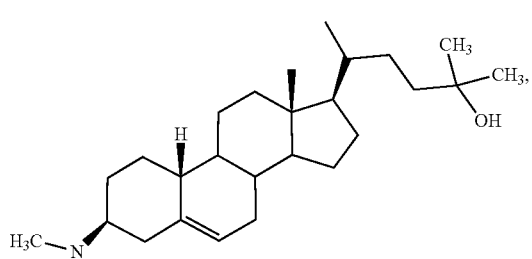
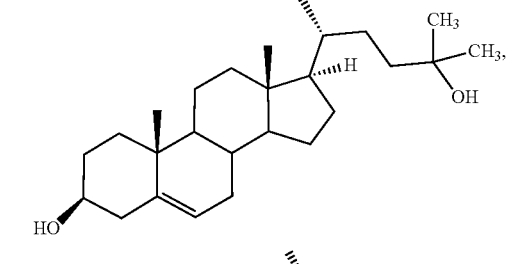
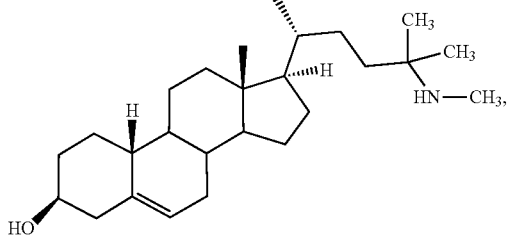
94
-continued
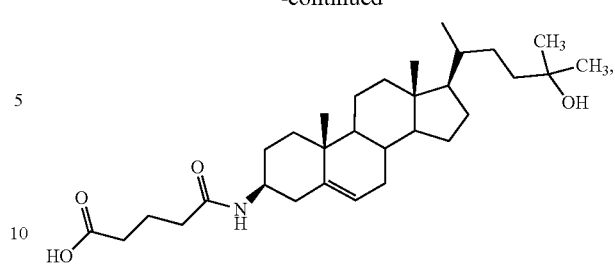
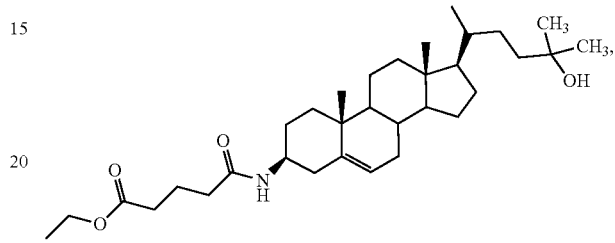
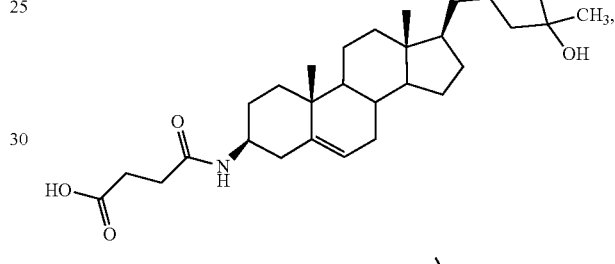
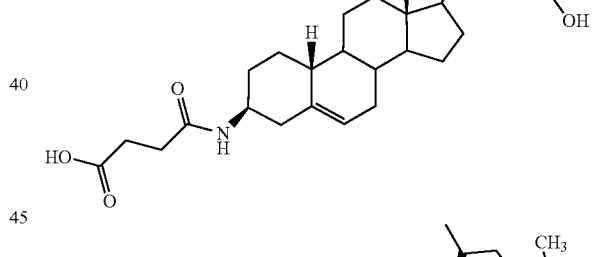
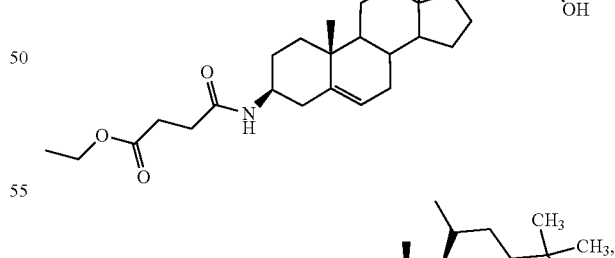
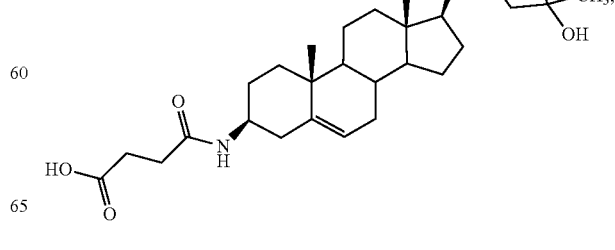

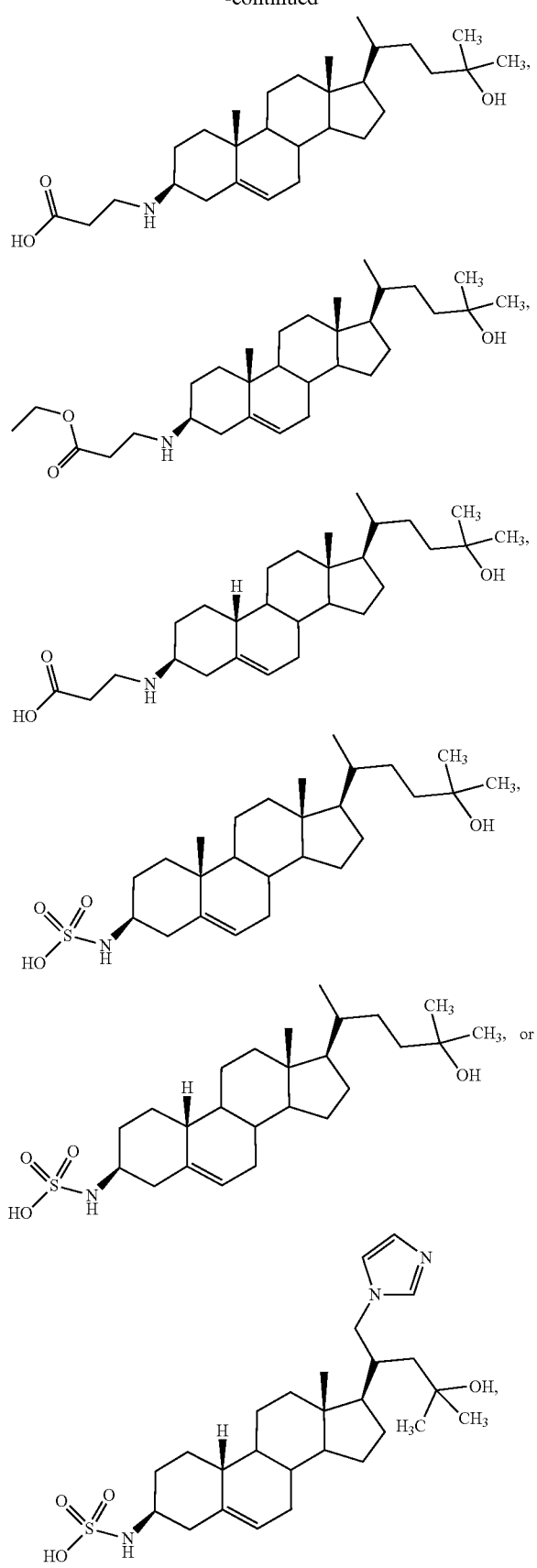
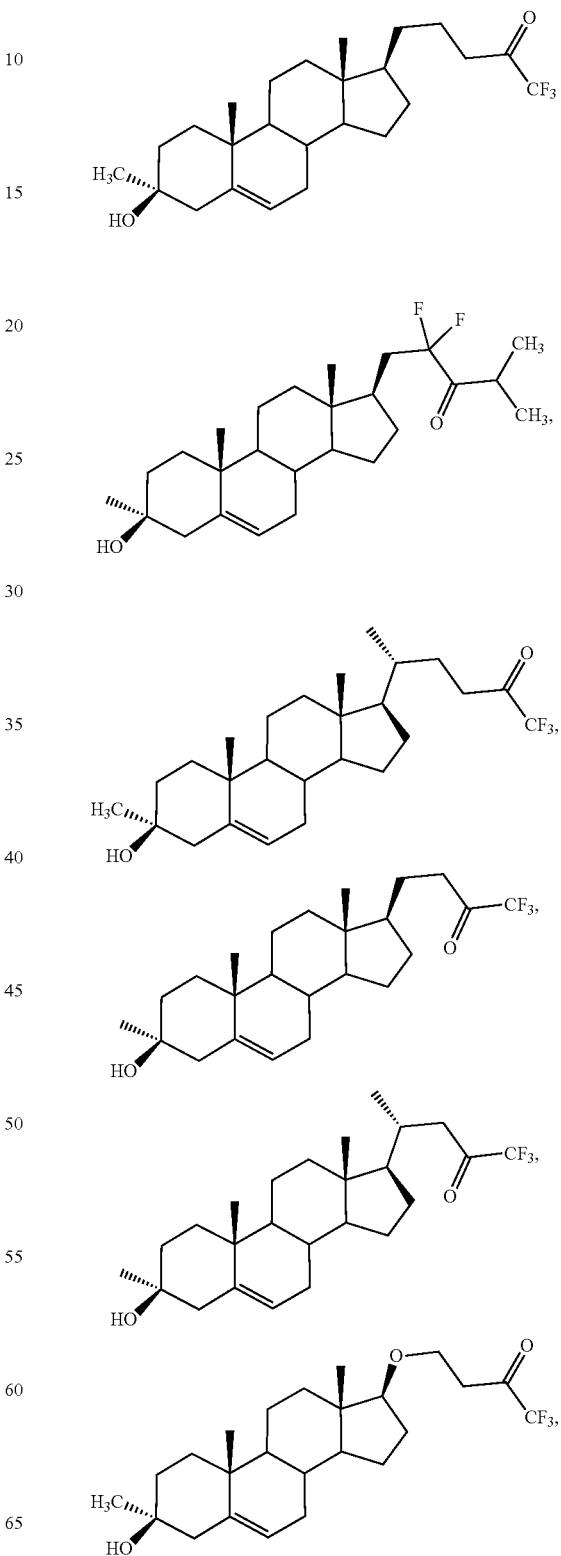
or a pharmaceutically acceptable salt, solvate, prodrug, stereoisomer, tautomer, isotopic variant, or N-oxide thereof, or a combination thereof.
In certain embodiments the compound is any one of the following compounds:

-continued
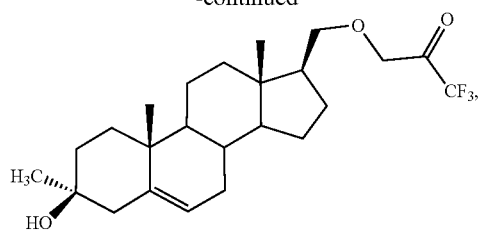
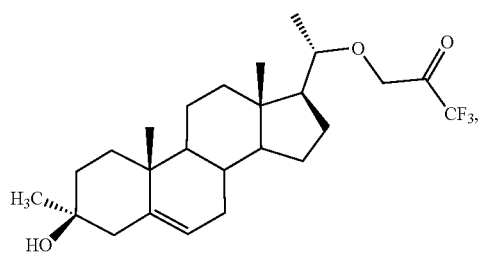
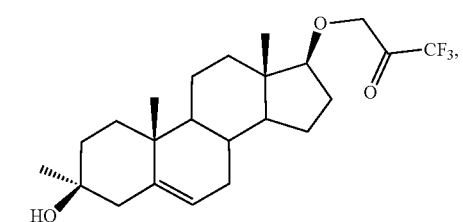
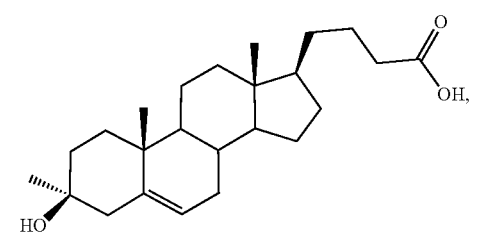
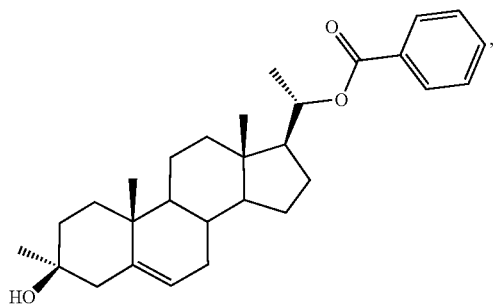
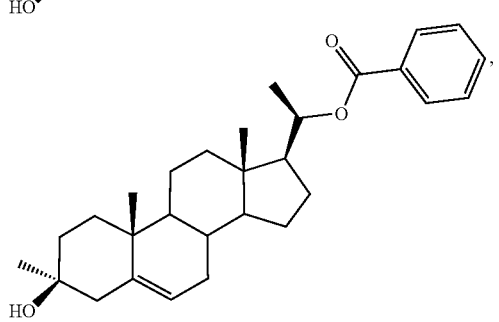
-continued
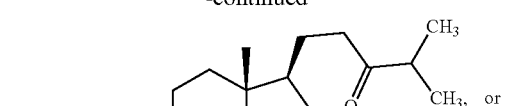
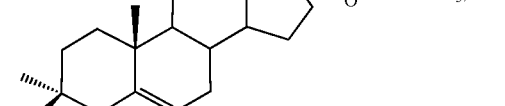
or a pharmaceutically acceptable salt, solvate, prodrug, stereoisomer, tautomer, isotopic variant, or N-oxide thereof, or a combination thereof.
In certain embodiments the compound is any one of the following compounds:
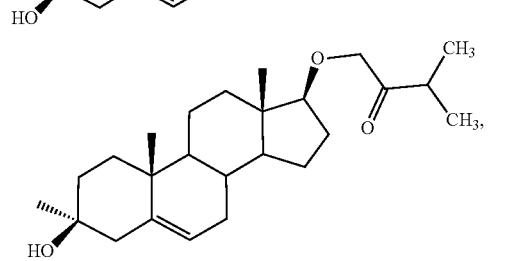
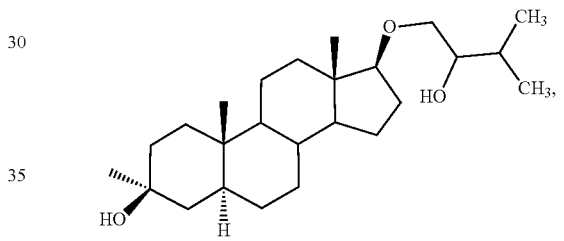
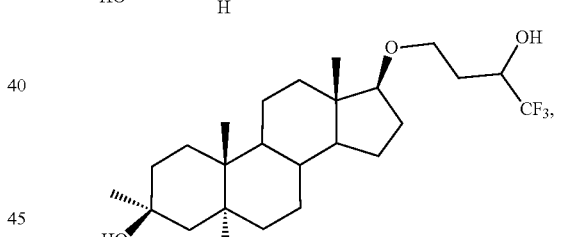
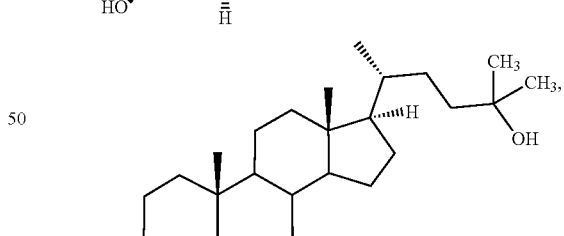
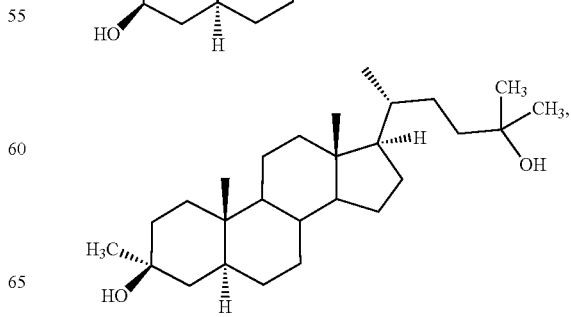

-continued
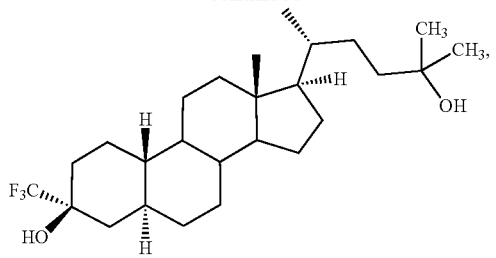
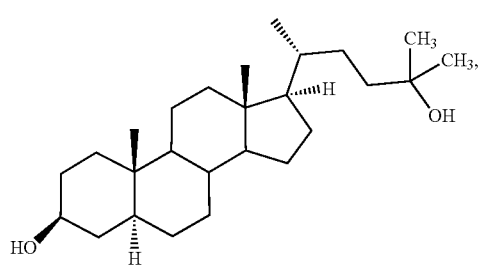
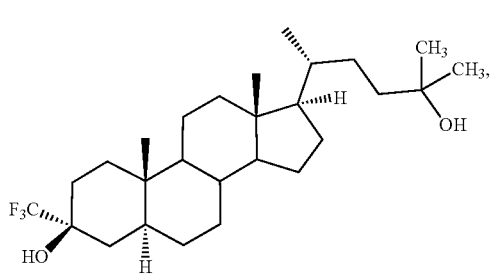
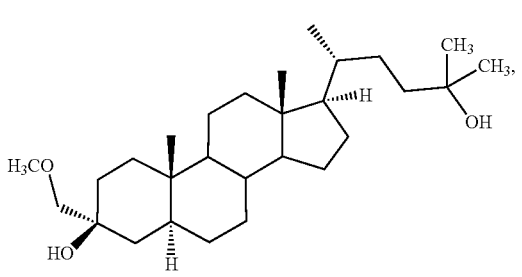
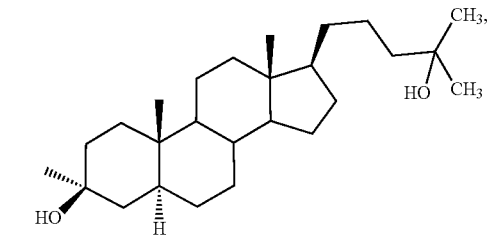
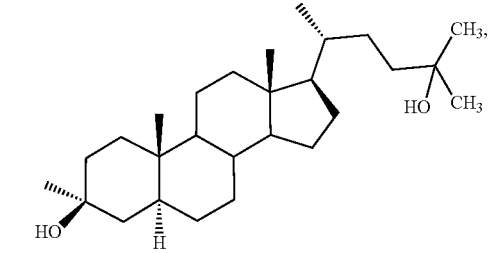
-continued
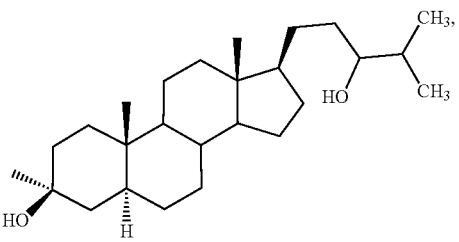
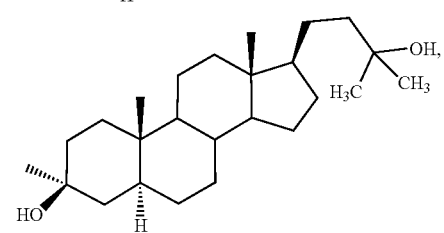
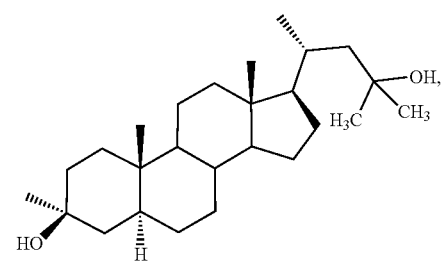
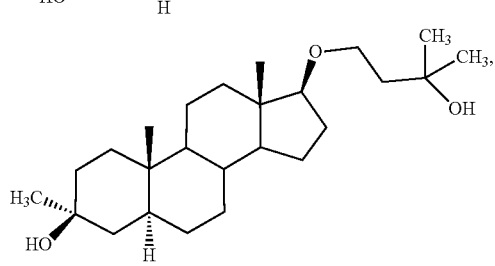
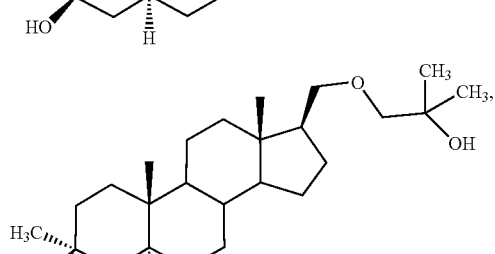
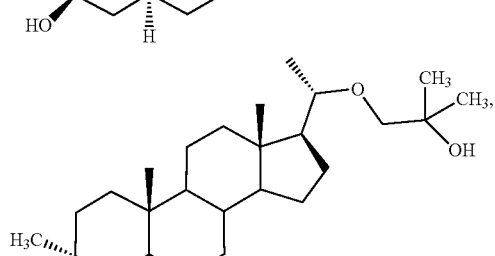
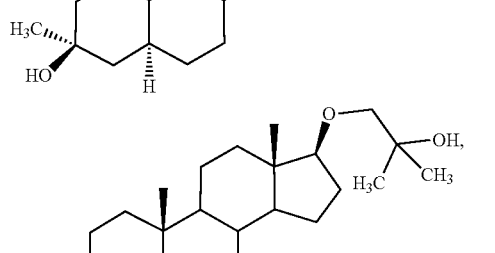
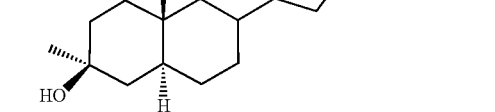

101
-continued
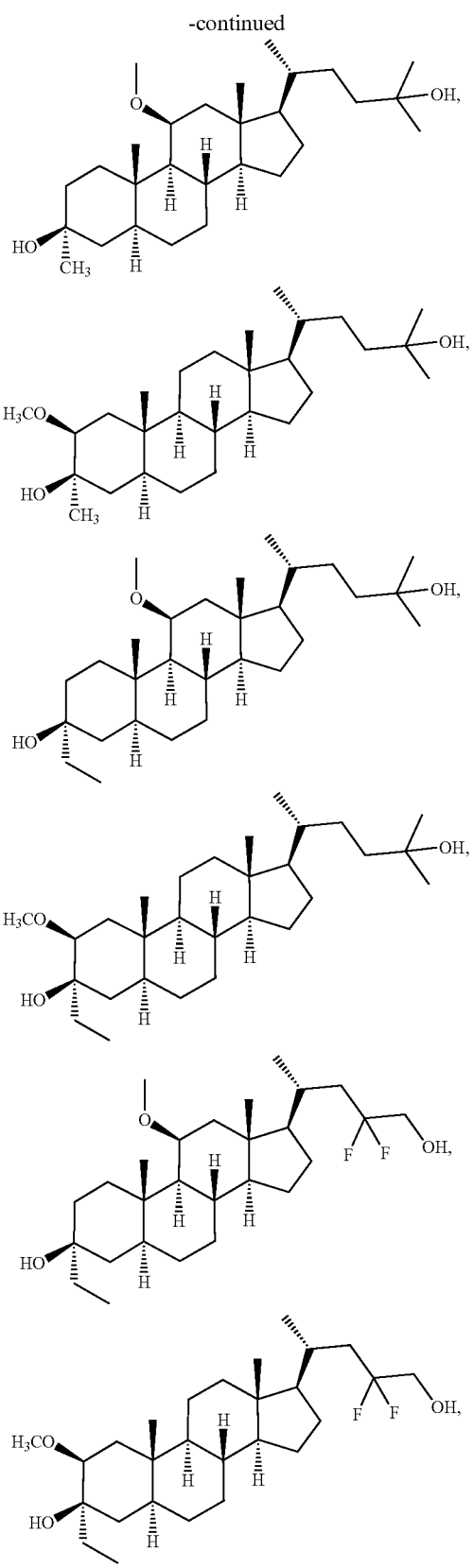
or a pharmaceutically acceptable salt, solvate, prodrug, stereoisomer, tautomer, isotopic variant, or N-oxide thereof, or a combination thereof.
102
In certain embodiments the compound is any one of the following compounds:
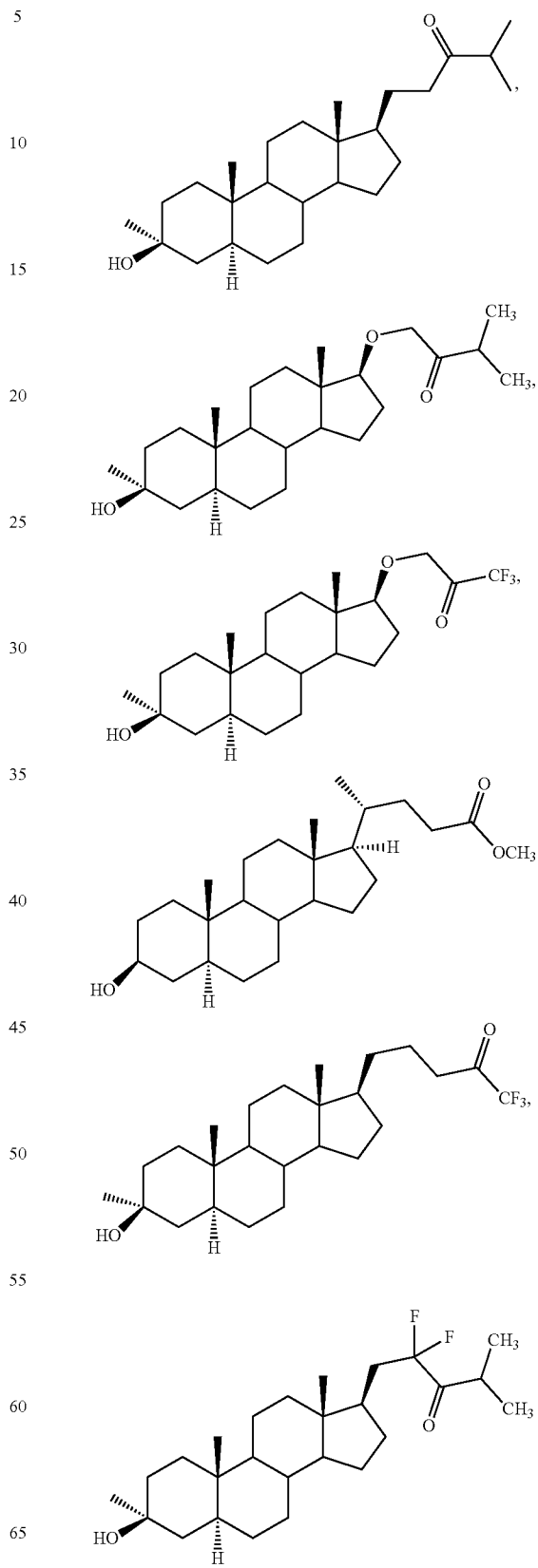

-continued

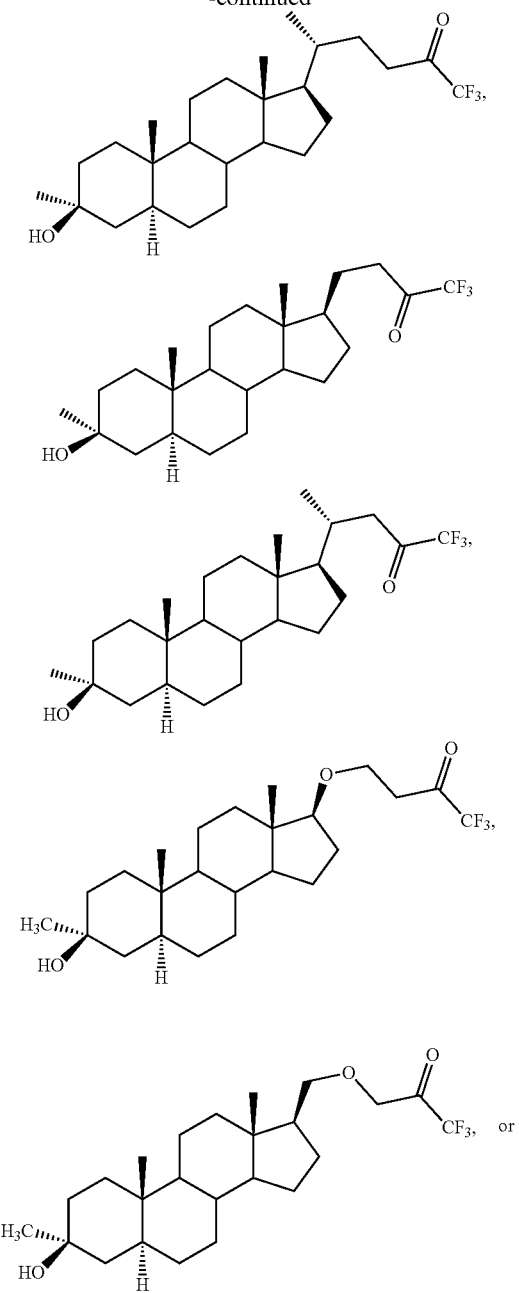

In certain embodiments the compound is any one of the following compounds:

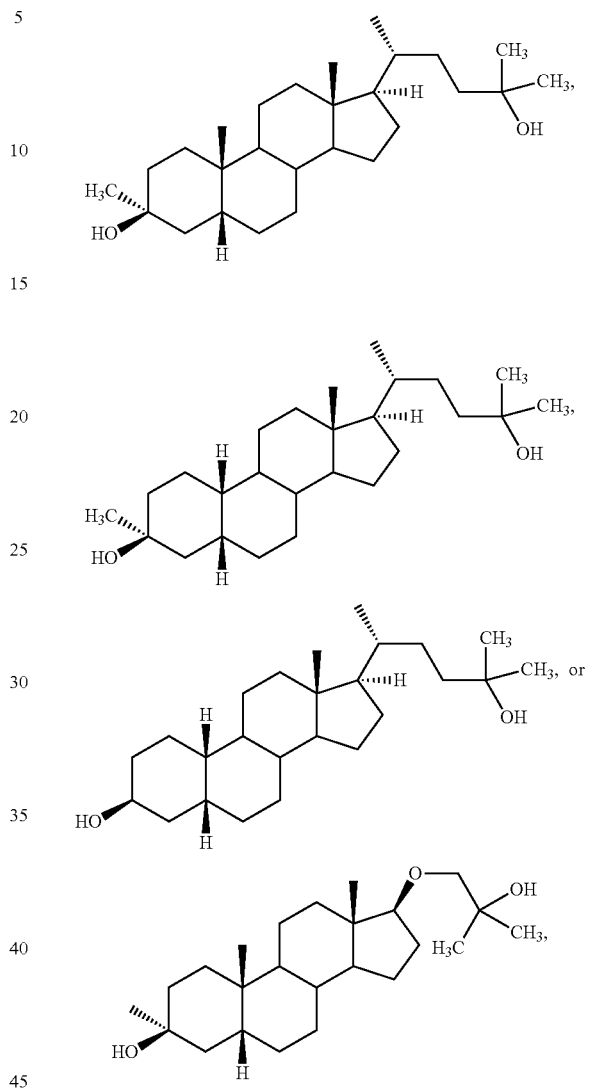

or a pharmaceutically acceptable salt, solvate, prodrug, stereoisomer, tautomer, isotopic variant, or N-oxide thereof, or a combination thereof.

In certain embodiments the compound is any one of the following compounds:

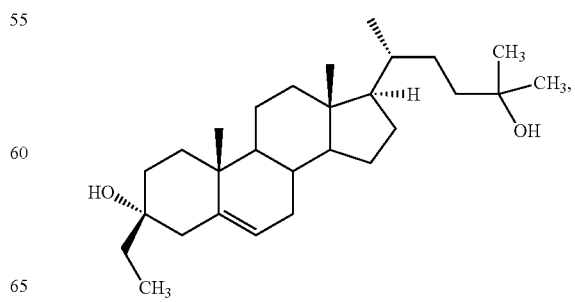

or a pharmaceutically acceptable salt, solvate, prodrug, stereoisomer, tautomer, isotopic variant, or N-oxide thereof, or a combination thereof.

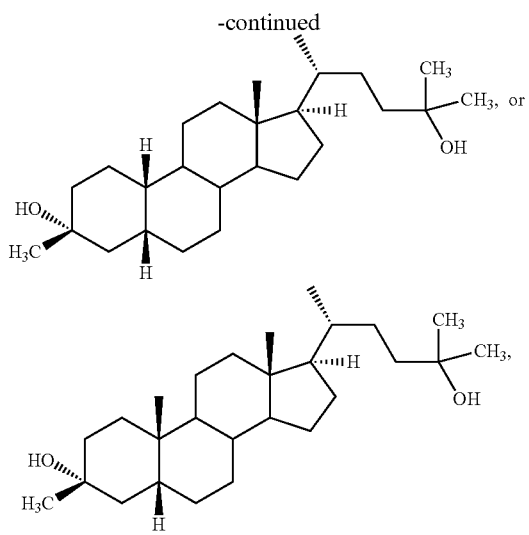

or a pharmaceutically acceptable salt, solvate, prodrug, stereoisomer, tautomer, isotopic variant, or N-oxide thereof, or a combination thereof.

In certain embodiments, the compound of the present invention is a pharmaceutically acceptable salt.

Pharmaceutical Compositions

In another aspect, the invention provides a pharmaceutical composition comprising a pharmaceutically acceptable carrier and a effective amount of a compound of Formula (I).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of the present invention or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound of the present invention. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of the present invention. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of the present invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of the present invention may be admixed as a dry powder with a starch diluent in an approximate 1:1 weight ratio. The mixture is filled into 250 mg capsules (125 mg of active compound per capsule).

Exemplary Formulation 3—Liquid: A compound of the present invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of the present invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of the present invention may be dissolved or suspended in a buffered sterile saline injectable aqueous medium to a concentration of approximately 5 mg/mL.

Exemplary Formulation 6—Tablets: A compound of the present invention may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of the present invention may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of the present invention may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of the present invention may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of the present invention may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Earlier studies (see, e.g., Gee et al., *European Journal of Pharmacology*, 136:419-423 (1987)) demonstrated that certain 3α-hydroxylated steroids are orders of magnitude more potent as modulators of the GRC than others had reported (see, e.g., Majewska et al., *Science* 232:1004-1007 (1986); Harrison et al., *J Pharmacol. Exp. Ther.* 241:346-353 (1987)). Majewska et al. and Harrison et al. taught that 3α-hydroxylated-5-reduced steroids are only capable of much lower levels of effectiveness. In vitro and in vivo experimental data have now demonstrated that the high potency of these steroids allows them to be therapeutically useful in the modulation of brain excitability via the GRC (see, e.g., Gee et al., *European Journal of Pharmacology*, 136:419-423 (1987); Wieland et al., *Psychopharmacology* 118(1):65-71 (1995)).

Various synthetic steroids have also been prepared as neuroactive steroids. See, for example, U.S. Pat. No. 5,232,917, which discloses neuroactive steroid compounds useful in treating stress, anxiety, insomnia, seizure disorders, and mood disorders, that are amenable to GRC-active agents, such as depression, in a therapeutically beneficial manner. Furthermore, it has been previously demonstrated that these steroids interact at a unique site on the GRC which is distinct from other known sites of interaction (e.g., barbiturates, benzodiazepines, and GABA) where therapeutically beneficial effects on stress, anxiety, sleep, mood disorders and seizure disorders have been previously elicited (see, e.g., Gee, K. W. and Yamamura, H. I., "*Benzodiazepines and Barbiturates: Drugs for the Treatment of Anxiety, Insomnia and Seizure Disorders*," in Central Nervous System Disorders, Horvell, ed., Marcel-Dekker, New York (1985), pp. 123-147; Lloyd, K. G. and Morselli, P. L., "*Psychopharmacology of GABAergic Drugs*," in Psychopharmacology: The Third Generation of Progress, H. Y. Meltzer, ed., Raven Press, N.Y. (1987), pp. 183-195; and Gee et al., *European Journal of Pharmacology*, 136:419-423 (1987). These compounds are desirable for their duration, potency and oral activity (along with other forms of administration).

Accordingly, the compounds and pharmaceutical compositions provided herein find use as therapeutics for preventing and/or treating CNS conditions in mammals including humans and non-human mammals. Thus, and as stated earlier, the present invention includes within its scope, and extends to, the recited methods of treatment, as well as to the compounds for such methods, and to the use of such compounds for the preparation of medicaments useful for such methods. It is contemplated that the novel 3α- and 3β-hydroxy steroids of the invention may act as negative allosteric modulators (NAM) of NMDA receptor and thus may be useful for preventing and/or treating a broad range of CNS conditions.

In one aspect, compounds of the present invention are contemplated as therapeutic agents, e.g., for the treatment of CNS conditions in mammals, such as for the treatment of schizophrenia, depression, bipolar disorder (e.g., I and/or II), schizoaffective disorder, mood disorders, anxiety disorders, personality disorders, psychosis, compulsive disorders, post-traumatic stress disorder (PTSD), Autism spectrum disorder (ASD), dysthymia (mild depression), social anxiety disorder, obsessive compulsive disorder (OCD), pain (e.g., a painful syndrome or disorder), sleep disorders, memory disorders, dementia, Alzheimer's Disease, a seizure disorder (e.g., epilepsy), traumatic brain injury (TBI), stroke, addictive disorders (e.g., addiction to opiates, cocaine, and/or alcohol), autism, Huntington's Disease, insomnia, Parkinson's disease, withdrawal syndromes, or tinnitus. In certain embodiments, the compounds of the present invention are useful in the treatment of depression, anxiety, mood disorders, sleep disorders, memory disorders, traumatic brain injury, stroke, epilepsy, and schizophrenia.

In another aspect, provided is a method of treating a mammal susceptible to or afflicted with a condition associated with brain excitability, which method comprises administering an effective amount of one or more of the pharmaceutical compositions described herein.

In yet another aspect, provided is the use of a compound of the present invention as a pharmaceutical, e.g., especially in the treatment or prevention of the aforementioned conditions and diseases.

In still yet another aspect, provided is a method of manufacture of a medicament for the treatment or prevention of one of the aforementioned conditions and diseases.

In still yet another aspect, the present invention provides a method for preventing, treating, ameliorating or managing a disease or condition which comprises administering to a subject in need of such prevention, treatment, amelioration or management, a prophylactically or therapeutically effective amount of a compound of the present invention, or the pharmaceutical composition thereof.

In yet another aspect, the present invention provides a use of a compound of the present invention for the manufacture of a medicament to treat a disease or condition associated with brain excitability. In one embodiment, the disease or condition is selected from depression, anxiety, schizophrenia, sleep disorders, memory disorders, and mood disorders.

In yet another aspect, the present invention provides a method of treatment of a mammal, e.g., a human being, to treat a disease associated with brain excitability, including treating said mammal with an effective amount of a compound of the present invention or composition thereof.

In yet another aspect, the present invention provides a combination of a compound of the present invention and another pharmacologically active agent.

The compounds provided herein can be administered as the sole active agent or they can be administered in combination with other agents. Administration in combination can proceed by any technique apparent to those of skill in the art including, for example, separate, sequential, concurrent and alternating administration.

EXAMPLES

In order that the invention described herein may be more fully understood, the following examples are set forth. The synthetic and biological examples described in this application are offered to illustrate the compounds, pharmaceutical compositions and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, or HPLC. The following schemes are presented with details as to the preparation of representative substituted biarylamides that have been listed herein. The compounds provided herein may be prepared from known or commercially available starting materials and reagents by one skilled in the art of organic synthesis.

The enantiomerically pure compounds provided herein may be prepared according to any techniques known to those of skill in the art. For instance, they may be prepared by chiral or asymmetric synthesis from a suitable optically pure precursor or obtained from a racemate by any conventional technique, for example, by chromatographic resolution using a chiral column, TLC or by the preparation of diastereoisomers, separation thereof and regeneration of the desired enantiomer. See, e.g., "*Enantiomers, Racemates and Resolutions*," by J. Jacques, A. Collet, and S. H. Wilen, (Wiley-Interscience, New York, 1981); S. H. Wilen, A. Collet, and J. Jacques, *Tetrahedron*, 2725 (1977); E. L. Eliel *Stereochemistry of Carbon Compounds* (McGraw-Hill, N Y, 1962); and S. H. Wilen *Tables of Resolving Agents and Optical Resolutions* 268 (E. L. Eliel ed., Univ. of Notre Dame Press, Notre Dame, IN, 1972, *Stereochemistry of Organic Compounds*, Ernest L. Eliel, Samuel H. Wilen and Lewis N. Manda (1994 John Wiley & Sons, Inc.), and *Stereoselective Synthesis A Practical Approach*, Mihály Nógrádi (1995 VCH Publishers, Inc., NY, NY).

In certain embodiments, an enantiomerically pure compound of the present invention may be obtained by reaction of the racemate with a suitable optically active acid or base. Suitable acids or bases include those described in Bighley et al., 1995, *Salt Forms of Drugs and Adsorption*, in *Encyclopedia of Pharmaceutical Technology*, vol. 13, Swarbrick & Boylan, eds., Marcel Dekker, New York; ten Hoeve & H. Wynberg, 1985, *Journal of Organic Chemistry* 50:4508-4514; Dale & Mosher, 1973, *J. Am. Chem. Soc.* 95:512; and *CRC Handbook of Optical Resolution via Diastereomeric Salt Formation*, the contents of which are hereby incorporated by reference in their entireties.

Enantiomerically pure compounds can also be recovered either from the crystallized diastereomer or from the mother liquor, depending on the solubility properties of the particular acid resolving agent employed and the particular acid enantiomer used. The identity and optical purity of the particular compound so recovered can be determined by polarimetry or other analytical methods known in the art. The diasteroisomers can then be separated, for example, by chromatography or fractional crystallization, and the desired enantiomer regenerated by treatment with an appropriate base or acid. The other enantiomer may be obtained from the racemate in a similar manner or worked up from the liquors of the first separation.

In certain embodiments, enantiomerically pure compound can be separated from racemic compound by chiral chromatography. Various chiral columns and eluents for use in the separation of the enantiomers are available and suitable conditions for the separation can be empirically determined by methods known to one of skill in the art. Exemplary chiral columns available for use in the separation of the enantiomers provided herein include, but are not limited to, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Synthetic Procedures

General processes for preparing compounds of the present invention are provided as further embodiments of the invention and are illustrated in generalized schemes 1-13 and Examples 1-36. For the purpose of Scheme 1-13, if not defined, R' is alkyl, $R^{23}$ is $R^{23a}$ or $R^{23b}$ and $X^1$, $L^1$, $R^1$, $R^{3a}$, $R^{3b}$, $R^{23a}$, and $R^{23b}$, are as described herein.

Scheme 1. Synthesis of 3α-Substituted-3β-hydroxy steroids

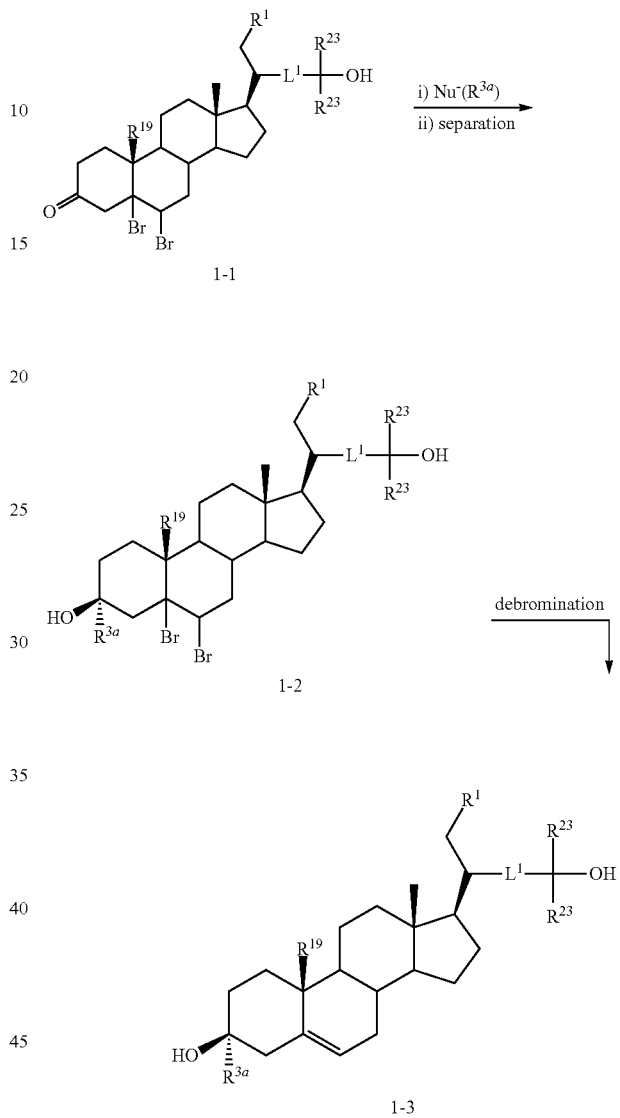

Scheme 2. Synthesis of 3α-Substituted-3β-hydroxy steriods

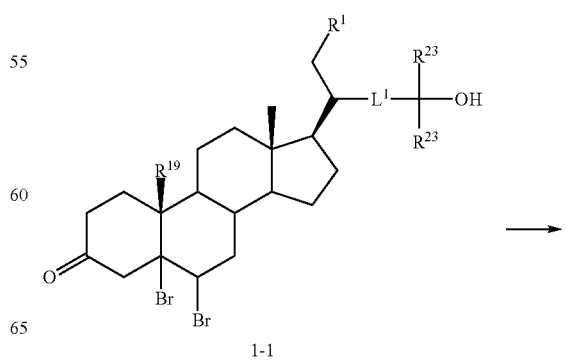

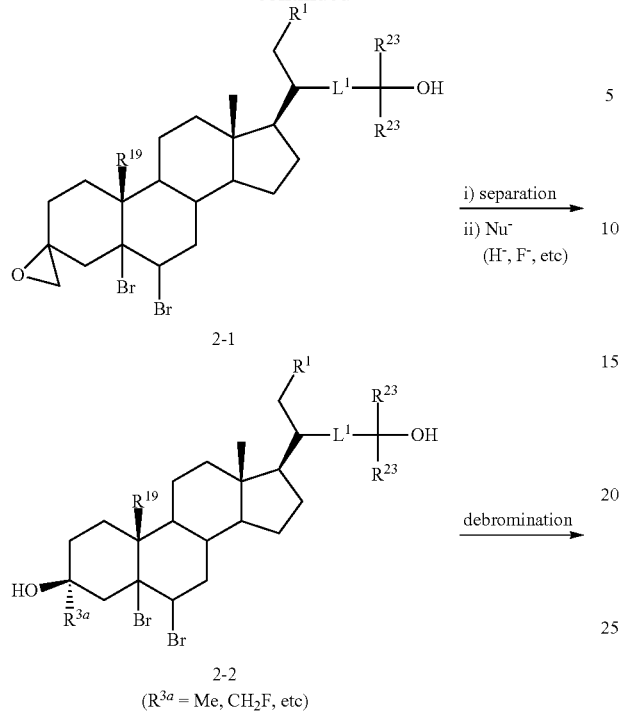
2-1
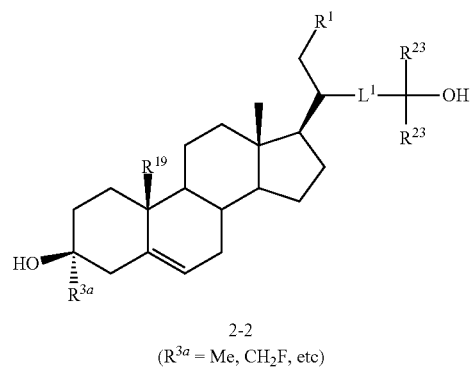
2-2
($R^{3a}$ = Me, $CH_2F$, etc)
2-2
($R^{3a}$ = Me, $CH_2F$, etc)
Scheme 3. Synthesis of 3β-Amino- and 3β-alkylamino steriods
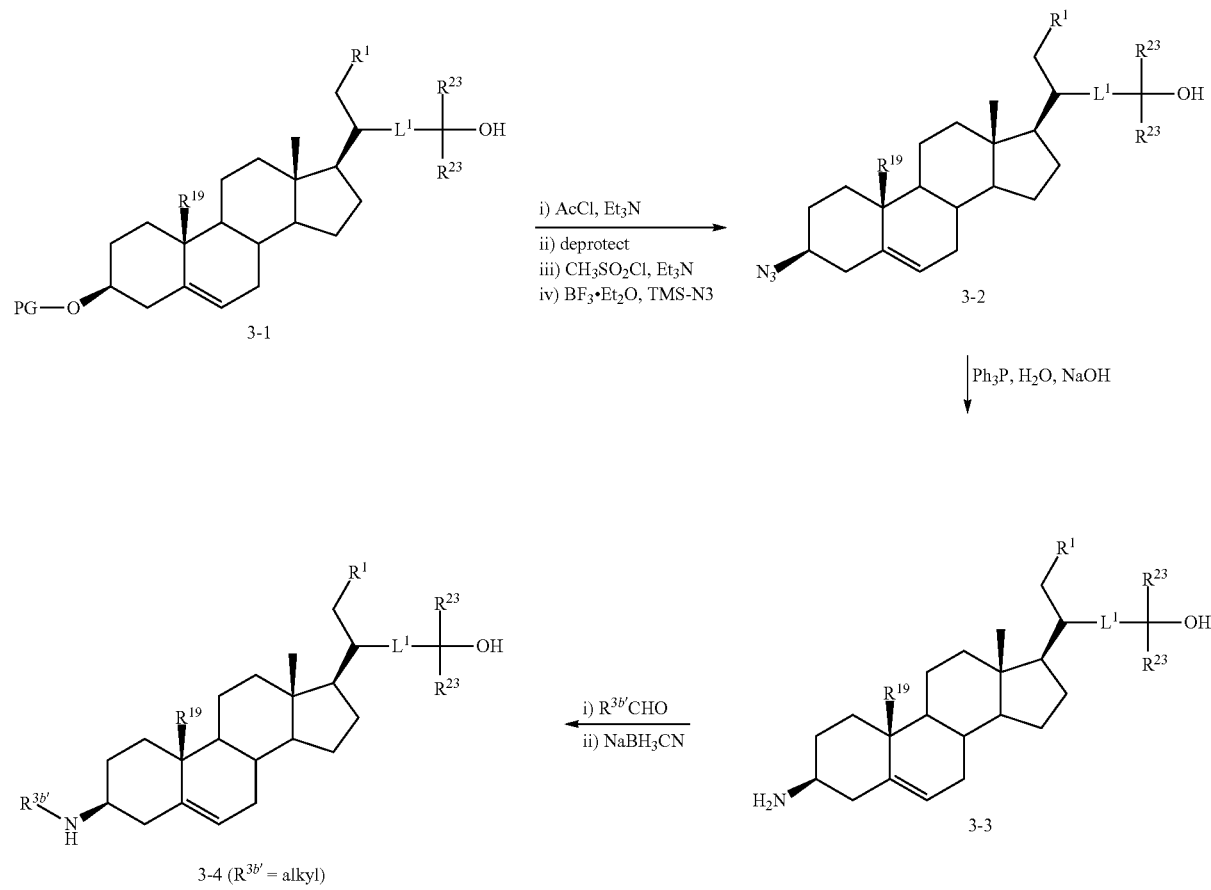

Scheme 4. Synthesis of Steroid sulfates
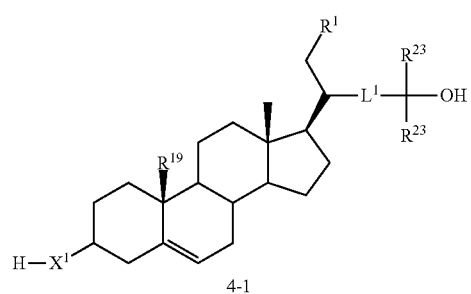
Scheme 5. Synthesis of Steriod 3β-ester and amide
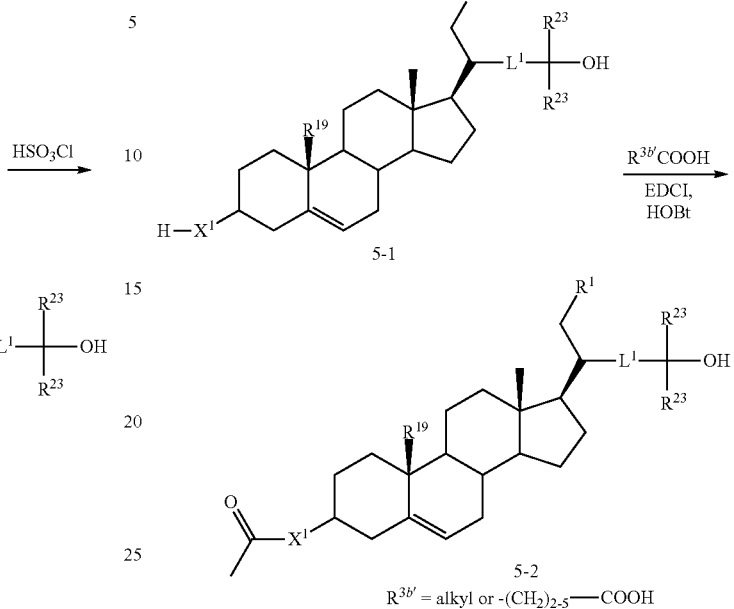
Scheme 6. Synthesis of 3-Oxo Steroids
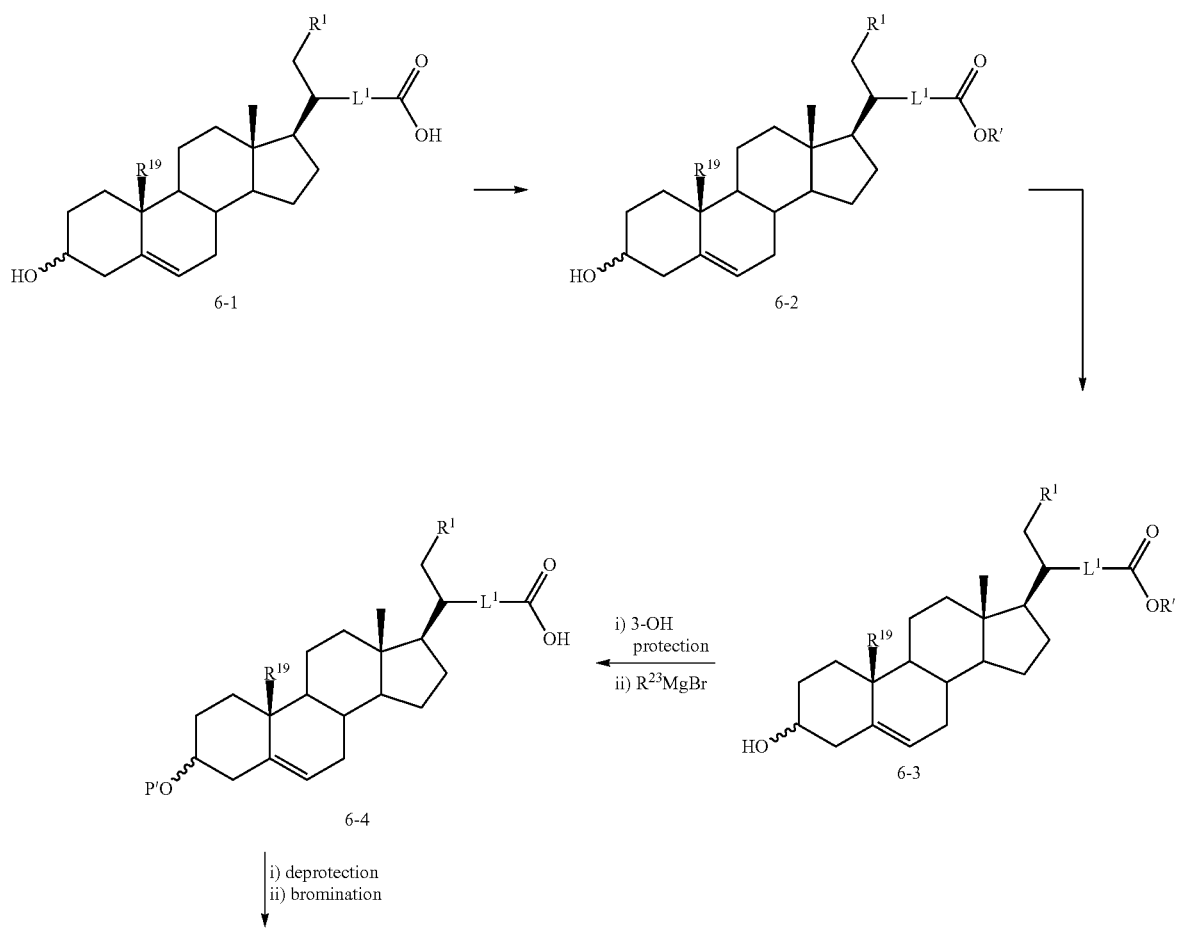

117
118
-continued
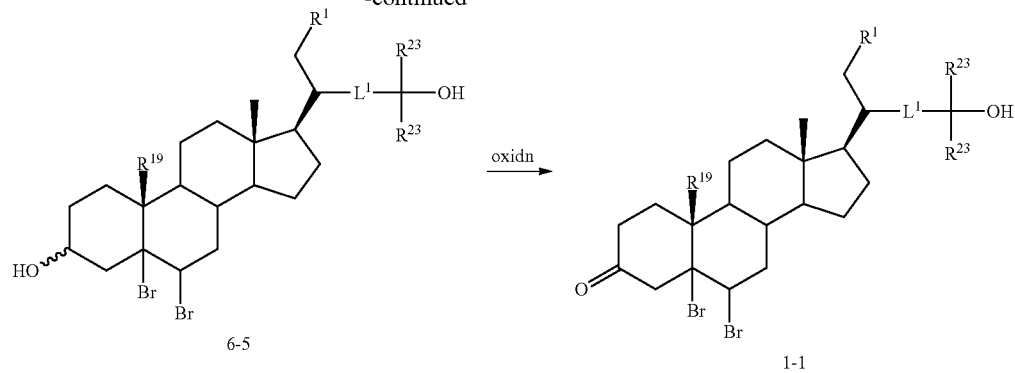
6-5 → (oxidn) → 1-1
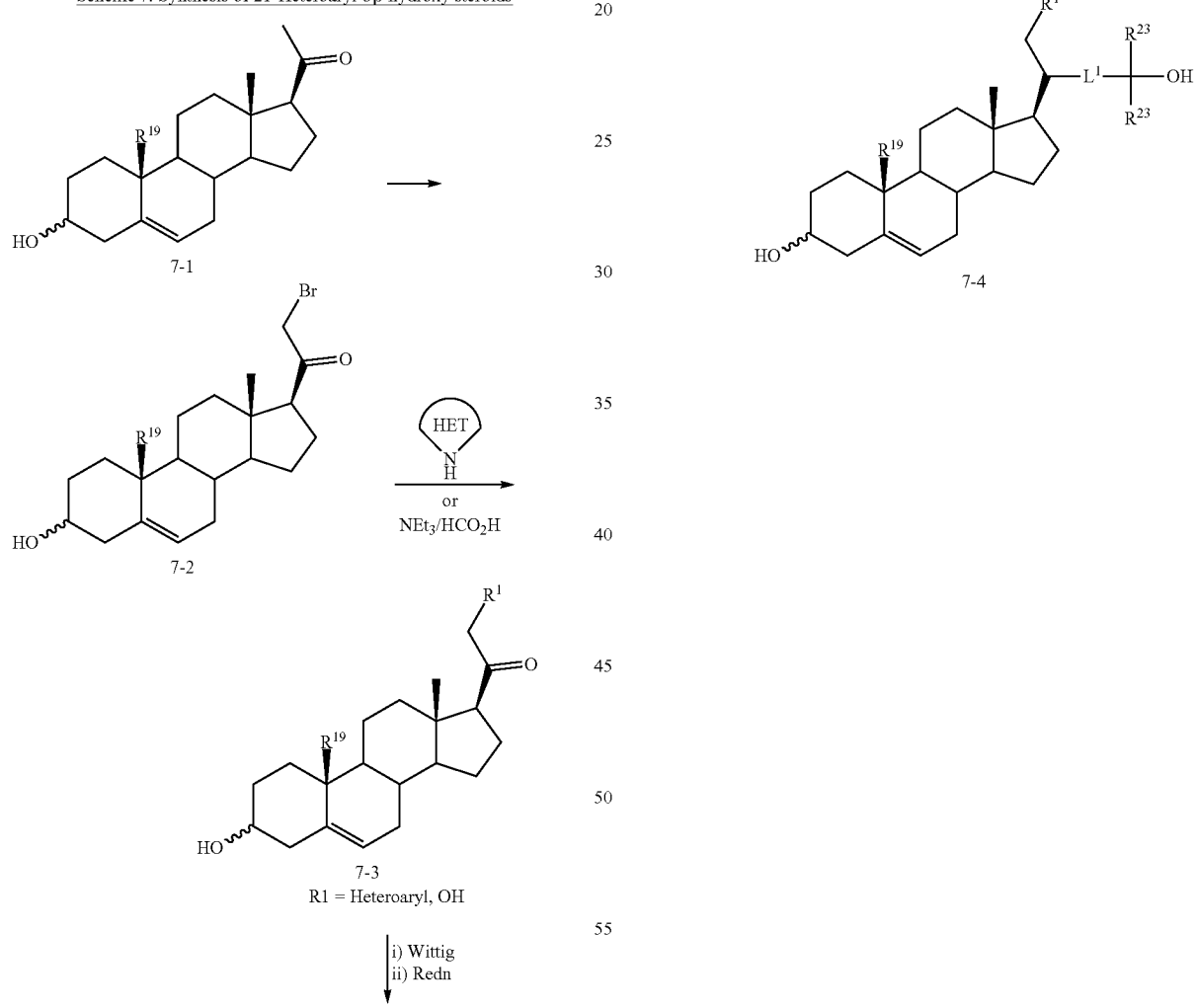
Scheme 7. Synthesis of 21-Heteroaryl-3β-hydroxy steroids
7-1 →
7-2 →(HET-NH or NEt₃/HCO₂H)→
7-3
R1 = Heteroaryl, OH
i) Wittig
ii) Redn
7-4
-continued Scheme 8. Synthesis of 3α-Substituted-3β-hydroxy steroids
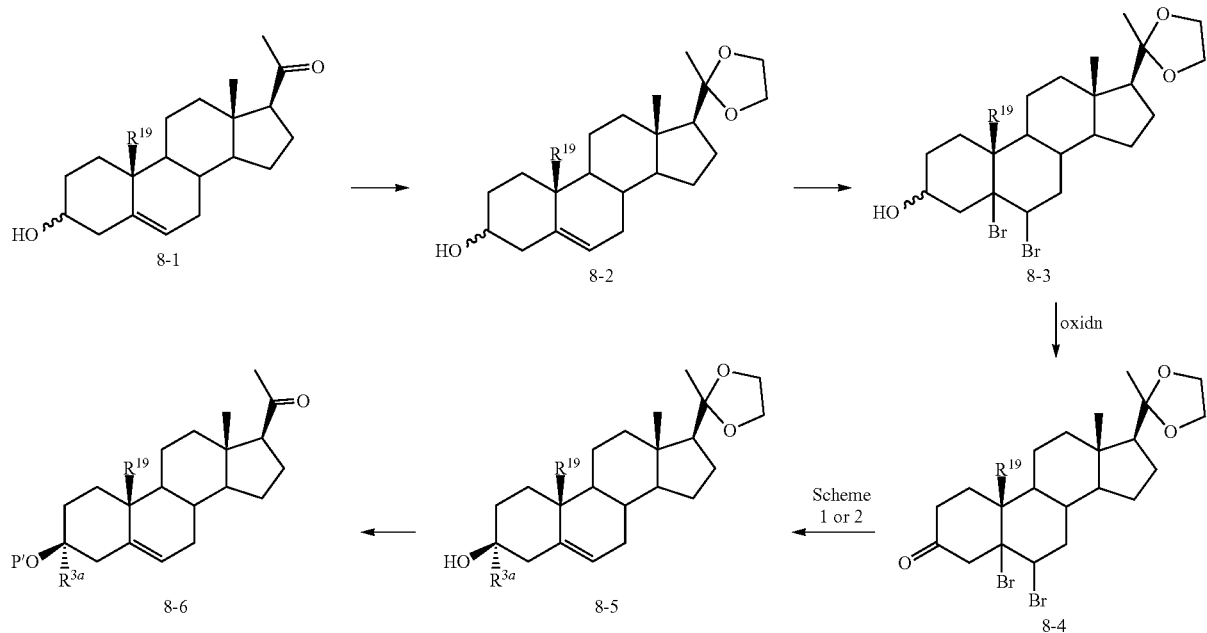
Scheme 9. Synthesis of 3α-substituted-3β-hydroxy steroids
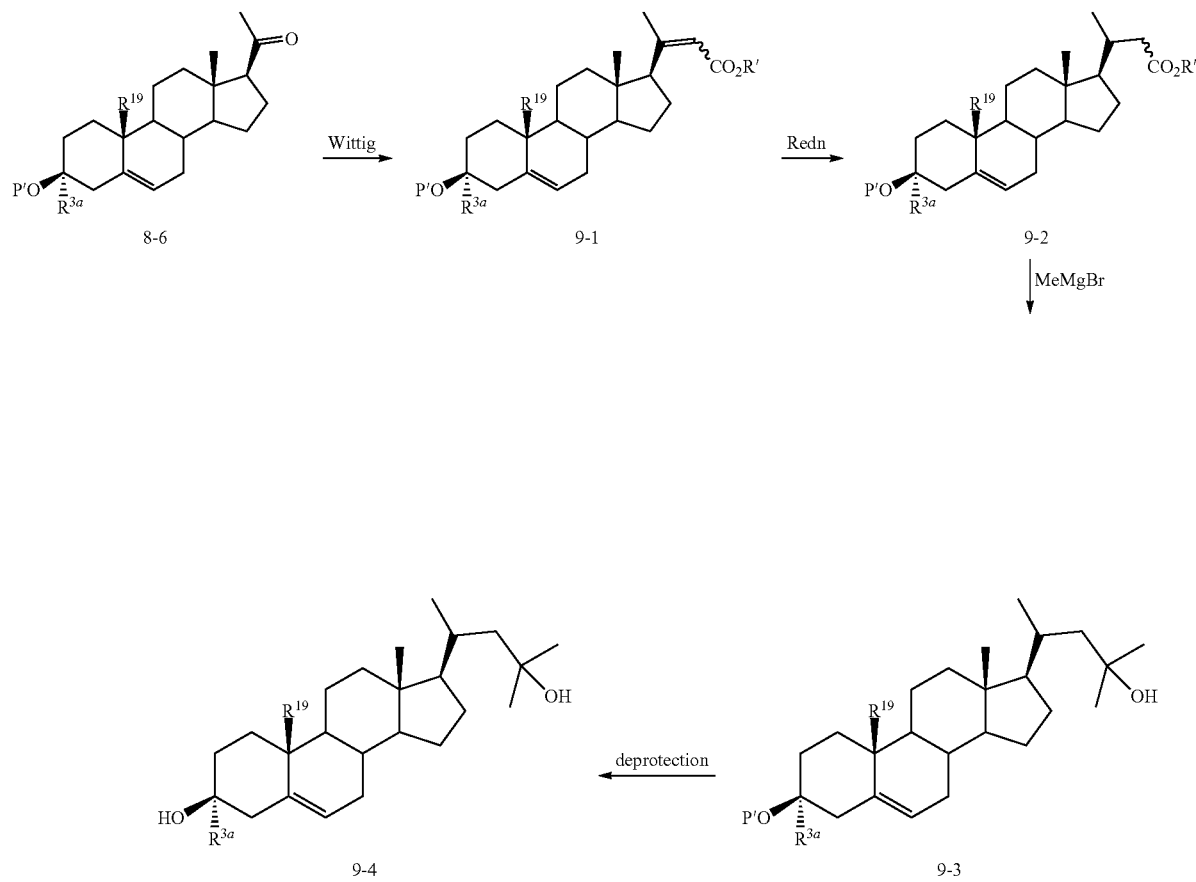

Scheme 10. Synthesis of 3α-substituted-3β-hydroxy steroids
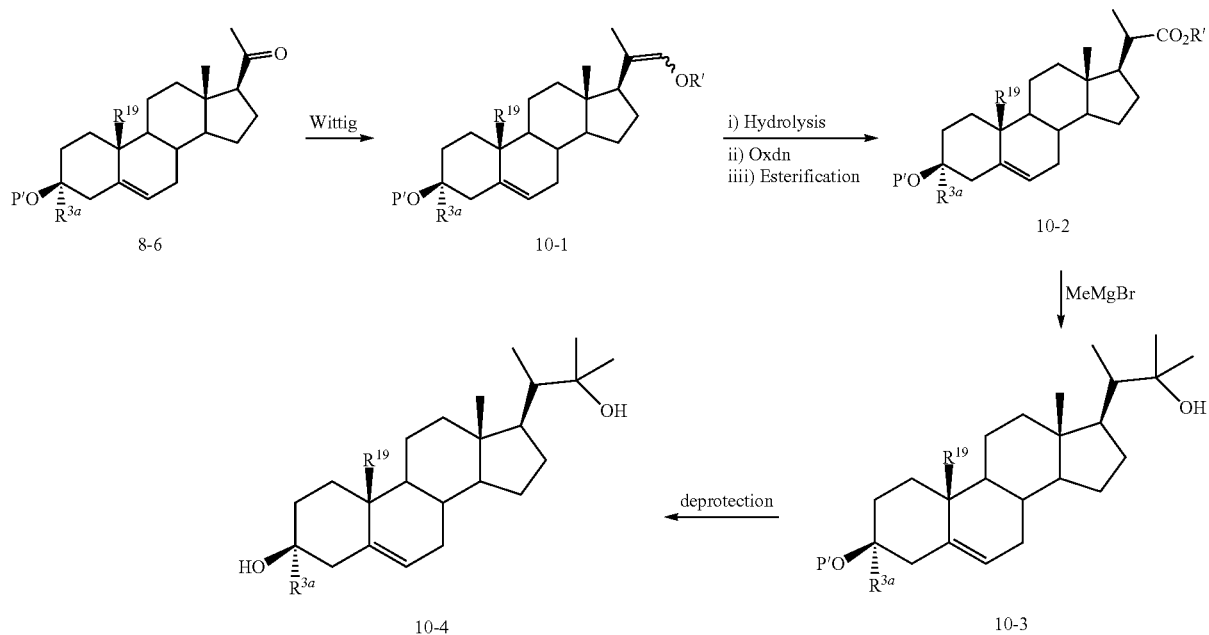
Scheme 11. Synthesis of 3α-substituted-3β-hydroxy steroids
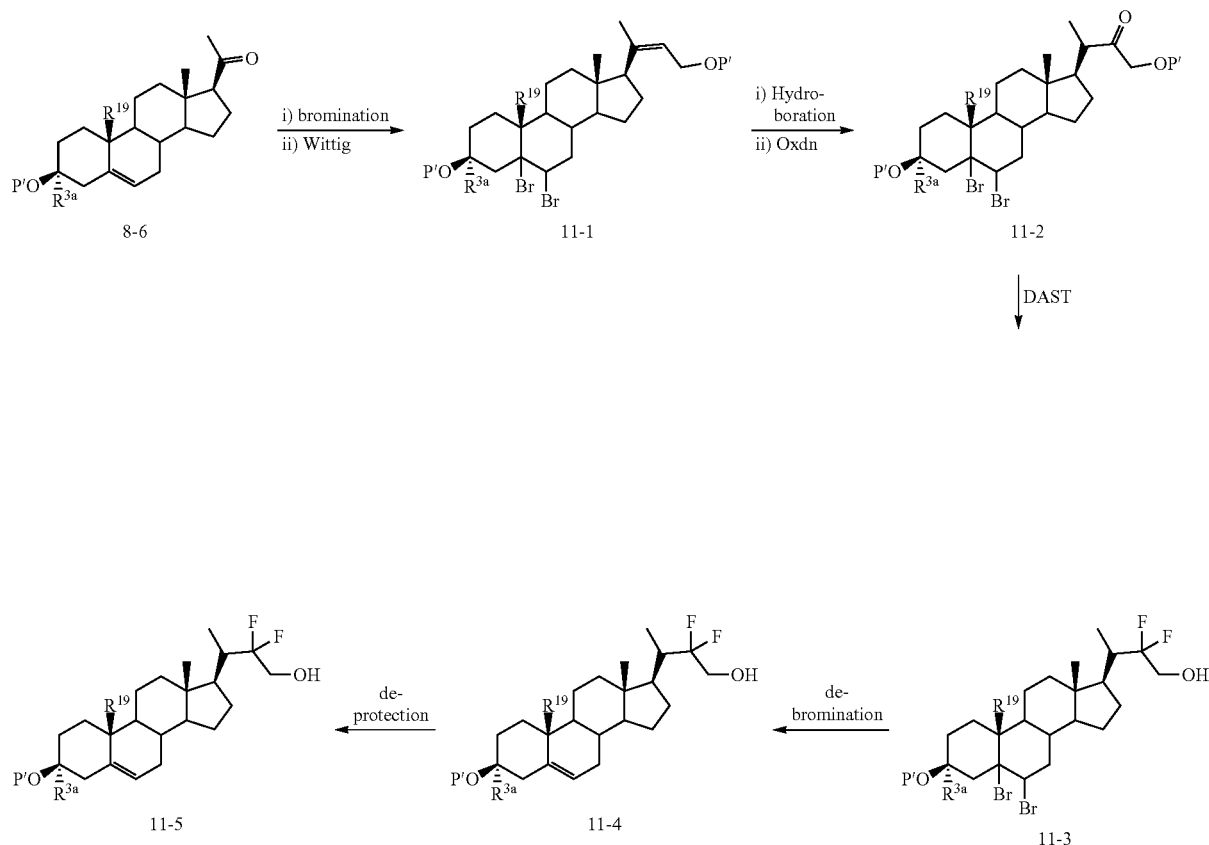

Scheme 12. Synthesis of 3α-Substituted-3β-hydroxy steroids
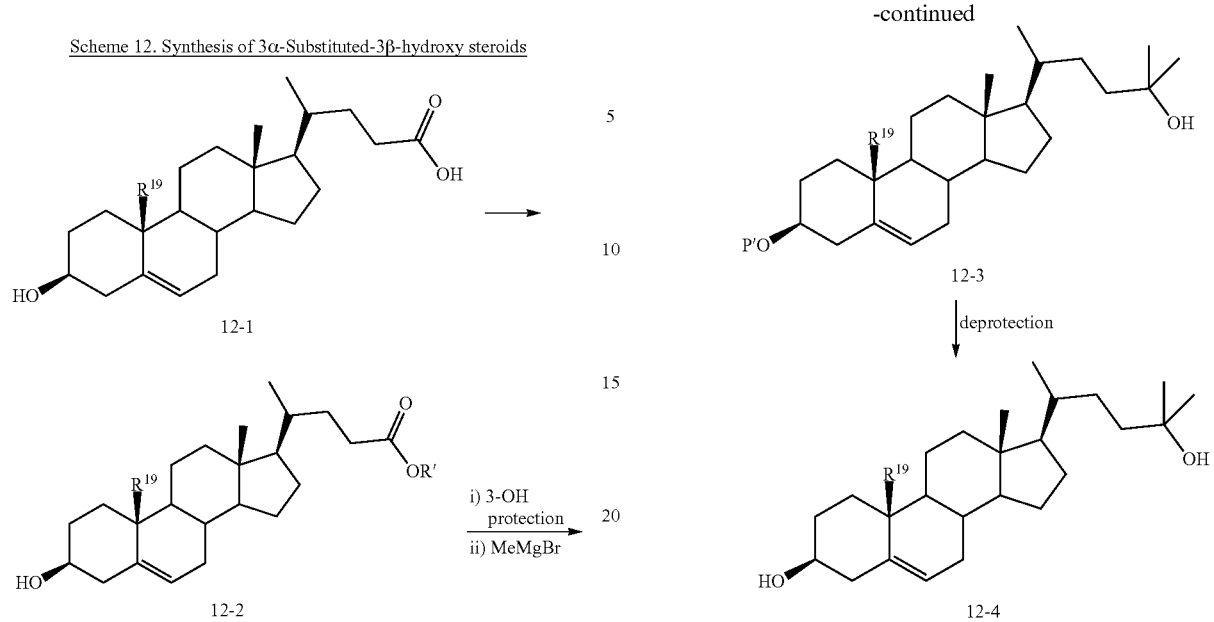
Scheme 13. Synthesis of 3α-Substituted-3β-hydroxy steroids
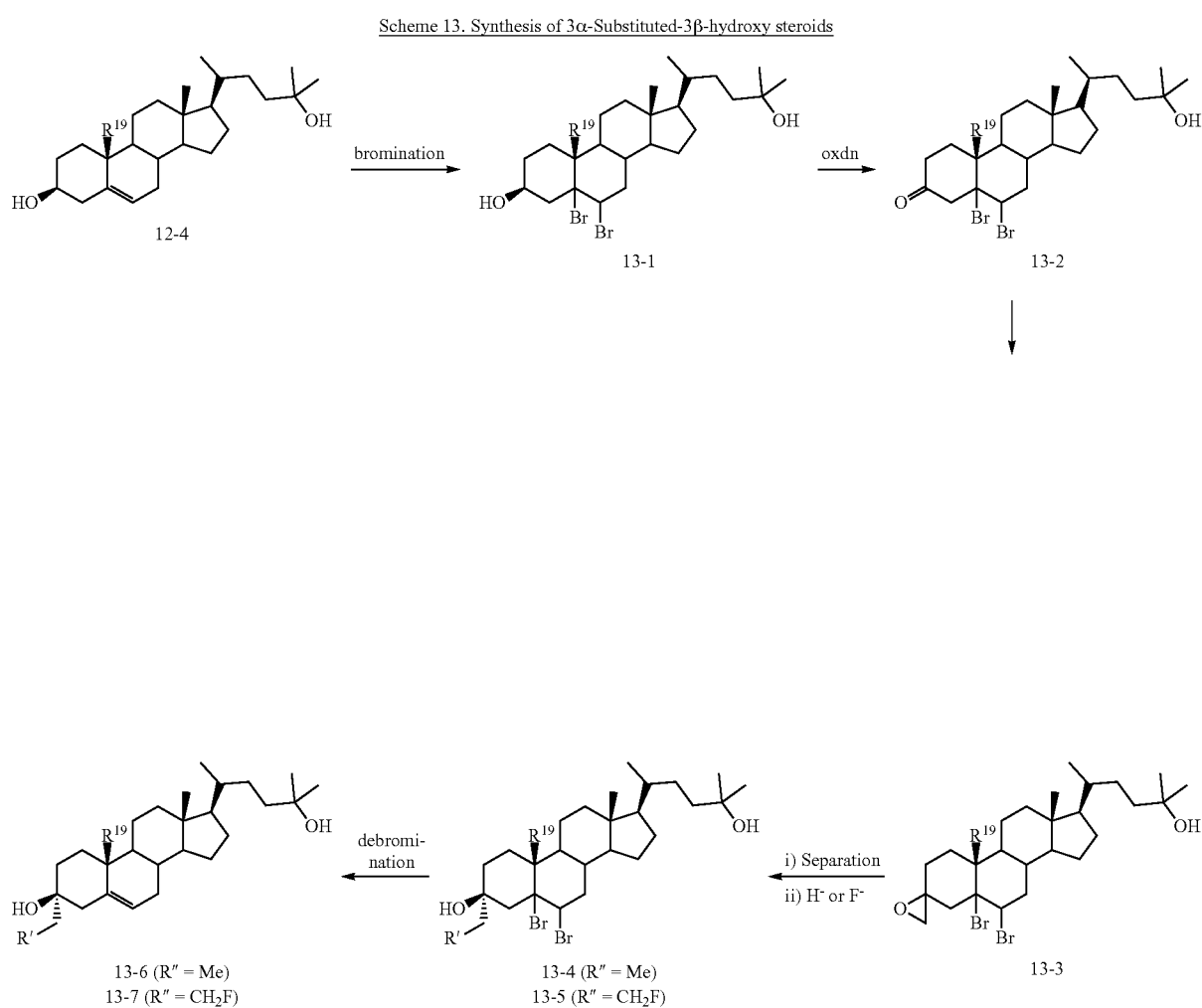

Example 1. Preparation of Compound ST-200-A-001

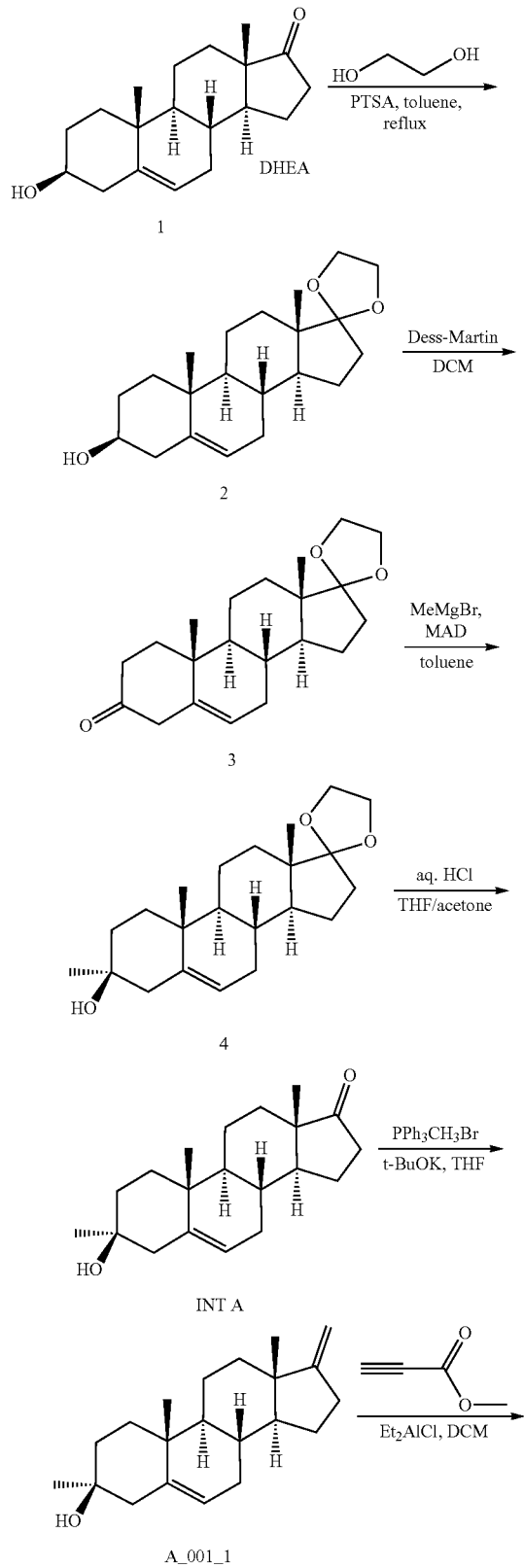

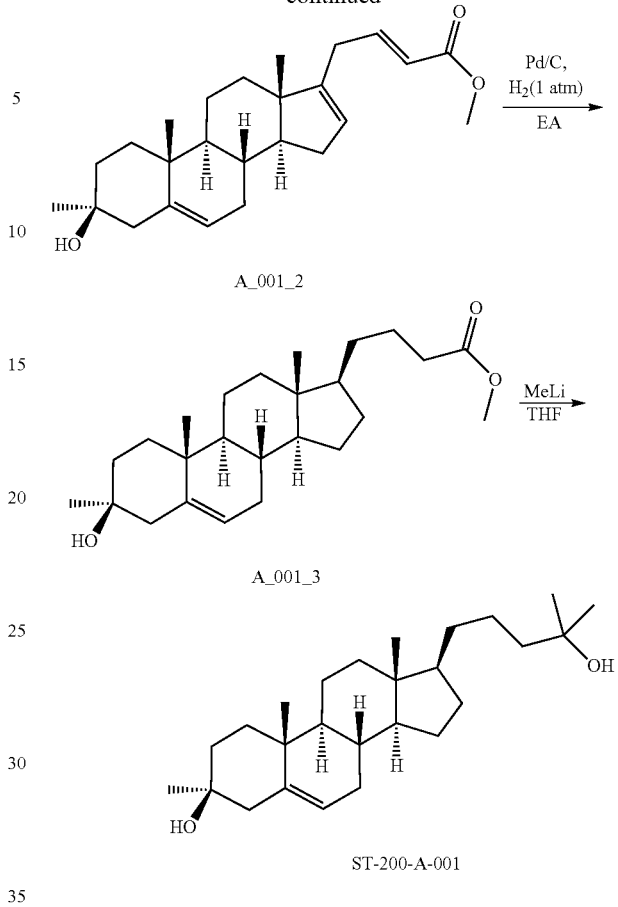

Preparation of Compound 2: To a solution of ketone 1 (50.0 g, 0.17 mol, 1.0 eq) and ethylene glycol (62 mL) in toluene (600 mL) was added p-toluenesulfonic acid (1.4 g, 7.28 mmol). The reaction mixture was heated at reflux overnight with a Dean-Stark trap. LCMS showed the starting material was consumed completely. The mixture was cooled to room temperature, diluted with ethyl acetate (500 mL), and washed with saturated aqueous sodium bicarbonate (300 mL×2) and brine (300 mL×2). The organic phase was dried over sodium sulfate and concentrated in vacuum to afford crude product 2 (64.0 g, 100%) which was directly used in the next step without further purification. $^1$H NMR: (400 MHz, CDCl3) δ 5.35 (d, J=5.6 Hz, 1H), 3.97-3.82 (m, 4H), 3.59-3.47 (m, 1H), 2.34-2.21 (m, 2H), 2.06-1.94 (m, 2H), 1.90-1.74 (m, 3H), 1.73-1.64 (m, 1H), 1.63-1.33 (m, 10H), 1.32-1.19 (m, 1H), 1.14-1.03 (m, 1H), 1.01 (s, 3H), 0.99-0.93 (m, 1H), 0.86 (s, 3H).

Preparation of Compound 3: To a solution of compound 2 (32 g, 96 mmol, 1.0 eq) in dry $CH_2Cl_2$ (1200 mL) was added Dess-Martin (81 g, 192 mmol, 2.0 eq) in portions at 0° C. Then the reaction mixture was stirred at room temperature for 3 h. TLC (PE:EA=3:1) showed the starting material was consumed completely. The mixture was quenched with saturated aqueous $NaHCO_3/Na_2S_2O_3$=1:3 (1 L). The organic phase was washed with brine (500 mL) and dried over $Na_2SO_4$, and the solvent was evaporated to afford crude product 3 (33.0 g, 100%), which was directly used in the next step without further purification. $^1$H NMR: (400 MHz, CDCl3) δ 5.34 (d, J=5.2 Hz, 1H), 3.77-4.00 (m, 4H), 3.19-3.39 (m, 1H), 2.83 (dd, J=16.44, 2.13 Hz, 1H), 2.38-2.59 (m, 1H), 2.21-2.37 (m, 1H), 1.95-2.09 (m, 3H), 1.54-

1.73 (m, 4H), 1.74-1.90 (m, 2H), 1.37-1.51 (m, 3H), 1.21-1.34 (m, 2H), 1.19 (s, 3H), 0.98-1.12 (m, 1H), 0.83-0.93 (m, 3H).

Preparation of MAD: To a solution of compound 5 (96 g, 436 mmol, 1.0 eq) in toluene (300 mL) was added a solution of AlMe$_3$ (109 mL, 218 mmol, 0.5 eq, 2 M in hexane) at room temperature, at which time the methane gas was evolved immediately. The resulting mixture was stirred at room temperature for 1 h and used as a solution of MAD in toluene in the next step without any purification.

Preparation of Compound 4: To a solution of MAD (218 mmol, 2.3 eq, freshly prepared) in toluene (300 mL) was added dropwise a solution of compound 4 (33 g, 96 mmol, 1.0 eq) in toluene (100 mL) at −78° C. during a period of 1 h under nitrogen. Then the reaction mixture was stirred for 30 min, a solution of MeMgBr (205 mL, 288 mmol, 3.0 eq, 1.4 M in toluene) was added dropwise at −78° C. The reaction mixture was warmed to −40° C. and stirred at this temperature for 3 h. TLC (PE:EA=3:1) showed that the starting material was consumed completely. The mixture was poured into saturated aqueous NH$_4$Cl solution (200 mL) and extracted with EA (150 mL×2). The combined organic phases were dried over Na$_2$SO$_4$, and the solvent was evaporated to afford crude product. The crude product was purified by silica gel chromatography eluted with PE:EA (15:1) to give the product (7.64 g, 22%) as white powder.

$^1$H NMR: (400 MHz, CDCl3) δ 5.30 (d, J=5.2 Hz, 1H), 3.75-4.04 (m, 4H), 2.42 (d, J=13.6 Hz, 1H), 1.88-2.12 (m, 3H), 1.73-1.86 (m, 2H), 1.64-1.72 (m, 2H), 1.52-1.63 (m, 4H), 1.35-1.51 (m, 4H), 1.19-1.32 (m, 1H), 1.12-1.18 (m, 1H), 1.10 (s, 3H), 0.99-1.03 (m, 3H), 0.92-0.98 (m, 1H), 0.86 (s, 3H).

Compound INT A: To a solution of compound 4 (6.0 g, 17.3 mmol, 1.0 eq) in THF (200 mL) was added aqueous HCl solution (35 mL, 1 M) and acetone (35 mL). The reaction mixture was stirred at room temperature overnight. TLC (PE:EA=3:1) indicated that the reaction was complete. Then the reaction mixture was diluted with EA (200 mL), washed with saturated aqueous NaHCO$_3$ solution (200 mL), dried over Na$_2$SO$_4$ and evaporated under reduced pressure to give the product (5.2 g, 99.2%). $^1$H NMR: (400 MHz, CDCl3) δ 5.27 (d, J=6.8 Hz, 1H), 2.45-2.35 (m, 2H), 2.09-1.84 (m, 4H), 1.82-1.57 (m, 6H), 1.50-1.35 (m, 4H), 1.26-1.08 (m, 4H), 1.05 (s, 3H), 0.95 (s, 3H), 0.86 (s, 3H).

Compound A_001_1: To a solution of PPh$_3$CH$_3$Br (28.3 g, 79.35 mmol) in THF (50 mL) was added a solution of t-BuOK (8.96 g, 79.35 mmol) in THF (20 mL) at room temperature. After stirring for 1 h, INT A (4.0 g, 13.22 mmol) dissolved in THF (10 mL) was added dropwise. The reaction mixture was refluxed for 3 h. The reaction mixture was cooled to room temperature and quenched with Sat. NH$_4$Cl, extracted with EA. The combined organic layer was washed with brine, dried and concentrated to give the crude product, which was purified by a flash column chromatography (PE/EA=15/1) to afford compound A_001_1 (3.2 g, Y=80%) as a white solid. $^1$H NMR: (400 MHz, CDCl3) δ 5.32 (d, J=5.2 Hz, 1H), 4.65-4.64 (m, 2H), 2.50-2.42 (m, 2H), 2.27-2.22 (m, 1H), 2.07-1.97 (m, 1H), 1.87-1.68 (m, 4H), 1.68-1.49 (m, 7H), 1.40-1.15 (m, 4H), 1.12 (s, 3H), 1.05 (s, 3H), 1.04-0.96 (m, 1H), 0.80 (s, 3H).

Preparation of Compound A_001_2: To a solution of compound A_001_1 (300 mg, 1.0 mmol, 1.0 eq) and methyl propiolate (250 mg, 3.0 mmol, 3.0 eq) in CH$_2$Cl$_2$ (5 mL) was added dropwise Et$_2$AlCl (4 mL, 4.0 mmol, 4.0 eq, 1 M in toluene) with stirring at 25° C., then the reaction mixture was stirred overnight. TLC (PE/EA=3/1) indicated that the starting material was consumed completely. The solution was washed with saturated aqueous NaHCO$_3$ (5 mL), dried over Na$_2$SO$_4$ and concentrated under reduced pressure to provide the crude product which was purified by silica gel chromatography eluted with PE:EA (15:1) to give the desired product (200 mg, 52%) as a white powder. $^1$H NMR: (400 MHz, CDCl$_3$) δ 7.03-6.97 (m, 1H), 5.86 (dd, J$_1$=1.2 Hz, J$_2$=15.6 Hz, 1H), 5.35 (d, J=1.2 Hz, 1H), 5.32 (d, J=5.2 Hz, 1H), 3.72 (s, 3H), 2.87 (d, J=6.8 Hz, 2H), 2.42 (d, J=13.2 Hz, 1H), 2.13-1.95 (m, 3H), 2.00-1.40 (m, 11H), 1.40-1.20 (m, 4H), 1.11 (s, 3H), 1.06 (s, 3H), 0.90-0.82 (m, 3H), 0.78 (s, 3H).

Preparation of Compound A_001_3: To a solution of compound A_001_2 (192 mg, 0.5 mmol, 1.0 eq) in EA (5 mL) was added Pd/C (5%, 40 mg) under N$_2$. The suspension was degassed under vacuum and purged with H$_2$ several times. Then the mixture was stirred under H$_2$ balloon at 30° C. for 1 h. TLC (PE:EA=3:1) showed that the reaction was complete. The suspension was filtered through a pad of celite and the pad was washed with EA (5 mL×2). The combined filtrates were concentrated to dryness to give the product (185 mg, 95%) as a white powder. $^1$H NMR: (400 MHz, CDCl$_3$) δ 5.31 (d, J=4.4 Hz, 1H), 3.67 (s, 3H), 2.42 (d, J=13.2 Hz, 1H), 2.35-2.28 (m, 2H), 2.02-1.92 (m, 2H), 1.90-1.60 (m, 6H), 1.55-1.30 (m, 6H), 1.30-1.13 (m, 5H), 1.12 (s, 3H), 1.02 (s, 3H), 1.00-0.75 (m, 4H), 0.58 (s, 3H).

Preparation of Compound ST-200-A-001: To a solution of compound A_001_3 (150 mg, 0.386 mmol, 1.0 eq) in THF (5 mL) was added dropwise MeLi (2 mL, 3.200 mmol, 8.3 eq, 1.6 M in THF) at −78° C. under nitrogen. After the addition the reaction mixture was warmed to −40° C. and stirred for 1 h. TLC (PE:EA=3:1) showed that the reaction was complete. The reaction mixture was quenched with saturated aqueous NH$_4$Cl (10 mL), extracted with EA (10 mL×2). The combined organic layers were concentrated under reduced pressure to provide the crude product which was purified by silica gel chromatography eluted with PE:EA (10:1) to give product (91 mg, 60%) as a white powder. $^1$H NMR: (400 MHz, CDCl$_3$) δ 5.31 (d, J=5.6 Hz, 1H), 2.43 (d, J=13.2 Hz, 1H), 2.05-1.95 (m, 2H), 1.90-1.60 (m, 6H), 1.21 (s, 6H), 1.12 (s, 3H), 1.11-1.04 (m, 1H), 1.03 (s, 3H), 1.01-0.92 (m, 2H), 0.58 (s, 3H).

Example 2. Preparation of Compound ST-200-A-003

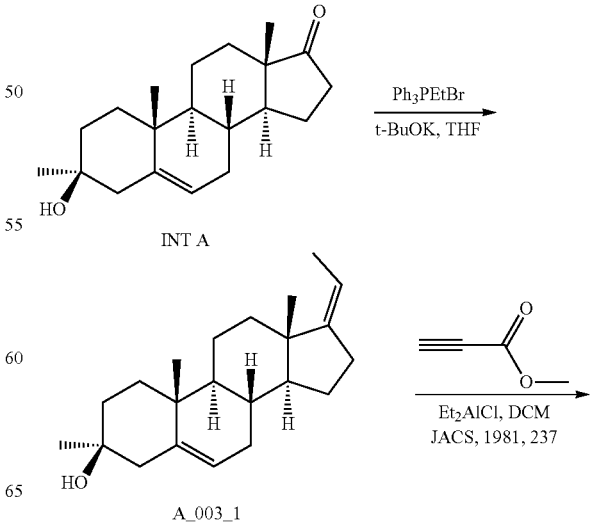

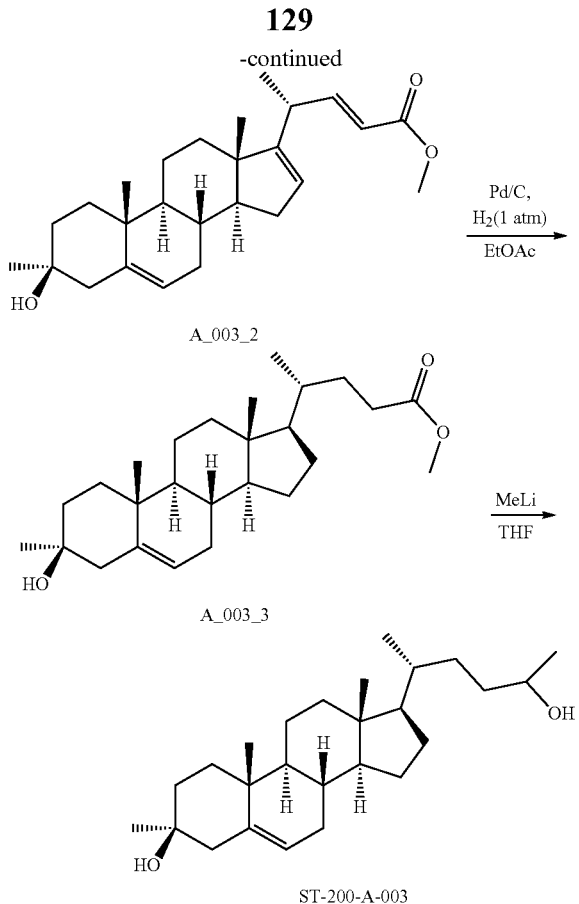

Preparation of Compound A_003_1: To a solution of Ph₃PEtBr (12.25 g, 33.00 mmol, 10.0 eq) in dry THF (15 mL) was added dropwise a solution of t-BuOK (3.70 g, 33.00 mmol, 10.0 eq) in dry THF (10 mL) under N₂ at 0° C. The mixture was stirred at room temperature for 1.5 h. Then a solution of INT A (1.00 g, 3.31 mmol, 1.0 eq) in THF (10 mL) was added dropwise and the resulting mixture was stirred at 70° C. for 4 h. TLC (PE:EA=3:1) indicated that the starting material was consumed completely. The reaction was quenched with saturated aqueous NH₄Cl solution (50 mL) and extracted with EA (30 mL×2). The combined organic phases were dried over Na₂SO₄ and concentrated in vacuum. The residue was purified by column chromatography on silica gel (eluent: PE:EA=12:1) to give the product (900 mg, 90.9%) as a white powder. ¹H NMR: (400 MHz, CDCl3) δ 5.32 (d, J=5.2 Hz, 1H), 5.15-5.12 (m, 1H), 2.44-2.30 (m, 3H), 2.29-2.21 (m, 1H), 2.05-1.97 (m, 2H), 1.81-1.45 (m, 14H), 1.30-1.15 (m, 3H), 1.12 (s, 3H), 1.02 (s, 3H), 0.95-1.01 (m, 1H), 0.90 (s, 3H).

Preparation of Compound A_003_2: To a solution of compound A_003_1 (1.00 g, 3.20 mmol, 1.0 eq) and methyl propiolate (0.67 g, 8.00 mmol, 2.5 eq) in dry DCM (15 mL) was added dropwise a solution of Et₂AlCl (12.8 mL, 12.8 mmol, 4.0 eq, 1 M in toluene) with stirring at 0° C. Then the reaction was warmed to room temperature and stirred overnight. TLC (PE:EA=5:1) indicated that the starting material was consumed completely. The mixture was quenched with saturated aqueous NaHCO₃ solution (30 mL) and extracted with DCM (30 mL×2). The combined organic phases were dried over Na₂SO₄ and concentrated in vacuum. The residue was purified by column chromatography on silica gel (eluent: PE:EA=10:1) to give product (1.00 g, 78.7%) as white powder. ¹H NMR: (400 MHz, CDCl3) δ 6.97-6.91 (m, 1H) 5.82 (d, J=16 Hz, 1H), 5.42-5.41 (m, 1H), 5.32 (d, J=5.2 Hz, 1H), 3.73 (s, 3H), 3.04-3.00 (m, 1H), 2.43 (d, J=12.8 Hz, 1H), 2.11-1.97 (m, 3H), 1.88-1.50 (m, 12H), 1.40-1.20 (m, 3H), 1.21-1.26 (m, 1H), 1.18 (d, J=6.78 Hz, 3H), 1.12 (s, 3H), 1.04 (s, 3H), 0.82 (s, 3H).

Preparation of Compound A_003_3: To a solution of compound A_003_2 (160 mg, 0.40 mmol) in EA (15 mL) was added Pd/C (30 mg, 5%). Then the reaction was stirred under 15 psi of H₂ pressure at room temperature for 2 h. TLC (PE/EA=3/1) showed that the starting material was consumed completely. And then the reaction mixture was filtered and the filtrate was evaporated under reduced pressure to give the product (150 mg, 92.8%). ¹H NMR: (400 MHz, CDCl3) δ 5.32 (d, J=5.2 Hz, 1H), 3.67 (s, 3H), 2.48-1.96 (m, 7H), 1.90-1.62 (m, 5H), 1.60-1.55 (m, 7H), 1.11 (s, 3H), 1.03-0.99 (m, 3H), 0.95-0.93 (m, 2H), 0.70-0.66 (m, 2H).

Preparation of Compound ST-200-A-003: To a solution of compound A_003_2 (100 mg, 0.25 mmol, 1.0 eq) in dry THF (1 mL) under N₂ protection was added dropwise MeLi (1.56 mL, 2.50 mmol, 1.6 M in THF) at −78° C. and the mixture was stirred at this temperature for 30 min. TLC (PE:EA=3:1) showed that the reaction was complete. The reaction mixture was quenched with saturated aqueous NH₄Cl (5 mL) and extracted with EA (5 mL×2). The combined organic layers were concentrated under reduced pressure to provide the crude product, which was purified by silica gel chromatography eluted with PE:EA (10:1) to give the product (45 mg, 45%) as a white powder. ¹H NMR: (400 MHz, CDCl3) δ 5.30 (d, J=5.2 Hz, 1H), 2.42 (d, J=12 Hz, 1H), 2.02-1.98 (m, 3H), 1.92-1.66 (m, 3H), 1.61-1.56 (m, 2H), 1.55-1.54 (m, 2H), 1.53-1.23 (m, 11H), 1.20 (s, 6H), 1.10 (s, 3H), 1.05 (s, 3H), 1.02 (s, 3H), 0.95-0.90 (m, 3H), 0.68 (s, 3H).

Example 3. Preparation of Compound ST-200-A-007

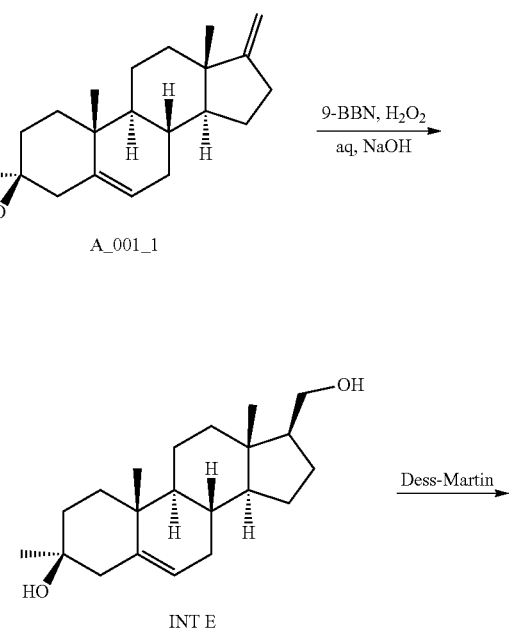

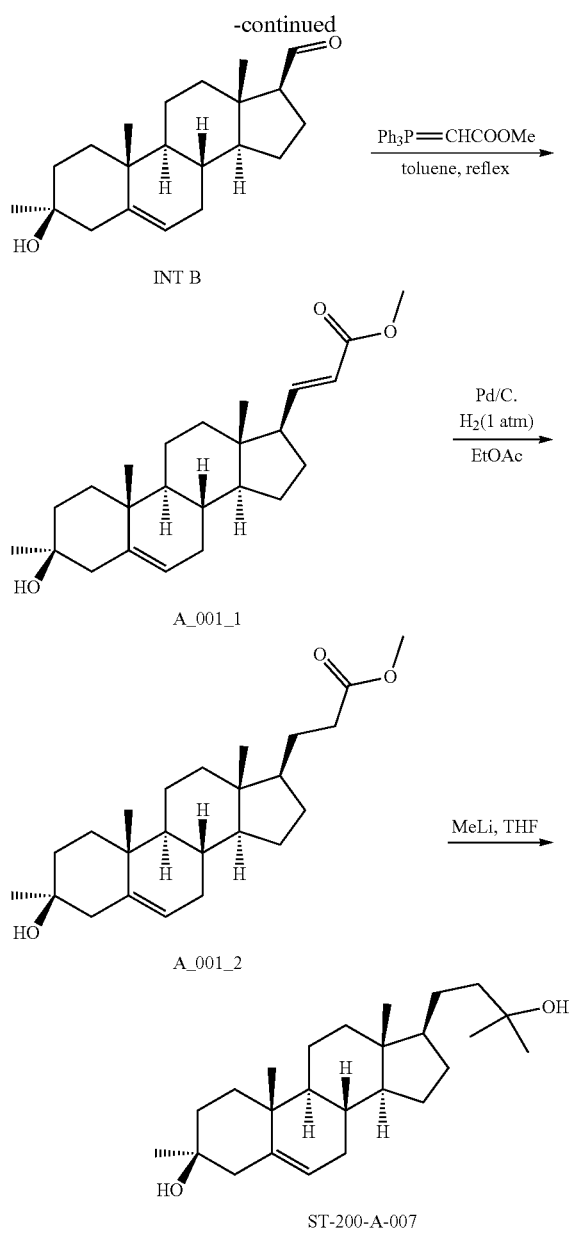

Preparation of Compound INT E: To a solution of 9-BBN (0.5 M in THF, 133 mL, 66.6 mmol, 10.0 eq) under ice-bath, a solution of A_001_1 (2.0 g, 6.66 mmol, 1.0 eq) in THF (10 mL) was added dropwise. The reaction mixture was heated to 60° C. and stirred for 20 h. The mixture was cooled to 0° C. and 10% aqueous NaOH solution (20 mL) followed by 30% aqueous $H_2O_2$ (30%, 10 mL) was added. The mixture was stirred for 2 h at 0° C. and then extracted with EA (30 mL×3). The combined organic layers were washed with brine (30 mL), dried over $Na_2SO_4$ and concentrated in vacuum to give the crude product, which was purified by a flash column chromatography eluted by PE/EA (10/1) to afford INT E (1.0 g, 47%) as a white solid. $^1$H NMR: (400 MHz, $CDCl_3$) δ 5.30 (d, J=5.2 Hz, 1H), 3.75-3.71 (dd, $J_1$=10.4 Hz, $J_2$=6.8 Hz, 1H), 3.58-3.53 (dd, $J_1$=10.4 Hz, $J_2$=7.6 Hz, 1H), 2.43-2.41 (d, J=10.4 Hz, 1H), 2.02-1.96 (m, 2H), 1.91-1.75 (m, 3H), 1.72-1.44 (m, 10H), 1.33-1.20 (m, 5H), 1.18 (s, 3H), 1.06 (s, 3H), 1.04-0.99 (m, 1H), 0.67 (s, 3H).

Preparation of Compound INT B: To a solution of INT E (100 mg, 0.314 mmol, 1.0 eq) in DCM (10 mL) under ice-bath, Dess-Martin reagent (265 mg, 0.628 mmol, 2.0 eq) was added. The reaction mixture was warmed to room temperature and stirred for 2 h. The mixture was poured into a solution of $NaS_2O_3$ (4.5 g) and $NaHCO_3$ (1.5 g) in water (20 mL), extracted with EA (20 mL×3). The combined organic layers were washed with brine (20 mL), dried over $Na_2SO_4$ and concentrated in vacuum to give the crude product (100 mg, 100%) which was used directly in the next step without further purification.

Preparation of Compound A_007_1: A mixture of INT B (100 mg, 0.316 mmol, 1.0 eq) and $Ph_3P$=$CHCOOCH_3$ (634 mg, 1.89 mmol, 6.0 eq) in toluene (10 mL) was stirred for 3 h at 80° C. and then concentrated in vacuum. The residue was purified by a flash column chromatography eluted by PE/EA (12/1) to afford product A_007_1 (65 mg, 55.2%) as a white solid. $^1$H NMR: (400 MHz, $CDCl_3$) δ 6.99-6.93 (dd, $J_1$=16 Hz, $J_2$=8.4 Hz, 1H), 5.82-5.77 (dd, $J_1$=15.6 Hz, $J_2$=1.2 Hz, 1H), 5.30 (d, J=5.2 Hz, 1H), 3.73 (s, 3H), 2.42 (d, J=12.4 Hz, 1H), 2.14-2.11 (m, 1H), 2.05-1.99 (m, 2H), 1.98-1.41 (m, 15H), 1.29-1.24 (m, 2H), 1.12-1.14 (m, 1H), 1.12 (s, 3H), 1.06 (s, 3H), 1.02-0.95 (m, 1H), 0.66 (s, 3H).

Preparation of Compound A_007_2: A mixture of compound A_007_1 (65 mg, 0.174 mmol, 1.0 eq) and Pd/C (5%, 20 mg) in EA (5 mL) was stirred for 2 h at room temperature under $H_2$ (1 atm). The mixture was filtered and the filtrate was concentrated in vacuum to give product A_007_2 (65 mg, 100%) which was used directly in the next step without further purification.

Preparation of Compound ST-200-A-007: To a solution of A_007_2 (65 mg, 0.17 mmol, 1.0 eq) in THF (2 mL) at −78° C., $CH_3L^1$ (1.6 M in THF, 1 mL, 1.7 mmol, 10.0 eq) was added dropwise under nitrogen. The reaction mixture was warmed to room temperature and stirred for 1 h. The mixture was quenched with saturated aqueous $NH_4Cl$ (10 mL) and then extracted with EA (5 mL×2). The combined organic layers were washed with brine (5 mL), dried over $Na_2SO_4$ and concentrated in vacuum to give the crude product, which was purified by a flash column chromatography (eluent: PE/EA=8/1) to afford ST-200-A-007 (27 mg, 41%) as a white solid. $^1$H NMR: (400 MHz, $CDCl_3$) δ 5.30 (d, J=5.2 Hz, 1H), 2.42 (d, J=15.2 Hz, 1H), 2.02-1.96 (m, 2H), 1.86-1.38 (m, 14H), 1.25-1.14 (m, 4H), 1.21 (s, 6H), 1.11 (s, 3H), 1.09-1.05 (m, 2H) 1.02 (s, 3H), 1.01-0.94 (m, 3H), 0.61 (s, 3H).

Example 4. Preparation of Compound ST-200-A-011

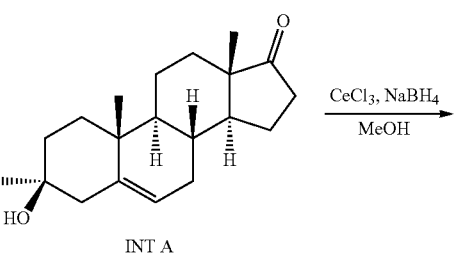

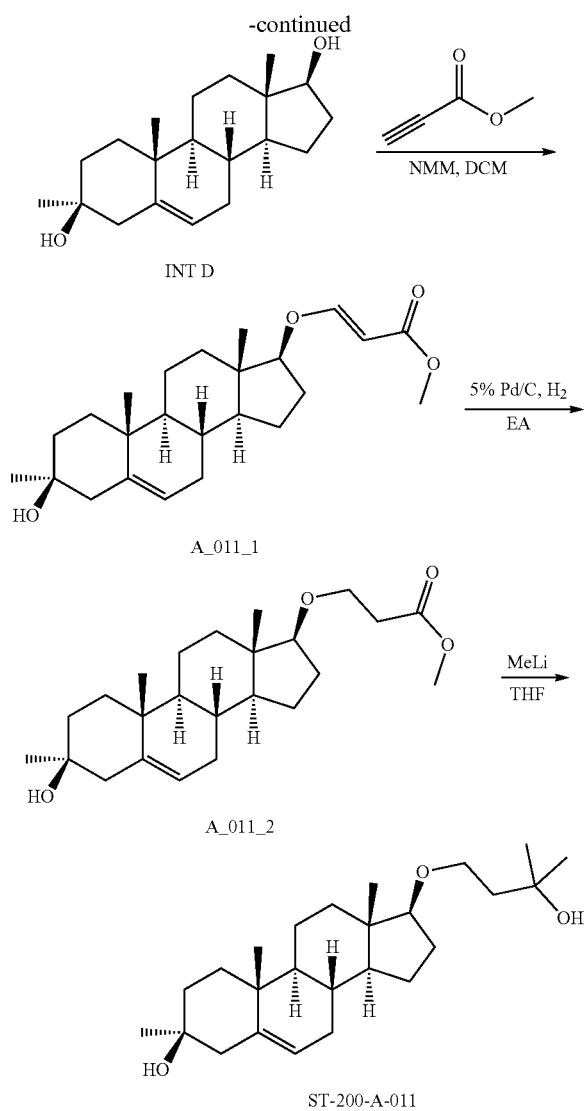

Preparation of Compound INT D: To a solution of INT A (2.00 g, 6.58 mmol, 1.0 eq) in MeOH (30 mL) and THF (15 mL) was added CeCl₃·7H₂O (2.45 g, 6.58 mmol, 1.0 eq). The reaction mixture was stirred at room temperature for 10 min. Then NaBH₄ (0.50 g, 13.16 mmol, 2.0 eq) was slowly added and the resulting mixture was stirred for 30 min at room temperature. TLC (PE/EA=3/1) showed that the reaction was complete. The reaction mixture was quenched by addition of saturated aqueous NH₄Cl (50 mL) and extracted with EA (50 mL×2). The combined organic layers were dried over Na₂SO₄ and evaporated to dryness to give the desired product (1.84 g, 91%) as a white solid. ¹H NMR: (400 MHz, CDCl3) δ 5.30 (d, J=5.2 Hz, 1H), 3.65 (t, J=8.6 Hz, 1H), 2.43 (d, J=13.2 Hz, 1H), 2.09-1.97 (m, 3H), 1.97-1.68 (m, 3H), 1.64-1.38 (m, 5H), 1.31-1.20 (m, 2H), 1.19-1.16 (m, 1H), 1.11 (s, 3H), 1.11-1.04 (m, 1H), 1.03 (s, 3H), 1.01-0.93 (m, 2H), 0.88-0.84 (m, 1H), 0.76 (s, 3H).

Preparation of Compound A_011_1: To a solution of INT D (500 mg, 1.63 mmol, 1.0 eq) in DCM (10 mL) was added methyl propiolate (325 mg, 3.30 mmol, 2.0 eq) and NMM (287 mg, 3.30 mmol, 2.0 eq) in turn. The reaction mixture was stirred at room temperature for two days. TLC (PE/EA=3/1) showed that the reaction was complete. The reaction mixture was washed with saturated aqueous NaHCO₃ (20 mL) and brine (20 mL), dried over Na₂SO₄ and evaporated to dryness to give the crude product. The residue was purified by silica gel chromatography eluted with PE:EA (15:1) to give the desired product (274 mg, 43%) as a white solid. ¹H NMR: (400 MHz, CDCl3) δ 7.54 (d, J=12.8 Hz, 1H), 5.29 (d, J=5.2 Hz, 1H), 5.24 (d, J=12.8 Hz, 1H), 3.88 (t, J=8.2 Hz, 1H), 3.68 (s, 3H), 2.42 (d, J=13.2 Hz, 1H), 2.19-2.09 (m, 1H), 2.00-1.89 (m, 2H), 1.88-1.84 (m, 1H), 1.80-1.70 (m, 2H), 1.62-1.50 (m, 5H), 1.49-1.41 (m, 2H), 1.39-1.29 (m, 1H), 1.19-1.10 (m, 2H), 1.11 (s, 3H), 1.02 (s, 3H), 1.00-0.91 (m, 2H), 0.79 (s, 3H).

Preparation of Compound A_011_2: To a solution of compound A_011_1 (50 mg, 0.128 mmol) in EA (5 mL) was added 5% Pd/C (50%, 25 mg) under argon. The suspension was degassed under vacuum and purged with H₂ several times. The mixture was stirred under H₂ balloon at room temperature for 4 h. TLC (PE/EA=3/1) showed that the starting material was consumed completely. Then the suspension was filtered through a pad of celite and the pad was washed with EA (5 mL×3). The combined filtrates were concentrated to dryness to give the product (48 mg, 96%) as a white solid which was used directly in the next step without purification. ¹H NMR: (400 MHz, CDCl3) δ 5.30 (d, J=5.2 Hz, 1H), 3.77-3.69 (m, 2H), 3.66 (s, 3H), 3.32 (t, J=8.4 Hz, 1H), 2.56 (t, J=6.4 Hz, 2H), 2.42 (d, J=12.4 Hz, 1H), 2.00-1.89 (m, 4H), 1.81-1.67 (m, 2H), 1.57-1.44 (m, 6H), 1.43-1.32 (m, 1H), 1.30-1.13 (m, 4H), 1.11 (s, 3H), 1.02 (s, 3H), 0.99-0.91 (m, 2H), 0.74 (s, 3H).

Preparation of Compound ST-200-A-011: To a solution of compound A_011_2 (60 mg, 0.16 mmol, 1.0 eq) in anhydrous THF (5 mL) was added dropwise MeLi (1 mL, 1.60 mmol, 10.0 eq, 1.6 M in Et₂O) at −78° C. under N₂. The reaction mixture was stirred at −78° C. for 30 min and then warmed to room temperature for another 30 min. TLC (PE/EA=3/1) showed that the starting material was consumed completely. The reaction mixture was quenched with saturated aqueous NH₄Cl (5 mL). The resulting solution was extracted with EA (5 mL×3). The combined organic layers were washed with brine (10 mL), and dried over Na₂SO₄ and concentrated in vacuum. The residue was purified by silica gel chromatography eluted with PE:EA (10:1) to give the target product (25 mg, 42%) as white solid. ¹H NMR: (400 MHz, CDCl3) δ 5.29 (d, J=4.8 Hz, 1H), 3.80-3.62 (m, 2H), 3.27 (t, J=8.4 Hz, 1H), 2.39 (d, J=13.2 Hz, 1H), 2.05-1.86 (m, 4H), 1.76-1.64 (m, 3H), 1.59-1.37 (m, 8H), 1.27-1.20 (m, 1H), 1.19 (s, 6H), 1.12-1.08 (m, 2H), 1.07 (s, 3H), 0.99 (s, 3H), 0.98-0.89 (m, 2H), 0.72 (s, 3H).

Example 5. Preparation of Compound ST-200-A-013

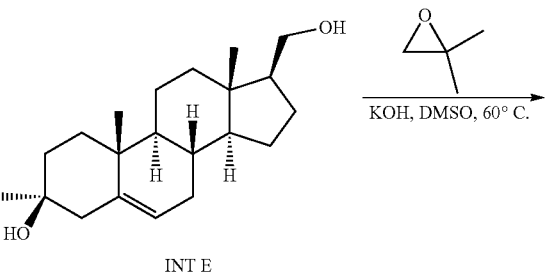

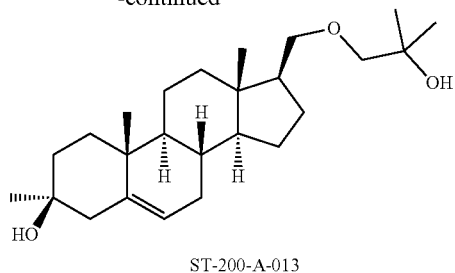

ST-200-A-013

To a solution of INT E (150 mg, 0.471 mmol, 1.0 eq) in DMSO (1 mL) was added KOH (53 mg, 0.942 mmol, 2.0 eq) and 2,2-dimethyloxirane (340 mg, 4.717 mmol, 10.0 eq). The reaction mixture was stirred at 50° C. for 16 h. TLC (PE/EA=3/1) showed the starting material was consumed completely. The mixture was cooled to room temperature, diluted with ethyl acetate (20 mL), and washed with saturated aqueous NH$_4$Cl (10 mL×2) and water (10 mL×2). The organic phase was dried over sodium sulfate and concentrated in vacuum to afford the crude product which was purified by column chromatography followed by prep-HPLC purification to afford pure product ST-200-A-013 (14 mg, 8%). $^1$H NMR (400 MHz, CDCl3) δ 5.30 (d, J=5.2 Hz, 1H), 3.57-3.48 (m, 1H), 3.38-3.35 (m, 1H), 3.20 (s, 2H), 2.42-2.40 (m, 1H), 2.03-1.85 (m, 3H), 1.76 (m, 4H), 1.55-1.43 (m, 4H), 1.25 (s, 3H), 1.28-1.25 (m, 6H), 1.17-1.13 (m, 2H), 1.11 (s, 3H), 1.06-0.96 (m, 5H), 0.92-0.79 (m, 2H), 0.65 (s, 3H).

Example 6. Preparation of Compound ST-200-A-017

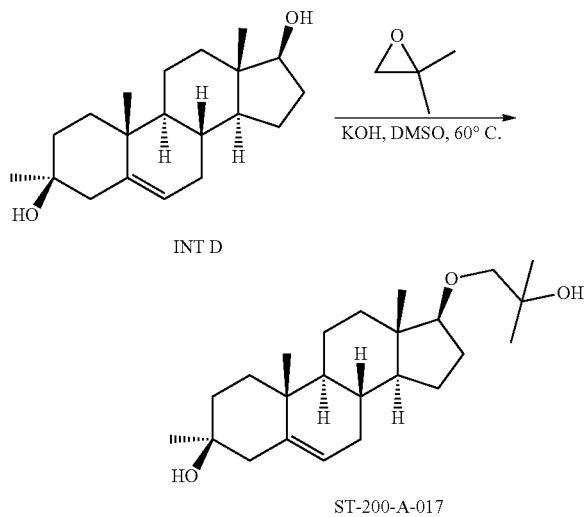

INT D

ST-200-A-017

To a solution of compound INT D (150 mg, 0.49 mmol, 1.0 eq) and 2, 2-dimethyloxirane (1.5 g, 20.8 mol, 42.0 eq) in DMSO (3 mL) was added KOH (56 mg, 1.0 mmol, 2.0 eq), then the reaction mixture was stirred at 60° C. for 5 h. TLC (PE:EA=3:1) indicated that the reaction was complete. The solution was cooled to room temperature, diluted with water (10 mL), extracted with EA (5 mL×2). The combined organic layers were concentrated under reduced pressure to provide the crude product which was purified by pre-HPLC to give the product (6.6 mg, 3.5%) as a white powder. $^1$H NMR: (400 MHz, CDCl$_3$) δ 5.30 (d, J=5.2 Hz, 1H), 3.33 (t, J=8.0 Hz, 1H), 3.29-3.22 (m, 2H), 2.40-2.50 (m, 2H), 2.05-1.85 (m, 4H), 1.82-1.65 (m, 2H), 1.60-1.35 (m, 9H), 1.34-1.22 (m, 1H), 1.20-1.15 (m, 6H), 1.14-1.11 (m, 1H), 1.12 (s, 3H), 1.05 (s, 3H), 0.90-1.00 (m, 2H), 0.79 (s, 3H).

Example 7. Preparation of Compound ST-200-A-021

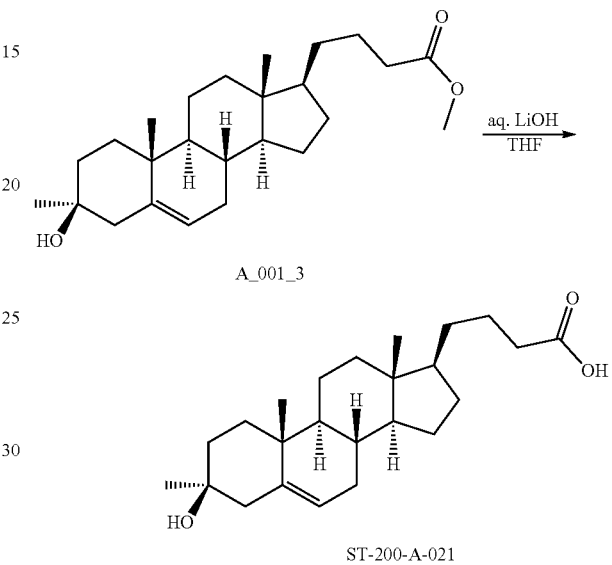

A_001_3

ST-200-A-021

To a solution of compound A_001_3 (150 mg, 0.39 mmol, 1.0 eq) in THF/H$_2$O (4 mL, 1/1), LiOH (90 mg, 2.20 mmol, 5.6 eq) was added. The reaction was stirred at room temperature overnight. TLC (PE/EA=3/1) showed that compound A_001_3 was consumed completely. The mixture was diluted with water (3 mL), washed with MTBE (5 mL×2) and then acidified to pH=4 with 1 M aqueous HCl. The precipitate was collected by filtration and dried in vacuum to give the product (54 mg, 37.3%). $^1$H NMR: (400 MHz, CDCl3) δ 5.30 (d, J=5.2 Hz, 2H), 2.43-2.37 (m, 1H), 2.37-2.33 (m, 2H), 2.05-1.93 (m, 2H), 1.90-1.79 (m, 2H), 1.78-1.61 (m, 6H), 1.61-1.50 (m, 6H), 1.50-1.37 (m, 3H), 1.34-1.13 (m, 4H), 1.12 (s, 3H), 1.02 (s, 3H), 0.93-1.01 (m, 3H), 0.61 (s, 3H).

Example 8. Preparation of Compounds ST-200-A-022 and ST-200-A-023

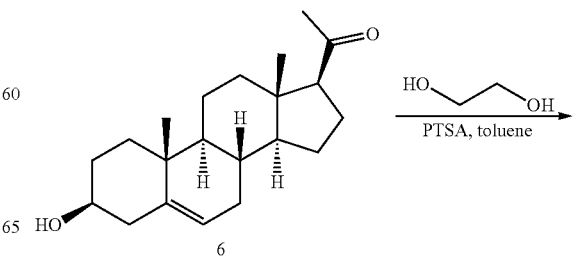

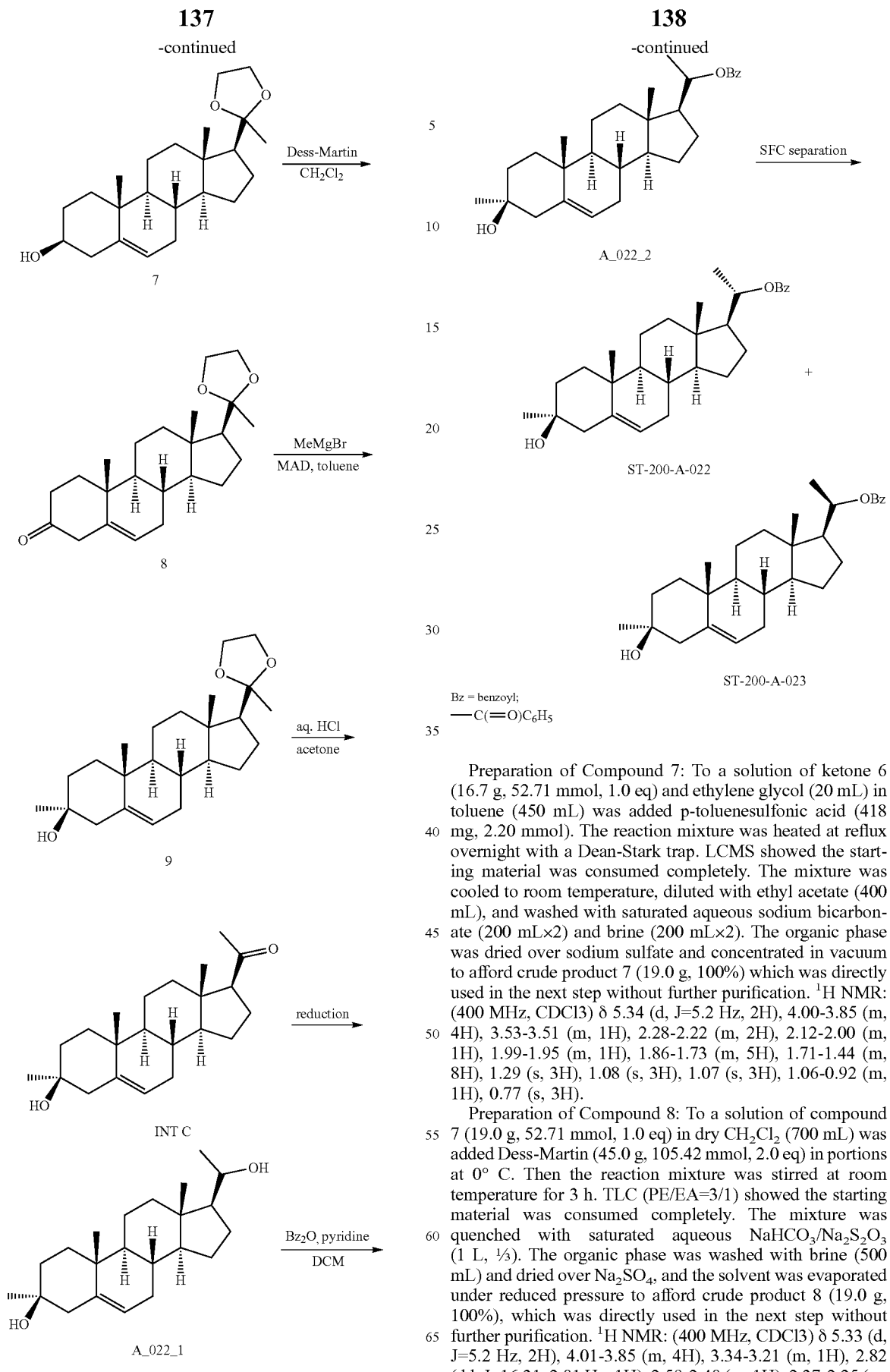

Bz = benzoyl;
—C(=O)C₆H₅

Preparation of Compound 7: To a solution of ketone 6 (16.7 g, 52.71 mmol, 1.0 eq) and ethylene glycol (20 mL) in toluene (450 mL) was added p-toluenesulfonic acid (418 mg, 2.20 mmol). The reaction mixture was heated at reflux overnight with a Dean-Stark trap. LCMS showed the starting material was consumed completely. The mixture was cooled to room temperature, diluted with ethyl acetate (400 mL), and washed with saturated aqueous sodium bicarbonate (200 mL×2) and brine (200 mL×2). The organic phase was dried over sodium sulfate and concentrated in vacuum to afford crude product 7 (19.0 g, 100%) which was directly used in the next step without further purification. $^1$H NMR: (400 MHz, CDCl3) δ 5.34 (d, J=5.2 Hz, 2H), 4.00-3.85 (m, 4H), 3.53-3.51 (m, 1H), 2.28-2.22 (m, 2H), 2.12-2.00 (m, 1H), 1.99-1.95 (m, 1H), 1.86-1.73 (m, 5H), 1.71-1.44 (m, 8H), 1.29 (s, 3H), 1.08 (s, 3H), 1.07 (s, 3H), 1.06-0.92 (m, 1H), 0.77 (s, 3H).

Preparation of Compound 8: To a solution of compound 7 (19.0 g, 52.71 mmol, 1.0 eq) in dry CH₂Cl₂ (700 mL) was added Dess-Martin (45.0 g, 105.42 mmol, 2.0 eq) in portions at 0° C. Then the reaction mixture was stirred at room temperature for 3 h. TLC (PE/EA=3/1) showed the starting material was consumed completely. The mixture was quenched with saturated aqueous NaHCO₃/Na₂S₂O₃ (1 L, ⅓). The organic phase was washed with brine (500 mL) and dried over Na₂SO₄, and the solvent was evaporated under reduced pressure to afford crude product 8 (19.0 g, 100%), which was directly used in the next step without further purification. $^1$H NMR: (400 MHz, CDCl3) δ 5.33 (d, J=5.2 Hz, 2H), 4.01-3.85 (m, 4H), 3.34-3.21 (m, 1H), 2.82 (dd, J=16.31, 2.01 Hz, 1H), 2.59-2.40 (m, 1H), 2.37-2.25 (m, 1H), 2.13-1.95 (m, 5H), 1.87-1.41 (m, 13H), 1.30 (s, 3H), 1.21-1.15 (m, 5H), 0.81 (s, 3H).

Preparation of Compound 9: To a solution of MAD (158 mL, 158 mmol, 3.0 eq, 1 M in toluene, prepared via the method as described in the synthesis of ST-200-A-001) was added a solution of compound 8 (19.0 g, 52.71 mmol, 1.0 eq) in toluene at −78° C. under nitrogen. Then the reaction mixture was stirred at this temperature for 30 min. A solution of MeMgBr (53 mL, 159 mmol, 3.0 eq, 3 M in Et$_2$O) was added dropwise at −78° C. The reaction mixture was warmed to −40° C. and stirred at this temperature for 3 h. TLC (PE:EA=3:1) showed that the starting material was consumed completely. The mixture was poured into saturated aqueous NH$_4$Cl solution (300 mL) and extracted with EA (150 mL×2). The combined organic phases were dried over Na$_2$SO$_4$, and the solvent was evaporated under reduced pressure to afford crude product. The crude product was purified by silica gel chromatography eluted with PE:EA (15:1) to give the product (7.70 g, 39%) as a white powder. $^1$H NMR: (400 MHz, CDCl3) δ 5.31 (d, J=5.2 Hz, 2H), 4.01-3.85 (m, 4H), 2.42 (d, J=12 Hz, 1H), 2.04-1.96 (m, 1H), 1.96-1.95 (m, 2H), 1.85-1.66 (m, 5H), 1.66-1.61 (m, 2H), 1.61-1.36 (m, 7H), 1.33 (s, 3H), 1.26-1.13 (m, 3H), 1.11 (s, 3H), 1.05 (s, 3H), 0.91-1.00 (m, 2H), 0.80 (s, 3H).

Preparation of Compound INT C: To a solution of compound 9 (2.7 g, 7.21 mmol, 1.0 eq) in THF (20 mL) was added aqueous HCl solution (10 mL, 1 M) and acetone (10 mL). The reaction mixture was stirred at room temperature overnight. TLC (PE:EA=3:1) indicated that the reaction was complete. Then the reaction mixture was diluted with EA (50 mL), washed with saturated aqueous NaHCO$_3$ solution (50 mL×2), dried over Na$_2$SO$_4$ and evaporated under reduced pressure to give the product (2.10 g, 88.2%) as a white powder. $^1$H NMR: (400 MHz, CDCl3) δ 5.31 (d, J=5.2 Hz, 2H), 2.55-2.50 (m, 1H), 2.40 (d, J=12 Hz, 1H), 2.20-2.19 (m, 1H), 2.15-2.10 (m, 3H), 2.08-1.94 (m, 3H), 1.83-1.76 (m, 1H), 1.74-1.65 (m, 3H), 1.62 (s, 3H), 1.61-1.39 (m, 7H), 1.30-1.13 (m, 4H), 1.12 (s, 3H), 1.01 (s, 3H), 0.61-0.65 (m, 3H).

Preparation of Compound A_022_1: To a solution of INT C (700 mg, 2.1 mmol, 1.0 eq) in MeOH (10 mL) and THF (5 mL) was added NaBH$_4$ (160 mg, 4.2 mmol, 2.0 feq) was added in five portions. The reaction mixture was stirred at room temperature for 1 h. TLC (PE/EA=3/1) showed the starting material was consumed completely. The mixture was quenched with saturated aqueous NH$_4$Cl (50 mL) and extracted with EA (20 mL×2). The combined organic layers were washed with water (20 mL) and brine (20 mL), dried over sodium sulfate and concentrated in vacuum to afford the desired product A_022_1 (600 mg, 86%).

Preparation of Compounds ST-200-A-022 and ST-200-A-023: To solution of A_022_1 (570 mmol, 1.717 mmol, 1.0 eq) in DCM (15 mL) was added TEA (867 mg, 8.585 mmol, 5.0 eq) and DMAP (63 mg, 0.515 mmol, 0.3 eq). Then BzCl (961 mg, 6.867 mmol, 4.0 eq) was added dropwise. The resulting mixture was stirred at room temperature for 16 h and then neutralized by addition of 1 M aqueous HCl. The aqueous layer was separated and extracted with DCM (10 mL×3). The combined organic layers were washed with saturated aqueous NaHCO$_3$ (10 mL) and brine (10 mL), dried over sodium sulfate and concentrated in vacuum. The residue was purified by silica gel chromatography eluted with PE:EA (15:1) to give product (360 mg, 46.6%) as a write solid which was applied to the SFC separation to afford the target ST-200-A-022 (100 mg) and ST-200-A-023 (70 mg). H NMR (ST-200-A-022): (400 MHz, CDCl3) δ 8.06 (d, J=7.2 Hz, 2H), 7.61-7.50 (m, 1H), 7.49-7.40 (m, 2H), 5.30 (d, J=5.2 Hz, 2H), 5.19-5.08 (m, 1H), 2.40 (d, J=12 Hz, 1H), 2.03-1.86 (m, 3H), 1.85-1.64 (m, 5H), 1.58-1.30 (m, 7H), 1.27 (d, J=6.0 Hz, 3H), 1.23-1.06 (m, 6H), 1.01-0.83 (m, 5H), 0.68 (s, 3H). $^1$H NMR (ST-200-A-023): (400 MHz, CDCl3) δ 8.01 (d, J=8.4 Hz, 2H), 7.58-7.50 (m, 1H), 7.47-7.39 (m, 2H), 5.31 (d, J=6.0 Hz, 2H), 5.24-5.14 (m, 1H), 2.43 (d, J=13.2 Hz, 1H), 2.05-1.87 (m, 4H), 1.82-1.61 (m, 5H), 1.55-1.38 (m, 4H), 1.36 (d, J=6.0 Hz, 3H), 1.29-1.14 (m, 4H), 1.12 (s, 3H), 1.04-0.95 (m, 4H), 0.74 (s, 3H)

Example 9. Preparation of Compound ST-200-C-001

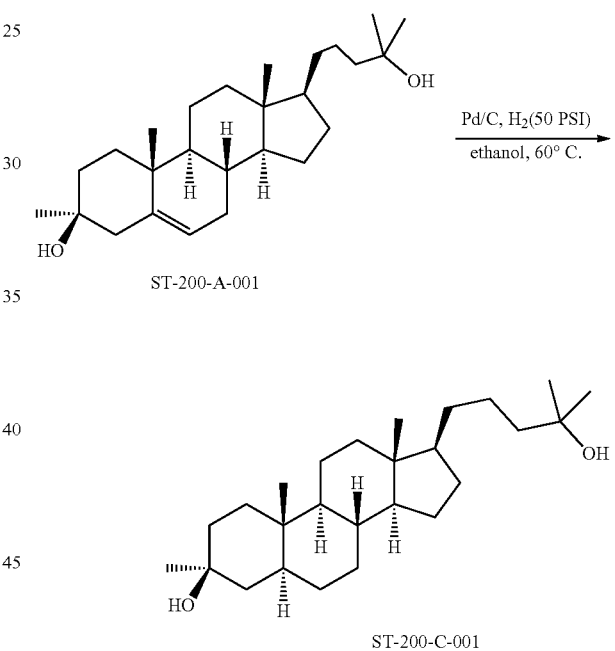

To a solution of compound ST-200-A-001 (65 mg, 0.167 mmol, 1.0 eq) in ethanol (10 mL) was added Pd/C (10%, 15 mg) under N$_2$. The suspension was degassed under vacuum and purged with H$_2$ several times. Then the mixture was stirred under 50 psi of hydrogen pressure at 60° C. for 24 h. TLC (PE:EA=3:1) showed that the reaction was complete. The suspension was filtered through a pad of celite and the pad was washed with ethanol (5 mL×2). The combined filtrates were concentrated to dryness to give the crude product, which was purified by silica gel chromatography eluted with PE:EA (10:1) to give the product (28 mg, 43%) as a white powder. $^1$H NMR: (400 MHz, CDCl$_3$) δ 1.90-1.87 (m, 1H), 1.75-1.60 (m, 4H), 1.82-1.65 (m, 2H), 1.55-1.30 (m, 12H), 1.27-1.23 (m, 6H), 1.22 (s, 6H), 1.18-0.95 (m, 8H), 0.82 (s, 3H), 0.72-0.65 (m, 1H), 0.55 (s, 3H).

Example 10. Preparation of Compounds ST-200-C-003 and ST-200-C-003A

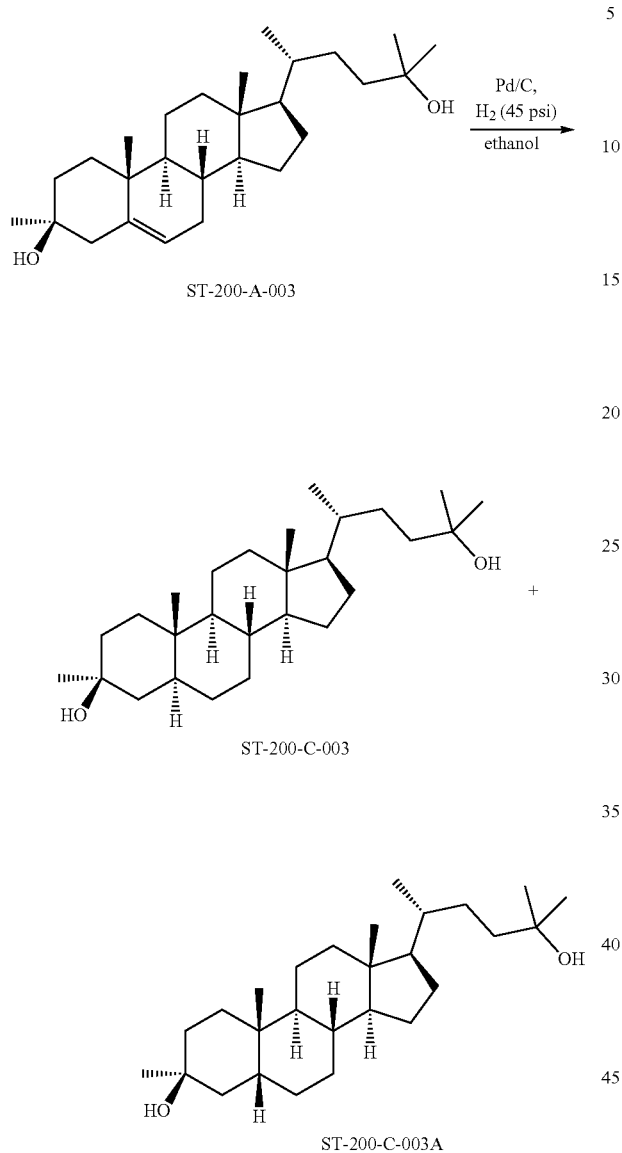

To a solution of compound ST-200-A-003 (40.0 mg, 0.10 mmol, 1.0 eq) in EtOH (30 mL) was added Pd/C (10 mg). The mixture was stirred at 60° C. overnight under 50 psi of hydrogen pressure. $^1$H NMR indicated that the reaction was complete. Then the mixture was filtered through a pad of celite and the filtrate was evaporated under reduced pressure. The residue was purified by column chromatography on silica gel (eluent: PE:EA=2:1) to afford the pure product ST-200-C-003 (12.0 mg, 29.8%) and ST-200-C-003A (0.8 mg, 2.3%) as a white powder. $^1$H NMR (ST-200-C-003): (400 MHz, CDCl3) δ 1.97-1.83 (m, 2H), 1.65-1.55 (m, 7H), 1.55-1.42 (m, 4H), 1.41-1.2841 (m, 6H), 1.27-1.21 (m, 5H), 1.20 (s, 6H), 1.16-0.95 (m, 7H), 0.92 (d, J=6.27 Hz, 3H), 0.81 (s, 3H), 0.65 (s, 3H). H NMR (ST-200-C-003A): (400 MHz, CDCl3) δ 1.98-1.79 (m, 4H), 1.64-1.53 (m, 6H), 1.52-1.29 (m, 7H), 1.25-1.22 (m, 6H), 1.22 (s, 3H), 1.20 (s, 3H), 1.05 (s, 3H), 0.96 (s, 3H), 0.91 (d, J=6.53 Hz, 3H), 0.86-0.80 (m, 2H), 0.65 (s, 3H).

Example 11. Preparation of Compound ST-200-C-007

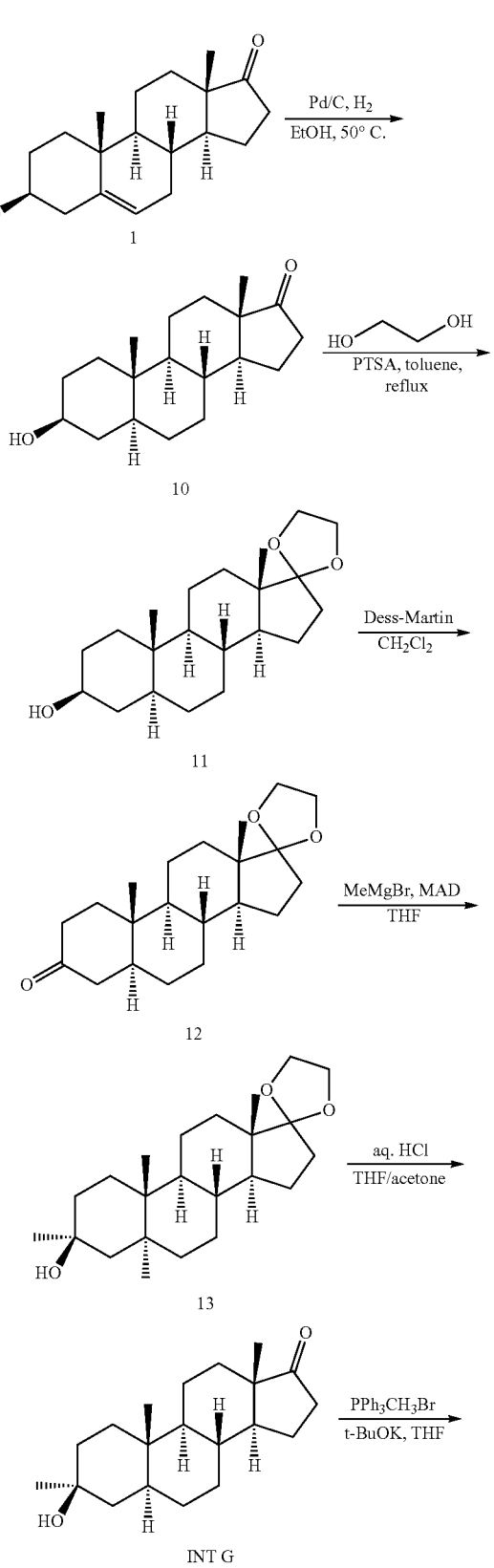

-continued

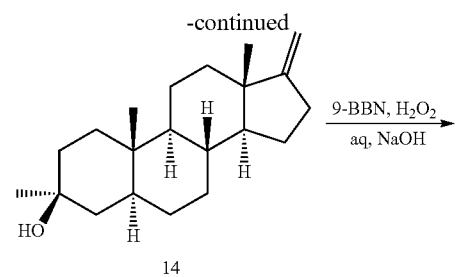
14

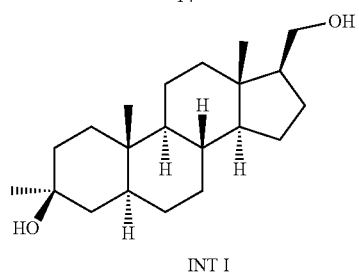
INT I

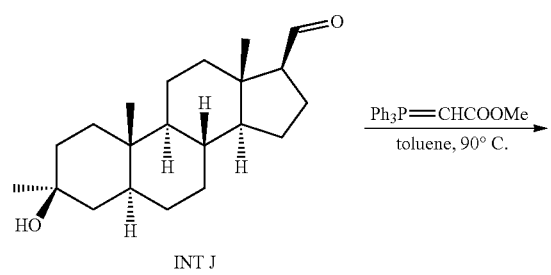
INT J

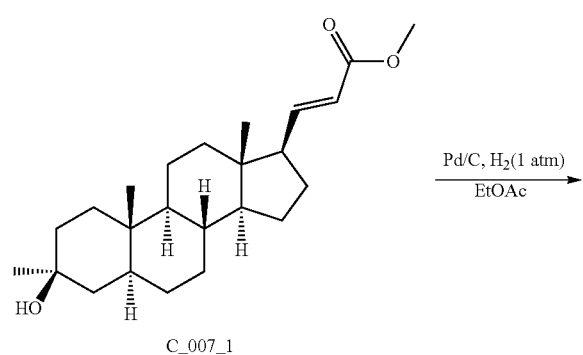
C_007_1

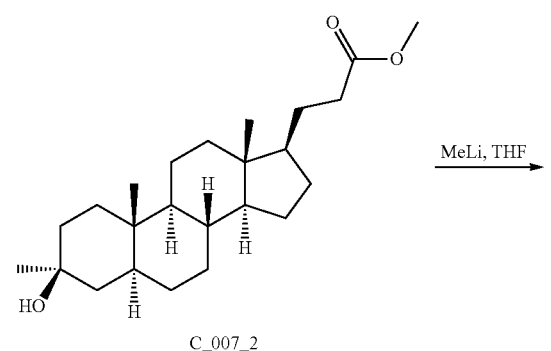
C_007_2

9-BBN, H₂O₂
aq, NaOH
→

Dess-Martin
CH₂Cl₂
→

Ph₃P═CHCOOMe
toluene, 90° C.
→

Pd/C, H₂(1 atm)
EtOAc
→

MeLi, THF
→

-continued

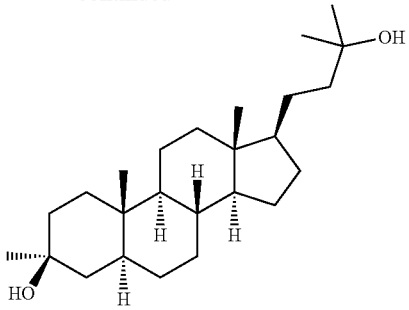
ST-200-C-007

Preparation of Compound 10: A mixture of compound 1 (28.0 g, 0.097 mol, 1.0 eq) and Pd/C (3.5 g) in ethanol (400 mL) was hydrogenated at room temperature overnight under 40 psi of hydrogen pressure. The suspension was filtered through a pad of celite and the pad was washed with ethanol (20 mL×3). The combined filtrates were concentrated to dryness to give the product (28.0 g, 0.097 mol, 100%) as the white solid. $^1$H NMR (400 MHz, CDCl3) δ 3.63-3.53 (m, 1H), 2.42 (dd, J=19.2, 8.4 Hz, 1H), 2.11-2.06 (m, 1H), 19.6-1.87 (m, 1H), 1.83-1.09 (m, 18H), 1.04-0.91 (m, 2H), 0.85 (s, 3H), 0.82 (s, 3H).

Preparation of Compound 11: To a solution of compound 10 (28.0 g, 0.097 mol, 1.0 eq) and ethylene glycol (30 mL) in toluene (300 mL) was added p-toluenesulfonic acid (0.7 g, 3.64 mmol). The reaction mixture was heated at reflux overnight with a Dean-Stark trap. LCMS showed the starting material was consumed completely. The mixture was cooled to room temperature, diluted with ethyl acetate (250 mL), and washed with saturated aqueous sodium bicarbonate (100 mL×2) and brine (100 mL×2). The organic phase was dried over sodium sulfate and concentrated in vacuum to afford crude product 11 (30.0 g, 0.090 mol, 93%) which was directly used in the next step without further purification. $^1$H NMR: (400 MHz, CDCl3) δ4.02-3.78 (m, 4H), 3.68-3.48 (m, 1H), 2.04-1.92 (m, 1H), 1.80-1.54 (m, 8H), 1.46-1.32 (m, 5H), 1.31-1.19 (m, 5H), 1.14-1.05 (m, 1H), 1.02-0.86 (m, 2H), 0.83 (s, 3H), 0.80 (s, 3H), 0.72-0.61 (m, 1H).

Preparation of Compound 12: To a solution of compound 11 (30.0 g, 0.090 mol, 1.0 eq) in dry DCM (300 mL) was added Dess-Martin oxidant (76.0 g, 0.180 mol, 2.0 eq) at 0° C. The reaction mixture was stirred at 0° C. for 30 min and then at room temperature for 2 h. LCMS showed the starting material was consumed completely. The mixture was quenched with a mixed aqueous solution of saturated NaHCO₃/Na₂SO₃ (200 mL, ⅓) and then diluted with DCM (250 mL). The organic layer was washed with saturated aqueous sodium bicarbonate (100 mL×2) and brine (100 mL×2), dried over sodium sulfate and concentrated in vacuum to afford crude product 12 (24.0 g, 0.072 mol, 80%) which was directly used in the next step without further purification.

Preparation of Compound 13: To a solution of MAD (2.16 mol, 3.0 eq, prepared via the method as described in synthesis of ST-200-A-001) in dry toluene (300 mL) was added dropwise compound 12 (24.0 g, 0.072 mol, 1.0 eq) at −78° C. and the mixture was stirred at −78° C. for 30 min under nitrogen. Then MeMgBr (72 mL, 2.16 mol, 3.0 eq, 3 M in ether) was added dropwise at −78° C. and the resulting mixture was stirred at the same temperature for 2 h. LCMS showed the starting material was consumed completely. The reaction mixture was poured into saturated aqueous NH₄Cl₄ solution (400 mL) and exacted with EA (300 mL×2). The combined organic layers were washed with brine (200 mL×2), dried over sodium sulfate and concentrated in vacuum. The residue was purified by silica gel chromatography eluted with PE:EA (15:1) to give product 13 (16.0 g, 0.046 mol, 72%) as a white solid. ¹H NMR: (400 MHz, CDCl3) δ 3.95-3.88 (m, 2H), 3.87-3.82 (m, 2H), 2.02-1.92 (m, 1H), 1.84-1.73 (m, 1H), 1.71-1.50 (m, 9H), 1.50-1.43 (m, 1H), 1.42-1.33 (m, 4H), 1.33-1.28 (m 1H), 1.27-1.19 (m, 7H), 1.08-0.88 (m, 2H), 0.83 (s, 3H), 0.81 (s, 3H).

Preparation of Compound INT G: A mixture of compound 13 (16.0 g, 46.0 mmol, 1.0 eq) in 1 M aqueous HCl (60 mL), acetone (60 mL) and THF (350 mmL) was stirred at room temperature overnight, and then diluted with water (200 mL) and neutralized with solid NaHCO₃ until no CO₂ was evolved. The mixture was extracted with EA (300 mL×2). The combined organic layers were washed with brine (200 mL×2), dried over sodium sulfate and concentrated in vacuum to afford product INT G (14.0 g, 46.0 mmol, 100%) as a white solid.

¹H NMR: (400 MHz, CDCl3) δ 2.44 (dd, J=19.20, 8.41 Hz, 1H), 2.13-2.01 (m, 1H), 1.98-1.89 (m, 1H), 1.85-1.76 (m, 2H), 1.69-1.60 (m, 3H), 1.59-1.42 (m, 5H), 1.33-1.13 (m, 10H), 1.08-0.94 (m, 2H), 0.86 (s, 3H), 0.84 (s, 3H), 0.68-0.77 (m, 1H).

Preparation of Compound 14: To a solution of PPh₃CH₃Br (1.4 g, 3.94 mmol, 5.0 eq) in THF (10 mL) was added a solution of t-BuOK (442 mg, 3.94 mmol, 5.0 eq) in THF (5 mL) at room temperature. After stirring for 1 h, a solution of INT G (0.2 g, 0.657 mmol, 1.0 eq) in THF (5 mL) was added dropwise. The reaction mixture was refluxed for 3 h, then cooled room temperature and quenched with saturated aqueous NH₄Cl (50 mL), extracted with EA (20 mL×2). The combined organic layers were washed with brine (20 mL), dried over sodium sulfate and concentrated in vacuum to give the crude product, which was purified by a flash column chromatography (eluent: PE/EA=15/1) to afford compound 14 (180 mg, 90%) as a white solid. ¹H NMR: (400 MHz, CDCl₃) δ 4.62 (d, J=6.4 Hz, 2H), 2.51-2.44 (m, 1H), 2.24-2.22 (m, 1H), 1.82-1.78 (m, 1H), 1.75-1.30 (m, 9H), 1.29-1.11 (m, 11H), 1.03-0.95 (m, 3H), 0.83 (s, 3H), 0.77 (s, 3H), 0.72-0.68 (m, 1H).

Preparation of Compound INT I: To a solution of 9-BBN (0.5 M in THF, 50 mL, 25.00 mmol, 8.0 eq) under ice-bath, a solution of compound 14 (0.95 g, 3.14 mmol, 1.0 eq) in THF (10 mL) was added dropwise. The reaction mixture was heated to 60° C. and stirred for 20 h. The mixture was cooled to 0° C. and 10% aqueous NaOH solution (20 mL) followed by 30% aqueous H₂O₂ (10 mL) was added. The resulting mixture was stirred for 2 h at 0° C. and then extracted with EA (10 mL×2). The combined organic layers were washed with brine (10 mL), dried over sodium sulfate and concentrated in vacuum to give the crude product, which was purified by a flash column chromatography (eluent: PE/EA=10/1) to afford INT I (0.63 g, 63%) as a white solid. ¹H NMR: (400 MHz, CDCl₃) δ 3.74-3.69 (dd, J₁=10.4 Hz, J₂=6.8 Hz, 1H), 3.56-3.52 (dd, J₁=10.4 Hz, J₂=7.6 Hz, 1H), 1.86-1.80 (m, 2H), 1.69-1.44 (m, 11H), 1.41-1.26 (m, 4H), 1.25-1.21 (m, 5H), 1.19-0.99 (m, 5H), 0.93-0.91 (m, 5H), 0.81 (s, 3H), 0.74-0.68 (m, 1H), 0.64 (s, 3H).

Preparation of Compound INT J: To a solution of INT I (500 mg, 1.56 mmol, 1.0 eq) in DCM (20 mL) under ice-bath, Dess-Martin reagent (1.3 g, 3.12 mmol, 2.0 eq) was added. The reaction mixture was warmed to room temperature and stirred for 2 h. The mixture was poured into a solution of NaS₂O₃ (5 g) and NaHCO₃ (1.5 g) in water (20 mL), extracted with EA (20 mL×2). The combined organic layers were washed with brine (20 mL), dried over sodium sulfate and concentrated in vacuum to give the crude product (500 mg, 100%), which was used directly in the next step without further purification.

Preparation of Compound C_007_1: A mixture of INT J (500 mg, 1.57 mmol, 1.0 eq) and Ph₃P=CHCOOCH₃ (3.1 g, 8.27 mmol, 6.0 eq) in toluene (30 mL) was stirred for 3 h at 80° C. The mixture was concentrated in vacuum and the residue was purified by a flash column chromatography (eluent: PE/EA=12/1) to afford product C_007_1 (188 mg, 32%) as a white solid.

Preparation of Compound C_007_2: A mixture of compound C_007_1 (188 mg, 0.5 mmol, 1.0 eq) and Pd/C (5%, 60 mg) in EA (10 mL) was stirred for 2 h at room temperature under H₂ (1 atm). The mixture was filtered and the filtrate was concentrated in vacuum to give product C_007_2 (189 mg, 100%), which was used directly in the next step without further purification.

Preparation of Compound ST-200-C-007: To a solution of compound C_007_2 (100 mg, 0.26 mmol, 1.0 eq) in THF (2 mL) at −78° C., CH₃L¹ (1.6 M in THF, 1.6 mL, 2.6 mmol, 10.0 eq) was added dropwise under nitrogen. The reaction mixture was warmed to room temperature and stirred for 1 h. Saturated aqueous NH₄Cl (10 mL) was added to quench the reaction and the mixture was extracted with EA (10 mL×2). The combined organic layers were washed with brine (10 mL), dried over sodium sulfate and concentrated in vacuum to give the crude product, which was purified by a flash column chromatography (eluent: PE/EA=8/1) to afford the target ST-200-C-007 (32.7 mg, 32.7%) as a white solid. ¹H NMR: (400 MHz, CDCl₃) δ 1.82-1.81 (m, 1H), 1.75-1.57 (m, 7H), 1.56-1.26 (m, 10H), 1.24 (s, 3H), 1.20 (s, 6H), 1.18-0.83 (m, 10H), 0.81 (s, 3H), 0.71-0.66 (m, 1H), 0.58 (s, 3H).

Example 12. Preparation of Compound ST-200-C-011

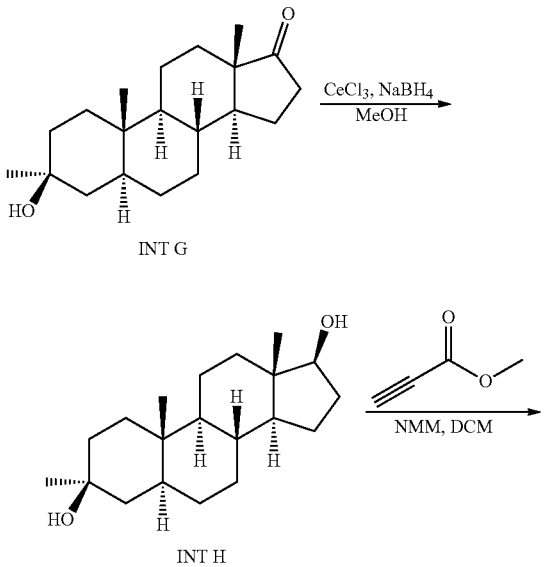

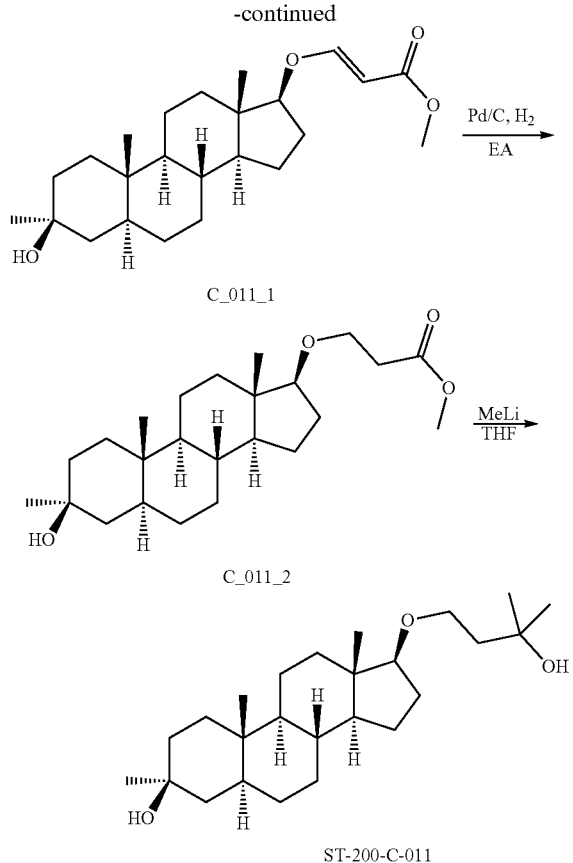

Preparation of Compound INT H: To a solution of INT G (1.00 g, 3.28 mmol, 1.0 eq) in MeOH (20 mL) and THF (8 mL) was added CeCl$_3$·7H$_2$O (1.22 g, 3.28 mmol, 1.0 eq). Then NaBH$_4$ (0.25 g, 6.56 mmol, 2.0 eq) was added in five portions and the mixture was stirred at room temperature for 1 h. The reaction slurry was quenched with saturated aqueous NH$_4$Cl (50 mL) and extracted with EA (20 mL×3). The combined organic layers were washed with brine (30 mL), dried over sodium sulfate and concentrated in vacuum to give the desired product (0.97 g, 97%) as a white solid. $^1$H NMR: (400 MHz, CDCl3) δ 3.62 (t, J=8.4 Hz, 1H), 2.10-2.04 (m, 1H), 1.79-1.77 (m, 1H), 1.70-1.35 (m, 13H), 1.31-1.15 (m, 11H), 1.14-0.84 (m, 5H), 0.81 (s, 3H), 0.72 (s, 3H), 0.70-0.61 (m, 1H)

Preparation of Compound C_011_1: To a solution of INT H (500 mg, 1.63 mmol, 1.0 eq) in DCM (20 mL), NMM (830 mg, 8.21 mmol, 5.0 eq) and methyl propiolate (690 mg, 8.21 mmol, 5.0 eq) were added. The mixture was stirred at room temperature for 16 h, then washed with water (30 mL) and brine (30 mL), dried over sodium sulfate and concentrated in vacuum. The residue was purified by silica gel chromatography eluted with PE:EA (15:1) to give the product (500 mg, 78.6%) as a white solid. $^1$H NMR: (400 MHz, CDCl3) δ=7.53 (d, J=12.4 Hz, 1H), 5.24 (d, J=12.4 Hz, 1H), 3.86 (t, J=8.4 Hz, 1H), 3.68 (s, 3H), 2.18-2.06 (m, 1H), 1.84-1.81 (m, 1H), 1.70-0.85 (m, 30H), 0.81 (s, 3H), 0.78 (s, 3H), 0.72-0.64 (m, 1H).

Preparation of Compound C_011_2: To a solution of C_011_1 (500 mg, 1.289 mmol, 1.0 eq) in EA (20 mL) was added Pd/C (10%, 50 mg). The suspension was degassed under vacuum and purged with H$_2$ several times. The mixture was stirred at 30° C. for 16 h under 30 psi of hydrogen pressure. TLC (PE/EA=3/1) showed the reaction was complete. The suspension was filtered through a pad of celite and the pad was washed with EA (20 mL×5). The combined filtrates were concentrated in vacuum to give the product (430 mg, 85.5%) as a white solid.

Preparation of Compound ST-200-C-011: To a solution of C_011_2 (100 mg, 0.256 mmol, 1.0 eq) in dry THF (1 mL), MeLi (1.3 mL, 2.048 mmol, 8.0 eq) was added dropwise at −78° C. under N$_2$. The resulting mixture was stirred at this temperature for 0.5 h, and then the temperature was allowed to warm to room temperature and stirred at this temperature for another 1 h. TLC (PE/EA=3/1) showed the reaction was complete. The mixture was quenched with saturated aqueous NH$_4$Cl and extracted with EA (10 mL×3). The combined organic layers were washed with brine (10 mL), dried over sodium sulfate and concentrated in vacuum. The residue was purified by silica gel chromatography eluted with PE:EA (10:1) to give the product (30 mg, 30%) as a white solid. $^1$H NMR (400 MHz, CDCl3) δ3.86 (s, 1H), 3.78-3.61 (m, 2H), 3.29 (t, J=8.3 Hz, 1H), 2.10-1.95 (m, 1H), 1.90-1.81 (m, 1H), 1.74 (t, J=5.6 Hz, 2H), 1.69-1.61 (m, 3H), 1.55-1.28 (m, 9H), 1.24-1.22 (m, 9H), 1.22-0.83 (m, 8H), 0.81 (s, 3H), 0.74 (s, 3H), 0.69-0.62 (m, 1H).

Example 13. Preparation of Compound ST-200-C-013

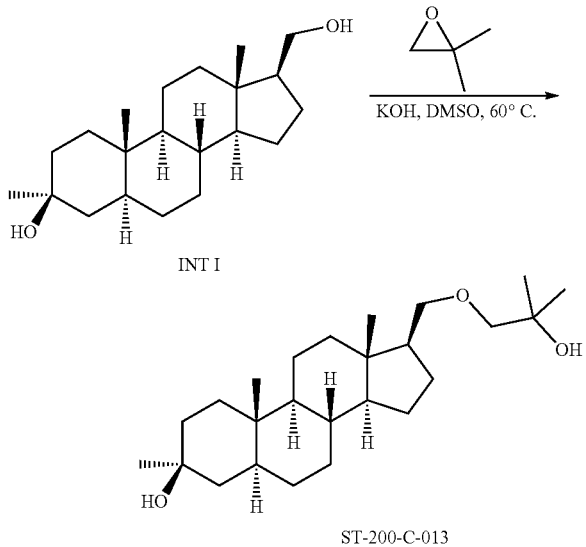

To a solution of INT I (150 mg, 0.469 mmol, 1.0 eq) in DMSO (1 mL) was added KOH (53 mg, 0.937 mmol, 2.0 eq) and 2,2-dimethyloxirane (337 mg, 4.687 mmol, 10.0 eq). The reaction mixture was stirred at 50° C. for 16 h. TLC (PE/EA=10/1) showed the starting material was consumed completely. The mixture was cooled to room temperature, diluted with ethyl acetate (20 mL) and washed with saturated aqueous NH$_4$Cl (10 mL×2) and water (10 mL×2). The organic phase was dried over sodium sulfate and concentrated in vacuum to afford crude product which was purified by column chromatography followed by prep-HPLC to afford pure product. ST-200-C-013 (26 mg, 15.8%). $^1$H NMR: (400 MHz, CDCl3) δ 3.72 (dd, J=7.3, 9.3 Hz, 1H), 3.35 (dd, J=6.8, 9.3 Hz, 1H), 3.21 (s, 2H), 2.34 (s, 1H), 1.84-1.80 (m, 1H), 1.79-1.63 (m, 5H), 1.54-1.27 (m, 8H), 1.25 (s, 3H), 1.19 (s, 6H), 1.18-0.83 (m, 7H), 0.81 (s, 3H), 0.74-0.65 (m, 1H), 0.63 (s, 3H)

Example 14. Preparation of Compounds ST-200-C-017 and ST-200-C-017A

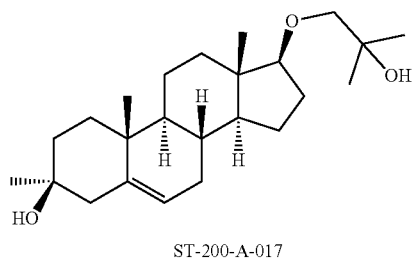

ST-200-A-017

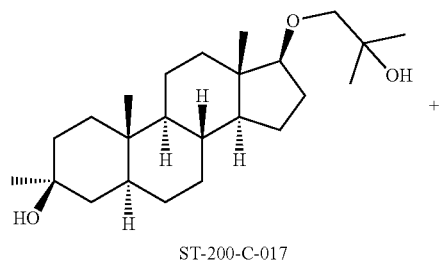

ST-200-C-017

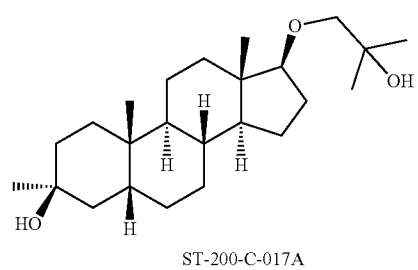

ST-200-C-017A

A solution of ST-200-A-017 (60 mg, 0.159 mmol, 1.0 eq) and Pd/C (10 mg) in EtOH (10 mL) was stirred at 50° C. under 50 psi of hydrogen pressure for 16 h. The reaction solution was filtered through a pad of celite and the filtrate was concentrated in vacuum. The residue was purified by silica gel chromatography eluted by PE:EA (20:1) to give ST-200-C-017 (21 mg) and ST-200-C-017A (4.6 mg) as a white solid. $^1$H NMR (ST-200-C-017): (400 MHz, CDCl3) δ 3.73-3.71 (m, 1H), 3.31 (t, J=8.4 Hz, 1H), 3.27-3.22 (m, 2H), 2.48 (s, 1H), 2.01-1.91 (m, 1H), 1.88-1.84 (m, 1H), 1.68-1.52 (m, 4H), 1.51-1.49 (m, 4H), 1.47-1.42 (m, 1H), 1.31-1.24 (m, 7H), 1.20-1.83 (m, 6H), 1.15-1.10 (m, 1H), 1.03-0.95 (m, 2H), 0.90-0.85 (m, 1H), 0.81 (s, 3H), 0.65 (s, 3H), 0.70-0.61 (m, 1H). H NMR (ST-200-C-017a): (400 MHz, CDCl3) δ 3.33 (t, J=8.4 Hz, 1H), 3.27-3.22 (m, 2H), 2.45 (s, 1H), 2.10-1.91 (m, 1H), 1.89-1.78 (m, 3H), 1.69-1.61 (m, 1H), 1.58-1.51 (m, 1H), 1.50-1.30 (m, 7H), 1.29-1.24 (m, 5H), 1.20 (s, 3H), 1.29-1.10 (m, 8H), 1.09-1.01 (m, 1H), 0.98 (s, 3H), 0.75 (s, 3H).

Example 15. Preparation of Compounds 3-alpha-A2 and 3-beta-A2

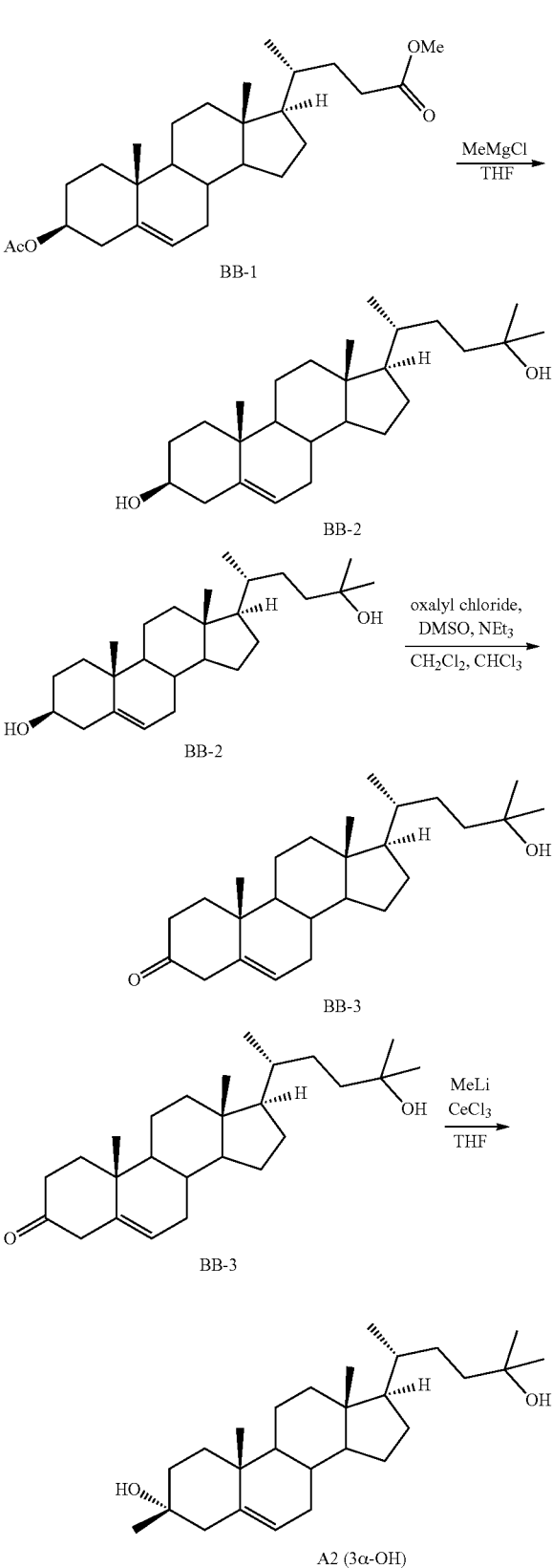

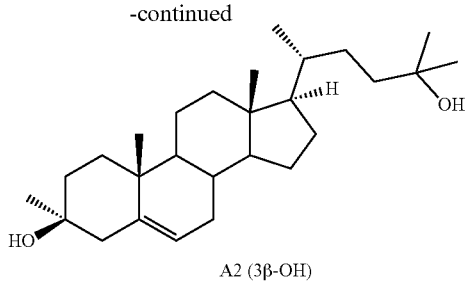

A2 (3β-OH)

Preparation of compound BB-2: Under nitrogen a solution of BB-1 (1.75 g, 4.06 mmol) in THF (35 mL), prepared as described in Steroids (2006) 71:18, was cooled to 0° C. Methylmagnesium chloride (22% (w/w) in THF, 19.5 mL, 58.1 mmol) was added dropwise. Stirring at 0° C. was continued for 15 minutes and reaction mixture was allowed to warm to room temperature and stirring was continued for two hours. Saturated aqueous NH$_4$Cl (5 mL) was added slowly. Precipitate formed and was dissolved by addition of water (10 mL). EtOAc (50 mL) and brine (20 mL) were added. Layers were separated. Aqueous layer was extracted with EtOAc (2×50 mL). Combined organic layers were dried with Na$_2$SO$_4$ and solvents were removed in vacuo. Residue was coevaporated with dichloromethane (50 mL). BB-2 (1.54 g, 3.95 mmol, 97%) was obtained as an off-white solid. $^1$HNMR (400 MHz, CDCl$_3$): δ (ppm): 5.32-5.43 (1H, m), 3.46-3.61 (1H, m), 1.20 (3H, s), 1.19 (3H, s), 1.01 (3H, s), 0.93 (3H, d, J=6.6 Hz), 0.68 (3H, s).

Preparation of compound BB-3: Under nitrogen in an oven dried flask a solution of oxalyl chloride (0.622 mL, 7.26 mmol) in dichloromethane (19 mL) was cooled to −78° C. Dimethyl sulfoxide (0.60 mL, 8.47 mmol) was added slowly. After 25 minutes a solution of BB-2 (0.470 g, 1.209 mmol) in CHCl$_3$ (38 mL) was added dropwise over 25 minutes The solution was stirred at −78° C. for 2.5 hours. Triethyl amine (3.36 ml. 24.19 mmol) was added dropwise at −78° C. Stirring was continued 15 minutes. Cooling bath was removed and stirring was continued for 10 min. Aqueous saturated NH$_4$Cl (10 mL) was added and reaction mixture was stirred for 5 minutes. Dichloromethane (50 mL) and water (20 mL) were added. Layers were separated and organic layer was washed with water (20 mL). Combined aqueous layers were diluted with brine (20 mL) and were extracted with EtOAc (2×75 mL). Combined organic layers were dried with Na$_2$SO$_4$ and solvents were removed in vacuo. Flash chromatography (heptane, 5%-30% EtOAc) afforded BB-3 (238 mg, 0616 mmol, 51%) as a white solid. $^1$HNMR (400 MHz, CDCl$_3$): δ (ppm): 5.31-5.38 (1H, m), 3.22-3.34 (1H, m), 2.83 (1H, dd, J=16.4 Hz, 2.1 Hz), 2.41-2.54 (1H, m), 2.25-2.34 (1H, m), 1.95-2.08 (3H, m), 1.82-1.93 (1H, m), 1.21 (3H, s), 1.20 (3H, s), 1.19 (3H, s), 0.94 (3H, d, J=6.5 Hz), 0.71 (3H, s).

Preparation of compounds 3-α-OH A2 and 3-β-OH A2: In a glove box in a flame dried flask, THF (degassed, 3 mL) was added to anhydrous cerium(III) chloride (0.319 g, 1.29 mmol). The suspension was stirred at RT overnight. The white, fine suspension was taken out of the glove box. THF (dry, 1 mL) was added and the mixture was stirred under argon for 15 minutes at RT. Under argon the white, fine suspension was cooled to −78° C. At this temperature methyllithium, 1.6M in Et2O (0.79 mL, 1.27 mmol) was added dropwise. A yellow suspension formed and was stirred at −78° C. for 1.5 h. A solution of BB-3 (0.100 g, 0.259 mmol) in THF (dry, 2 mL) was added dropwise over 5 min. The colour of the reaction mixture changed from yellow to brown. Reaction mixture was stirred at −78° C. for 45 min. Cooling bath was removed and reaction mixture was stirred for 10 min. 5% aq. AcOH (2 mL) was added. Reaction mixture turned into a colourless, clear solution. EtOAc (10 mL) was added. Mixture was allowed to warm to RT. Layers were separated and aq. layer was extracted with EtOAc (2×10 mL). Combined org. layers were dried with sodium sulfate and solvents were removed in vacuo. Flash chromatography (H, 5%-20% EtOAc) afforded compound A2 (3α—OH) (33 mg, 0.082 mmol; 63.5%) and compound A2 (3β—OH) (13 mg, 0.032 mmol; 25.0%). (3α—OH): $^1$H-NMR (400 MHz, CDCl$_3$): δ (ppm): 5.43-5.38 (m, 1H), 2.46-2.37 (m, 1H), 2.05-1.80 (m, 4H), 1.73-1.23 (m, 15H), 1.22 (s, 3H), 1.20 (s, 3H), 1.19 (s, 3H), 1.18-0.99 (m, 9H), 0.98 (s, 1H), 0.94 (d, J=6.5 Hz, 3H), 0.68 (s, 3H). (3β—OH): $^1$H-NMR (400 MHz, CDCl$_3$): δ (ppm): 5.34-5.28 (m, 1H), 2.47-2.38 (m, 1H), 2.07-1.92 (m, 3H), 1.91-1.66 (m, 3H), 1.63-1.24 (m, 13H), 1.20 (s, 3H), 1.19 (s, 3H), 1.18-1.12 (m, 3H), 1.11 (s, 3H), 1.10-1.02 (m, 2H), 1.01 (s, 3H), 1.00-0.94 (m, 1H), 0.93 (d, J=6.5 Hz, 3H), 0.91-0.82 (m, 1H), 0.68 (s, 3H).

Example 16. Preparation of Compounds 3-alpha-A28 and 3-beta-A28

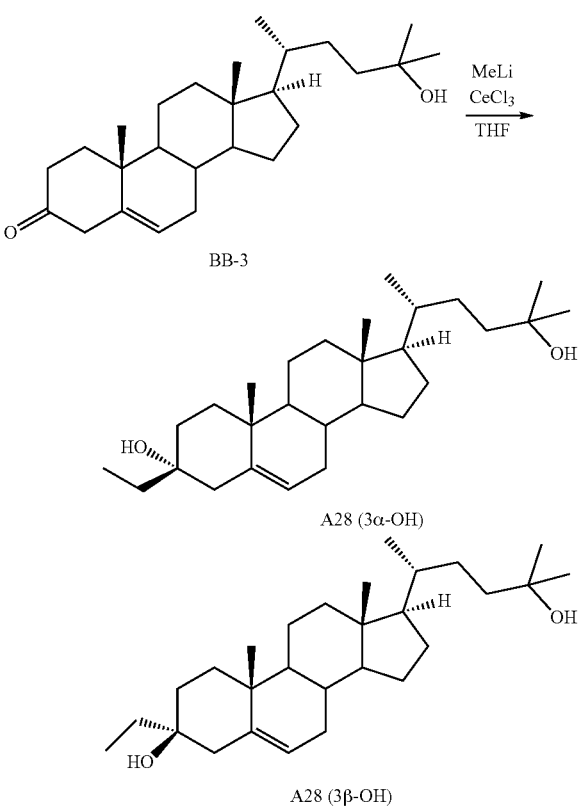

In a glove box in a flame dried flask THF (degassed, 1.5 mL) was added to anhydrous cerium(III) chloride (0.207 g, 0.841 mmol). The suspension was stirred at RT overnight. The white, fine suspension was taken out of the glove box and stirred under argon for 15 min. Under argon the white, fine suspension was cooled to −78° C. At this temperature ethyllithium, 0.5M in benzene/cyclohexane (1.68 mL, 0.841 mmol) was added dropwise. A yellow suspension formed and was stirred at −78° C. for 30 min. A solution of BB-3 (0.065 g, 0.168 mmol) in THF (dry, 1.5 mL) was added dropwise over 3 min. The colour of the reaction mixture changed from yellow to brown. Reaction mixture was stirred at −78° C. for 45 min. A brown, milky suspension was obtained, TLC (H/E; 2:1) showed complete conversion of the starting material and formation of a more polar spot. Cooling bath was removed and reaction mixture was stirred for 10 min. 5% aq. AcOH (2 mL) was added. After addition of brine (2 mL), reaction mixture turned into a colourless, clear solution. EtOAc (5 mL) was added. Mixture was allowed to warm to RT. Layers were separated and aq. layer was extracted with EtOAc (2×5 mL). Combined org. layers were dried with sodium sulfate and solvents were removed in vacuo. 60 mg of a white solid were obtained. Separation on silicagel impregnated with AgNO$_3$ (H, 5%-20% EtOAc) afforded compound A28 (3α—OH) (6 mg, 0.014 mmol; 8.56%) and compound A28 (3β—OH) (4 mg, 0.0096 mmol; 5.71%). (3α—OH): $^1$H-NMR (400 MHz, CDCl$_3$): δ (ppm): 5.45-5.38 (m, 1H), 2.40-2.33 (m, 1H), 2.05-1.93 (m, 2H), 1.92-1.80 (m, 2H), 1.75-1.23 (m, 15H), 1.20 (s, 3H), 1.19 (s, 3H), 1.18-0.98 (m, 7H), 0.97 (s, 3H), 0.96-0.90 (m, 6H), 0.89-0.81 (m, 2H), 0.68 (s, 3H). (3β—OH): $^1$H-NMR (400 MHz, CDCl$_3$): δ (ppm): 5.33-5.25 (m, 1H), 2.41-2.31 (m, 1H), 2.06-1.93 (m, 3H), 1.90-1.78 (m, 1H), 1.77-1.23 (m, 20H), 1.20 (s, 3H), 1.19 (s, 3H), 1.17-1.05 (m, 5H), 1.03 (s, 3H), 1.01-0.95 (m, 1H), 0.93 (d, J=6.5 Hz, 3H), 0.92-0.88 (m, 1H), 0.84 (t, J=7.4 Hz, 3H), 0.67 (s, 3H).

Example 17. Preparation of Compound B6

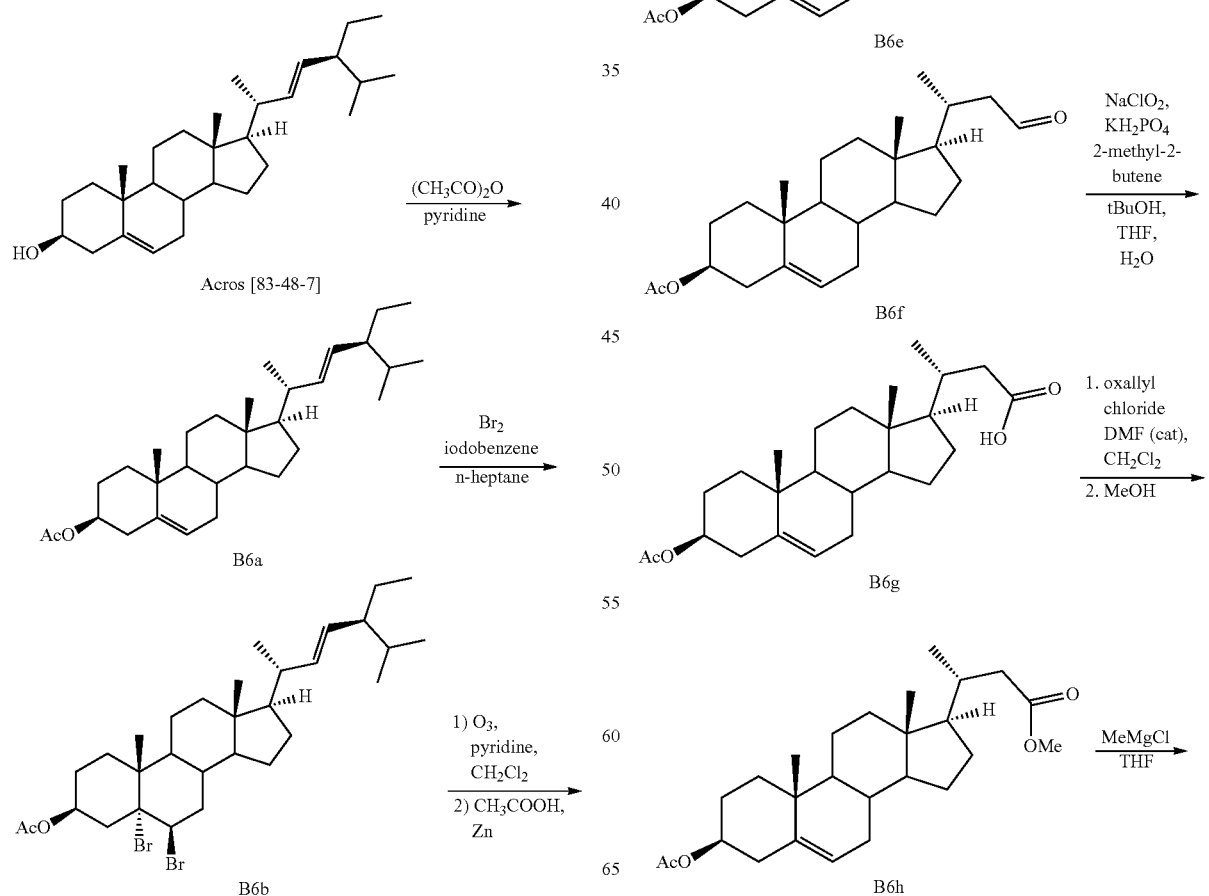
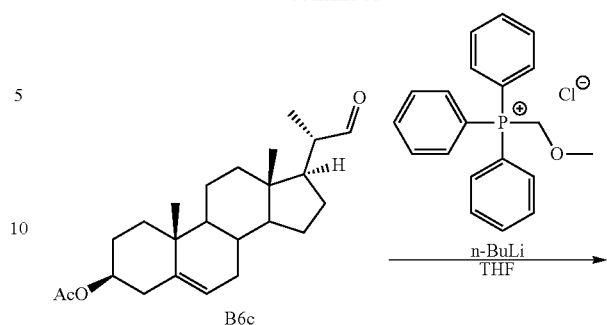
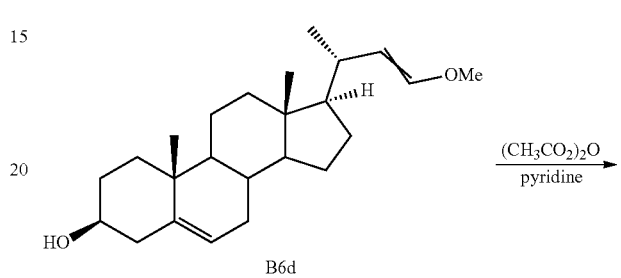
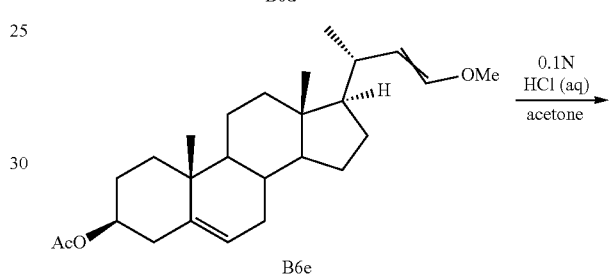
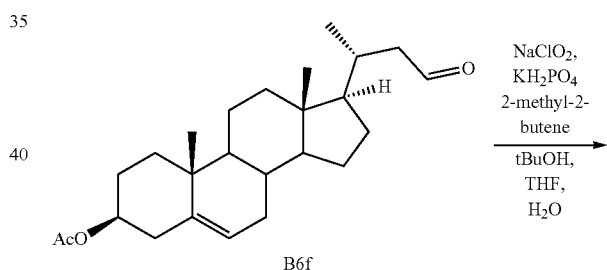
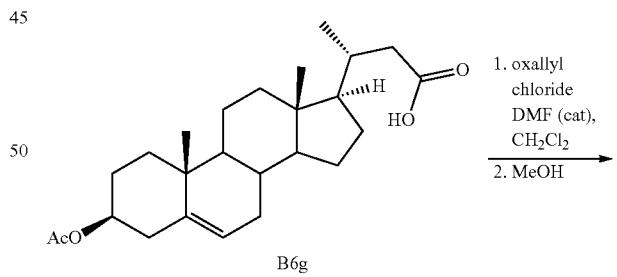
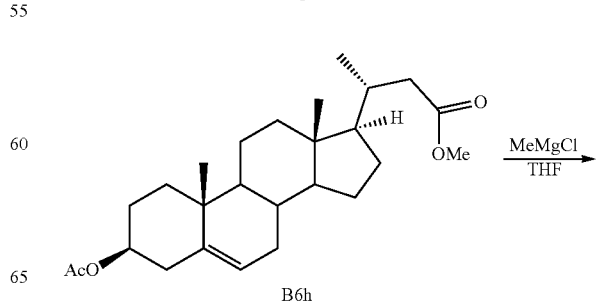

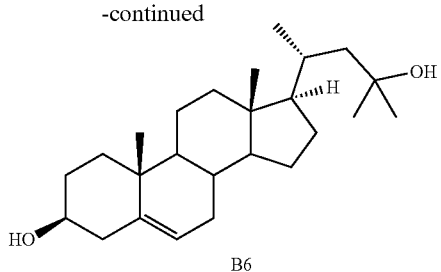

B6

Preparation of compound B6a. Acetic anhydride (15.36 ml, 164 mmol) was added to a suspension of Stigmasterol (22.5 g, 54.5 mmol) in pyridine (90 ml) under nitrogen atmosphere, and the mixture was incubated at room temperature for 42 h. TLC[heptane(2): ethyl acetate(1)] showed complete conversion to a higher eluting product after p-anisaldehyde staining. Water (300 ml) was added to the reaction mixture to quench the excess acetic anhydride. After stirring for 1 h, the white solid was filtered and thoroughly washed with water (9×250 ml). The white solid was dried in a vacuum oven at 40° C. in presence of a beaker of sodium hydroxide over the weekend to obtain product B6a (24.63 g, 54.2 mmol, Yield=99%) as white powder. B6a was used as such in the following experiment(s). $^1$HNMR (400 MHz, CDCl$_3$) δ (ppm): 5.38-5.37 (1H, m), 5.15 (1H, dd, J=15.1, 8.6 Hz), 5.01 (1H, dd, J=15.1, 8.6 Hz), 4.64-4.56 (1H, m), 2.33-2.31 (2H, m), 2.03 (3H, s), 1.90-1.82 (2H, m), 1.75-1.65 (1H, m), 1.02 (6H, t, J=3.2 Hz), 0.86-0.78 (9H, m), 0.68 (3H, s).

Preparation of compound B6b. Bromine (1.754 ml, 34.1 mmol) was added to a solution of iodobenzene (3.66 ml, 32.7 mmol) in n-heptane (100 ml) and the solution was cooled to −5° C. under nitrogen atmosphere. A solution of Stigmasteryl acetate B6a (13.5 g, 29.7 mmol) in n-heptane (700 ml) was also cooled to −5° C. under nitrogen atmosphere, stirred vigorously, and the solution prepared above was added dropwise over a period of 2.5 h under a nitrogen atmosphere to maintain the solution a pale yellow color. The resulting solution was stirred overnight and then filtered. TLC[heptane(9):ethyl acetate(1)] showed complete conversion to a slightly lower eluting product after vanillin staining. The solution was concentrated under vacuum until dryness. The residue was purified by column (900 g) chromatography [heptane (95): diisopropyl ether(5)]. The pure product containing fractions were collected and evaporated under reduced pressure to obtain B6b (9.06 g, 14.7 mmol, Yield=50%) as a white powder. B6b was used as such in the following experiment(s).

$^1$HNMR (400 MHz, CDCl$_3$) δ (ppm): 5.48 (1H, sep, J=5.4 Hz), 5.15 (1H, dd, J=15.1, 8.6 Hz), 5.02 (1H, dd, J=15.1, 8.6 Hz), 4.84 (1H, brd), 2.05 (3H, s), 1.46 (3H, s), 1.01 (3H, d, J=6.6 Hz), 0.90-0.79 (15H, m), 0.72 (3H, s).

Preparation of compound B6c. A solution of 5α,6β-Dibromostigmastan-3β-yl acetate B6b (8.11 g, 13.20 mmol) in molecular sieves dried dichloromethane (240 ml) and pyridine (3.05 ml, 37.7 mmol) was cooled in a liquid nitrogen/ethyl acetate bath. A stream of ozone rich oxygen was passed into the solution through a sintered glass sprayer for one hour. The color of reaction mixture turned slightly blue. TLC[heptane(9):ethyl acetate(1)] showed complete conversion of the starting material under UV$_{254}$. The ozonolysis reaction was stopped. The reaction mixture was immediately poured into a mixture of glacial acetic acid (33.2 ml, 581 mmol) and zinc, dust (21.57 g, 330 mmol) and stirred at room temperature overnight. The solution was filtered, washed successively with water (200 ml), 10% aqueous sodium hydrogen carbonate (200 ml), 5% aqueous sodium hydroxide (200 ml) and brine (200 ml), and then dried over anhydrous sodium sulfate. Evaporation of the solvent afforded crude Cholest-5-en-3β-ol-22-al B6c which was purified by flash column (300 g) chromatography [heptane(100=>90):ethyl acetate(0=>10)]. The product containing fractions were collected and evaporated under reduced pressure to obtain Cholest-5-en-3β-ol-22-al B6c (2.58 g, 6.93 mmol, Yield=53%) as a white powder. B6c was used as such in the following experiment(s). $^1$HNMR (400 MHz, CDCl3) δ(ppm): 9.57 (1H, d, J=3.3 Hz), 5.38 (1H, brd), 4.65-4.56 (1H, m), 2.41-2.28 (3H, m), 2.04 (3H, s), 2.03-1.92 (2H, m), 1.91-1.81 (3H, m), 1.13 (3H, d, J=6.8 Hz), 1.03 (3H, s), 0.73 (3H, s).

Preparation of compound B6d. To a solution of (methoxymethyl)triphenyl-phosphonium chloride (0.789 g, 2.30 mmol) in dry THF (6.4 mL) at −10° C. under an atmosphere of argon was added n-BuLi 1.6M in hexanes (1.342 mL, 2.15 mmol). The solution was stirred for 5 min at room temperature, followed by addition of B6c (0.2 g, 0.54 mmol) in dry THF (1.3 mL). The mixture was stirred for 30 min at room temperature. The reaction mixture was poured in saturated aqueous NH$_4$Cl (75 mL) and extracted twice with CH$_2$Cl$_2$ (50 mL). The combined organic layers were washed with brine dried on Na$_2$SO$_4$ and the crude product was purified by flash column chromatography (silica, heptane/ethylacetate, 1:0->88:12) to afford B6d (103 mg, 0.29 mmol, yield=54%). B6d was obtained as 1:1 E/Z-mixture according to NMR. $^1$HNMR (400 MHz, CDCl3) δ(ppm): 6.24 (0.5H, d, J=12.6 Hz), 5.74 (0.5H, d, J=6.2 Hz), 5.34 (1H, brd), 4.59 (0.5H, dd, J=12.5, 9.3 Hz), 4.17 (0.5H, dd, J=9.8, 6.3 Hz), 3.58-3.46 (1H, m), 3.55 (1.5H, s), 3.47 (1.5H, s), 2.67-2.54 (0.5H, m), 2.33-2.18 (2H, m), 2.04-1.78 (6H, m), 1.77-1.65 (1H, m), 1.04 (1.5H, d, J=6.6 Hz), 1.01 (3H, s), 0.98 (1.5H, d, J=6.7 Hz), 0.72 (1.5H, s), 0.69 (1.5H, s).

Preparation of compound B6e. Acetic anhydride (0.079 mL, 0.84 mmol) was added to a suspension of B6d (0.1 g, 0.279 mmol) in pyridine (3 mL) under nitrogen atmosphere, and the mixture was incubated at room temperature for 42 h. Water (60 mL) was added to the reaction mixture to quench the excess acetic anhydride. After stirring for 1 h, the white solid was filtered and thoroughly washed with water (9×250 mL). The white solid was dried in a vacuum oven at 40° C. overnight to obtain product B6e (111 mg, 0.28 mmol, Yield=99%). $^1$HNMR (400 MHz, CDCl3) δ(ppm): 6.24 (0.5H, d, J=12.6 Hz), 5.73 (0.5H, d, J=6.2 Hz), 5.37 (1H, brd), 4.66-4.55 (1H, m), 4.59 (0.5H, dd, J=12.5, 9.3 Hz), 4.17 (0.5H, dd, J=9.8, 6.3 Hz), 3.55 (1.5H, s), 3.47 (1.5H, s), 2.66-2.54 (0.5H, m), 2.35-2.28 (2H, m), 2.03 (3H, s), 2.02-1.91 (3H, m), 1.90-1.81 (2H, m), 1.77-1.66 (1H, m), 1.04 (1.5H, d, J=6.6 Hz), 1.02 (3H, s), 0.99 (1.5H, d, J=6.6 Hz), 0.72 (1.5H, s), 0.69 (1.5H, s).

Preparation of compound B6f. To a solution of B6e (0.111 g, 0.28 mmol) in acetone (9 mL) was added 0.1 M aqueous HCl (1 mL, 0.10 mmol). The resulting white suspension was stirred for 1 h at room temperature, followed by 1 h at 70° C. and at room temperature overnight. The mixture heated at 70° C. for 2 h, cooled to room temperature and diluted with H$_2$O (50 mL). The reaction mixture was evaporated until dryness, coevaporated with MeOH (50 mL) and CH$_2$Cl$_2$ (10 mL). This seems to be a mixture of the desired product and the dimethyl acetal. To a solution of this mixture (0.12 g, 0.28 mmol) in acetone (10 mL) was added 0.1 M aqueous HCl (1 mL, 0.10 mmol). The resulting white suspension was stirred for 2 h at 70° C. 1,4-Dioxane (5 mL) was added, which caused the insoluble to dissolve. The reaction mixture was heated to 70° C. for another 2 h, allowed to cool to room temperature and stirred over the weekend. The reaction mixture was diluted with H₂O (50 mL) and extracted with CH₂Cl₂ (3×50 mL). The combined organic layers were washed with brine, dried on Na₂SO₄ and the solvents evaporated. The crude product was coevaporated with CH₂Cl₂ (10 mL) to yield B6f (119 mg, 0.31 mmol, yield=111%). ¹HNMR (400 MHz, CDCl3) δ(ppm): 9.75 (1H, m), 5.37, (1H, brd), 4.66-0.454 (1H, m), 2.47 (1H, dd, J=15.8, 2.4 Hz), 2.36-2.28 (2H, m), 2.17 (1H, ddd, J=15.8, 9.3, 3.3 Hz), 2.03 (3H, s), 1.02 (3H, d, J=6.4 Hz), 1.02 (3H, s), 0.70 (3H, s).

Preparation of compound B6g. Compound B6f (0.11 g, 0.285 mmol) was dissolved in t-butanol (5 mL), dry THF (1 mL) and 2-methyl-2-butene (0.512 mL, 4.84 mmol). The solution was stirred and cooled with an iced bath. A solution of NaClO₂ (0.028 g, 0.313 mmol) and K₂HPO₄ (0.043 g, 0.313 mmol) in demineralized Water (3 ml) was slowly added to the solution over a period of 5 minutes and the mixture was stirred 2 h at 0° C. The mixture was stirred at room temperature overnight. Extra NaClO₂ (0.028 g, 0.313 mmol) and K₂HPO₄ (0.043 g, 0.313 mmol) dissolved in H₂O (3 mL) was added slowly to the reaction mixture and stirring was continued for 2 h. The reaction mixture was poured into saturated aqueous NH₄Cl (250 mL) and extracted three times with CH₂Cl₂ (75 mL). The combined organic layers were dried over Na₂SO₄, filtered and evaporated under reduced pressure. The white solid residue (2.26 g, 163%) was triturated in petroleum ether 40-60 (10 mL). The white solid was filtered, washed twice with petroleum ether 40-60 (5 mL) and dried on air for 0.5 h to obtain B6f (0.089 g, 0.22 mmol, Yield=78%). ¹HNMR (400 MHz, CDCl3) δ(ppm): 10.0 (1H, bs), 5.37 (1H, brd), 4.66-4.55 (1H, m), 2.53-2.44 (1H, m), 2.36-2.26 (2H, m), 2.04 (3H, s), 1.04 (3H, d, J=6.4 Hz), 1.02 (3H, s), 0.72 (3H, s).

Preparation of compound B6 h. To a solution of B6g (0.09 g, 0.224 mmol) in CH₂Cl₂ (10 mL) were added oxalyl chloride (0.048 mL, 0.56 mmol) and DMF (cat). The solution was stirred for 2 h at room temperature. The reaction mixture was diluted with dry MeOH (150 mL, 3703 mmol) and stirred at 40° C. till all solids were dissolved. The reaction mixture was evaporated till dryness and the crude product was purified by flash column chromatography (silica, heptane/ethylacetate, 1:0->95:5) and coevaporated with THF twice to afford B6 h (85 mg, 0.20 mmol, yield=91%). ¹HNMR (400 MHz, CDCl3) δ(ppm): 5.37 (1H, brd), 4.66-4.55 (1H, m), 3.66 (3H, s), 2.43 (1H, dd, J=14.1, 2.9 Hz), 2.38-2.25 (2H, m), 2.04 (3H, s), 1.02 (3H, s), 0.99 (3H, d, J=6.2 Hz), 0.72 (3H, s).

Preparation of compound B6. A solution of B6 h (0.085 g, 0.20 mmol) in dry THF (3 mL) was cooled to 0° C. under an atmosphere of argon. MeMgCl 3.0M in THF (0.68 mL, 2.04 mmol) was added drop wise using a syringe. The reaction mixture was stirred for 1 h at 0° C., followed by 2 h at room temperature. MeMgCl 3.0M in THF (0.68 mL, 2.04 mmol) was added again at room temperature and stirring was continued overnight. The reaction mixture was quenched with saturated aqueous NH₄Cl (75 mL) and extracted three times with CH₂Cl₂ (3×50 mL). The combined organic layers were washed with brine dried on Na₂SO₄ and the crude product was purified by flash column chromatography (silica, heptane/ethylacetate, 1:0->4:1) to afford B6 (45 mg, 0.12 mmol, yield=59%) as a white fluffy solid. ¹HNMR (400 MHz, CDCl3) δ(ppm): 5.35 (1H, brd), 3.53 (1H, sep, J=5.1 Hz), 2.34-2.17 (2H, m), 2.03 (1H, dt, J=12.6, 3.3 Hz), 2.01-1.94 (1H, m), 1.93-1.79 (3H, m), 1.23 (6H, s), 1.06 (3H, d, J=6.5 Hz), 1.01 (3H, s), 0.72 (3H, s).

Example 18. Preparation of Compound B7

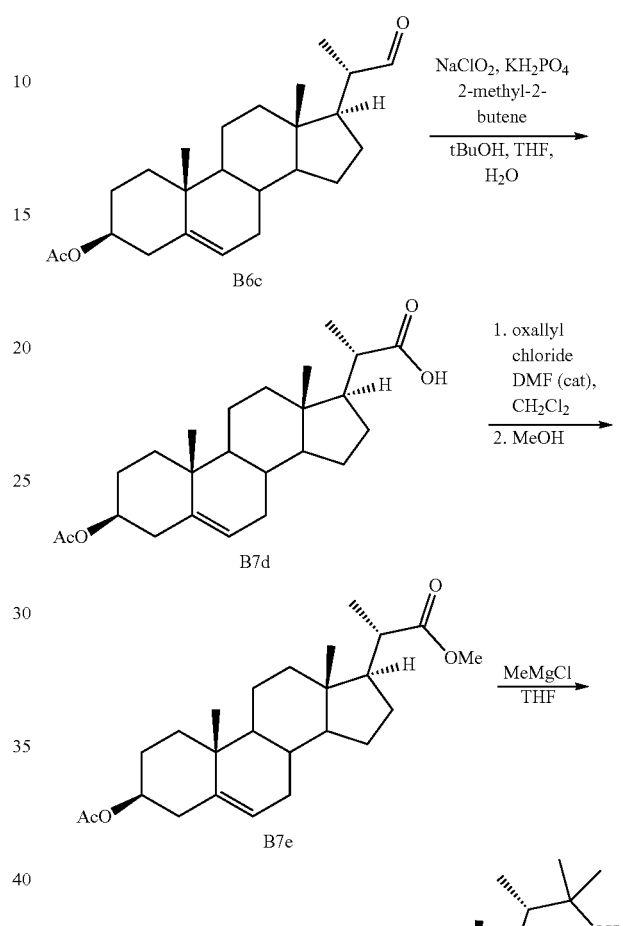

Preparation of compound B7d: Cholest-5-en-3β-ol-22-al B7c (1.33 g, 3.57 mmol) was dissolved in t-butanol (75 ml), tetrahydrofuran (dry) (15 ml) and 2-methyl-2-butene (13.22 ml, 125 mmol). The solution was stirred and cooled with an iced bath. A freshly prepared solution of sodium chlorite (0.355 g, 3.93 mmol) and potassium phosphate, monobasic, p.a. (0.534 g, 3.93 mmol) in demineralized water (45 ml) was slowly added to the solution over a period of 30 minutes and the mixture was stirred 2 hour at 0° C. The ice bath was removed, the temperature of the mixture was raised to room temperature, and stirred overnight. TLC[heptane(2):ethyl acetate(1)] showed partial conversion to a lower eluting product after vanillin staining. Extra sodium chlorite (0.355 g, 3.93 mmol) and potassium phosphate, monobasic, p.a. (0.534 g, 3.93 mmol) dissolved in water (45 ml) was added slowly to the reaction mixture and stirring was continued for 2 h. TLC[heptane(2):ethyl acetate(1)] showed complete conversion to a lower eluting product after vanillin staining. The reaction mixture was poured into saturated aqueous ammonium chloride (250 ml) and extracted three times with dichloromethane (100 ml). The combined organic layers were dried over sodium sulfate, filtered and evaporated under reduced pressure. The residue was twice stripped with toluene (50 ml) followed by dichloromethane (50 ml). The white solid residue (2.26 g, 163%) was triturated in petroleum ether 40-60 (10 ml) for 0.5 h. The white solid was filtered, washed twice with petroleum ether 40-60 (10 ml) and dried on air (leaving the vacuum pump on) for 0.5 h to obtain B7d (1.27 g, 3.26 mmol, Yield=91%) as a white powder. B7d was used as such in the following experiment(s). $^1$HNMR (400 MHz, CDCl3) δ(ppm): 10.31 (1H, bs), 5.37 (1H, brd), 4.65-4.56 (1H, m), 2.47-2.39 (1H, m), 2.36-2.26 (2H, m), 2.04 (3H, s), 2.01-1.92 (2H, m), 1.90-1.76 (3H, m), 1.24 (3H, d, J=6.8 Hz), 1.02 (3H, s), 0.71 (3H, s).

Preparation of compound B7e. Carboxylic acid B7d (0.1 g, 0.257 mmol) was dissolved in dichloromethane (10 ml). Oxalyl chloride (0.044 mL, 0.515 mmol) and N,N-dimethylformamide (one drop) were added, and the reaction mixture was stirred for 1 h. A sample of the reaction was poured out in methanol, evaporated until dryness, and analyzed on TLC[heptane(3):ethyl acetate(1)] which showed complete conversion to the methyl ester after vanillin staining. The reaction mixture was diluted with methanol (50 mL, 1234 mmol) (dried on mol. sieves), evaporated under reduced pressure, stripped with anhydrous toluene, and dichloromethane. The residue was purified by flash column (4 g) chromatography [heptane(99=>80):ethyl acetate(1=>20)]. The product containing fractions were collected and evaporated under reduced pressure to obtain B7e (0.104 g, 0.257 mmol, Yield=100%). B7e was stripped with toluene (2×5 ml), dichloromethane (2×5 ml) and anhydrous tetrahydrofuran (2×5 ml) and used as such in the next reaction step. 1HNMR (400 MHz, CDCl3) δ(ppm): 5.37 (1H, brd), 4.65-4.56 (1H, m), 3.65 (3H, s), 2.47-2.38 (1H, m), 2.36-2.26 (2H, m), 2.03 (3H, s), 2.01-1.92 (2H, m), 1.90-1.82 (2H, m), 1.19 (3H, d, J=6.8 Hz), 1.02 (3H, s), 0.69 (3H, s).

Preparation of compound B7. Methyl ester B7e (0.104 g, 0.258 mmol) was dissolved in tetrahydrofuran (dry) (2.6 ml) and cooled in an ice bath under argon. After 20 minutes, methylmagnesium chloride 3.0M in THF (0.861 ml, 2.58 mmol) was added dropwise via a syringe. Some gas evolution was observed. After stirring the reaction mixture for 0.5 h, the cooling bath was removed, and stirring was continued for 2 h. TLC [heptane(3):ethyl acetate(1)] showed complete conversion of the starting material to two lower eluting products after vanillin staining. Stirring was continued for 1 h. The reaction mixture was poured out into saturated aqueous solution of ammonium chloride (75 ml) under stirring and extracted with dichloromethane (3×50 ml). The extracts were combined, dried over sodium sulfate and evaporated. The residue was triturated in methanol (2 ml) for 0.5 h, the white solid was filtered, and the filter residue was washed with methanol (2 ml). Almost no material was left on the filter, most of it was present in the filtrate. Filtrate and filter residue were combined and purified by flash column chromatography [heptane (99=>70): ethyl acetate (1=>30)]. The product containing fractions were collected and evaporated. The residue was dried at 40° C. in a vacuum oven overnight to obtain B7 (0.044 g, 0.122 mmol, Yield=47%) as a white solid. $^1$HNMR (400 MHz, CDCl3) δ(ppm): 5.35 (1H, m), 3.53 (1H, sep, J=5.2 Hz), 2.34-2.19 (2H, m), 2.10 (1H, dt, J=12.6, 3.4 Hz), 2.03-1.88 (2H, m), 1.88-1.79 (2H, m), 1.20 (3H, s), 1.15 (3H, s), 1.00 (3H, s), 0.98 (3H, d, J=6.9 Hz), 0.73 (3H, s).

Example 19. Preparation of Compound B8

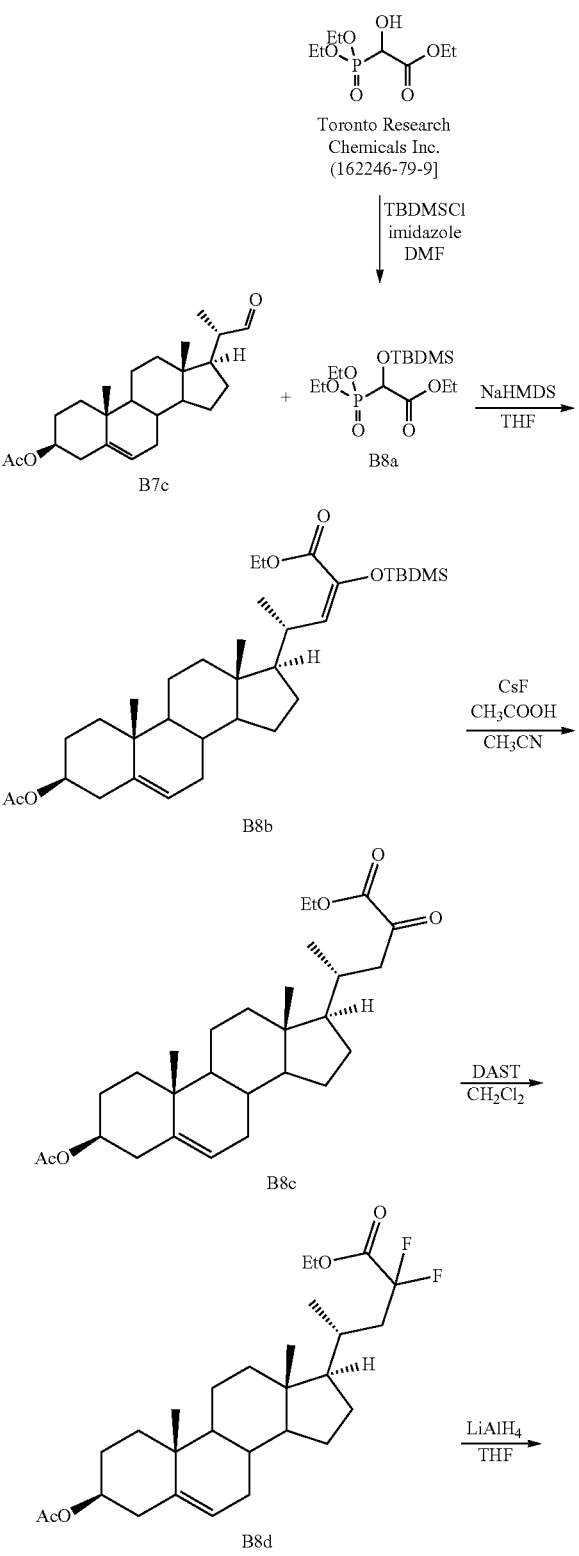

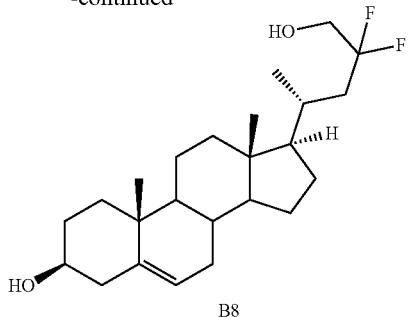

B8

Preparation of compound B8b. In a flame dried round bottom flask, a solution of NaHMDS (0.070 ml, 0.349 mmol) in tetrahydrofuran (dry) (1 ml) was added to a solution of silyloxyphosphonate ester B8a (0.143 g, 0.403 mmol) in tetrahydrofuran (dry) (1 ml) at −78° C. The solution was stirred for 15 minutes at −78° C. under argon atmosphere. Then a solution of Cholest-5-en-3β-ol-22-al B7c (0.1 g, 0.268 mmol) in tetrahydrofuran (dry) (1 ml) was slowly added via a syringe. The reaction mixture was slowly warmed to room temperature and stirred for 20 h. TLC [heptane(3):ethyl acetate(1)] showed partial conversion to an higher eluting product after vanillin staining. The reaction mixture was quenched by the addition of aqueous saturated ammonium chloride (50 ml) and extracted with dichloromethane (3×50 ml). The combined organic layers were washed with water (50 ml), dried over sodium sulfate, and concentrated in vacuo. The residue was purified by flash column (4 g) chromatography [heptane(100=>90): diisopropyl ether (0=>10)]. The product containing fractions were collected and evaporated under reduced pressure to afford product B8b (0.117 g, 0.187 mmol, Yield=70%) as white powder. According to NMR a 7:3 mixture of E- and Z-isomers was obtained. $^1$HNMR (400 MHz, CDCl$_3$) δ (ppm): 5.70 (1H, d, J=10.4 Hz), 5.23 (1H, brd), 5.17-5.13 (1H, m), 4.51-4.40 (1H, m), 4.11-4.00 (2H, m), 3.16-3.07 (0.3H[Z-isomer], m), 2.68-2.57 (0.7H[E-isomer], m), 2.20-2.10 (2H, m), 1.89 (3H, s), 1.89-1.77 (2H, m), 1.75-1.67 (2H, m), 0.89-0.85 (6H, m), 0.84-0.77 (10H, m), 0.59 (0.9H[Z-isomer], s), 0.57 (2.1H[E-isomer], s), 0.05-0.00 (6H, m).

Preparation of compound B8c. Glacial acetic acid (0.060 ml, 1.047 mmol) and cesium fluoride (0.080 g, 0.524 mmol) were added to a suspension of B8b (0.1 g, 0.175 mmol) in acetonitrile (anhydrous) (4 ml) under nitrogen atmosphere at 0° C. The resulting mixture was stirred at 0° C. for 30 min and at room temperature for 2 h. LCMS-NQAD (acid) showed little conversion of the starting material to a product with unclear product mass. Dichloromethane (2 ml) was added to the reaction mixture, and the reaction mixture immediately turned to a yellow clear solution. The reaction mixture was stirred overnight. Extra cesium fluoride (0.080 g, 0.524 mmol) was added to the reaction mixture and stirring was continued for 24 h. Extra cesium fluoride (0.080 g, 0.524 mmol) was added to the reaction mixture again and stirring was continued for 4 h. Although TLC[heptane(3): ethyl acetate(1)] showed still a little bit of starting material present in the reaction mixture, the reaction mixture was diluted with dichloromethane (75 ml) and washed with saturated aqueous sodium hydrogen carbonate (50 ml). The organic layer was dried over sodium sulfate and concentrated under reduced pressure. The residue was purified by flash column (25 g) chromatography [heptane(100=>90): ethyl acetate(0=>10)] to remove the remaining starting material (only visible on TLC). The product containing fractions were collected and evaporated under reduced pressure to afford product B8c (0.051 g, 0.111 mmol, Yield=64%). $^1$HNMR (400 MHz, CDCl$_3$) δ (ppm): 5.37 (1H, brd), 4.65-4.55 (1H, m), 4.31, (2H, q, J=7.1 Hz), 2.89 (1H, dd, J=16.8, 3.0 Hz), 2.57 (1H, dd, J=16.8, 9.9 Hz), 2.37-2.25 (2H, m), 2.04 (3H, s), 2.09-1.91 (2H, m), 1.90-1.77 (3H, m), 1.37 (3H, t, J=7.1 Hz), 1.02 (3H, s), 0.97 (3H, d, J=6.5 Hz), 0.72 (3H, s).

Preparation of compound B8d. A solution of B8c (0.051 g, 0.111 mmol) in dichloromethane (1 ml) was cooled in an ice bath under nitrogen atmosphere for 0.5 h. Diethylaminosulfur trifluoride (DAST) (0.027 ml, 0.222 mmol) was added and the reaction mixture was allowed to warm to room temperature and stirred overnight. Extra diethylaminosulfur trifluoride (DAST) (0.027 ml, 0.222 mmol) was added and stirring was continued for 20 h. TLC[heptane(3): ethyl acetate(1)] showed still no complete consumption of the starting material after vanillin staining. LCMS-ELSD (base): 47% product at rt=3.43 with m/z(+)=421, corresponds to desired product were acetate group is eliminated [M-CH$_3$COOH+H]$^+$. The reaction mixture was diluted with dichloromethane (50 ml) and washed with saturated sodium hydrogen carbonate (50 ml). The aqueous layer was separated and twice extracted with dichloromethane (50 ml). The extracts were combined with the former organic layer, dried over sodium sulfate and evaporated under reduced pressure. The residue was purified by flash column chromatography [heptane(100=>90):ethyl acetate(0=>90)]. The product containing fractions were collected, evaporated under reduced pressure and stripped with dichloromethane (5 ml) to afford product B8d (0.027 g, 0.056 mmol, Yield=51%). $^1$HNMR (400 MHz, CDCl$_3$) δ (ppm): 5.37 (1H, brd), 4.65-4.55 (1H, m), 4.32, (2H, q, J=7.1 Hz), 2.37-2.28 (2H, m), 2.27-2.09 (1H, m), 2.03 (3H, s), 2.04-1.92 (2H, m), 1.90-1.81 (3H, m), 1.35 (3H, t, J=7.1 Hz), 1.06 (3H, d, J=6.1 Hz), 1.02 (3H, s), 0.88 (6H, t, J=6.8 Hz), 0.70 (3H, s).

Preparation of compound B8. Compound B8d (0.027 g, 0.056 mmol) was dissolved in tetrahydrofuran (dry) (1 ml) under argon atmosphere. The mixture was cooled in an ice bath for 15 minutes and lithium aluminium hydride, 2.4M in THF (0.047 ml, 0.112 mmol) was added gradually. Some gas evolution was observed. The reaction mixture was cooled and stirred for 1 h. TLC[heptane(3):ethyl acetate(1)] showed complete conversion to mainly one lower eluting product after vanillin staining. The ice bath was removed and stirring was continued for 1 h. The reaction mixture was quenched with saturated aqueous ammonium chloride (50 ml) and extracted three times with dichloromethane (50 ml). The combined extracts were dried over sodium sulfate and evaporated under reduced pressure. The residue was purified by flash column (4 g silica) chromatography [heptane (100=>85):ethyl acetate(0=>15)]. The product containing fractions were collected and evaporated under reduced pressure. The residue was transferred to a vial (4 ml) with methanol and the methanol was evaporated at 37° C. under a stream of nitrogen. The residue was dried at 40° C. in a vacuum oven overnight to afford product B8 (0.011 g, 0.028 mmol, Yield=49%). $^1$HNMR (400 MHz, CDCl$_3$) δ (ppm): 5.35 (1H, m), 3.71 (2H, t, J=12.8 Hz), 3.58-3.48 (1H, m), 2.35-2.18 (2H, m), 2.15-1.93 (3H, m), 1.92-1.73 (5H, m), 1.70-1.40 (9H, m), 1.08 (3H, d, J=6.5 Hz), 1.01 (3H, s), 0.72 (3H, s).

Example 20. Preparation of Compound B10

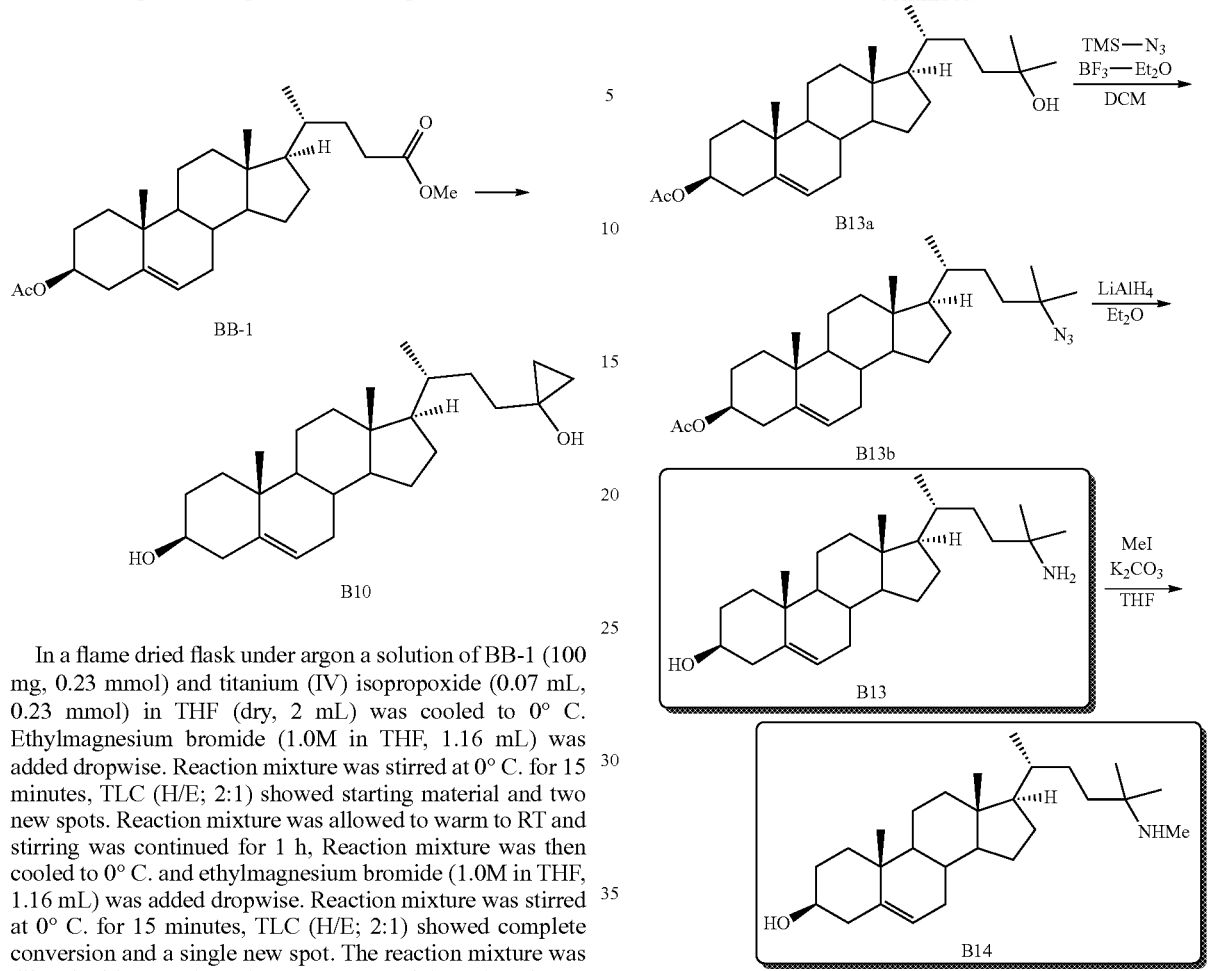

In a flame dried flask under argon a solution of BB-1 (100 mg, 0.23 mmol) and titanium (IV) isopropoxide (0.07 mL, 0.23 mmol) in THF (dry, 2 mL) was cooled to 0° C. Ethylmagnesium bromide (1.0M in THF, 1.16 mL) was added dropwise. Reaction mixture was stirred at 0° C. for 15 minutes, TLC (H/E; 2:1) showed starting material and two new spots. Reaction mixture was allowed to warm to RT and stirring was continued for 1 h, Reaction mixture was then cooled to 0° C. and ethylmagnesium bromide (1.0M in THF, 1.16 mL) was added dropwise. Reaction mixture was stirred at 0° C. for 15 minutes, TLC (H/E; 2:1) showed complete conversion and a single new spot. The reaction mixture was diluted with $Et_2O$ (2 mL). Aq. sat. $NH_4Cl$ (2 mL) and $H_2O$ (2 mL) were added at 0° C. Solids were filtered off over cotton and the filter cake was washed with $Et_2O$ (10 mL). The colourless layers were separated and the aq. layer was extracted with $Et_2O$ (20 mL) and a mixture of $Et_2O$ and EtOAc (20 mL; 1:1). Org. layers were dried with Na2SO4 and solvents were removed in vacuo. 125 mg of a white solid were obtained. Flash chromatography (heptane, 5%-30% EtOAc) afforded compound B10 (37 mg, 0.096 mmol; 41.2%). 1H-NMR (400 MHz, $CDCl_3$) δ (ppm): 5.36-5.35 (m, 1H), 3.58-3.46 (m, 1H), 2.32-2.21 (m, 2H), 2.03-1.93 (m, 2H), 1.91-1.80 (m, 3H) 1.77 (s, 1H), 1.69-1.37 (m, 10H), 1.34-0.82 (m, 9H), 1.01 (s, 3H), 0.93 (d, J=6.6 Hz, 3H), 0.75-0.71 (m, 2H), 0.69 (s, 3H), 0.46-0.39 (m, 2H).

Example 21. Preparation of Compounds B13α-B14

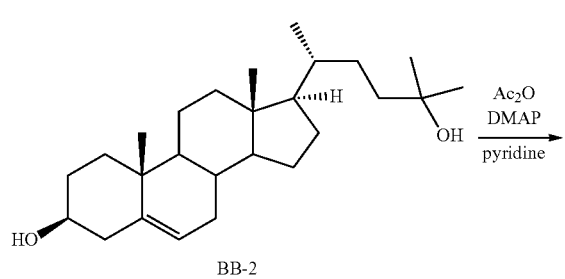

Preparation of compound B13α. To a solution of BB-2 (762 mg, 1.961 mmol) in Pyridine (15 ml) at 0° C. was added acetic anhydride (0.185 ml, 1.961 mmol) and DMAP (23.95 mg, 0.196 mmol) (a slightly yellowish suspension which slowly dissolves). The mixture was stirred at RT overnight. TLC (Heptane/EtOAc 2:1) showed full conversion. The RM was diluted with EtOAc (100 ml) and water (100 ml) and the layers were separated. The water layer was extracted with EtOAc (2×). The organic layers were combined and washed with water (3×) and brine, dried with Na2SO4 and concentrated. The obtained solid was co-evaporated three times with toluene, EtOH and DCM. The material was purified by flash chromatography (40 gr silica, 4-40% EtOAc in heptane, loaded with DCM). Compound B13a (687 mg, 1.595 mmol; 81%) was obtained as a white solid. $^1$HNMR (300 MHz, $CDCl_3$): δ (ppm): 5.37 (1H, d, 5.1 Hz), 4.60 (1H, m), 1.99 (3H, s), 1.20 (6H, s), 1.01 (3H, s), 0.93 (3H, d, J=6.6 Hz), 0.68 (3H, s).

Preparation of compound B13b. To a solution of compound B13a (687 mg, 1.595 mmol) in Dichloromethane (8.5 ml) under nitrogen, was added TMS-$N_3$ (0.233 ml, 1.755 mmol), followed by $BF_3 \cdot OEt_2$ (0.842 ml, 3.19 mmol). The mixture was stirred at RT for 2 hours. TLC showed almost complete conversion into a higher eluting spot. Impurities present. Stirred for another 30 minutes after which the RM was diluted with 2M NaOH (25 ml) and DCM (25 ml). The layers were separated. The water layer was extracted with DCM (2×). The organic layers were combined and washed with brine, dried over Na₂SO₄ and concentrated and purified by flash chromatography (40 gr silica, 4-40% EtOAc in heptane, loaded with DCM to give compound B13b (660 mg, 1.376 mmol; 86%). ¹HNMR (300 MHz, CDCl₃): δ (ppm): 5.37 (1H, d, 4.8 Hz), 4.60 (1H, m), 2.03 (3H, s), 1.20 (6H, s), 1.01 (3H, s), 0.93 (3H, d, J=6.6 Hz), 0.68 (3H, s).

Preparation of compound B13. To a solution of compound B13b (660 mg, 1.448 mmol) in Diethyl ether (dry) (15 ml) at 0° C. under argon, was added LiAlH₄ in Et2O (0.797 ml, 3.19 mmol) (white suspension was formed). The mixture was stirred for 30 minutes at 0° C. and for 1 hour at RT, after which TLC showed complete conversion of the SM into a low eluting spot (amine). The mixture was cooled to 0° C. again and WATER (0.057 ml, 3.19 mmol) and NaOH, 4M solution in water (0.797 ml, 3.19 mmol) were added. Stirred for 30 minutes at RT and filtered over Celite with diethyl ether and THF. The organic layer was dried with Na2SO4 and the solvent evaporated. The crude product was purified by gravity column chromatography (100 gr silica, loaded with DCM). First, the column was eluted with DCM:MeOH (95:5), to flush off all the impurities. Then, the column was eluted with DCM:7M NH3 in MeOH (95:5), to obtain compound B13 (400 mg, 1.032 mmol; 71.2%). ¹HNMR (300 MHz, CDCl₃): δ (ppm): 5.35 (1H, d, 5.1 Hz), 3.51 (1H, m), 1.07 (6H, s), 1.01 (3H, s), 0.93 (3H, d, J=6.6 Hz), 0.68 (3H, s).

Preparation of compound B14. Compound B13 (50 mg, 0.129 mmol) was dissolved in Tetrahydrofuran (dry) (2 ml) by slightly heating, then MeI (8.07 µl, 0.129 mmol) (1 mL from a stock solution of 81 microliter MeI in 10 mL of THF) and K2CO3 (21.39 mg, 0.155 mmol) were added. Stirring overnight at rt. The solid was filtered off, washed with water and dried. The mixture was purified on a 12 g pre-packed flash column (GraceResolve™) run in DCM/7N NH₃ in MeOH 97.5/2.5 15 ml/min, 1 min. fractions. Compound B14 (18 mg, 0.045 mmol, 34.7%) was thus obtained. ¹HNMR (400 MHz, CDCl₃): δ (ppm): 5.35 (1H, d, 4.8 Hz), 3.53 (1H, m), 2.30 (3H, s), 1.02 (9H, s), 0.93 (3H, d, J=6.6 Hz), 0.68 (3H, s).

Example 22. Preparation of Compound B17

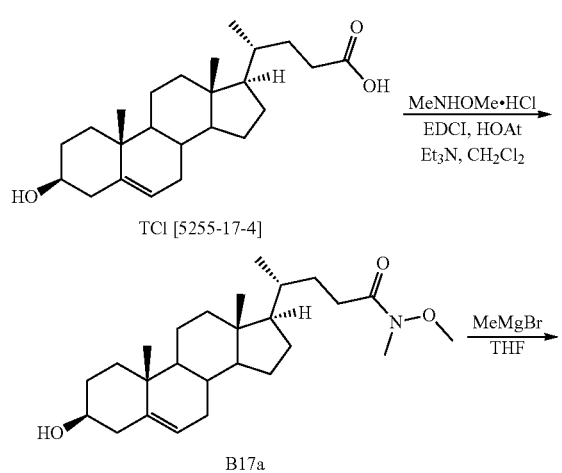

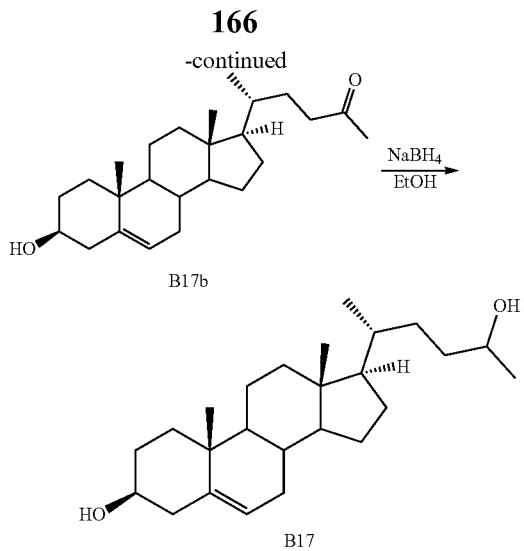

Preparation of compound B17a. 1-(3-Dimethylaminopropyl)-3-ethylcarbodiimide hydrochloride (EDCI) (0.282 g, 1.468 mmol), and 1-hydroxy-7-azabenzotriazole (HOAt) (0.018 g, 0.133 mmol) were added at 0° C. to a solution of 3β-hydroxy cholenic acid (0.5 g, 1.335 mmol), N,O-dimethylhydroxylamine hydrochloride (0.143 g, 1.468 mmol), and N,N-diisopropylethylamine (0.256 ml, 1.468 mmol) in dichloromethane (15 ml) under nitrogen atmosphere. The reaction mixture was allowed to warm to room temperature over the weekend. Extra 1-(3-dimethylaminopropyl)-3-ethylcarbodiimide hydrochloride (EDCI) (0.282 g, 1.468 mmol) and 1-hydroxy-7-azabenzotriazole (HOAt) (0.018 g, 0.133 mmol) were added and stirring was continued for 2 h. The reaction was diluted with dichloromethane (100 ml), washed with 0.5N aqueous potassium hydrogen sulfate (75 ml), and saturated aqueous sodium hydrogen carbonate (75 ml), dried over sodium sulfate and evaporated under reduced pressure. The residue was purified by flash column (4 g silica) chromatography[heptane(80=>66):ethyl acetate (20=>33)]. The product containing fractions were collected and evaporated under reduced pressure. The residue was stripped with methanol and dried at 40° C. overnight to afford B17a (0.495 g, 1.185 mmol, Yield=89%) as a white powder. ¹HNMR (400 MHz, CDCl₃) δ (ppm): 5.36-5.35 (1H, m), 3.69 (3H, s), 3.58-3.48 (1H, m), 3.18 (3H, s), 2.49-2.41 (1H, m), 2.37-2.20 (3H, m), 2.03-1.96 (2H, m), 1.96-1.75 (4H, m), 1.01 (3H, s), 0.95 (3H, d, J=6.5 Hz), 0.69 (3H, s).

Preparation of compound B17b. Under argon atmosphere, B17a (0.2 g, 0.479 mmol) was dissolved in Tetrahydrofuran (dry) (5 ml) and cooled to −75° C. Methylmagnesium bromide 3.0M in diethylether (0.798 ml, 2.394 mmol) was added dropwise (exothermic, temperature raised to −40° C.). After the addition, the reaction mixture dropped down to −75° C. The cooling bath was removed and the reaction mixture was allowed to warm to room temperature over a period of 20 minutes, and stirred 5 h. TLC[heptane(2):ethyl acetate(1)] showed complete conversion to a higher eluting product after vanillin staining. The reaction mixture was quenched by addition of a saturated aqueous ammonium chloride (75 ml) and extracted with dichloromethane (2×75 ml). The combined extracts were dried over sodium sulfate and evaporated under reduced pressure. The residue was purified via flash column (4 g) chromatography [heptane (80=>66):ethyl acetate (20=>33)]. The product containing fractions were collected and evaporated under reduced pressure. The residue was stripped with methanol and dried at 40° C. overnight to afford B17b (0.117 g, 0.314 mmol, Yield=66%) as a white solid. The product was used as such in the next step. $^1$HNMR (400 MHz, CDCl$_3$) δ (ppm): 5.36-5.34 (1H, m), 3.56-3.48 (1H, m), 2.50-2.30 (2H, m) 2.30-2.19 (2H, m), 2.14 (3H, s), 2.02-1.94 (2H, m), 1.90-1.81 (3H, m), 1.01 (3H, s), 0.91 (3H, d, J=6.5 Hz), 0.67 (3H, s).

Preparation of compound B17. Compound B17b (0.117 g, 0.314 mmol) was dissolved in ethanol (Abs) (5 ml) under nitrogen atmosphere and cooled to 0° C. Sodium borohydride (0.018 g, 0.471 mmol) was added in one portion (beware for foaming) and the reaction mixture was allowed to warm slowly to room temperature. After stirring for 3 h, TLC[heptane(2):ethyl acetate(1)] showed complete consumption of the starting material after vanillin staining. Excess sodium borohydride was decomposed with a saturated aqueous solution of ammonium chloride (50 ml). The reaction mixture was extracted with dichloromethane (3×50 ml). The extracts were combined, dried over sodium sulfate and evaporated under reduced pressure. The residue was dried at 40° C. in a vacuum oven overnight to afford B17 (0.105 g, 0.280 mmol, Yield=89%) as a white solid. 1HNMR (400 MHz, CDCl3) δ(ppm): 5.36-5.34 (1H, m), 3.75 (1H, q, J=5.8 Hz), 3.53 (1H, sep, J=5.5 Hz), 2.32-2.20 (2H, m), 2.02-1.95 (2H, m), 1.90-1.79 (3H, m), 1.19 (3H, dd, J=6.1, 2.1 Hz), 1.01 (3H, s), 0.93 (3H, d, J=5.5 Hz), 0.68 (3H, s).

Example 23. Preparation of Compound B18

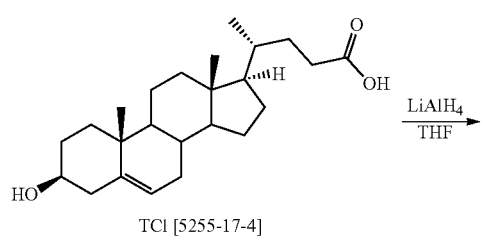

TCI [5255-17-4]

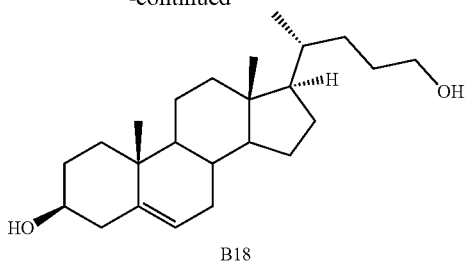

B18

3β-hydroxy cholenic acid (0.1 g, 0.267 mmol) was suspended in tetrahydrofuran (dry) (5 ml) under argon atmosphere. Lithium aluminium hydride, 2.4M in THF (0.222 ml, 0.534 mmol) was added gradually. Some gas evolution was observed. The reaction mixture was heated to 60° C. and stirred overnight. TLC[heptane(2):ethyl acetate(1)] showed complete conversion to a higher eluting product after molybdenum staining. Ethyl acetate (50 ml) and water (50 ml) were added carefully to destroy the excess reagent. The insoluble was filtered and washed with ethyl acetate (3×5 ml). The washings were combined with the filtrate and the organic phase was separated. The aqueous phase was twice more extracted with ethyl acetate (25 ml), and the combined extracts were washed with brine (75 ml), dried over sodium sulfate and evaporated under reduced pressure to afford product B18 (0.032 g, 0.089 mmol, Yield=33%) as white powder. $^1$HNMR (400 MHz, CDCl$_3$) δ (ppm): 5.36-5.35 (1H, m), 3.65-3.58 (2H, bs), 3.57-3.48 (1H, m), 2.32-2.20 (2H, m), 2.03-1.93 (2H, m), 1.89-1.79 (3H, m), 1.01 (3H, s), 0.94 (3H, d, J=6.5 Hz), 0.68 (3H, s).

Example 24. Preparation of C12, C32, and C33

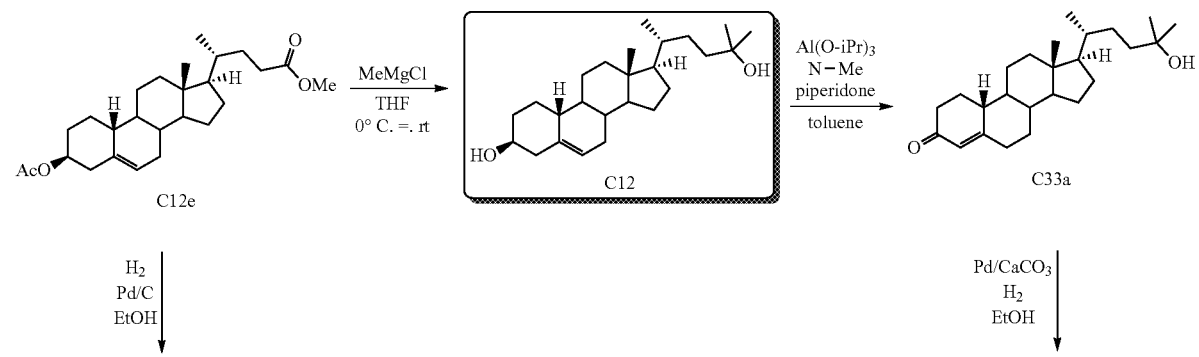

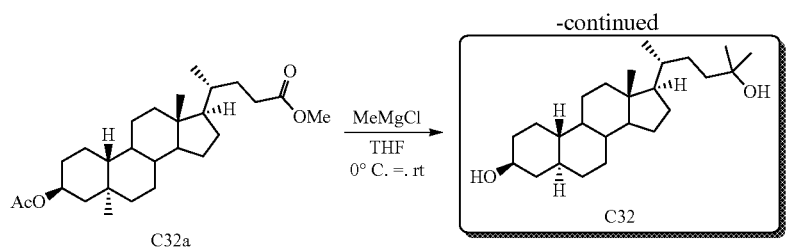
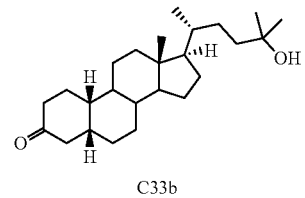
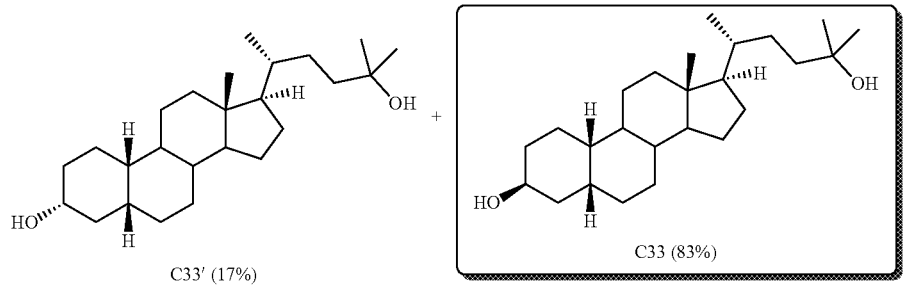

Preparation of compound C12. Compound C12e (300 mg, 0.720 mmol) was dissolved in Tetrahydrofuran (dry) (7 ml) and cooled to 4° C. under Argon. Then, Methylmagnesium chloride, 3M in THF (2.400 ml, 7.20 mmol) was added via a syringe at such a speed that the temperature did not exceed 7° C. Stirring at 4° C. for 20 min and then at rt. After 2 h, TLC revealed complete reaction. The rx was dropped onto a stirred saturated solution of NH$_4$Cl and extracted with EtOAc (2×). Some MeOH was added to assure that all the product dissolves in the organic layer. The extract was dried (Brine, Na$_2$SO$_4$) and evaporated. The residue was stirred in a little MeOH (~5 ml) and the white solid was filtered off and dried: Compound C12 (168 mg, 0.448 mmol; 62.3%). $^1$HNMR (400 MHz, DMSO-D$_6$): δ (ppm): 5.36 (1H, d, 4.6 Hz), 4.61 (1H, d, J=4.3 Hz), 4.03 (1H, s), 3.26 (1H, m), 2.32 (1H, m), 1.03 (6H, s), 0.87 (3H, d, J=6.6 Hz), 0.65 (3H, s).

Preparation of compound C32a. Compound C12e (74 mg, 0.178 mmol) was dissolved in Ethanol (Abs) (10 ml) and Palladium, 10% On Charcoal (18.90 mg, 0.018 mmol) was added. The rx was flushed with nitrogen and consecutively with hydrogen. It was stirred vigorously at rt. LCMS after 2 h indicated complete conversion whereas TLC did not show any change. The rx was again flushed with nitrogen and the Pd/C was filtered off through a fritted tube (3 frits). Still Pd/C in the filtrate. The EtOH was evaporated and the residue was dissolved in DCM and filtered through a small cotton plug. This gave a clear solution. DCM was evaporated to give compound C32a (68 mg, 0.162 mmol; 91% yield). Used as such without further purification. $^1$HNMR (400 MHz, CDCl$_3$): δ (ppm): 4.68 (1H, m), 3.66 (3H, s), 2.02 (3H, s), 0.91 (3H, d, J=6.6 Hz), 0.66 (3H, s).

Preparation of compound C32. Compound C32a (68 mg, 0.162 mmol) was dissolved in Tetrahydrofuran (dry) (1.5 ml) and cooled to 0° C. under argon. Then, Methylmagnesium chloride (0.541 mL, 1.624 mmol) was added. Vigorous gas evolution is seen. Stirring at 0° C. and after 3 min. at rt. A little more methylmagnesium chloride (0.1 mL, 0.300 mmol) was added after 2 hours. Stirring overnight at rt. Next day, the rx was poured into 50 ml of sat. aq. NH4Cl and extracted 3× with EtOAc. EtOAc dried (brine, sulfate) and evaporated. The residue was purified by column chromatography: The crude mixture was dissolved in DCM with a few drops MeOH to aid dissolution and applied to a pre-packed flash silica column. It was eluted 30 ml/min fractions of 30 sec. with: 5 min 100% heptane; 20 min 0=>20% EtOAc/heptane and 20 min 20% EtOAc/Heptane isocratic. The product fractions were combined, the solvent evaporated and the white solid residue was triturated in Et2O, filtered off and dried to give compound C32 (25 mg, 0.063 mg; 38.8% yield). $^1$HNMR (400 MHz, CDCl$_3$): δ (ppm): 3.58 (1H, m), 1.19 (6H, s), 0.91 (3H, d, J=6.6 Hz), 0.66 (3H, s).

Preparation of compound C33α. Compound C12 (110 mg, 0.294 mmol) was suspended in Toluene (dry) (7 ml) and 1-methyl-4-piperidone (1.666 mg, 0.015 mmol) and Aluminium isopropoxide (93 mg, 1.028 mmol) were added. Stirring at reflux temp. for 4 h. TLC: still s.m. present. More Aluminium isopropoxide (100 mg, 0.884 mmol) was added. Continue reflux. After 2 h, more Aluminium isopropoxide (100 mg, 0.884 mmol) was added. Continue reflux for 3 h. Then the last amount of Aluminium isopropoxide (100 mg, 0.884 mmol) was added. Reflux for 2 h more. Then the rx was allowed to cool to rt, diluted with EtOAc and extracted with 1N HCl to remove the 3. The yellow-colored aqueous layer was extracted 2× with EtOAc. The combined EtOAc fractions was washed with 1N HCl (3×), dried (brine, sulfate) and evaporated. The residue was stripped with DIPE to leave behind a white powder. This crude mixture was purified on a 40 g pre-packed flash column (GraceResolve™) applied in CHCl3 with a little MeOH; run in a gradient 30 ml/min: 2 min 100% Heptane; 38 min 0=>20% Heptane/EtOAc; 10 min 20% Heptane/EtOAc; fraction size 30 sec. Product C33a (84 mg, 0.225 mmol; 77%) was thus obtained. $^1$HNMR (400 MHz, CDCl$_3$): (ppm): 5.82 (1H, s), 1.20 (6H, s), 0.93 (3H, d, J=6.5 Hz), 0.73 (3H, s).

Preparation of compound C33b. Compound C33a (84 mg, 0.225 mmol) was dissolved in Ethanol (25 ml) and flushed with nitrogen. Then, Palladium on calcium carbonate, (~10% as Pd; 23.99 mg, 0.023 mmol, 10%) was added and the rx was again flushed with nitrogen. Then the rx was flushed with hydrogen and vigorously stirred under hydrogen. After 3 h, TLC indicated completion of the reaction. It was again flushed with nitrogen and the catalyst was filtered off over hyflo, the EtOH evaporated. The mixture was purified on a 12 g pre-packed flash column (GraceResolve™) run isocratic in Heptane/EtOAc 9/1; sample applied in DCM; 15 ml/min 1 min fraction-size; Product C33b (40 mg, 0.107 mmol; 47.4%) was thus obtained. $^1$HNMR (400 MHz, CDCl$_3$): δ (ppm): 2.60 (1H, t, J=14.4 Hz), 1.20 (6H, s), 0.93 (3H, d, J=6.5 Hz), 0.70 (3H, s).

Preparation of compound C33. Compound C33b (5 mg, 0.013 mmol) was dissolved in Tetrahydrofuran (dry) (1 ml) and cooled to −78° C. Then, K-Selectride (0.020 mmol, 0.020 ml) was added and the reaction mixture was stirred for 6 hours under nitrogen. The reaction was stopped by the addition of a 10% NaOH solution (0.1 mL) followed by the addition of 30% hydrogen peroxide solution (0.2 mL). The reaction mixture was warmed to room temperature and stirring was continued for 30 minutes. The mixture was extracted with ethyl acetate, the combined organic layers were washed with brine, dried over Na2SO4, filtered and evaporated. The crude product was purified by flash column chromatography using 2:1 Heptane/EtOAc. Compound C33 (2.2 mg, 0.00502 mmol; 37.6%) was thus obtained. LCMS: 83% pure, contains 17% of the 3α—OH isomer. $^1$HNMR (400 MHz, CDCl$_3$): δ (ppm): 4.12 (1H, t, J=2.7 Hz), 1.20 (6H, s), 0.92 (3H, d, J=6.6 Hz), 0.67 (3H, s).

Example 25. Preparation of D15

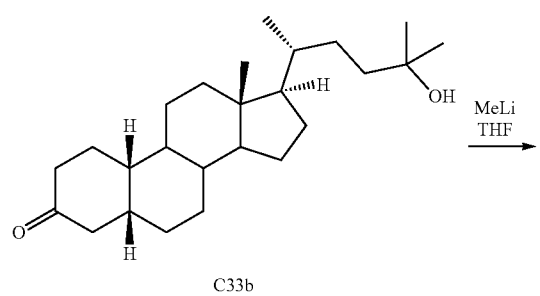

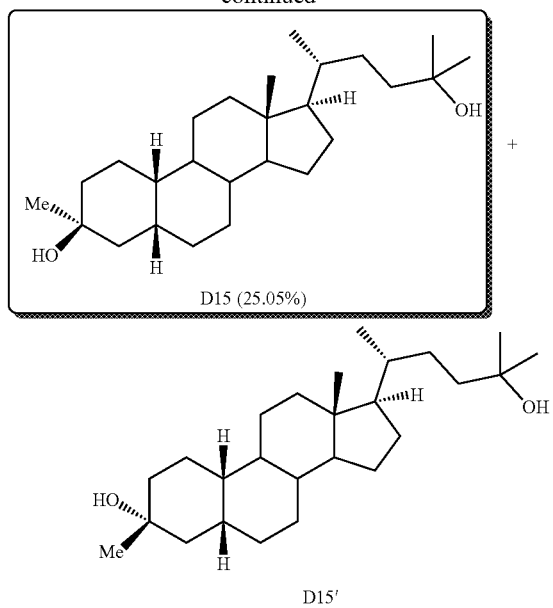

Compound C33b (40 mg, 0.107 mmol) was dissolved in tetrahydrofuran (dry) (1 ml) under argon and cooled to −78° C. Then, Methyllithium 1.6M (0.320 mmol, 0.200 ml) was added. Stirring at −78° C. TLC after 2 h: still much s.m. present. The rx was allowed to reach r.t. slowly. TLC after 1 h: still much s.m. present and a thick precipitate present. more Tetrahydrofuran (dry) (1 mL) was added to aid dissolution. After 30 min; the rx was almost completely dissolved. Continue stirring for 1 h. TLC: s.m. still present but 90+% conversion. The rx was stirred 30 min. longer and then quenched. Sat. aq. NH4Cl was added and the product was extracted with DCM (3×). 32 mg yield (crude). The aq. layer was saturated with NaCl and extracted again this time with EtOAc (3×). Now 36 mg crude product. The mixture was purified on a 12 g pre-packed flash column (GraceResolve™) run in a gradient 15 ml/min: 2 min 100% Heptane; 28 min 0=>15% Heptane/EtOAc; 20 min 15% Heptane/EtOAc; fraction size 60 sec. The product D15 (11 mg, 0.027 mmol; 25.05%) was thus obtained. $^1$HNMR (400 MHz, CDCl$_3$): δ (ppm): 1.21 (3H, s), 1.20 (6H, s), 0.92 (3H, d, J=6.5 Hz), 0.67 (3H, s).

Example 26. Preparation of D10 and D16

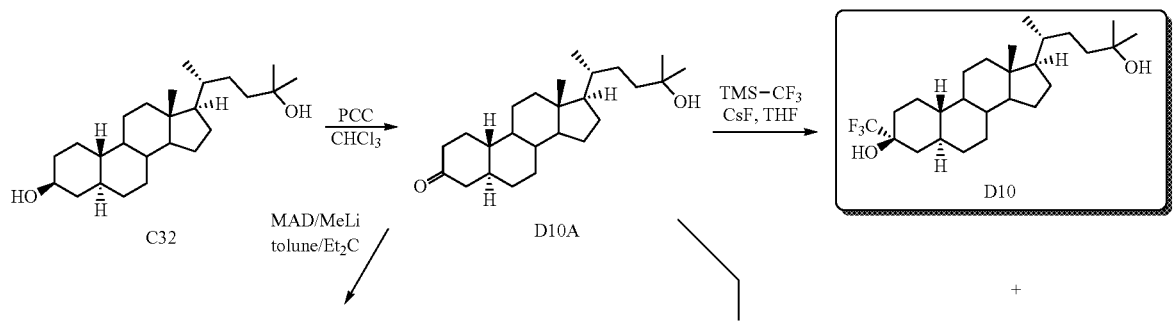

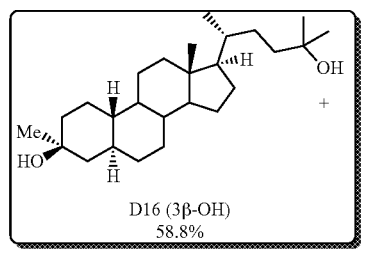

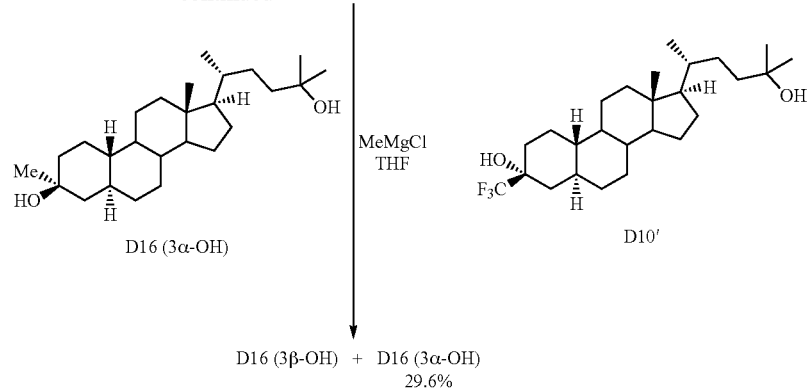

Preparation of 3-alpha-D16 compound. Compound D10a (68 mg, 0.182 mmol) was dissolved in Tetrahydrofuran (dry) (2 ml) under argon and cooled to 0° C. Then, Methylmagnesium chloride (0.605 ml, 1.815 mmol) was added. After 10 min, the rx was stirred at rt for 3 h. The rx was then added to 100 mL of sat. aq. NH4Cl, rx vessel rinsed with THF and DCM, and stirred for 0.5 h with DCM. The product was extracted twice more with DCM. DCM dried (brine, sulfate) and evaporated and Purification on a silica column run in 30 ml/min fractions 30 sec. Gradient: 5 min 100% heptane; 25 min 100/0 H/EtOAc=>80/20 heptane/EtOAc; 20 min 80/20 heptane/EtOAc. Compound D16 (3α—OH) (21 mg, 0.054 mmol; 29.6%) was thus obtained. $^1$HNMR (400 MHz, CDCl$_3$): δ (ppm): 1.19 (9H, s), 0.91 (3H, d, J=6.6 Hz), 0.66 (3H, s).

Preparation of 3-beta-D16 compound. Compound D10a (57 mg, 0.152 mmol) was dissolved in Toluene (dry) (1 ml) under argon and cooled to −78° C. Then, MAD, 0.4 M solution in toluene (1.141 ml, 0.456 mmol) was added. After 10 min. stirring at −78° C., Methyllithium, 1.6 M solution in diethyl ether (0.285 ml, 0.456 mmol) was added. Stirring for 2 h at −78° C. under argon. After 2 h at that temperature, the reaction was allowed to stir and warm to rt. After 2 additional hour it was quenched by adding it to saturated NH4Cl. The rx vessel was rinsed with EtOAc. Product extracted with EtOAc (2×). EtOAc dried (brine, Na2SO4) and evaporated. The mixture was purified on a 12 g pre-packed flash column (GraceResolve™) applied in DCM and run in a gradient 30 ml/min: 5 min 100% Heptane; 25 min 0=>15% Heptane/EtOAc; 20 min 15% Heptane/EtOAc; fraction size 30 sec. Product D16 (3β-OH) (35 mg, 0.090 mmol; 58.8%) was thus obtained. $^1$HNMR (400 MHz, CDCl$_3$): δ (ppm): 1.23 (3H, s), 1.20 (6H, s), 0.91 (3H, d, J=6.6 Hz), 0.66 (3H, s).

Preparation of compound D10a. Compound C32 (222 mg, 0.589 mmol) was dissolved in Chloroform (dry) (15 ml) by slightly heating. Then the solution was cooled in a water bath (did not crystallize upon cooling) and PCC (191 mg, 0.884 mmol) was added. Stirring while still in the water-bath. TLC after 1 h: ~60-70% conversion. Stirring overnight. The solution was then transferred to a separatory funnel and the deposit was extensively washed with DCM and added to the separatory funnel. Washing with 0.5N KHSO$_4$. The aq. phase was washed with DCM, org. phase combined and dried over Na$_2$SO$_4$ (no brine) and evaporated.

The mixture was purified on a 12 g pre-packed flash column (GraceResolve™) run in a gradient 30 ml/min: 5 min 100% H; 25 min 0=>15% H/EA; 20 min 15% H/EA; fraction size 30 sec. 100 tubes. Compound D10a (132 mg, 0.352 mmol; 59.8%) was thus obtained. $^1$HNMR (400 MHz, CDCl$_3$): δ (ppm): 1.20 (6H, s), 0.92 (3H, d, J=6.6 Hz), 0.69 (3H, s).

Preparation of compound D10. Compound D10a (73 mg, 0.195 mmol) was dissolved in tetrahydrofuran (dry) (2 ml) under argon and trifluoromethyltrimethylsilane (0.086 ml, 0.585 mmol) and Cesium fluoride (2.96 mg, 0.019 mmol) were added. Stirring at rt. The solution became slightly yellow slowly. TLC after 3 h: full conversion. The rx was diluted with DCM and extracted with water. No phase separation. Brine (equal volume) was added. Good separation. The aq. layer was again extracted with DCM; DCM combined and dried (Na2SO4) and evaporated. 103 mg crude product (102%). Flash column on a 12 g pre-packed column run in 30 min. gradient from 0=>2.5% DIPE in heptane. The impure TMS-intermediate was thus obtained as an impure mixture of the 3α- and 3β—OH products and used as such: The intermediate was dissolved in 1,4-Dioxane (4 ml) and 1N HCl (1 mL, 1.000 mmol) is added. Stirring at rt. TLC after 1 h: s.m. gone. Water was added and the product was extracted with DCM 3× and dried over Na2SO4 and evaporated. The crude product was purified on a C18-column run in a gradient of MeCN/water 95/5=>0/100 12 min then 12 min isocratic 100% water. Compound D10 (14 mg, 0.030 mmol; 22.9%) was thus obtained. $^1$HNMR (400 MHz, CDCl$_3$): δ (ppm): 1.19 (6H, s), 0.91 (3H, d, J=6.6 Hz), 0.67 (3H, s).

Example 27. Preparation of Compound D1

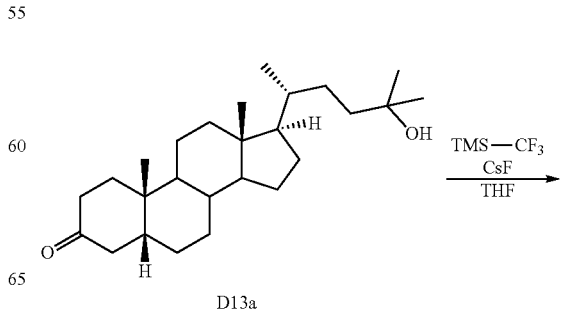

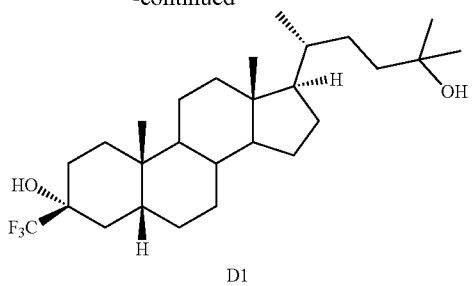

D1

In a flame dried tube a colorless clear solution of compound D13a (97 mg, 0.250 mmol) and Trifluoromethyltrimethylsilane (0.119 ml, 0.749 mmol) in THF (dry, 1 mL) was cooled to 0° C. under argon. Cesium fluoride (20 mg, 0.132 mmol) was added. Reaction mixture stayed colorless and was stirred at 0° C. for 5 min. Cooling bath was removed and stirring was continued at RT for 1.5 h. Reaction mixture had turned brown-yellow, TLC (Heptane/EtOAc, 1:1) complete conversion. Reaction mixture was left standing at RT overnight. H2O (1 mL) and EtOAc (5 mL) were added. Layers were separated and aq. layer was extracted with EtOAc (2×5 mL). Combined org. layers were dried with Na2SO4 and solvents were removed in vacuo. Flash chromatography (Heptane, 5%-20% EtOAc) afford the impure 3-OTMS intermediate. This was used as such: Aq. HCl (1N, 1 mL) was added to a solution of the 3-OTMS intermediate in THF (1 mL). Reaction mixture was stirred at RT overnight, TLC (H/E; 1:1) complete conversion. Solvents were removed in vacuo. A yellow solid was obtained, Purification by flash chromatography (Heptane; 15%-35% EtOAc) afforded compound D1 (36 mg, 0.078 mmol; 31.4%). $^1$H-NMR (400 MHz, CDCl$_3$): (ppm): 1.20 (6H, s), 0.96 (3H, s), 0.89 (3H, d, J=10.6 Hz), 0.65 (3H, s).

Example 28. Preparation of D2a-D2 Compounds

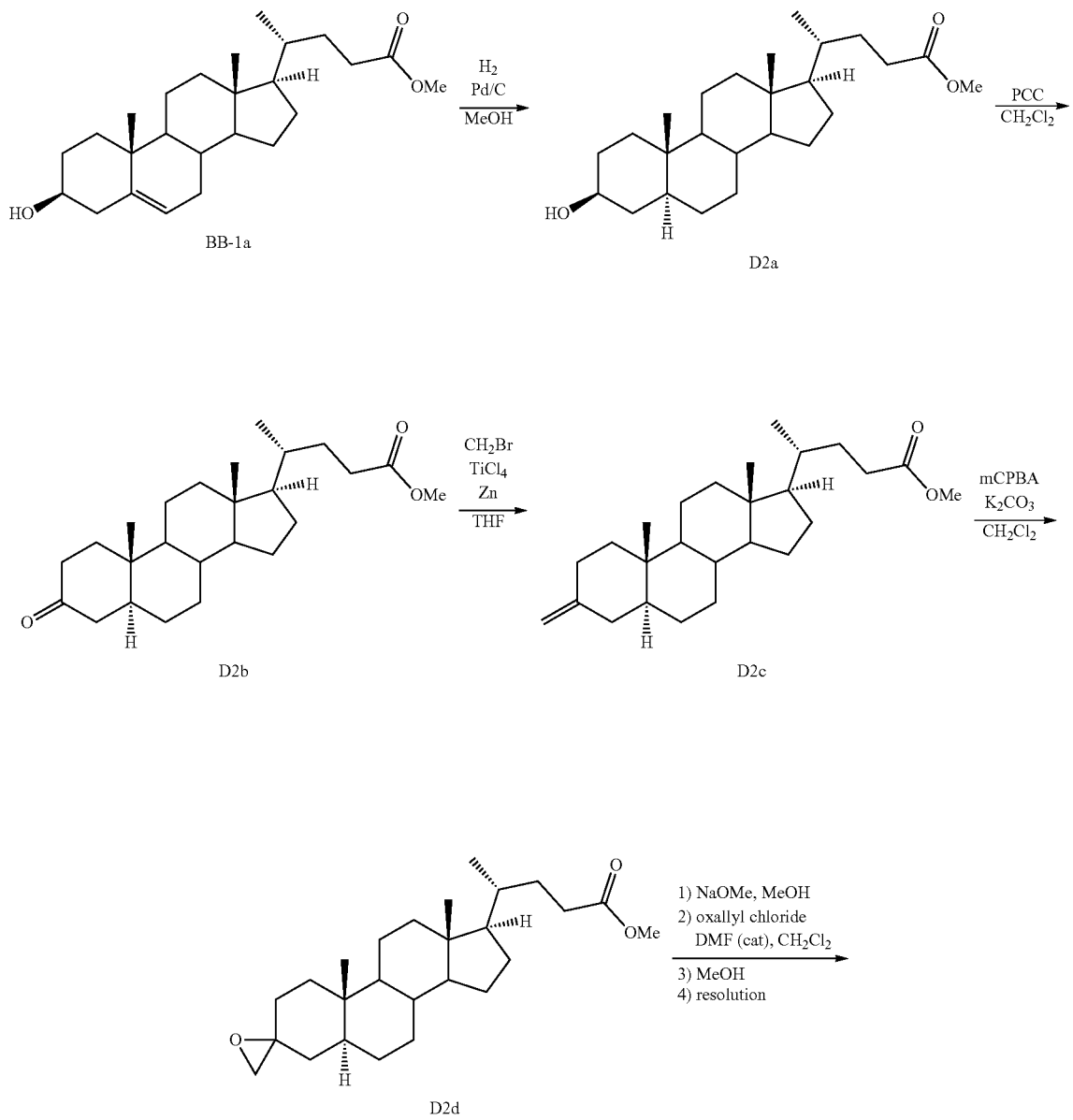

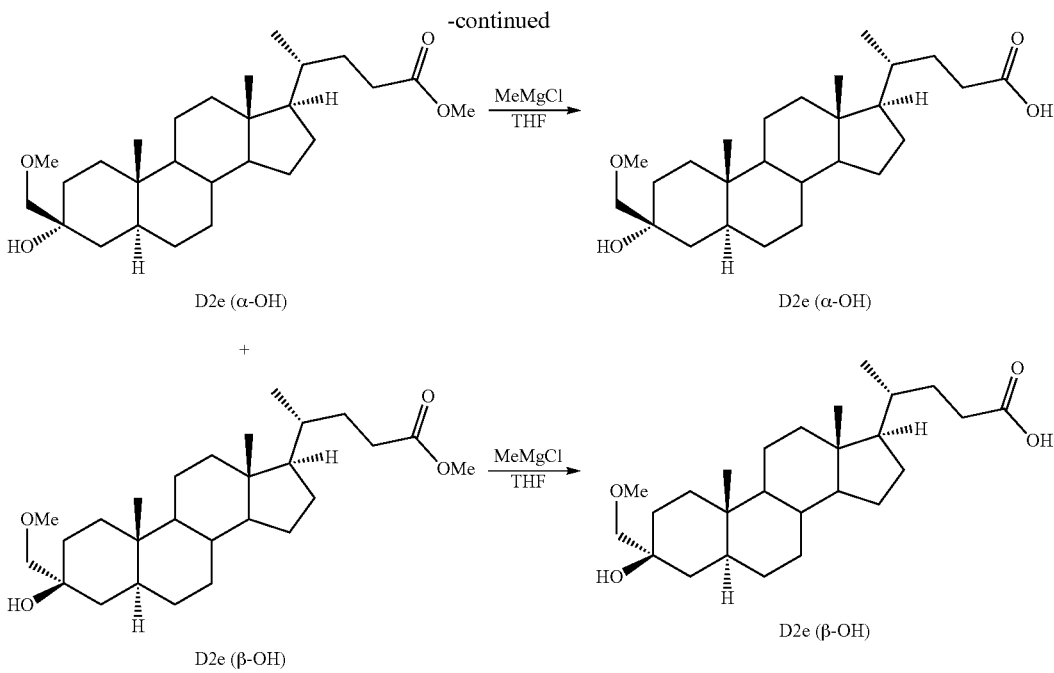

Preparation of compound D2a. Under an atmosphere of argon, compound BB-1a (1 g, 2.57 mmol) was dissolved in methanol (25 ml), and palladium, 10% on activated carbon (0.137 g, 0.129 mmol) was added. The argon atmosphere was replaced by hydrogen (balloon) and the reaction mixture was vigorously stirred at room temperature overnight. The reaction mixture was filtered over hyflo and the filter residue was washed with methanol (50 ml) and dichloromethane (2×50 ml). The filtrate and washings were combined and evaporated under reduced pressure to afford product D2a (1.01 g, 2.57 mmol, Yield=100%) as white powder. $^1$HNMR (400 MHz, CDCl$_3$) δ (ppm): 3.66 (3H, s), 3.59 (1H, oct, J=5.1 Hz), 2.35 (1H, ddd, J=15.4, 10.3, 5.1 Hz), 2.21 (1H, ddd, J=15.8, 9.5, 6.3 Hz), 1.94 (1H, dt, J=12.4, 3.3 Hz), 0.91 (3H, d, J=6.4 Hz), 0.65 (3H, s), 0.62 (1H, ddd, J=14.8, 8.1, 4.1 Hz).

Preparation of compound D2b. A suspension of pyridinium chlorochromate (PCC) (0.969 g, 4.49 mmol) in dichloromethane (10 ml) (dried over molecular sieves) was cooled to 0° C. under nitrogen atmosphere. A solution of D2a (0.585 g, 1.498 mmol) in dichloromethane (5 ml) (dried over molecular sieves) was added gradually. After stirring for 1 h, a color change from orange to dark brown was observed. The ice bath was removed and stirring was continued for 3.5 h. TLC[heptane(2):ethyl acetate(1)] showed complete clean conversion to a higher eluting product after vanillin staining. The reaction mixture was diluted with a 2:1 mixture of heptane/ethyl acetate (15 ml), eluted over a short pad of silica (30 g) and the pad was twice rinsed with heptane/ethyl acetate/dichloromethane 2:1:1 (60 ml). The elute was washed with 0.5N aqueous potassium hydrogen sulfate (90 ml). The washing was back extracted with dichloromethane (90 ml) and this extract was combined with the former organic layer, dried over sodium sulfate, filtered and evaporated under reduced pressure. The residue was stripped twice with dichloromethane to afford D2b (0.555 g, 1.428 mmol, Yield=95%) as a white solid. $^1$HNMR (400 MHz, CDCl$_3$) δ (ppm): 3.66 (3H, s), 2.04-1.94 (2H, m), 1.91-1.74 (2H, m), 1.73-1.66 (1H, m), 1.01 (3H, s), 0.92 (3H, d, J=6.4 Hz), 0.64 (3H, s).

Preparation of compound D2c. Under an atmosphere of argon, dibromomethane (1.268 ml, 18.01 mmol) was added to a stirred suspension of zinc (3.99 ml, 57.9 mmol) in tetrahydrofuran (dry) (30 ml) (slightly exothermic). The mixture was cooled to −40° C. in a dry ice/acetonitrile bath and stirring for 10 minutes. Titanium(IV) chloride (1.533 ml, 13.90 mmol) was added gradually at such a rate that the temperature did not exceed −30° C. (very exothermic). The dry ice/acetonitrile bath was removed and the mixture was stirred in an ice bath for 4 h at an internal temperature between 0-5° C. Part of the black suspension (~3 ml) was added at room temperature to a solution of D2b (0.1 g, 0.257 mmol) in tetrahydrofuran (dry) (10 ml). The mixture was stirred for 10 minutes. TLC[Heptane (2) ethyl acetate (1)] showed mainly starting material present in the reaction mixture after molybdenum staining. Another part of the suspension (~3 ml) was added and stirring was continued for 5 minutes. TLC[Heptane(2):ethyl acetate(1)] showed still mainly starting material present in the reaction mixture after molybdenum staining. The rest of the suspension was added and after stirring for 5 minutes, TLC[Heptane(2):ethyl acetate(1)] showed complete conversion of the starting material to mainly one very apolar product after molybdenum staining. The reaction mixture was poured out in saturated aqueous sodium hydrogen carbonate (100 ml) (beware for foaming) and extracted three times with ethyl acetate (100 ml). The combined extracts were washed with brine (150 ml), dried over sodium sulfate and evaporated under reduced pressure. The residue was chromatographed on silica gel (12 g flash column) using an eluent with gradient of 0-5% diisopropyl ether in heptane to provide D2c (0.058 g, 0.150 mmol, Yield=58%) as a white solid product. $^1$HNMR (400 MHz, CDCl$_3$) δ (ppm): 4.55 (2H, brd), 3.66 (3H, s), 2.35 (1H, ddd, J=15.4, 10.3, 5.1 Hz), 2.21 (1H, ddd, J=15.8, 9.7, 6.4 Hz), 2.19-2.09 (2H, m), 2.06-1.71 (6H, m), 1.69-1.61 (1H, m), 0.91 (3H, d, J=6.4 Hz), 0.85 (3H, s), 0.69-0.60 (1H, m), 0.65 (3H, s).

Preparation of compound D2d. To a solution of D2c (0.058 g, 0.150 mmol) in dry dichloromethane (2 ml) (dried on molsieves) was added potassium carbonate (anhydrous) (0.027 g, 0.195 mmol) under nitrogen atmosphere. The resulting mixture was cooled in an ice/water bath, and solid 3-chloroperoxybenzoic acid (70-75%) (mCPBA) (0.039 g, 0.158 mmol) was added in a one portion. The reaction mixture was stirred overnight. TLC[heptane(9):ethyl acetate (1)] showed partial clean conversion after vanillin staining. Extra potassium carbonate (anhydrous) (0.027 g, 0.195 mmol) and 3-chloroperoxybenzoic acid (70-75%) (m-CPBA) (0.039 g, 0.158 mmol) was added and stirring was continued for 2 h. TLC[heptane(9):ethyl acetate(1)] showed complete conversion after vanillin staining. The reaction mixture was filtered and the precipitated benzoate salt was washed with dichloromethane (2×5 ml). The solvent was removed in vacuo to afford D2d (0.060 g, 0.149 mmol, Yield=99%) as a white solid residue. According to NMR a 2:1 mixture of α-O— and β-O-diastereoisomers was obtained. $^1$HNMR (400 MHz, CDCl$_3$) δ (ppm): 3.66 (3H, s), 2.62 (0.33H[α-diastereoisomer], d, J=4.8 Hz), 2.61 (0.33H [α-diastereoisomer], d, J=4.9 Hz), 2.57 (0.33H[β-diastereoisomer], bs), 2.35 (1H, ddd, J=15.4, 10.3, 5.1 Hz), 2.21 (1H, ddd, J=15.7, 9.4, 6.3 Hz), 2.10-1.99 (1H, m), 1.99-1.92 (1H, m), 0.91 (3H, d, J=6.4 Hz), 0.86 (1H[β-diastereoisomer], s), 0.84 (2H[α-diastereoisomer], s), 0.66 (3H, s).

Preparation of compound D2e (α-OH and β-OH). A mixture of D2d (0.055 g, 0.137 mmol) in methanol (extra dry) (5.5 ml) was heated until a clear colorless solution was obtained. The solution was allowed to cool to room temperature under a nitrogen atmosphere and sodium methoxide, 5.4M (30 wt. %) solution in methanol (0.239 mmol, 0.080 ml) was added. The reaction mixture was heated to reflux and stirred overnight. TLC[heptane(4):ethyl acetate (1)] showed complete conversion after vanillin staining, product not visible. The reaction mixture was poured out in a saturated aqueous solution of ammonium chloride (50 ml) and three times extracted with dichloromethane (50 ml). The combined extracts were dried over sodium sulfate and evaporated. According to TLC, a very polar product was formed. The methyl ester moiety was hydrolyzed to the carboxylic acid due to presence of water in the reaction mixture. The residue was dissolved in dichloromethane (10 ml). Oxalyl chloride (0.078 g, 0.612 mmol, 0.053 ml) and N,N-dimethylformamide (cat.) were added, and the reaction mixture was stirred for 2 h. A sample was poured out in methanol, evaporated until dryness, and analyzed on TLC [dichloromethane(98):methanol(2)] which showed complete conversion to the methyl ester after molybdenum staining. The reaction mixture was diluted with methanol (150 ml) (dried on mol. sieves), and evaporated under reduced pressure at 40° C. The residue was purified by flash column (12 g) chromatography [heptane (100=>80): ethyl acetate (0=>20)]. Two product fractions were obtained, which were separately collected and evaporated under reduced pressure to afford D2e (α-OH) (0.035 g, 0.081 mmol, Yield=33%) and D2e (β-OH) (0.032 g, 0.074 mmol, Yield=30%) as white solids. D2e (α-OH) and D2e (β-OH) were used as such in the following experiment. D2e (α—OH): $^1$HNMR (400 MHz, CDCl$_3$) δ (ppm): 3.66 (3H, s), 3.38 (3H, s), 3.18 (2H, s), 2.35 (1H, ddd, J=15.4, 10.3, 5.1 Hz), 2.21 (1H, ddd, J=15.7, 9.4, 6.3 Hz), 2.02 (1H, bs), 1.94 (1H, dt, J=12.3, 3.0 Hz), 1.90-1.73 (2H, m), 0.91 (3H, d, J=6.4 Hz), 0.74 (3H, s), 0.65 (3H, s). D2e (β-OH): $^1$HNMR (400 MHz, CDCl$_3$) δ (ppm): 3.66 (3H, s), 3.39 (3H, s), 3.37 (2H, d, J=4.3 Hz), 2.54 (1H, bs), 2.35 (1H, ddd, J=15.4, 10.3, 5.1 Hz), 2.21 (1H, ddd, J=15.8, 9.5, 6.3 Hz), 1.95 (1H, dt, J=12.5, 3.0 Hz), 1.90-1.73 (2H, m), 0.91 (3H, d, J=6.4 Hz), 0.83 (3H, s), 0.65 (3H, s).

Preparation of compound D2 (α—OH). In a flame dried round bottom flask (100 ml), D2e (α—OH) (0.035 g, 0.081 mmol) was dissolved in tetrahydrofuran (dry) (1 ml) and cooled in an ice bath under argon for 0.5 h. Methylmagnesium chloride 3.0M in THF (0.805 mmol, 0.268 ml) was added via a syringe. Some gas evolution was observed. After stirring the reaction mixture for 2 h, TLC[heptane(1):ethyl acetate(1)] showed complete conversion of the starting material to a lower eluting product after molybdenum staining. The reaction mixture was partitioned between a saturated aqueous solution of ammonium chloride (20 ml) and dichloromethane (20 ml) and left for two days. The organic layer was separated and the aqueous layer was twice more extracted with dichloromethane (20 ml). The extracts were combined, dried over sodium sulfate and evaporated. The residue was purified by flash column (12 g) chromatography [heptane(100=>80):ethyl acetate(0=>20)]. The product containing fractions were collected and evaporated under reduced pressure at 40° C. The residue was transferred to a vial as a solution in dichloromethane/methanol and evaporated at 37° C. under a stream of nitrogen. The white solid residue was dried at 45° C. in a vacuum oven overnight to afford D2 (α—OH) (0.025 g, 0.055 mmol, Yield=68%) as white powder. $^1$HNMR (400 MHz, CDCl$_3$) δ (ppm): 3.38 (3H, s), 3.18 (2H, s), 1.98 (1H, bs), 1.95 (1H, dt, J=12.5, 3.2 Hz), 1.88-1.79 (1H, m), 1.68-1.61 (1H, m), 1.20 (3H, s), 1.19 (3H, s), 0.91, (3H, d, J=6.5 Hz), 0.74 (3H, s), 0.65 (3H, s).

Preparation of compound D2 (β-OH). In a flame dried round bottom flask (100 ml), D2e (β—OH) (0.035 g, 0.081 mmol) was dissolved in tetrahydrofuran (dry) (1 ml) and cooled in an ice bath under argon for 0.5 h. Methylmagnesium chloride 3.0M in THF (0.805 mmol, 0.268 ml) was added via a syringe. Some gas evolution was observed. After stirring the reaction mixture for 2 h, TLC[heptane(1):ethyl acetate(1)] showed complete conversion of the starting material to a lower eluting product after molybdenum staining. The reaction mixture was partitioned between a saturated aqueous solution of ammonium chloride (20 ml) and dichloromethane (20 ml) and left for two days. The organic layer was separated and the aqueous layer was twice more extracted with dichloromethane (20 ml). The extracts were combined, dried over sodium sulfate and evaporated. The residue was purified by flash column (12 g) chromatography [heptane (100=>80): ethyl acetate (0=>20)]. The product containing fractions were collected and evaporated under reduced pressure at 40° C. The residue was transferred to a vial as a solution in dichloromethane/methanol and evaporated at 37° C. under a stream of nitrogen. The white solid residue was dried at 45° C. in a vacuum oven overnight to afford D2 (β-OH) (0.018 g, 0.039 mmol, Yield=53%) as white powder. $^1$HNMR (400 MHz, CDCl$_3$) δ (ppm): 3.40 (3H, s), 3.39 (1H, d, J=9.2 Hz), 3.36 (1H, d, J=9.2 Hz), 2.51 (1H, bs), 1.96 (1H, dt, J=12.4, 3.1 Hz), 1.89-1.77 (1H, m), 1.20 (6H, s), 0.91, (3H, d, J=6.5 Hz), 0.83 (3H, s), 0.65 (3H, s).

Example 29. Preparation of 3-alpha-D3 and 3-beta-D6

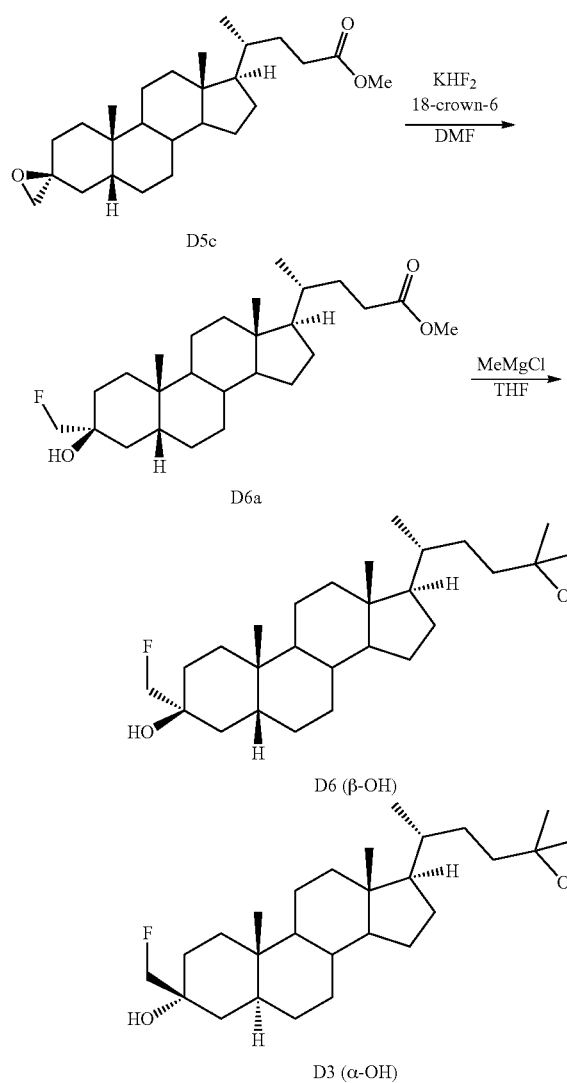

Preparation of compound D6a. To a solution of 18-crown-6 (0.315 g, 1.192 mmol) and KHF₂ (0.233 g, 2.98 mmol) in dry DMF (7.5 mL) under an argon atmosphere was added D5c (0.3 g, 0.745 mmol) The reaction mixture was heated till 150° C. overnight. More KHF₂ (0.233 g, 2.98 mmol) was added and heating was continued for 8 h. The mixture was cooled to room temperature poured out in H₂O (150 mL) and stirred with EtOAc (100 mL) for 30 min. The aqueous layer was extracted twice with EtOAc (200 mL). The combined organic layers were washed with brine (2×) dried over Na₂SO₄, filtered and evaporated under reduced pressure. The crude product was purified by flash column chromatography (silica, heptane/ethylacetate, 1:0->85:15) to afford product D6a (71 mg, 0.17 mmol, yield=23%). According to NMR D6a was obtained as a 3:1 cis/trans mixture. ¹HNMR (400 MHz, CDCl3) δ(ppm): 4.18 (1.5H [cis-isomer (β-OH)], d, J=47.8 Hz), 4.15 (0.5H [trans-isomer (α—OH)], d, J=48 Hz), 3.66 (3H, s), 2.35 (1H, ddd, J=15.4, 10.3, 5.2 Hz), 2.21 (1H, ddd, J=15.8, 9.5, 6.3 Hz), 0.98 (3H, s), 0.91 (3H, d, J=6.4 Hz), 0.65 (3H, s).

Preparation of compound D6 (β-OH) and D3 (α—OH). Compound D6a (0.071 g, 0.168 mmol) was coevaporated with toluene (50 mL) and dissolved in dry THF (2 mL) under an atmosphere of argon and cooled to 0° C. MeMgCl 3.0M in THF (0.560 mL, 1.680 mmol,) was added using a syringe. The reaction mixture was stirred for 2 h at 0° C. The reaction mixture was quenched with saturated aqueous NH₄Cl (50 mL) and extracted three times with CH₂Cl₂ (100 mL). The combined organic layers were washed with brine dried on Na₂SO₄ and the crude product was purified by flash column chromatography (silica, heptane/ethylacetate, 1:0->85:15) to afford D6 (β-OH) (23 mg, 0.05 mmol, yield=32%) and D3 (α—OH) (8 mg, 0.007 mmol, yield=4%). D6 (β-OH): ¹HNMR (400 MHz, CDCl3) δ(ppm): 4.19 (2H, d, J=47.8 Hz), 2.00-1.94 (1H, m), 1.76-1.69 (1H, m), 1.20 (6H, s), 0.98 (3H, s), 0.91 (3H, d, J=6.5 Hz), 0.65 (3H, s). D3 (α—OH): ¹HNMR (400 MHz, CDCl3) δ(ppm): 4.15 (2H, d, J=47.8 Hz), 1.96 (1H, dt, J=12.4, 3.2 Hz), 1.89-1.78 (1H, m), 1.20 (3H, s), 1.19 (3H, s), 0.92 (3H, d, J=6.5 Hz), 0.76 (3H, s), 0.65 (3H, s).

Example 30. Preparation of Compound D4

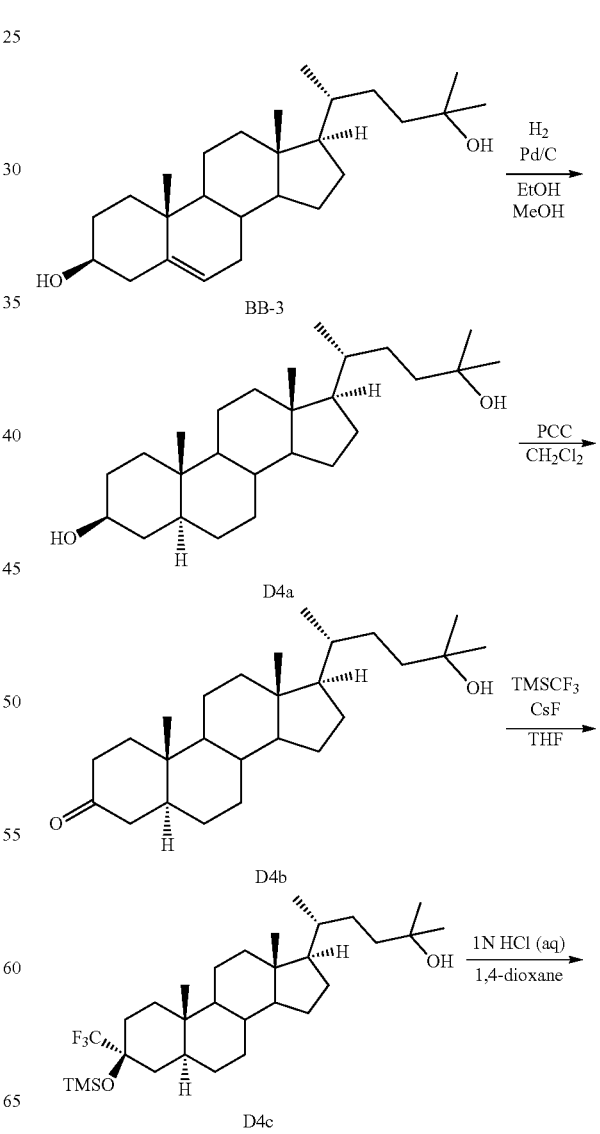

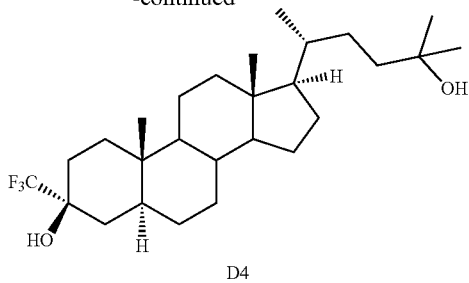

D4

Preparation of compound D4a. BB-3 (0.448 g, 1.153 mmol) was suspended in EtOH (abs) (12 mL) and MeOH (6 mL) under an atmosphere of argon and palladium, 10% on activated carbon (0.012 g, 0.012 mmol) was added. The argon atmosphere was replaced by hydrogen (atmospheric) and the reaction mixture was vigorously stirred at room temperature for 2 h. Stirring was continued for 3 days. The reaction mixture was filtered over hyflo and evaporated till dryness. The residue was suspended in acetic acid (5 mL), EtOAc (5 mL) and 1,4-dioxane (5 mL) and heated till a clear solution was obtained. The reaction mixture was cooled to room temperature and palladium, 10% on activated carbon (0.012 g, 0.012 mmol) was added under an Argon atmosphere. The argon atmosphere was replaced by hydrogen (atmospheric) and the reaction mixture was vigorously stirred at room temperature overnight. The reaction mixture was filtered over hyflo and washed with MeOH (2×50 mL) and CH$_2$Cl$_2$ (50 mL). The solvents were evaporated and the residue triturated with saturated aqueous NaHCO$_3$, filtered off and dried in a vacuum oven at 40° C. overnight to afford D4a (385 mg, 0.99 mmol, yield=85%) as a white solid. $^1$HNMR (400 MHz, CDCl$_3$) δ (ppm): 3.59 (1H, sep, J=5.3 Hz), 1.96 (1H, dt, J=9.3, 3.1 Hz), 1.98-1.75 (2H, m), 1.71 (1H, dt, J=13.2, 3.4 Hz), 1.65 (1H, dq, J=13.0, 3.4 Hz), 1.19 (6H, s), 0.91, (3H, d, J=6.5 Hz), 0.80 (3H, s), 0.65 (3H, s).

Preparation of compound D4b. To an ice cooled solution of pyridinium chlorochromate (PCC) (0.248 g, 1.152 mmol) in dry CH$_2$Cl$_2$ (4 mL) under a nitrogen atmosphere was added a suspension of D4a (0.3 g, 0.768 mmol) in dry CH$_2$Cl$_2$ (4 mL). The solid material was added drop wise redissolved as a solution in dry CHCl$_3$ (4 mL). The reaction mixture was stirred for 30 min at 0° C., followed by 2 h at room temperature. Again pyridinium chlorochromate (PCC) (0.248 g, 1.152 mmol) was added in one portion at room temperature, and the reaction mixture was stirred overnight. The reaction mixture was eluted over a short pad of sand, silica (5 g) and hyflo, and the pad was rinsed with CH$_2$Cl$_2$ (100 mL). The elute was washed twice with aqueous 0.5N KHSO$_4$ (100 ml). The combined washings were extracted once with CH$_2$Cl$_2$ (100 mL), and the combined organic layers were dried over Na$_2$SO$_4$, filtered and evaporated under reduced pressure to afford D4b (306 mg, 0.79 mmol, yield=103%) an orange/brown solid. $^1$HNMR (400 MHz, CDCl$_3$) δ (ppm): 2.38 (1H, td, J=14.5, 6.4 Hz), 2.32-2.21 (2H, m), 2.15-1.93 (3H, m), 1.90-1.79 (1H, m), 1.75-1.65 (1H, m), 1.20 (6H, s), 1.01 (3H, s), 0.92 (3H, d, J=6.4 Hz), 0.78-0.64 (1H, m), 0.68 (3H, s).

Preparation of compound D4c. In a flame dried reaction tube, a solution of D4b (0.1 g, 0.257 mmol) and (trifluoromethyl)trimethylsilane (0.053 mL, 0.34 mmol) in dry THF (2.5 mL) was cooled to 0° C. under argon. CsF (spatula tip) was added and the reaction mixture was stirred at 0° C. for 5 minutes. The cooling bath was removed and stirring was continued at room temperature overnight. Extra (trifluoromethyl)trimethylsilane (0.053 ml, 0.34 mmol) and CsF (spatula tip) were added to the reaction mixture and stirring under argon atmosphere was continued for 3 h. H$_2$O (50 mL) and EtOAc (50 mL) were added. Layers were separated after stirring for 30 minutes. The aqueous layer was extracted twice with EtOAc (50 mL). The combined organic layers were dried with Na$_2$SO$_4$ and solvents were removed in vacuo. D4c (163 mg, 0.31 mmol, yield=119%) was obtained as a light yellow oil. $^1$HNMR (400 MHz, CDCl$_3$) δ (ppm): 2.04-1.92 (1H, m), 1.90-1.68 (2H, m), 1.09 (3H, s), 1.08 (3H, s), 0.80 (3H, s), 0.73 (3H, s), 0.55 (3H, s), 0.03 (12H, m).

Preparation of compound D4. To a solution of D4c (0.137 g, 0.258 mmol) in 1,4-dioxane (8 mL) was added 1 M aqueous HCl (2 mL, 2.0 mmol). The yellow solution was stirred for 3 h at room temperature. The reaction mixture was diluted with H$_2$O (50 mL) and extracted with CH$_2$Cl$_2$ (3×50 mL). The combined organic layers were washed with saturated aqueous NaHCO$_3$, brine, dried on Na$_2$SO$_4$ and the solvents evaporated. The crude product was purified by flash column chromatography (silica, heptane/EtOAc, 1:0->4:1) and crystallized from CH$_2$Cl$_2$ to afford D4 (44 mg, 0.10 mmol, yield=37%) as a white solid. $^1$HNMR (400 MHz, CDCl$_3$) δ (ppm): 2.09-2.02 (1H, m), 1.98 (1H, s), 1.96 (1H, dt, J=12.8, 3.4 Hz), 1.88-1.77 (2H, m), 1.72-1.61 (3H, m), 1.20 (3H, s), 1.19 (3H, s), 0.92 (3H, d, J=6.6 Hz), 0.85 (3H, s), 0.65 (3H, s).

Example 31. Preparation of Compound D5

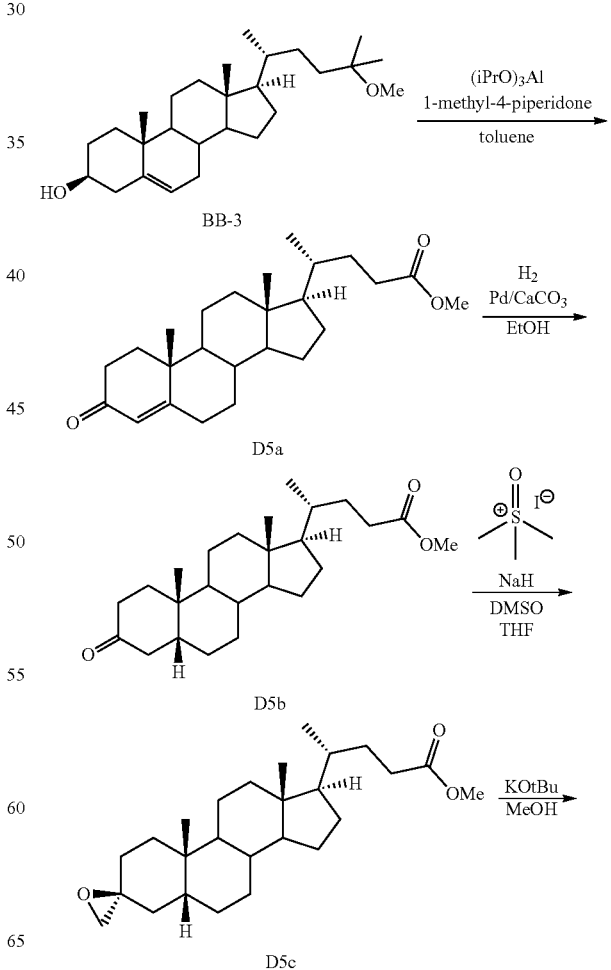

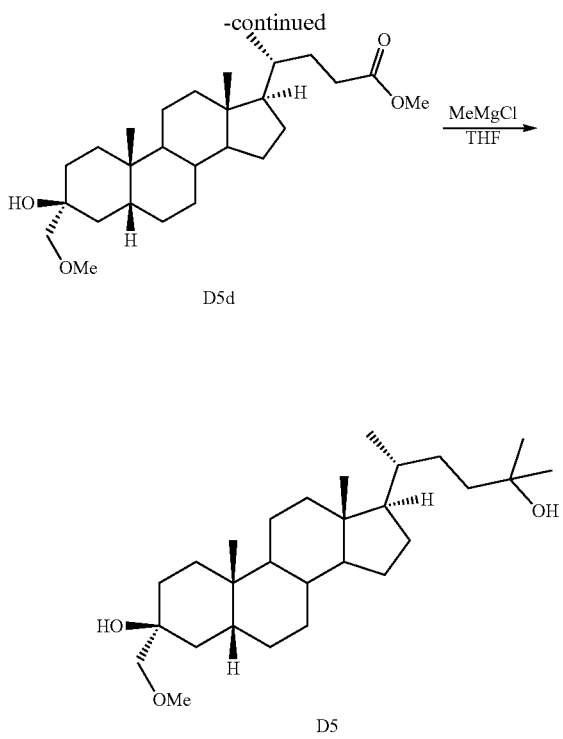

Preparation of compound D5a. To a solution BB-1 (2 g, 5.15 mmol) and Al(iPrO)₃ (3.68 g, 18.01 mmol) in dry toluene (80 mL) was added 1-methyl-4-piperidone (29.1 g, 257 mmol, 29.7 mL). The solution was stirred at reflux for 3 h. The reaction mixture was cooled to room temperature and diluted with aqueous 0.5 M HCl (80 mL), brine (80 mL) and Et₂O (120 mL). The organic layer was extracted with EtOAc (3×100 mL). The combined organic layers were dried with Na₂SO₄, filtered and the solvents were removed in vacuo. The residue was diluted with aqueous 1 M HCl (250 mL) and extracted with EtOAc (2×250 mL). The organic solvents were washed with brine, dried with Na₂SO₄ and evaporated till dryness. The crude product was purified by flash column chromatography (silica, heptane/ethylacetate, 1:0->9:1) and coevaporated with CH₂Cl₂ to afford D5a (1.27 g, 3.27 mmol, yield=64%). ¹HNMR (400 MHz, CDCl3) δ(ppm): 5.72 (1H, s), 3.67 (3H, s), 2.48-2.17 (6H, m), 2.02 (1H, dt, J=9.6, 3.8 Hz), 1.94-1.75 (3H, m), 1.69 (1H, td, J=14.0, 4.7 Hz), 1.18 (3H, s), 0.92 (3H, d, J=6.4 Hz), 0.71 (3H, s).

Preparation of compound D5b. A suspension of D5a (1.26 g, 3.26 mmol) in absolute EtOH (150 mL) was heated till the starting material was dissolved. The solution was cooled to room temperature and made under an argon atmosphere. Palladium on calcium carbonate, 10% (w/w) (cat.) was added, and hydrogen (atmospheric) was flushed through the reaction mixture for 15 minutes. The reaction mixture was stirred at room temperature under hydrogen atmosphere overnight. The reaction mixture was flushed with argon, the solids were filtered over Celite/silica gel, and the filter was washed with EtOH (75 ml). The solvents were removed in vacuo and the crude product was purified by flash column chromatography (silica, heptane/ethylacetate, 1:0->9:1) to obtain product D5b (1.12 g, 2.16 mmol, Yield=75%). According to NMR D5b was obtained as a 3:1 cis/trans mixture. ¹HNMR (400 MHz, CDCl3) δ(ppm): 3.67 (3H, s), 2.70 (1H, t, J=14.2 Hz), 1.02 (2H[cis-isomer], s), 1.00 (1H[trans-isomer], s), 0.92 (3H, d, J=6.4 Hz), 0.68 (3H, s).

Preparation of compound D5c. To a solution of trimethylsulfoxonium iodide (0.747 g, 3.39 mmol) in dry DMSO (10 mL) under an nitrogen atmosphere was added NaH (60% dispersion in mineral oil) (0.075 g, 3.13 mmol) in 1 portion. The reaction mixture was stirred for 30 min and a solution of D5b (1.014 g, 2.61 mmol) in dry THF (10 mL) was added. The reaction mixture was stirred for 1 h, followed by the addition of extra trimethylsulfoxonium iodide (0.747 g, 3.39 mmol) and NaH (60% dispersion in mineral oil) (0.075 g, 3.13 mmol). The mixture stirred for 2 h. The reaction mixture was partitioned between saturated aqueous NH₄Cl (150 mL) and CH₂Cl₂ (150 mL). The aqueous layer extracted with CH₂Cl₂ (100 mL) and the combined organic layers were washed with brine, dried on Na₂SO₄ and evaporated till dryness. The crude product was purified by flash column chromatography (silica, heptane/ethylacetate, 1:0->88:12) to afford product D5c (1 g, 2.48 mmol, Yield=75%). According to NMR D5c was obtained as a cis/trans mixture. ¹HNMR (400 MHz, CDCl3) δ(ppm): 3.67 (3H, s), 2.64-2.60 (2H, m), 2.42-2.30 (2H, m), 2.27-2.16 (1H, m), 0.99 (3H, s), 0.92 (3H, d, J=6.4 Hz), 0.66 (3H, s).

Preparation of compound D5d. To a suspension of D5c (0.1 g, 0.248 mmol) in MeOH (2.5 mL) under a nitrogen atmosphere was added KOtBu (0.056 g, 0.497 mmol) in one portion. The reaction mixture was heated till reflux for 3 hours and cooled to room temperature overnight. The mixture was diluted with CH₂Cl₂ (5 mL) and poured out in saturated aqueous NH₄Cl (25 mL). The aqueous layer was extracted with CH₂Cl₂ (3×25 mL). The combined organic layers were dried over Na₂SO₄, filtered and evaporated under reduced pressure. The crude product was purified by flash column chromatography (silica, heptane/ethylacetate, 1:0->9:1) and coevaporated with CH₂Cl₂ (5 mL) to afford product D5d (0.08 g, 0.18 mmol, Yield=74%). According to NMR D5d was obtained as a ~2:1 cis/trans mixture. ¹HNMR (400 MHz, CDCl3) δ(ppm): 3.66 (3H, s), 3.39 (2H [cis-isomer (β-OH)], s), 3.38 (1H [trans-isomer (α—OH)], s), 3.24-3.12 (2H [cis-isomer (β-OH)/trans-isomer (α—OH)], m), 2.35 (1H, ddd, J=15.4, 10.3, 5.1 Hz), 2.21 (1H, ddd, J=15.8, 9.5, 6.3 Hz), 2.04 (1H, bs), 1.98-1.92 (1H, m), 1.92-1.75 (3H, m), 0.96 (3H, s), 0.91 (3H, d, J=6.4 Hz), 0.64 (3H, s).

Preparation of compound D5. In a flame dried round bottom flask (100 mL) D5d (0.080 g, 0.184 mmol) was dissolved in dry THF (3 mL) under an atmosphere of nitrogen and cooled to 0° C. MeMgCl 3.0M in THF (0.614 mL, 1.841 mmol) was added using a syringe The reaction mixture was stirred for 1.5 h at 0° C. The reaction mixture was quenched with saturated aqueous NH₄Cl (20 mL) and extracted three times with CH₂Cl2 (3×20 mL). The combined organic layers were washed with brine dried on Na₂SO₄ and the crude product was purified by flash column chromatography (silica, heptane/ethylacetate, 1:0->85:15) to afford D5 (36 mg, 0.08 mmol, yield=45%). ¹HNMR (400 MHz, CDCl3) δ(ppm): 3.39 (3H, s), 3.22 (1H, d, J=9.0 Hz), 3.20 (1H, d, 9.0 Hz), 1.20 6H, s), 0.97 (3H, s), 0.91 (3H, d, J=6.5 Hz), 0.65 (3H, s).

Example 32. Preparation of C3-alpha-D13 and C3-beta-D13 Compounds

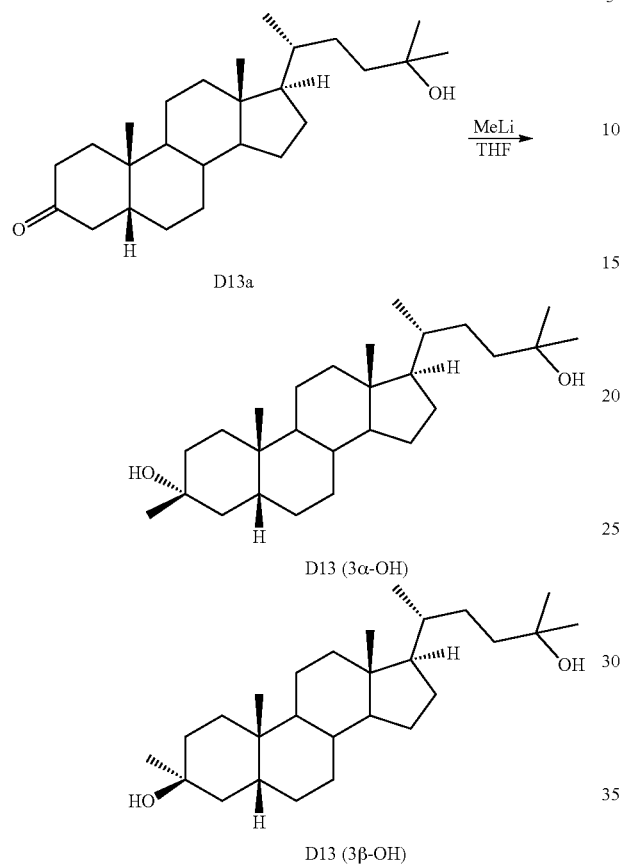

D13a

D13 (3α-OH)

D13 (3β-OH)

Under argon at 0° C. methyllithium, 1.6M in diethyl ether (0.26 mL, 0.412 mmol) was added dropwise to a solution of D13a (0.080 g, 0.206 mmol) in THF (dry, 1 mL). A white precipitate formed upon addition. THF (dry, 5 mL) was added. Stirring at 0° C. was continued for 10 min. Reaction mixture was allowed to warm to RT and stirring was continued for 1 h, TLC (H/E, 1:1) showed starting material and two more polar spots. Methyllithium, 1.6M in diethyl ether (0.39 mL, 0.618 mmol) was added at RT under argon. Stirring was continued overnight. Reaction mixture had turned into a yellow solution. Solvent was removed in vacuo. THF (dry, 1 mL) was added under argon at RT. Methyllithium, 1.6M in diethyl ether (0.26 mL, 0.412 mmol) was added dropwise and reaction mixture was stirred at RT for 3 h. Aq. sat. ammonium chloride (10 mL), $H_2O$ (5 mL) and diethyl ether (20 mL) were added. Layers were separated and aq. layer was extracted with diethyl ether (2×25 mL). Combined org. layers were dried with sodium sulfate and solvents were removed in vacuo. Flash chromatography (H, 5%-25% EtOAc) afforded 13 mg of the 3beta-hydroxy diastereoisomer and 12 mg of the 3alpha-hydroxy diastereoisomer. Compound D13 (3α—OH) (12 mg, 0.030 mmol; 14.4%) and compound D13 (β-OH) (13 mg, 0.032 mmol; 15.6%). (3α—OH): $^1$H-NMR (400 MHz, $CDCl_3$): δ (ppm): 2.03-1.92 (m, 2H), 1.90-1.79 (m, 2H), 1.78-1.70 (m, 1H), 1.63-0.99 (m, 25H), 1.25 (s, 3H), 1.20 (s, 3H), 1.19 (s, 3H), 0.93 (s, 3H), 0.91 (d, J=6.5 Hz, 3H), 0.64 (s, 3H). (β-OH): $^1$H-NMR (400 MHz, $CDCl_3$): δ (ppm): 2.00-1.78 (m, 4H), 1.67-0.99 (m, 25H), 1.22 (s, 3H), 1.20 (s, br, 6H), 0.96 (s, 3H), 0.94-0.86 (m, 4H), 0.65 (s, 3H).

Example 33. Preparation of Compounds C3-alpha and C3-beta D14

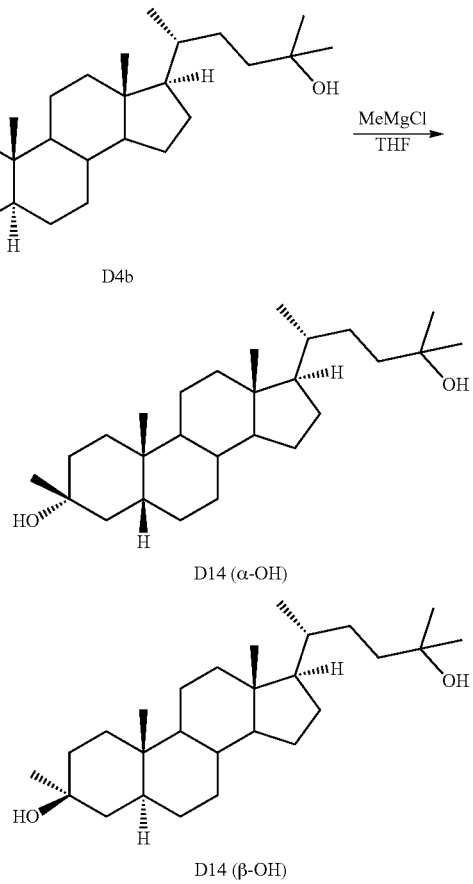

D4b

D14 (α-OH)

D14 (β-OH)

In a flame dried reaction tube (20 mL) D4b (0.1 g, 0.257 mmol) was dissolved in dry THF (3 mL) under an atmosphere of argon and cooled to −10° C. MeMgCl 3.0M in THF (0.86 mL, 2.57 mmol) was added drop wise using a syringe MeMgCl 3.0M in THF (0.68 mL, 2.04 mmol). The reaction mixture was coming up to room temperature during 1.5 h and stirred for 2 h at room temperature. The reaction mixture was poured into a stirred solution of saturated aqueous $NH_4Cl$ (100 mL) and extracted three times with $CH_2Cl_2$ (3×75 mL). The combined organic layers were washed with brine dried on $Na_2SO_4$ and the crude product was purified by flash column chromatography (silica, heptane/ethylacetate, 1:0->4:1) to afford D14 (α—OH) (28 mg, 0.07 mmol, yield=27%) and D14 (β-OH) (21 mg, 0.05 mmol, yield=20%) both as a white solid. D14 (α—OH): $^1$HNMR (400 MHz, $CDCl_3$) δ (ppm): 1.95 (1H, dt, J=12.3, 3.1 Hz), 1.89-1.77 (1H, m), 1.65 (1H, dq, J=12.7, 3.3 Hz), 1.20 (9H, s), 0.92 (3H, d, J=6.5 Hz), 0.75 (3H, s), 0.78-0.69 (1H, m), 0.65 (3H, s). D14 (β-OH): $^1$HNMR (400 MHz, $CDCl_3$) δ (ppm): 1.96 (1H, dt, J=12.5, 3.3 Hz), 1.89-1.77 (1H, m), 1.25 (3H, s), 1.20 (3H, s), 1.19 (3H, s), 0.92 (3H, d, J=6.5 Hz), 0.81 (3H, s), 0.65 (3H, s), 0.70-0.61 (1H, m).

Example 34. Synthesis of 6-difluoro Analogs
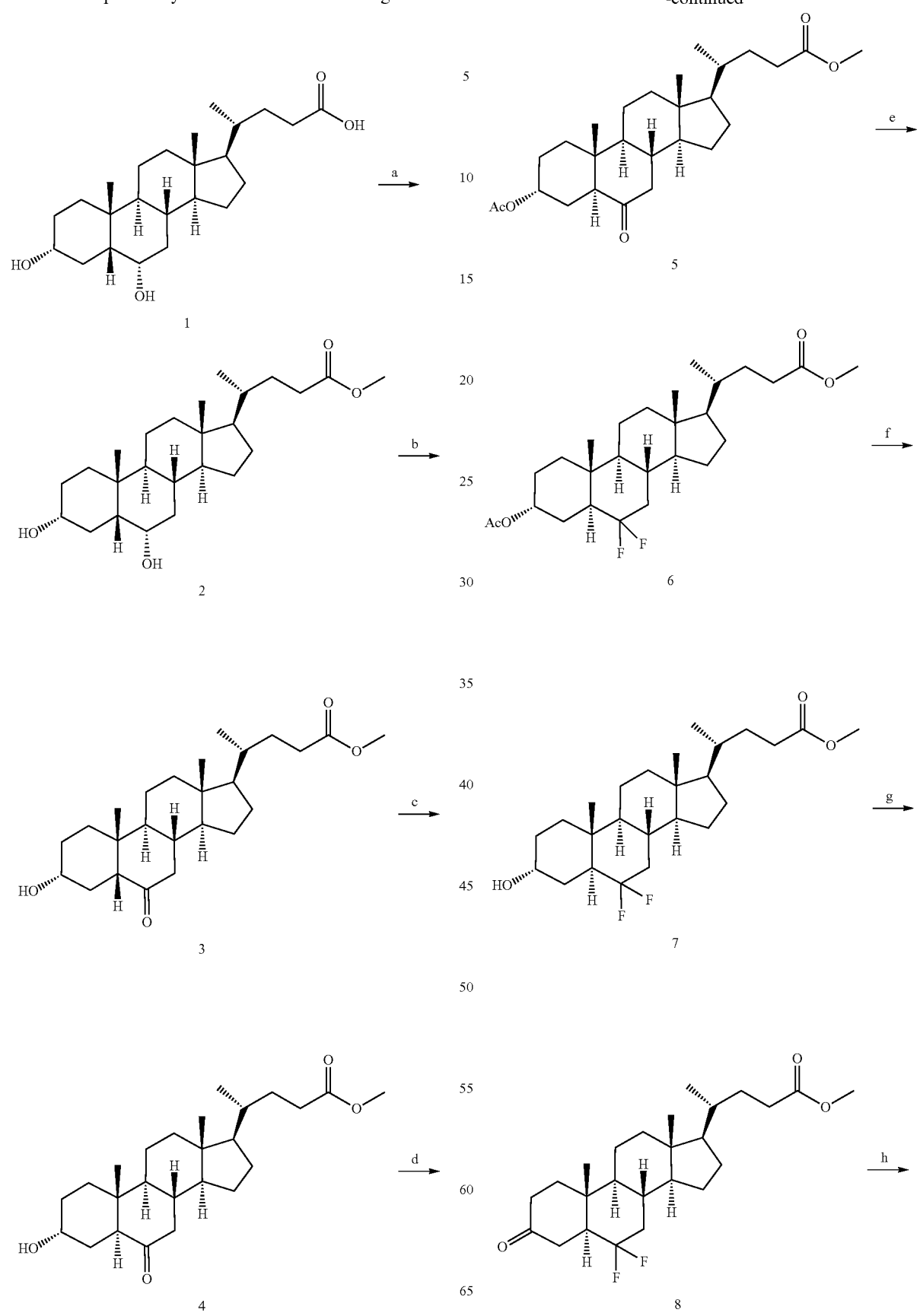

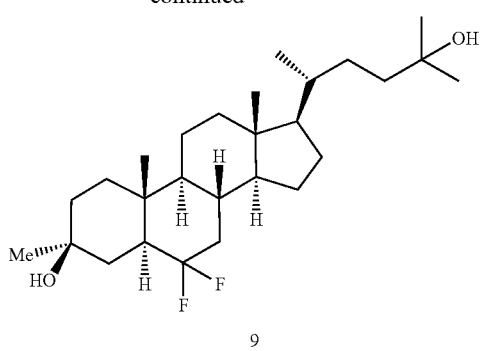
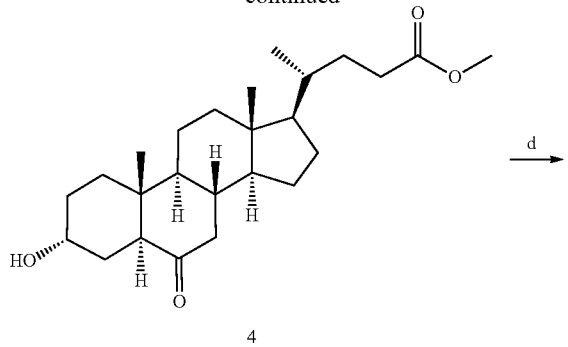
(a) H2SO4, MeOH, reflux overnight, 97%; (b) Jones reagent, acetone, 0° C. 30 min, 60%; (c) HCl, MeOH, rt overnight, 44%; (d) Ac2O, pyridine, 70° C., overnight, 92%; (e) DAST(neat), 40° C., 4 days, 42%; (f) HCl, MeOH, THF, rt overnight; (g) Dess-Marin periodinane, CH2Cl2, rt overnight; (h) MeMgBr, THF, 0° C.
Example 35. Synthesis of 5,6-alkenyl-6-monofluoro Analogs
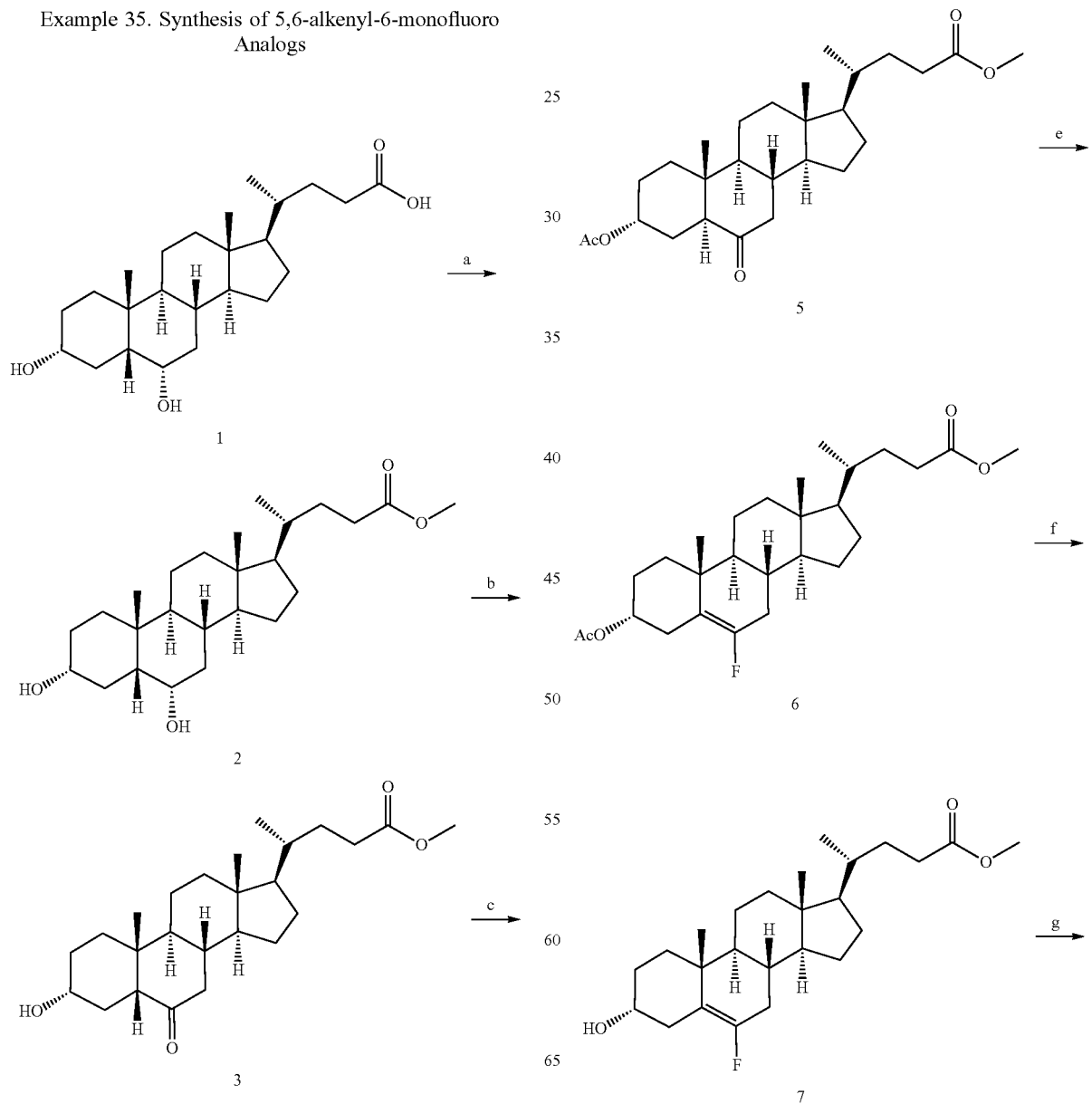

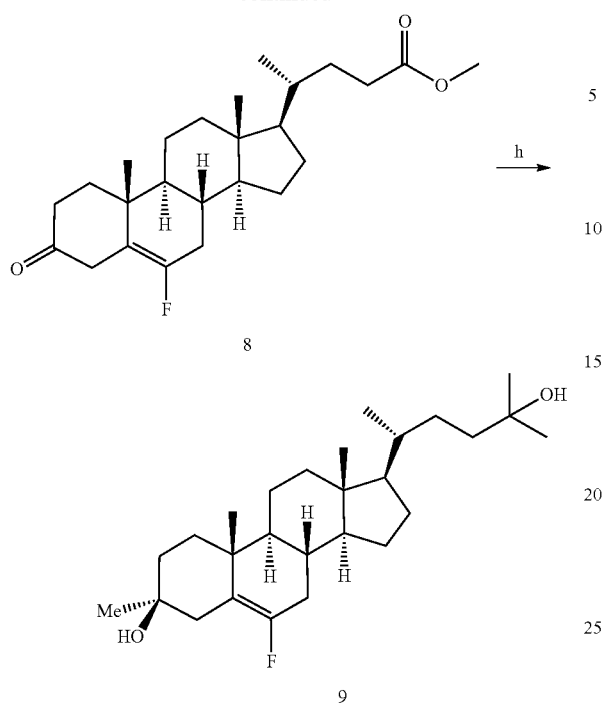
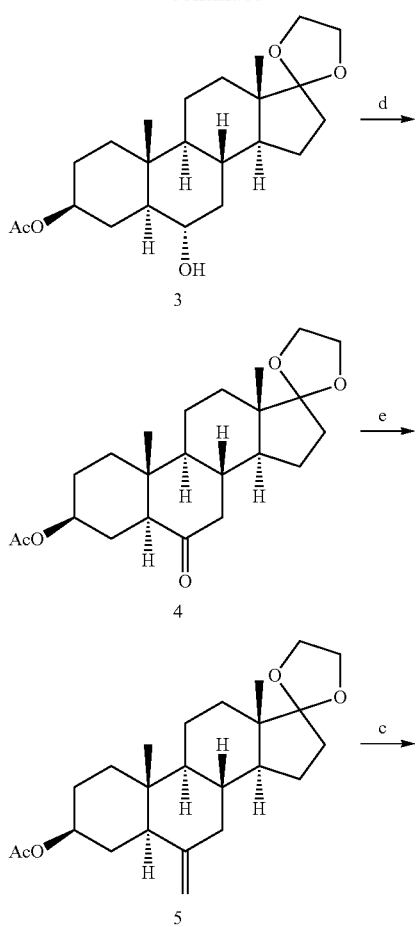
(a) H₂SO₄, MeOH, reflux overnight, 97%; (b) Jones reagent, acetone, 0° C. 30 min, 60%; (c) HCl, MeOH, rt overnight, 44%; (d) Ac₂O, pyridine, 70° C., overnight, 92%; (e) DAST(neat), cat. fuming H₂SO₄; (f) HCl, MeOH, THF, rt overnight; (g) Dess-Marin periodinane, CH2Cl2, rt overnight; (h) MeMgBr, THF, 0° C.
Example 36. Synthesis of 6-beta-methyl Analogs
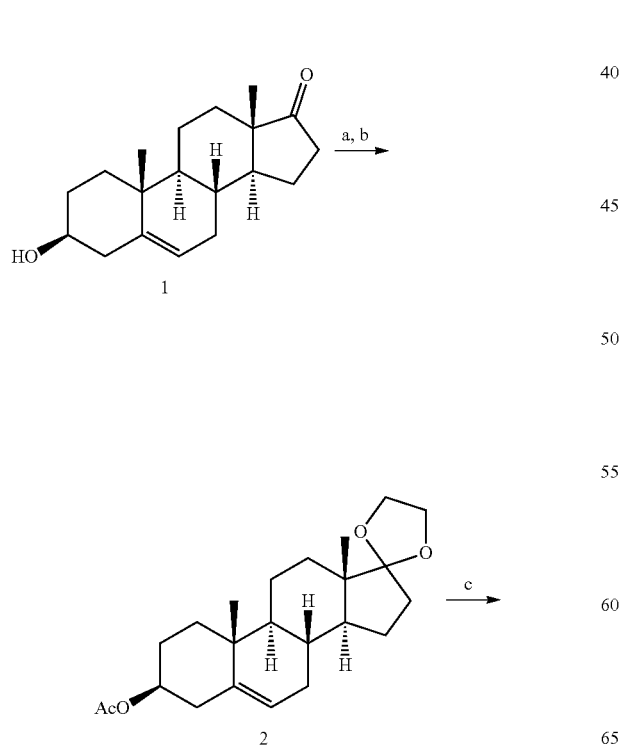
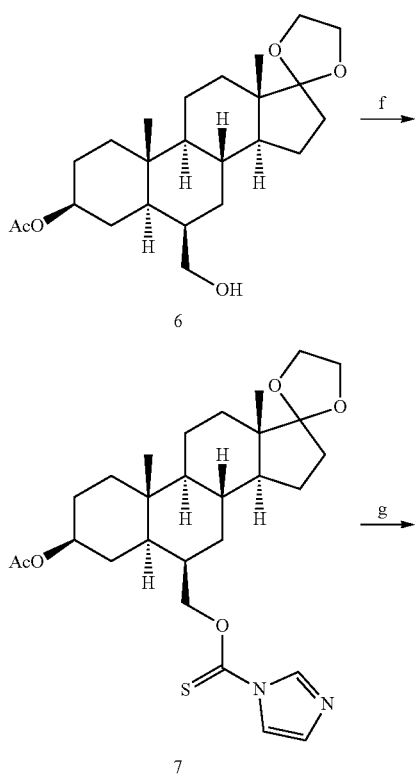

195
-continued

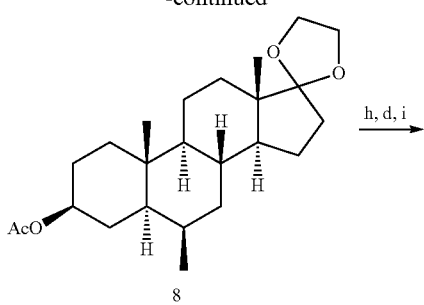

8

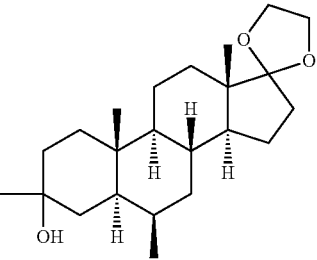

9a, α-OH
9b, β-OH (a) Ethane-1,2-diol, cat·TsOH, toluene, reflux overnight; (b) Ac₂O, pyridine, rt overnight; (c) BH₃, THF, NaOH/H₂O₂, 0° C. then rt; (d) Dess-Martin periodinane, CH₂Cl₂, rt overnight; (e) methyltriphenylphosphonium bromide, potassium tert-butoxide, THF, room temperature; (f) TCDI, DMAP, CH2Cl2, 40° C.; (g) Ph3SnH, AIBN, toluene, 100° C.; (h) potassium carbonate, MeOH, rt overnight; (i) MeMgBr, THF, 0° C.

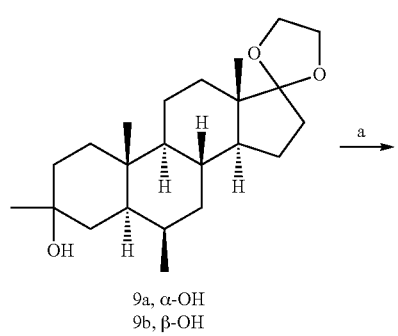

9a, α-OH
9b, β-OH

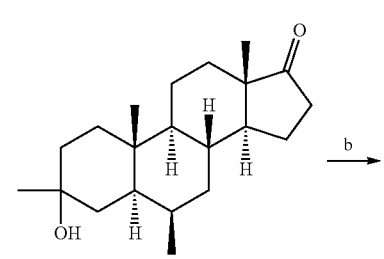

10a, α-OH
10b, β-OH

196
-continued

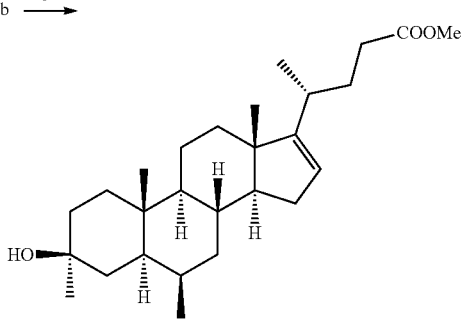

11a, α-OH
11b, β-OH

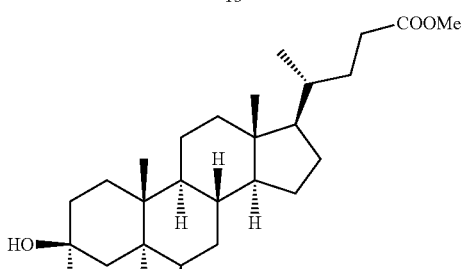

13

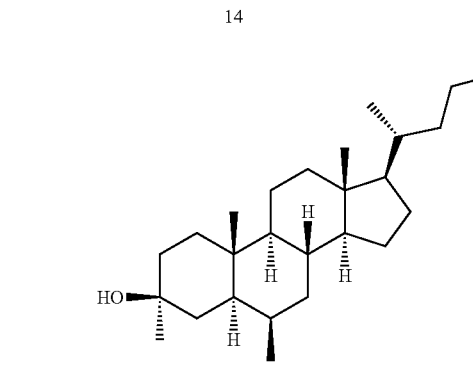

14

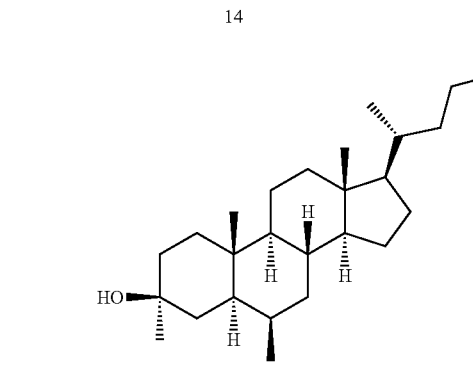

15

(a) 3M HCl, acetone; (b)(ethyl)-triphenylphosphonium bromide, t-BuOK, THF, 65° C.; (e) methylacrylate, EtAlCl2, DCM, rt; (f) 10% Pd/C, H2, EtOAc; (g) MeMgBr, THF, 0° C.

Assay Methods

Compounds of the present invention can be evaluated using various in vitro and in vivo assays described in the literature; examples of which are described below.

The following examples are offered to illustrate the biological activity of the compounds, pharmaceutical compositions, and methods provided herein and are not to be construed in any way as limiting the scope thereof.

NMDA Modulation Activity Assay

The compounds of the invention are or can be tested for their NMDA modulation activity using the assay described by Paul et al., in *J. Pharm. and Exp. Ther.* 1994, 271, 677-682. The assay protocol is reproduced below.

(1) Cell Culture

Hippocampal neurons from 19-day-old Sprague-Dawley rat embryos are maintained in primary culture, as described previously (Segal, J. NeurophysioL 50 1249-1264, 1983). Briefly, hippocampal tissue is dissected and mechanically disrupted and the cell suspension is plated onto poly-L-lysine (Sigma, St. Louis, MO)-coated, glass-bottom, 35-mm culture dishes that contained modified Eagle's medium with Earle's salts supplemented with 10% fetal bovine serum, 10% horse serum and 2 mM glutamine (Sigma). $N_3$ serum supplement (modified from Guthrie et al., Brain Res. 420 313-323, 1987) consisted of: bovine serum albumin, 0.001%; transferrin, 20 mg/liter; insulin, 10 mg/liter; selenium, 60 nM; corticosterone, 40 μg/liter; triiodothyronine, 20 μg/liter; progesterone, 40 nM; and putrescine, 200 M, which is added to the media. Cells are incubated in a humidified atmosphere that contained 10% $CO_2$ and 90% air. Culture media that lacked fetal bovine serum is added every 7 days after plating. The cells are used after 7 to 14 days in culture.

(2) Measurement of Intracellular $Ca^{++}$

Cultures are washed three times with buffer that contained (in millimolar quantities) the following: NaCl, 145; KCl, 2.5; HEPES, 10; $CaCl_2$, 1; and glucose, 10 (adjusted to pH 7.4 with NaOH and to an osmolality of 315-325 mOsm with sucrose). The cultures are then incubated with fura-2 acetoxymethyl ester 2 to 5 μM for 30 to 45 min in the dark at 37° C. After the incubation period, the cultures are again ished three times with buffer and allowed to stand for ≥15 mm to permit complete hydrolysis of the ester. The neuron of interest is perfused with buffer at a rate of approximately 250 μl/min (37° C.). The perfusion device consisted of a water-jacketed array of 10 tubes that emptied into a common tip positioned approximately 500 m from the cell. All solutions contained 0.5 μM tetrodotoxin to eliminate voltage-sensitive $Na^+$ currents and 2 to 5 μM glycine to saturate the strychnine-insensitive glycine site on NMDA receptors.

$[Ca^{++}]$ is measured by microspectrofluorimetry with the $Ca^{++}$ sensitive indicator fura-2 (Groden et al., Cell Calcium 12: 279-287, 1991). The neurons are illuminated on a Nikon inverted microscope with a dual-wavelength illumination-photometry system (SPEX-DM3000 AR-CM, SPEX Industries, Edison, NJ).

Excitation of fura-2 occurred at 340 and 380 nm with emitted light monitored at 510 nm. The neurons are visualized by phase-contrast microscopy and are easily identified by their characteristic morphology. Light reaching the photomultiplier is limited to that emitted by the cell of interest by a pinhole. The photon counts are stored in digital form for subsequent analysis. Calibration is carried out as described by Grynkiewicz et at. (J. Biol. Chem. 280, 34440-3450, 1985). The fluorescence ratio at saturating $Ca^{++}$ ($R_{max}$) is determined in situ by bathing the cells in buffer that contained (in millimolar quantities) the following: KCl, 130; NaCl, 17; HEPES, 10; glucose, 10; $CaCl_2$, 2; and ionomycin, 0.015 (pH 7.2, 37° C. Some calibration buffers contained 10 μM carbonyl cyanide-m-chlorophenyl-hydrazone to uncouple mitochondrial oxidative phosphorylation. For the determination of the fluorescence ratio at zero $Ca^{++}$ ($R_{min}$), the buffer is modified so that 3 mM EGTA and 80 M EGTA acetoxymethyl ester is substituted for $CaCl_2$. An apparent $K_d$ of 285 nM (Groden et at., 1991) is used for $[Ca^{++}]$; calculations.

Electrophysiology Assay

The compounds of the invention are or can be tested in electrophysiology assay as described by Petrovic et al., in *J. Neuroscience* 160 (2009) 616-628. The assay protocol is reproduced below.

(1) Hippocampal Cultures

Primary dissociated hippocampal cultures are prepared from 1- to 2-day-old postnatal rats. Animals are decapitated, and the hippocampi are dissected. Trypsin digestion, followed by mechanical dissociation, is used to prepare cell suspension. Single cells are plated at a density of 500,000 cells/$cm^2$ on 31- or 12-mm polylysine-coated glass coverslips. Neuronal cultures are maintained in Neurobasal™-A (Invitrogen, Carlsbad, CA, USA) medium supplemented with glutamine (0.5 mM) and B27 Serum-Free Supplement (Invitrogen).

(2) Transfection and Maintenance of HEK293 Cells

HEK293 cells (American Type Culture Collection, ATTC No. CRL1573, Rockville, MD, USA) are cultured in Opti-MEM® I (Invitrogen) with 5% fetal bovine serum at 37° C. and transfected with NR1-1a/NR2B/green fluorescent protein (GFP) plasmids as described previously (Cais et al., Neuroscience 151: 428-438, 2008). Briefly, equal amounts (0.3 μg) of cDNAs coding for NR1, NR2 and GFP (pQBI 25, Takara, Otsu, Shiga, Japan) are mixed with 0.9 μl Matra-A Reagent (IBA, Göttingen, Germany) and added to confluent HEK293 cells on a 24-well plate. After trypsinization, the cells are resuspended in Opti-MEM® I containing 1% fetal bovine serum supplemented with 20 mM MgCl2.1 mM D,L-2-amino-5-phosphonopentanoic acid and 3 mM kynurenic acid and plated on 30-mm polylysine-coated glass coverslips. The following genes encoding NMDAR subunits are used: NR1-1a (GenBank accession no. U08261) (Hollmann et al., Neuron 10:943-954 1993) and NR2B (GenBank accession no. M91562) (Monyer et al., *Science,* 256: 1217-1221, 1992).

(3) Recording from Cultured Cells and Drug Application

Experiments are performed 24-48 h after the end of HEK293 transfection; neurons maintained in culture for 5-8 days are used. Whole-cell voltage-clamp recordings are made with a patch-clamp amplifier after a capacitance and series resistance (<10 MΩ) compensation of 80%-90%. Agonist-induced responses are low-pass filtered at 1 kHz with an eight-pole Bessel filter (Frequency Devices, Haverhill, MA, USA), digitally sampled at 5 kHz and analyzed using pCLAMP software version 9 (Axon Instruments). Patch pipettes (3-4 MΩ) pulled from borosilicate glass are filled with $Cs^+$ based intracellular solution (Cs-ICS) containing (in mM) 125 gluconic acid, 15 CsCl, 5 EGTA, 10 Hepes, 3 MgCl2, 0.5 $CaCl_2$), and 2 ATP-Mg salt (pH-adjusted to 7.2 with CsOH). Extracellular solution (ECS) contained (in mM) 160 NaCl, 2.5 KCl, 10 Hepes, 10 glucose, 0.2 EDTA and 0.7 $CaCl_2$) (pH-adjusted to 7.3 with NaOH). In some experiments, the concentration of $CaCl_2$ is lowered to 0.2 mM (with no EDTA) or increased to 2 mM as indicated. Glycine (10 μM), an NMDAR coagonist, is present in the control and test solutions. Tetrodotoxin (0.5 μM) and bicuculline methochloride (10 μM) are used in experiments on cultured hippocampal neurons. The solutions of compounds of invention are made from freshly prepared 20 mM stock in dimethyl sulfoxide (DMSO). The same concentration of DMSO is maintained in all ECSs. A microprocessor-controlled multibarrel fast perfusion system, with a time constant of solution exchange around cells of ~10 ms, is used to apply test and control solutions (Vyklicky et al., *J Physiol Lond* 470:575-600 1990).

The compounds of the invention are prepared according to synthetic methods described herein and their purity is tested by using conventional methods known to one skilled in the art.

NMDA Binding In Vitro

Compounds can be screened to determine their potential as modulators of NMDA binding in vitro. These assays are or can be performed in accordance with the above discussed procedures.

In Vivo Pharmacology.

Male NSA mice weighing between 15-20 g are obtained from Harlan Sprague-Dawley (San Diego, CA). Upon arrival they are housed in standard polycarbonate cages (4 per cage) containing a sterilized bedding material in a room of constant temp (23.0°±2.5° C.) with a 12 h (07.00-19.00 light) light/dark cycle. Food (Teklad LM 485) and water are freely available. Mice are acclimated a minimum of 4 days prior to experimentation.

Hanging Wire Test

The hanging-wire test used a custom-built apparatus that consisted of a metal wire (2 mm diameter) suspended horizontally above a padded surface (25 cm). Mice are held by the base of the tail, their forepaws placed in contact with the wire, and then released. Animals are required to bring both hindpaws in contact with the wire within 5 sec in order to be scored as a pass. Results are treated quantally.

Drug Metabolism and Pharmacokinetics: HERG Assay

HEK 293 cells which stably express the HERG potassium channel are used for electrophysiological study. The methodology for stable transfection of this channel in HEK cells can be found elsewhere (Zhou et al., *Biophys. J.* 74:230-41, 1998). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95% $O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MOhm and seal resistances >1 GOhm are accepted for further experimentation. Series resistance compensation was applied up to a maximum of 80%. No leak subtraction is done. However, acceptable access resistance depended on the size of the recorded currents and the level of series resistance compensation that can safely be used.

Following the achievement of whole cell configuration and sufficient time for cell dialysis with pipette solution (>5 min), a standard voltage protocol is applied to the cell to evoke membrane currents. The voltage protocol is as follows. The membrane is depolarized from a holding potential of −80 mV to +40 mV for 1000 ms. This was followed by a descending voltage ramp (rate 0.5 mV msec-1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 min by a peristalic pump. Provided there were minimal changes in the amplitude of the evoked current response in the vehicle control condition, the test compound of either 0.3, 1, 3, or 10 mM is applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There is a subsequent wash period of a 10-20 min to assess reversibility. Finally, the cells is exposed to high dose of dofetilide (5 mM), a specific IKr blocker, to evaluate the insensitive endogenous current.

All experiments are performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, is measured off line on the computer.

The arithmetic mean of the ten values of amplitude is calculated under vehicle control conditions and in the presence of drug. Percent decrease of IN in each experiment was obtained by the normalized current value using the following formula: IN=(1−ID/IC)×100, where ID is the mean current value in the presence of drug and IC is the mean current value under control conditions. Separate experiments are performed for each drug concentration or time-matched control, and arithmetic mean in each experiment is defined as the result of the study.

Drug Metabolism and Pharmacokinetics: Half-Life in Human Liver Microsomes (HLM)

Test compounds (1 μM) are incubated with 3.3 mM $MgCl_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of P450 group is collected at 0, 10, 30, and 60 min time point, where 0 min time point indicated the time when NADPH was added into the reaction mixture of P450 group. An aliquot of samples of non-P450 group is collected at −10 and 65 min time point. Collected aliquots are extracted with acetonitrile solution containing an internal standard. The precipitated protein is spun down in centrifuge (2000 rpm, 15 min). The compound concentration in supernatant is measured by LC/MS/MS system. The half-life value is obtained by plotting the natural logarithm of the peak area ratio of compounds/internal standard versus time. The slope of the line of best fit through the points yields the rate of metabolism (k), and is converted to a half-life value using following equation: Half-life=ln 2/k.

Example 37. NMDA Potentiation Data

The whole-cell patch-clamp technique was used to investigate the effects of compounds (0.1 mM and 1.0 mM) on the NMDA receptor (GRIN1/GRIN2A subunits) expressed in HEK cells. NMDA/Glycine peak and steady-state currents were recorded from stably transfected cells expressing the NMDA receptor and the modulatory effects of the test items on these currents were investigated.

Cells were stably transfected (Lipofectamine™) with human GRIN1 (variant NR1-3). These cells were transiently transfected with GRIN2A cDNA and CD8 (pLeu) antigene cDNA. About 24-72 hours following transfection 1 μl Dynabeads M-45 CD8 was added to identify successfully transfected cells (Jurman et al., *Biotechniques* (1994) 17:876-881). Cells were passaged to a confluence of 50-80%. Whole cell currents were measured with HEKA EPC-10 amplifiers using PatchMaster software. Cell culture dishes for recordings were placed on the dish holder of the microscope and continuously perfused (1 ml/min) with bath solution. All solutions applied to cells including the pipette solution were maintained at room temperature (19° C.-30° C.). After formation of a Gigaohm seal between the patch electrodes and transfected individual HEK 293 cells (pipette resistance range: 2.5 MW-6.0 MW; seal resistance range:>1 GW) the cell membrane across the pipette tip was ruptured to assure electrical access to the cell interior (whole-cell patch-configuration). Once a stable seal could be established NMDA inward currents were measured upon application of 30 μM NMDA (and 5.0 μM Glycine) to patch-clamped cells (2 applications) for 5 s. The cells were voltage clamped at a holding potential of −80 mV.

| Structure | NMDA 1a2A (%) Potentiation 0.1 uM | NMDA 1a2A (%) Potentiation 1 uM |
|---|---|---|
| 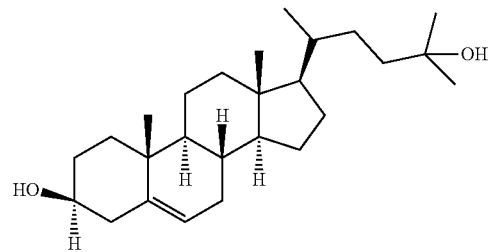 $C_{26}H_{44}O_2$ Compound 1 (Org-1) | 55 | 197 |
| 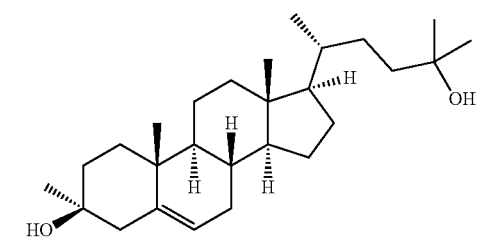 $C_{27}H_{46}O_2$ | 128 | 348 |
| 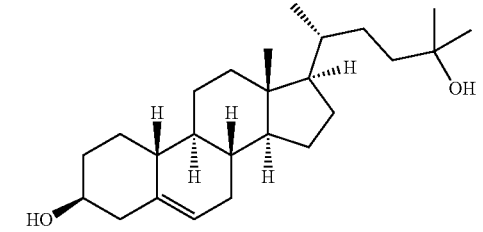 $C_{25}H_{42}O_2$ | 28 | 66 |
| 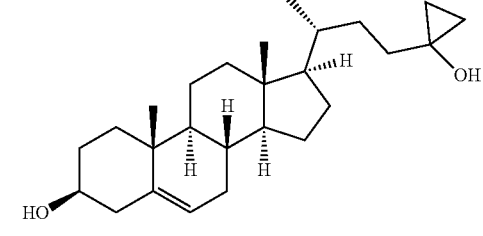 $C_{26}H_{42}O_2$ | 74 | 171 |

-continued
| Structure | NMDA 1a2A (%) Potentiation 0.1 uM | NMDA 1a2A (%) Potentiation 1 uM |
|---|---|---|
| 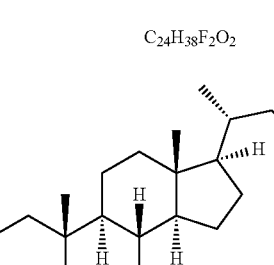<br>$C_{24}H_{38}F_2O_2$ | 31 | 95 |
| 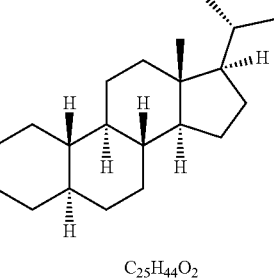<br>$C_{24}H_{40}O_2$ | 39 | 127 |
| 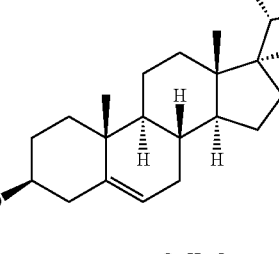<br>$C_{25}H_{44}O_2$ | 19 | 44 |
| 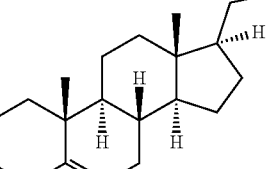<br>$C_{24}H_{40}O_2$ | 4 | 24 |
| 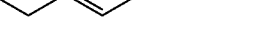<br>$C_{25}H_{42}O_2$ | 42 | 98 |

-continued
| Structure | NMDA 1a2A (%) Potentiation 0.1 uM | NMDA 1a2A (%) Potentiation 1 uM |
|---|---|---|
| 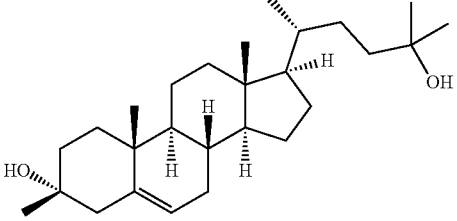 C₂₇H₄₆O₂ | 13 | 60 |
| 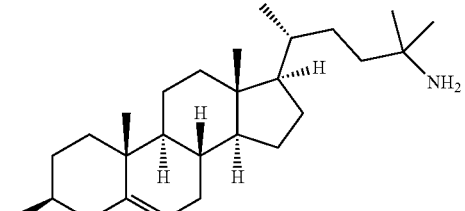 C₂₆H₄₅NO | −8 | −19 |
| 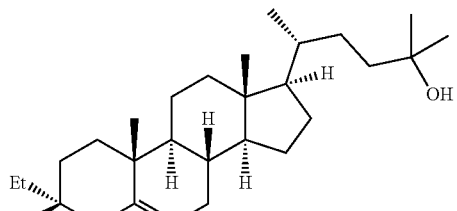 C₂₈H₄₈O₂ | 181 | 286 |
| 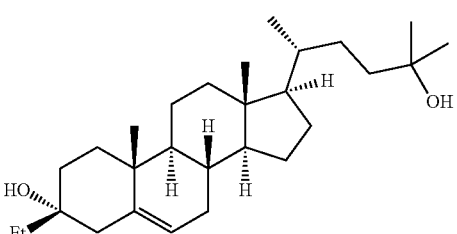 C₂₈H₄₈O₂ | 23 | 139 |
| 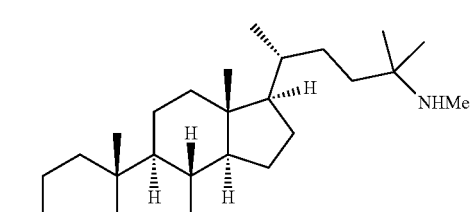 C₂₇H₄₇NO | 25 | 19 |

-continued

| Structure | NMDA 1a2A (%) Potentiation 0.1 uM | NMDA 1a2A (%) Potentiation 1 uM |
|---|---|---|
| C₂₆H₄₆O₂ | 25 | 114 |
| C₂₆H₄₆O₂ | 21 | 52 |
| C₂₆H₄₄F₃O₂ | 14 | 85 |
| C₂₆H₄₆O₂ | 18 | 85 |
| C₂₇H₄₅F₃O₂ | 59 | 172 |

-continued
| Structure | NMDA 1a2A (%) Potentiation 0.1 uM | NMDA 1a2A (%) Potentiation 1 uM |
|---|---|---|
| 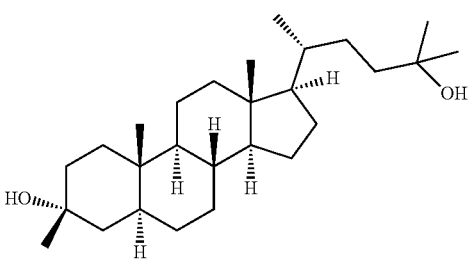 $C_{27}H_{48}O_2$ | 19 | 30 |
| 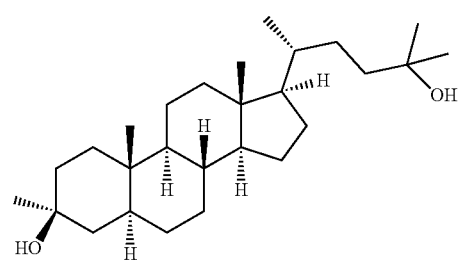 $C_{27}H_{48}O_2$ | 87, 70 | 278, 238 |
| 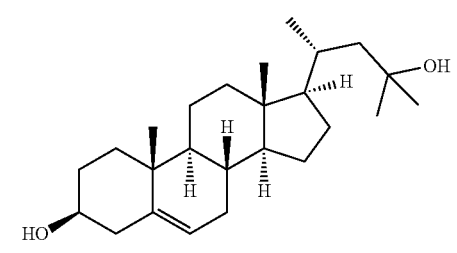 $C_{25}H_{42}O_2$ | −5 | 27 |
| 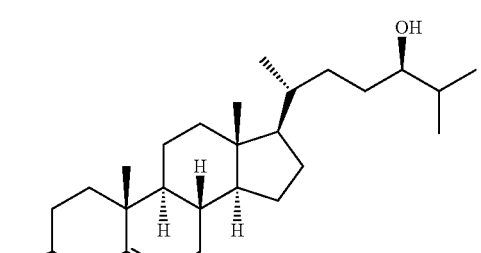 $C_{27}H_{46}O_2$ | 82 | 137 |
| 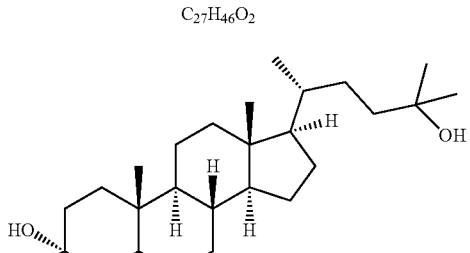 $C_{27}H_{45}F_3O_2$ | 9 | 18 |

-continued

| Structure | NMDA 1a2A (%) Potentiation 0.1 uM | NMDA 1a2A (%) Potentiation 1 uM |
|---|---|---|
| C₂₈H₅₀O₃ | 8 | 25 |
| C₂₈H₅₀O₃ | 14 | 110 |
| C₂₆H₄₆O₂ | 17 | 105 |
| C₂₅H₄₄O₃ | 6 | 27 |
| C₂₅H₄₂O₃ | −5 | −14 |

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I-b1), (I-b2) or (I-b3):

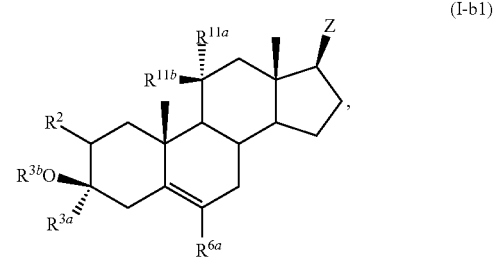

(I-b1)

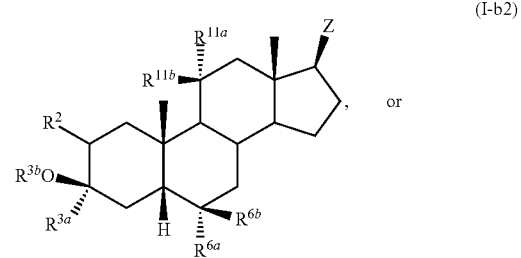

(I-b2)

or

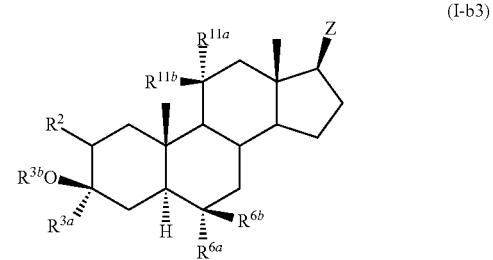

(I-b3)

or a pharmaceutically acceptable salt thereof;

wherein:

Z is selected from the group consisting of

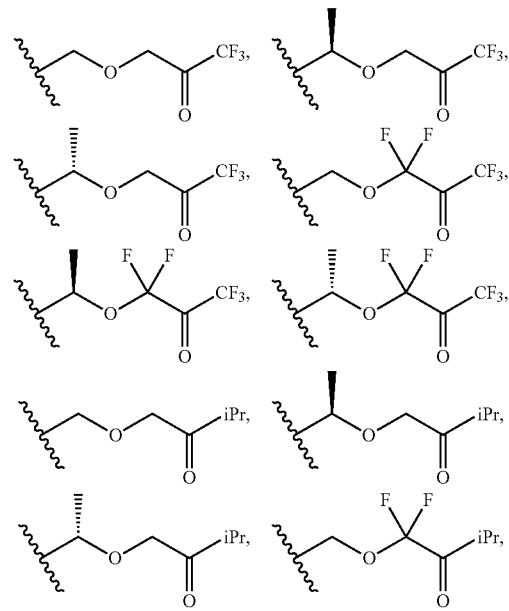

-continued

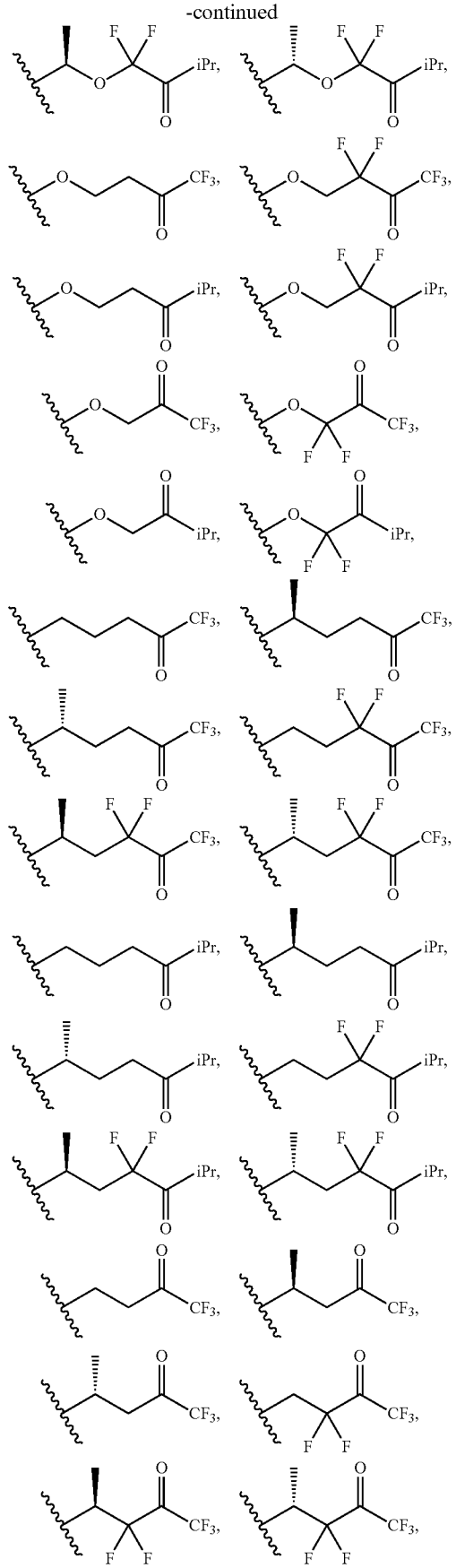

-continued

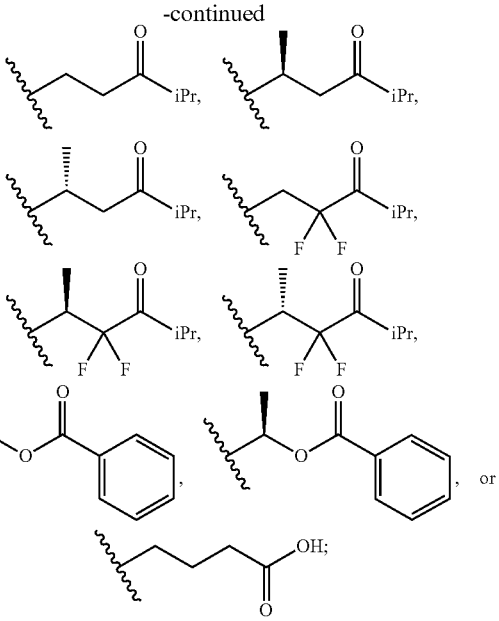

$R^{3b}$ is hydrogen;

$R^{3a}$ is substituted or unsubstituted alkyl, substituted or unsubstituted alkenyl, or substituted or unsubstituted alkynyl;

each instance of $R^2$, $R^{11a}$, and $R^{11b}$ is independently hydrogen or —$OR^{B1}$, wherein $R^{B1}$ is hydrogen or substituted or unsubstituted alkyl, or $R^{11a}$ and $R^{11b}$ are joined to form an oxo (=O) group; and each of $R^{6a}$ and $R^{6b}$ is independently hydrogen, halo, or substituted or unsubstituted alkyl.

2. The compound of claim 1, or a pharmaceutically acceptable salt thereof, wherein $R^{3a}$ is substituted or unsubstituted alkyl.

3. The compound of claim 1, or a pharmaceutically acceptable salt thereof wherein $R^{6b}$ is halo or substituted or unsubstituted alkyl.

4. The compound of claim 1, or a pharmaceutically acceptable salt thereof, wherein $R^2$ is hydrogen.

5. The compound of claim 1, or a pharmaceutically acceptable salt thereof, wherein $R^2$ is —$OR^{B1}$.

6. The compound of claim 1, or a pharmaceutically acceptable salt thereof, wherein $R^{11b}$ is hydrogen or —$OR^{B1}$, and $R^{11a}$ is hydrogen.

7. The compound of claim 1, or a pharmaceutically acceptable salt thereof, wherein $R^{11a}$ and $R^{11b}$ are joined to form an oxo group.

8. The compound of claim 1, wherein the compound is selected from the group consisting of:

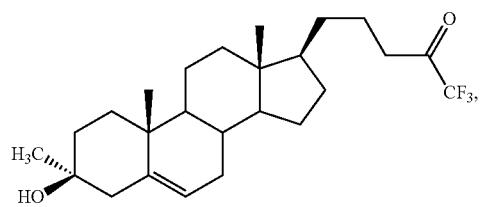

217
-continued
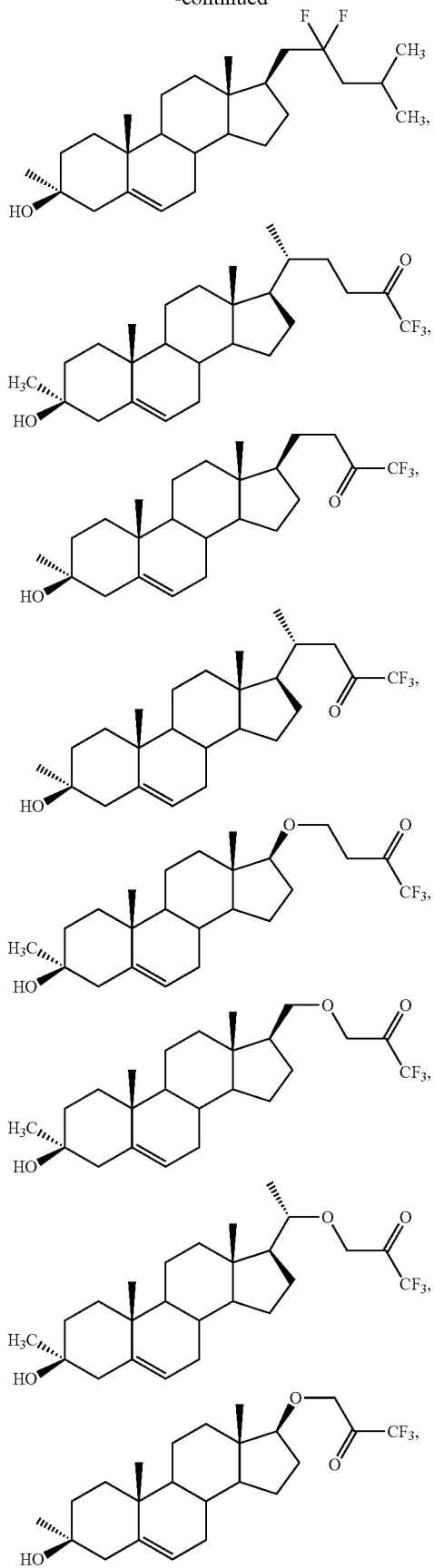
218
-continued
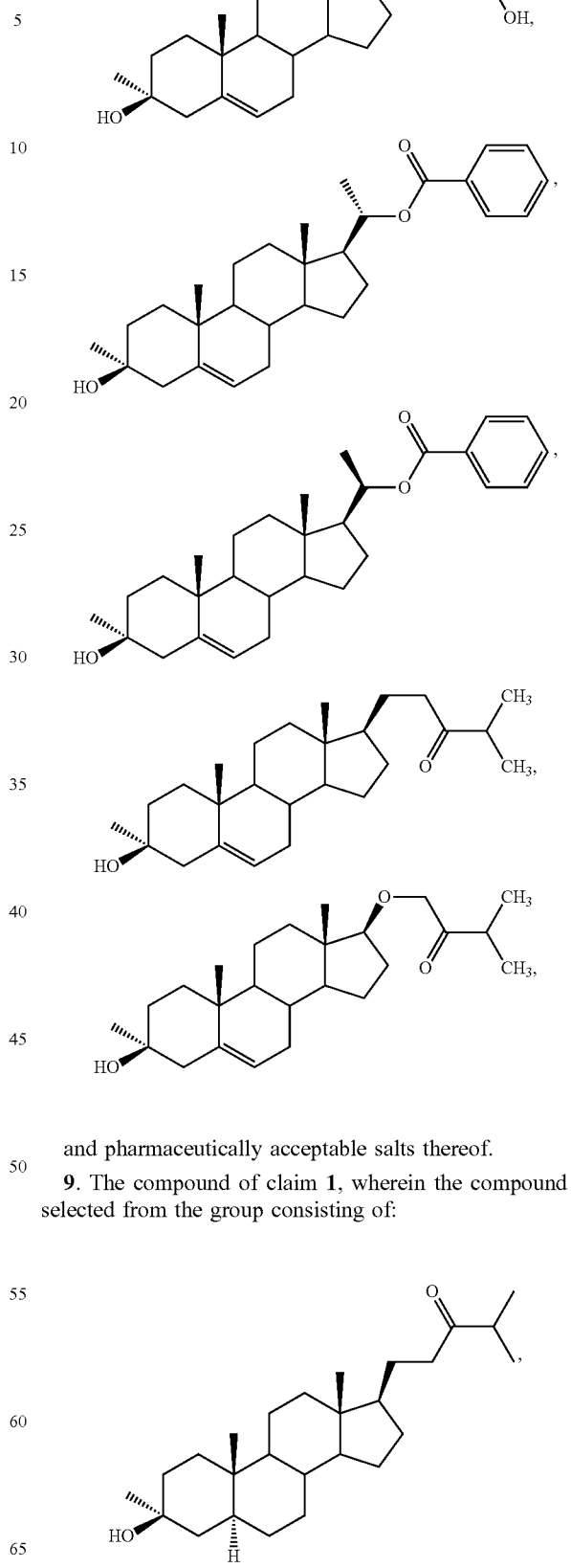
and pharmaceutically acceptable salts thereof.
9. The compound of claim 1, wherein the compound is selected from the group consisting of:
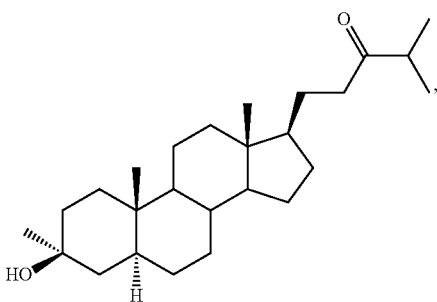

219
-continued
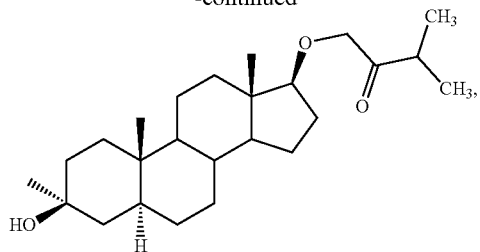
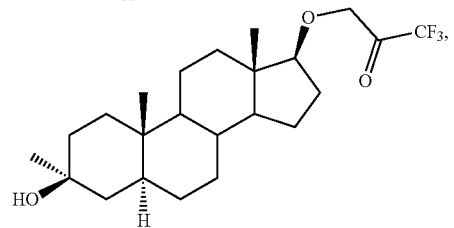
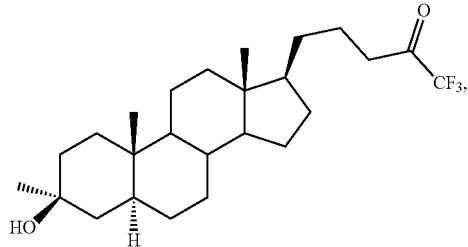
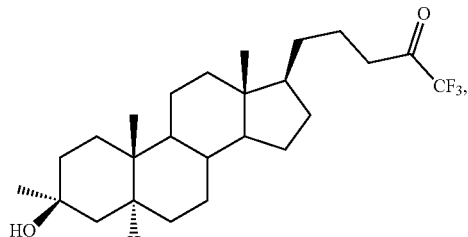
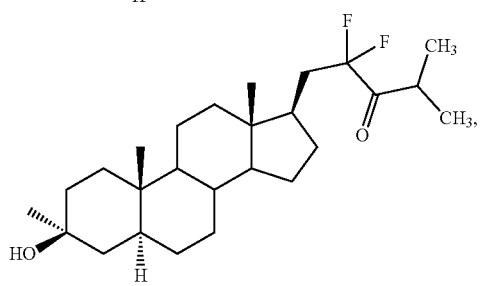
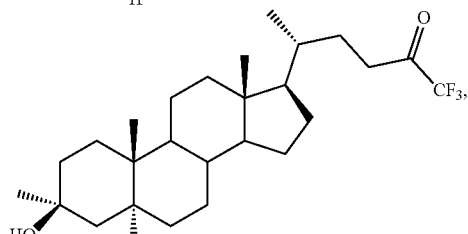
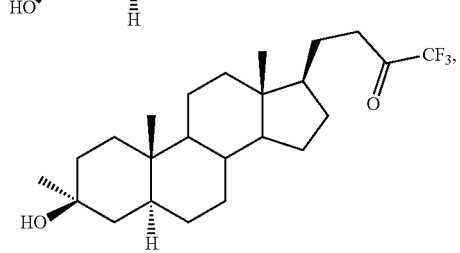
220
-continued
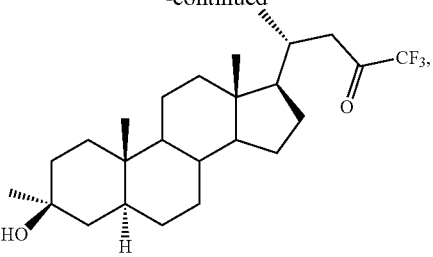
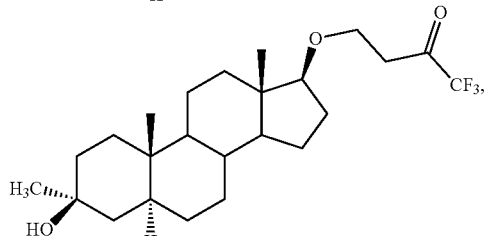
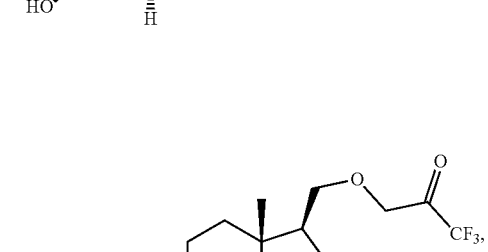
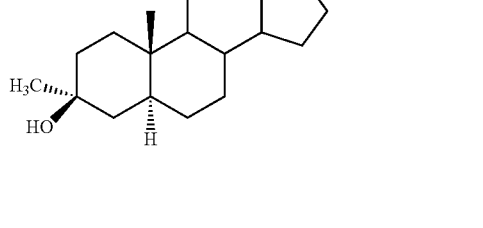
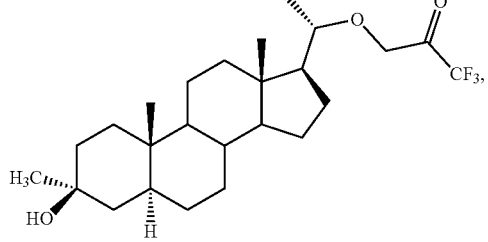
and pharmaceutically acceptable salts thereof.
10. A pharmaceutical composition comprising a pharmaceutically acceptable carrier and a compound of claim 1 or a pharmaceutically acceptable salt thereof.
11. The compound of claim 8, wherein the compound is selected from the group consisting of:
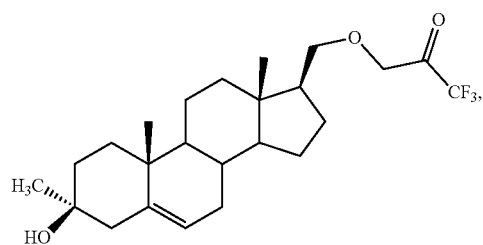

221
-continued
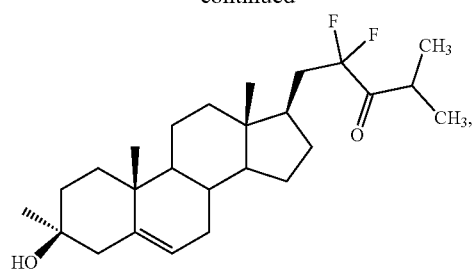
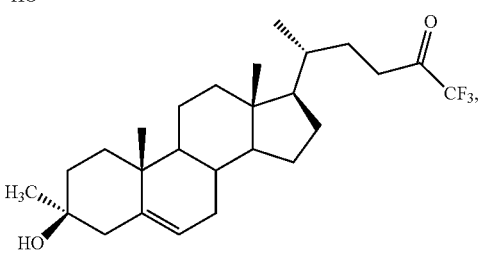
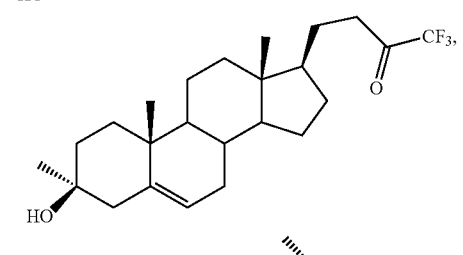
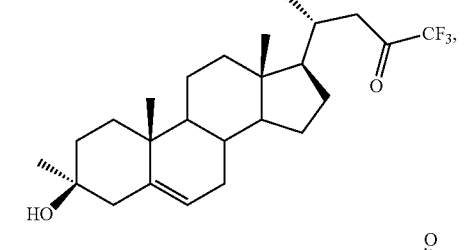
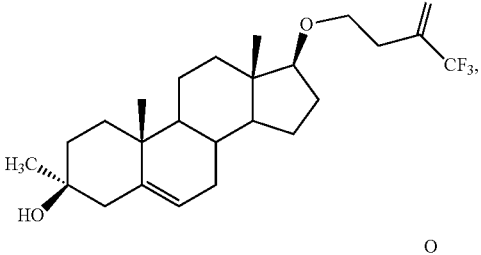
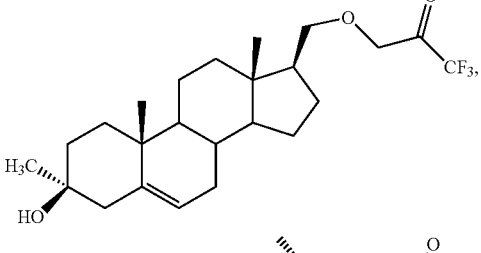
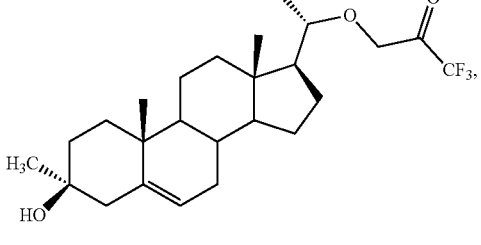
222
-continued
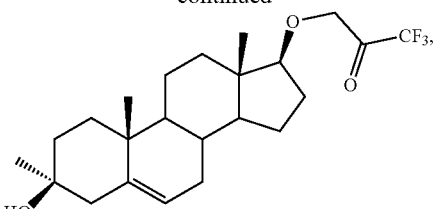
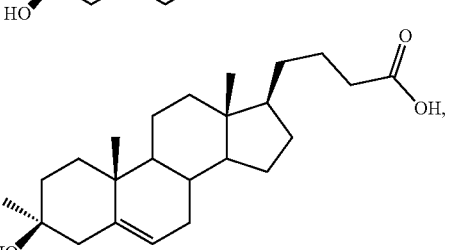
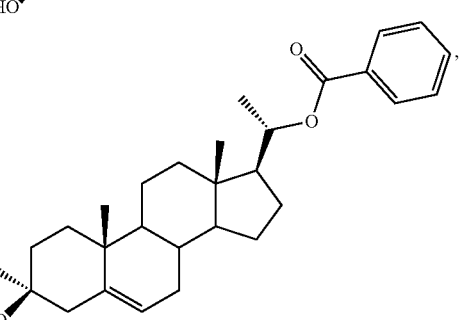
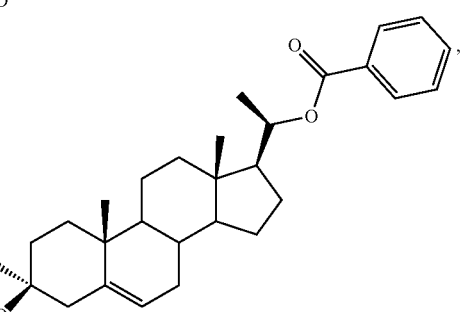
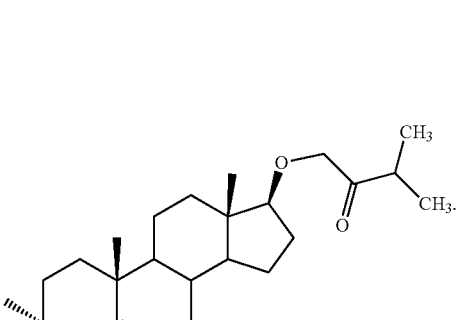

12. The compound of claim 9, wherein the compound is selected from the group consisting of:
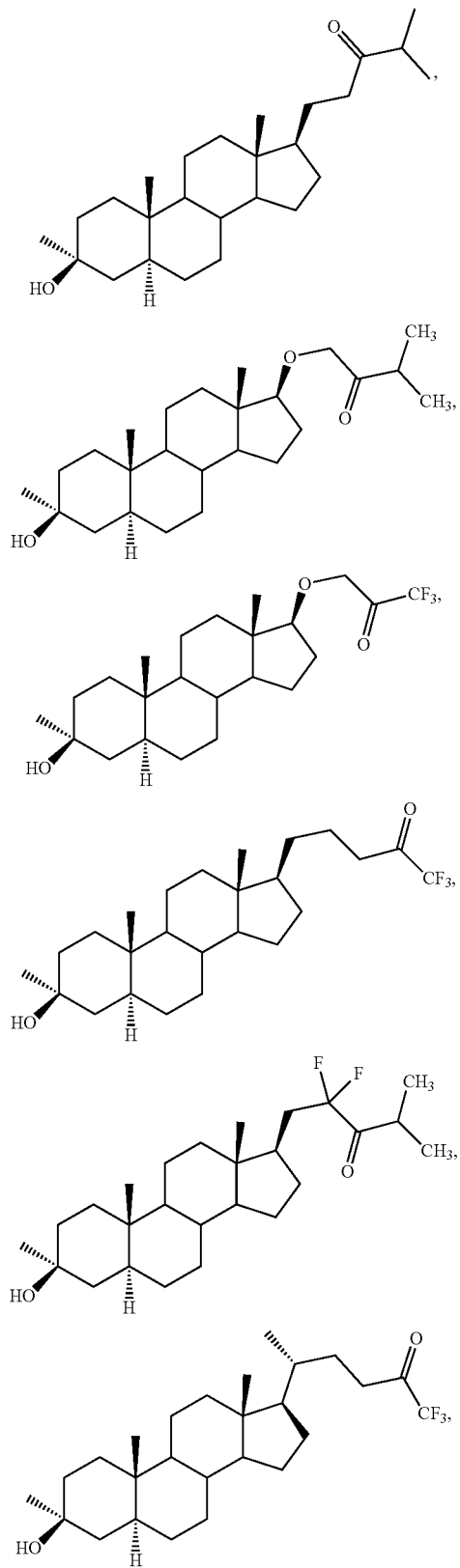
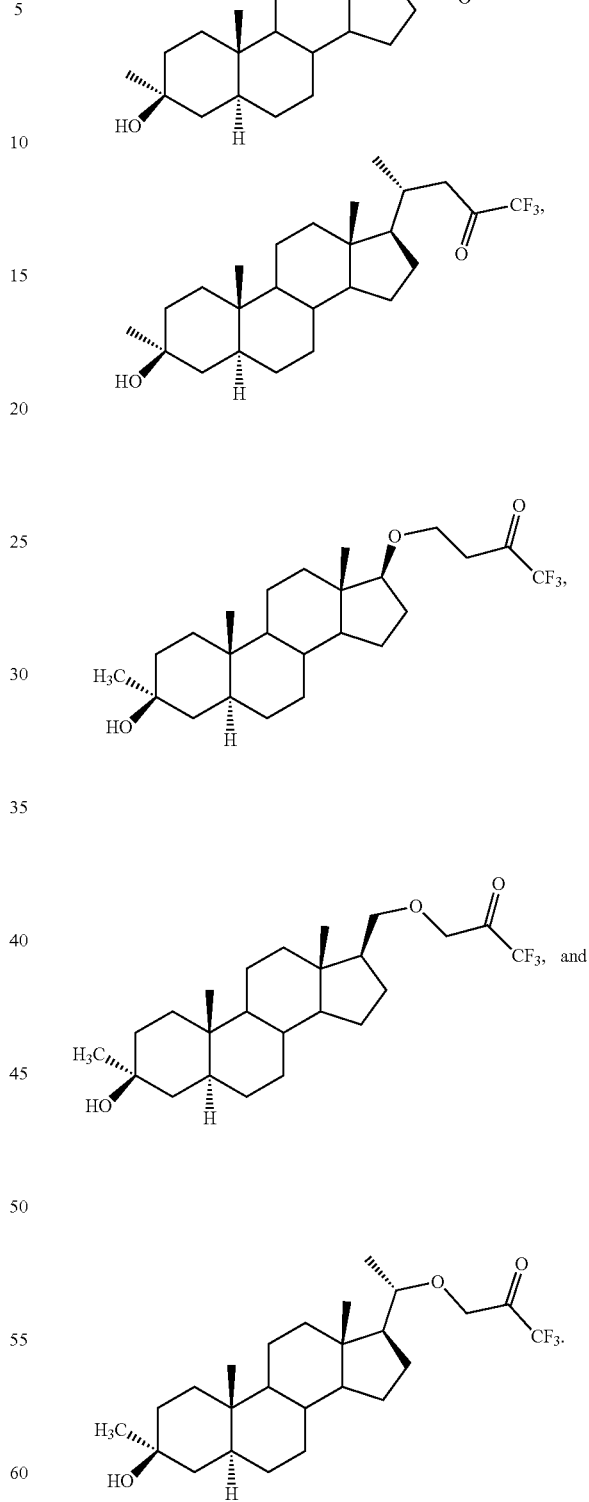
13. A pharmaceutical composition comprising a pharmaceutically acceptable carrier and a compound of claim 11.
14. A pharmaceutical composition comprising a pharmaceutically acceptable carrier and a compound of claim 12.

15. The compound of claim 8, wherein the compound is a pharmaceutically acceptable salt of a compound selected from the group consisting of:
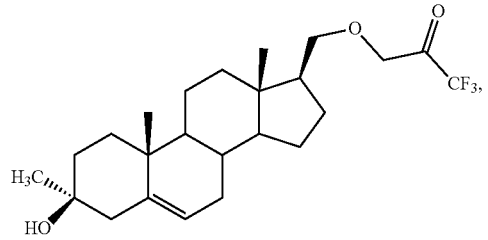
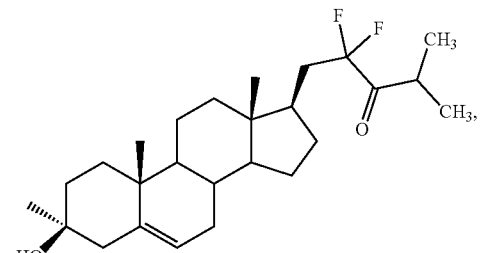
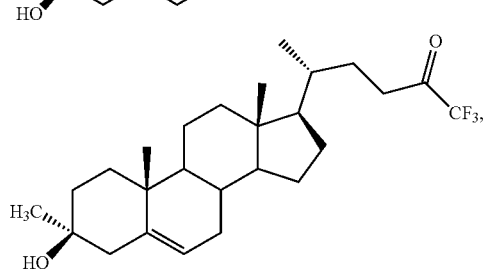
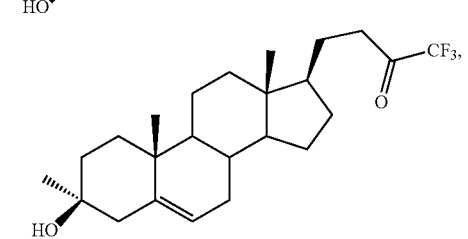
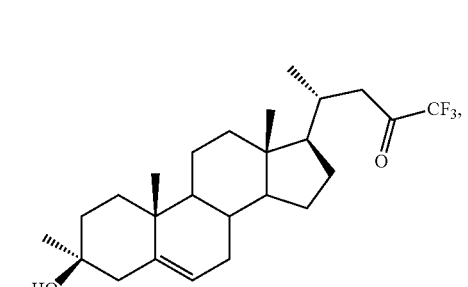
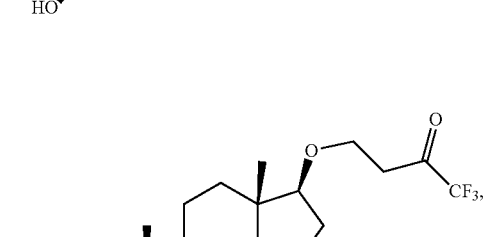
-continued
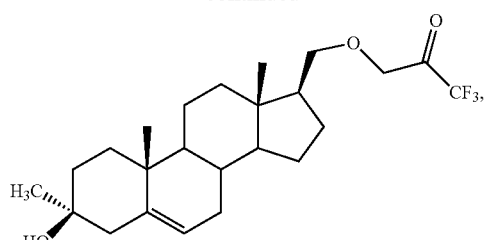
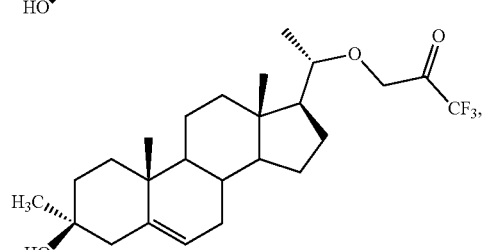
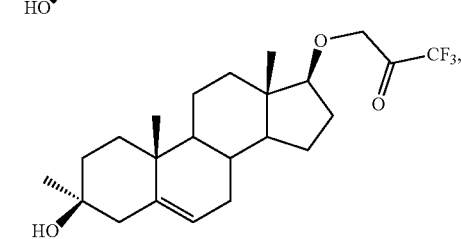
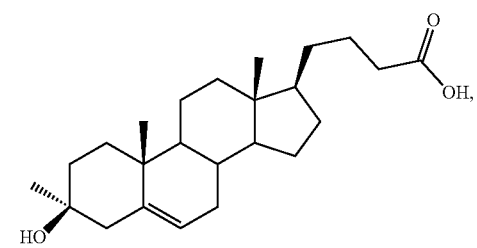
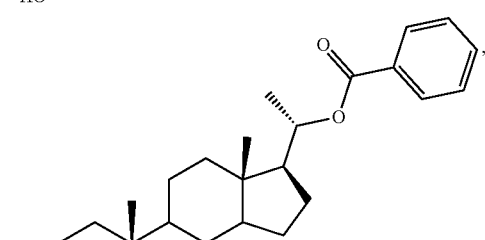
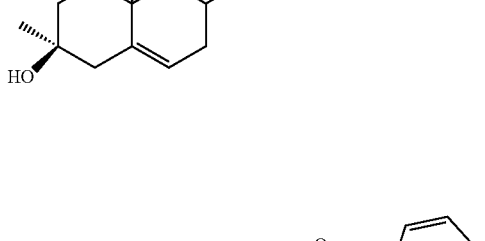
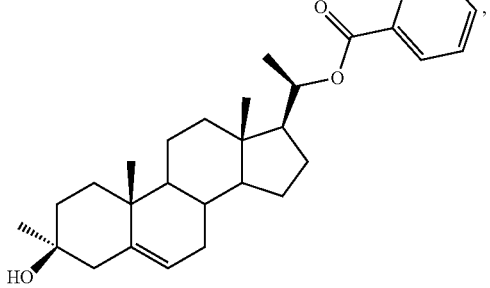

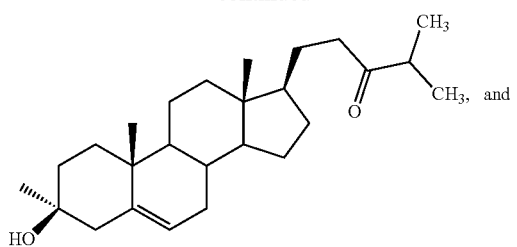
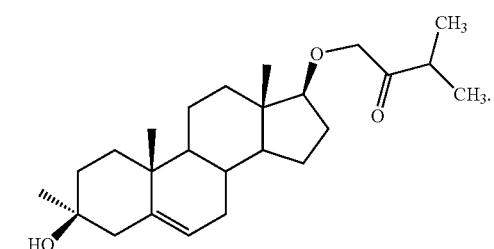
16. The compound of claim 9, wherein the compound is a pharmaceutically acceptable salt of a compound selected from the group consisting of:
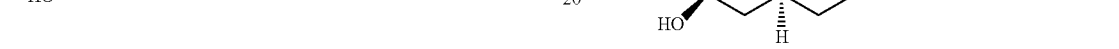
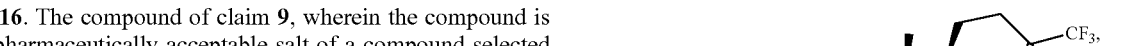
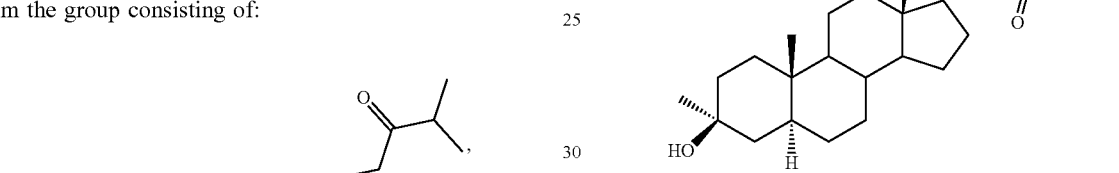
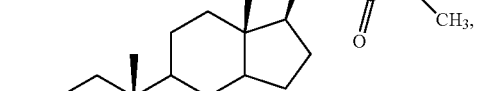
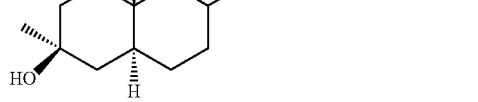
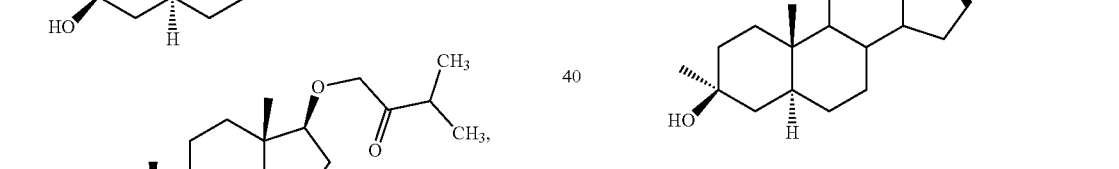
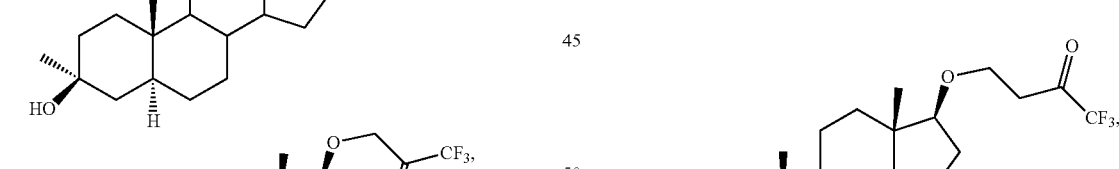
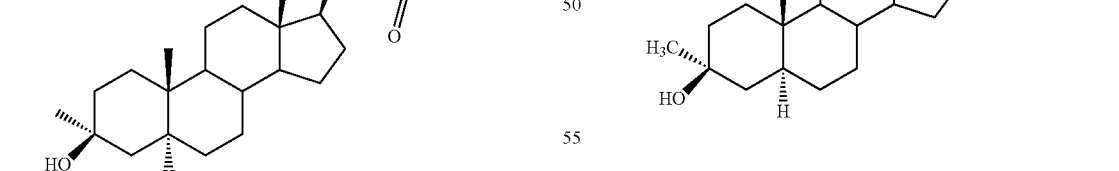
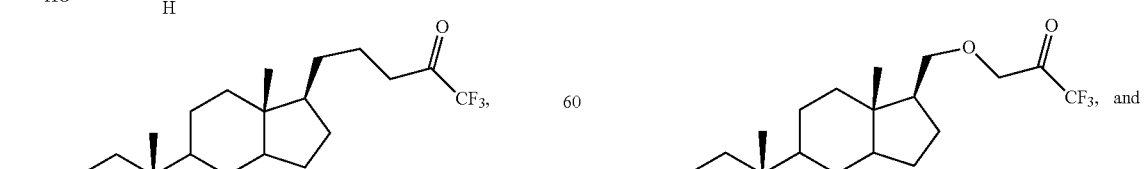

-continued
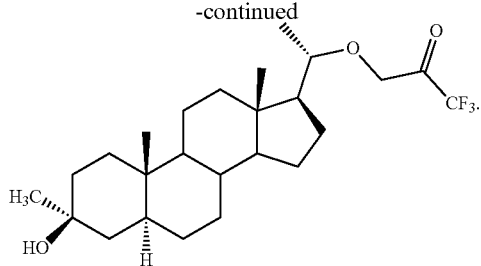
17. A pharmaceutical composition comprising a pharmaceutically acceptable carrier and a compound of claim 15.
18. A pharmaceutical composition comprising a pharmaceutically acceptable carrier and a compound of claim 16.
* * * * *